United States Patent
Lehmann-Lintz et al.

(10) Patent No.: US 8,754,079 B2
(45) Date of Patent: *Jun. 17, 2014

(54) CYCLOALKYL CONTAINING THIENOPYRIMIDINES FOR PHARMACEUTICAL COMPOSITIONS

(75) Inventors: Thorsten Lehmann-Lintz, Ochsenhausen (DE); Armin Heckel, Biberach (DE); Joerg Kley, Mittelbiberach (DE); Elke Langkopf, Warthausen (DE); Norbert Redemann, Biberach (DE); Achim Sauer, Ravensburg-Torkenweiler (DE); Leo Thomas, Biberach (DE); Dieter Wiedenmayer, Biberach (DE); Matthias Austen, Goettingen (DE); John Danilewicz, Canterbury (GB); Martin Schneider, Goettingen (DE); Kay Schreiter, Goettingen (DE); Phillip Black, Saffron Walden (GB); Wesley Blackaby, Saffron Walden (GB); Ian Linney, Saffron Walden (GB)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 379 days.

This patent is subject to a terminal disclaimer.

(21) Appl. No.: 13/034,855

(22) Filed: Feb. 25, 2011

(65) Prior Publication Data

US 2011/0217311 A1 Sep. 8, 2011

(30) Foreign Application Priority Data

Feb. 26, 2010 (EP) .................................. 10154922

(51) Int. Cl.
| | |
|---|---|
| *C07D 495/04* | (2006.01) |
| *A61K 31/519* | (2006.01) |
| *A61K 31/496* | (2006.01) |
| *A61K 31/5355* | (2006.01) |
| *C07D 413/12* | (2006.01) |
| *A61P 25/28* | (2006.01) |
| *A61P 29/00* | (2006.01) |
| *A61P 35/00* | (2006.01) |

(52) U.S. Cl.
CPC .................... *C07D 495/04* (2013.01)
USPC .............. 514/234.2; 514/260.1; 514/252.16; 544/117; 544/278

(58) Field of Classification Search
CPC ..................... C07D 495/04; A61K 31/519
USPC ....................... 544/278; 514/260.1
See application file for complete search history.

(56) References Cited

U.S. PATENT DOCUMENTS

| | | | |
|---|---|---|---|
| 5,686,457 | A | 11/1997 | Traxler et al. |
| 6,096,749 | A | 8/2000 | Traxler et al. |
| 6,395,733 | B1 | 5/2002 | Arnold et al. |
| 6,784,174 | B1 | 8/2004 | Cumming |
| 8,071,607 | B2 | 12/2011 | Coulter et al. |
| 2001/0027197 | A1 | 10/2001 | Bridges et al. |
| 2003/0162795 | A1 | 8/2003 | Munchhof et al. |
| 2006/0020042 | A1 | 1/2006 | McDonald et al. |
| 2007/0099877 | A1 | 5/2007 | Cai et al. |
| 2009/0163520 | A1 | 6/2009 | Coulter et al. |
| 2010/0015708 | A1 | 1/2010 | Quay et al. |
| 2010/0056548 | A1 | 3/2010 | Aicher et al. |
| 2010/0143341 | A1 | 6/2010 | Taylor et al. |
| 2010/0247517 | A1 | 9/2010 | Austen et al. |
| 2011/0021203 | A1 | 1/2011 | Yamada et al. |
| 2011/0212102 | A1 | 9/2011 | Lehmann-Lintz et al. |
| 2011/0217311 | A1 | 9/2011 | Lehmann-Lintz et al. |
| 2012/0128686 | A1 | 5/2012 | Austen et al. |
| 2013/0056914 | A1 | 3/2013 | Frankowski et al. |

FOREIGN PATENT DOCUMENTS

| | | |
|---|---|---|
| CA | 2038521 A1 | 9/1991 |
| CH | 408945 A | 3/1966 |
| DE | 3036390 A1 | 5/1982 |
| DE | 248593 A1 | 8/1987 |
| EP | 0447891 A1 | 9/1991 |
| EP | 0452002 A2 | 10/1991 |
| EP | 0682027 A1 | 11/1995 |
| EP | 0729758 A2 | 9/1996 |
| EP | 1724268 A1 | 11/2006 |
| JP | 2005503345 A | 2/2005 |

(Continued)

OTHER PUBLICATIONS

Banker, Gilbert S., et al; Modern Pharmaceutics (1996) 3rd Ed. Marcel Dekker, Inc. New York, p. 596.

(Continued)

*Primary Examiner* — Susanna Moore
(74) *Attorney, Agent, or Firm* — Michael P. Morris; Edward S. Lazer

(57) ABSTRACT

The present invention relates to novel thienopyrimidine compounds of general formula

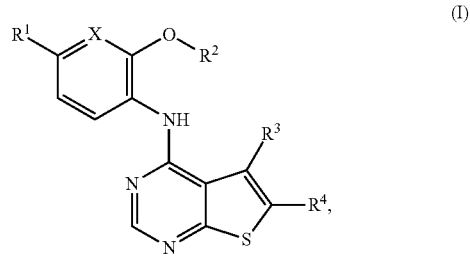

pharmaceutical compositions comprising these compounds and their therapeutic use for the prophylaxis and/or treatment of diseases which can be influenced by the inhibition of the kinase activity of Mnk1 and/or Mnk2 (Mnk2a or Mnk2b) and/or variants thereof.

13 Claims, No Drawings

(56) References Cited

FOREIGN PATENT DOCUMENTS

| WO | 9413677 | A1 | 6/1994 |
|---|---|---|---|
| WO | 9713771 | A1 | 4/1997 |
| WO | 9924440 | A1 | 5/1999 |
| WO | 0056738 | A1 | 9/2000 |
| WO | 0075145 | A1 | 12/2000 |
| WO | 02088138 | A1 | 11/2002 |
| WO | 03037362 | A2 | 5/2003 |
| WO | 2004037159 | A2 | 5/2004 |
| WO | 2004106340 | A2 | 12/2004 |
| WO | 2004113347 | A1 | 12/2004 |
| WO | 2005010008 | A1 | 2/2005 |
| WO | 2005042537 | A1 | 5/2005 |
| WO | 2005080377 | A1 | 9/2005 |
| WO | 2005117890 | A2 | 12/2005 |
| WO | 2006014325 | A2 | 2/2006 |
| WO | 2006066937 | A2 | 6/2006 |
| WO | 2006094791 | A1 | 9/2006 |
| WO | 2006124874 | A2 | 11/2006 |
| WO | 2006136402 | A1 | 12/2006 |
| WO | 2007056214 | A2 | 5/2007 |
| WO | 2007056215 | A2 | 5/2007 |
| WO | 2007059905 | A2 | 5/2007 |
| WO | 2007081517 | A2 | 7/2007 |
| WO | 2007084815 | A2 | 7/2007 |
| WO | 2007115822 | A1 | 10/2007 |
| WO | 2007147874 | A1 | 12/2007 |
| WO | 2008006547 | A2 | 1/2008 |
| WO | 2008041053 | A2 | 4/2008 |
| WO | 2009065596 | A2 | 5/2009 |
| WO | 2010023181 | A1 | 3/2010 |
| WO | 2011104334 | A1 | 9/2011 |
| WO | 2011104337 | A1 | 9/2011 |
| WO | 2011104338 | A1 | 9/2011 |
| WO | 2011104340 | A1 | 9/2011 |

OTHER PUBLICATIONS

Baumgartner, A., et al; Uber Thieno-Verbindungen: 14. Mitteilung: Darstellung 4-Aminosubstituierter Thieno[2.3-d]pyrimidyn-6-carbosa bsauurederivate; Institut fur Pharnazeutischer, (1993).

Cheng, C.C., et al; Potential Purine Antagonists. VI. Synthesis of 1-Alkyl- and 1-Aryl-4-substituted Pyrazolo[3,4-d] pyrimidines1,2; Journal of Organic Chemistry, American Chemical Society (1956) vol. 21 pp. 1240-1256.

Dörwald, Florencio Zaragoza, et al; Side Reactions in Organic Synthesis: A Guide to Successful Synthesys Design; (2005) Wiley; VCH, Weinheim p. IX of preface.

http://www.medterms.com/script/main/art.asp?articlekey=12063, last accessed on Aug. 24, 2010.

International Search Report for PCT/EP2006/005980 mailed Nov. 16, 2006.

International Search Report for PCT/EP2007/003186 mailed Jun. 8, 2007.

International Search Report for PCT/EP2007/006109 mailed Dec. 20, 2007.

International Search Report for PCT/EP2009/060876 mailed Nov. 10, 2009.

International Search Report for PCT/EP2011/052810 mailed May 16, 2011.

International Search Report for PCT/EP2011/052811/mailed May 18, 2011.

International Search Report for PCT/EP2011/052813 mailed May 30, 2011.

International Search Reportfor PCT/EP2008/009880 mailed Jun. 25, 2009.

Jorgensen, Anker, et al; Phosphorus Pentoxide in Organic Synthesis. XX [1]. Synthesis of N-Aryl-7H-pyrrolo [2,3-d]pyrimidin-4-amines; Journal of Heterocyclic Chemistry (1985) pp. 859-863.

Mogensen, Jorgen, et al; Phosphorus Pentoxide in Organic Synthesis: XXXIV*. Synthesis of 3-Arylthieno[2,3-d] pyrimidin-4(3H)-imines and their Rearrangement to N-arylthieno[2,3-d]pyrimidin-4-amines; Chemica Scripta (1988) vol. 28 pp. 195-200.

Munchhof, Michael J., et al; Design and SAR of Thienopyrimidine and Thienopyridine Inhibitors of VEGFR-2 Kinase Activity; Bioorganic & Medicinal Chemistry Letters (2004) vol. 14 pp. 21-24.

Peat, Andrew, J., et al; Novel Pyrazolopyrimidine Derivates as GSK-3 Inhibitors; Bioorganic & Medicinal Chemistry Letters (2004) vol. 14 pp. 2121-2125.

Showalter, H. D. Hollis, et al; Tyrosine Kinase Inhibitors. 16. 6,5,6-Tricyclic Benzothieno[3-,2-d]pyrimidines and Pyrimido[5,4-b]- and -[4,5-b]indoles as Potent Inhibitors of the Epidermal Growth Factor Receptor Tyrosine Kinase; Journal of Medicinal Chemistry (1999) vol. 42 pp. 5464-5474.

Sobolov, Susan B., et al; Selective N-Alkylation of Pyrrolopyrimidines and Indoles by "Transfer of Activation"; Tetrahedron Letters (1998) vol. 39 pp. 5685-5688.

Traxler, Peter, et al; Use of a Pharmacophore Model for the Design of EGF-R Tyrosine Kinase Inhibitors: 4-(Phenylamino)pyrazolo[3,4-d]pyrimidines; Journal of Medicinal Chemistry (1997) vol. 40, No. 22 pp. 3601-3616.

Traxler, Peter, M., et at; 4-(Phenylamino)pyrrolopyrimidines: Potent and Selective, ATP Site Directed Inhibitors of the EGF-Receptor Protein Tyrosine Kinase; Journal of Medicinal Chemistry (1996) vol. 39 pp. 2285-2292.

West, R. A., et al; 2-Alkyl(aryl)-and2,7-Dimethyl-4-substituted Aminopyrrolo [2,3-d]pyrimidines; Journal of Organic Chemistry (1961) vol. 26 pp. 3809-3812.

Wolff, Manfred, E.; Principles and Practice; Burger's Medicinal Chemistry and Drug Discovery (1995) 5ed, vol. 1 pp. 975-977.

Young, Rodney, C., et al; Purine Derivates as Competitive Inhibitors of Human Erythrocyte Membrane Phosphatidylinositol 4-Kinase; Journal of Medicinal Chemistry (1990) vol. 33 pp. 2073-2080.

CYCLOALKYL CONTAINING THIENOPYRIMIDINES FOR PHARMACEUTICAL COMPOSITIONS

SEQUENCE LISTING

The instant application contains a Sequence Listing which has been submitted in ASCII format via EFS-Web and is hereby incorporated by reference in its entirety. Said ASCII copy, created on Apr. 29, 2011, is named 012597.txt and is 2,116 bytes in size.

The present invention relates to thienopyrimidine compounds and to novel pharmaceutical compositions comprising thienopyrimidine compounds.

Moreover, the present invention relates to the use of the thienopyrimidine compounds of the invention for the production of pharmaceutical compositions for the prophylaxis and/or treatment of diseases which can be influenced by the inhibition of the kinase activity of Mnk1 (Mnk1a or MnK1b) and/or Mnk2 (Mnk2a or Mnk2b) or further variants thereof. Particularly, the present invention relates to the use of the thienopyrimidine compounds of the invention for the production of pharmaceutical compositions for the prophylaxis and/or therapy of metabolic diseases, such as diabetes, hyperlipidemia and obesity, hematopoietic disorders, neurodegenerative diseases, kidney damage, inflammatory disorders, and cancer and their consecutive complications and disorders associated therewith.

Metabolic diseases are diseases caused by an abnormal metabolic process and may either be congenital due to an inherited enzyme abnormality or acquired due to a disease of an endocrine organ or failure of a metabolically important organ such as the liver or the pancreas.

The present invention is more particularly directed to the treatment and/or prophylaxis of in particular metabolic diseases of the lipid and carbohydrate metabolism and the consecutive complications and disorders associated therewith.

Lipid disorders cover a group of conditions which cause abnormalities in the level and metabolism of plasma lipids and lipoproteins. Thus, hyperlipidemias are of particular clinical relevance since they constitute an important risk factor for the development of atherosclerosis and subsequent vascular diseases such as coronary heart disease.

Diabetes mellitus is defined as a chronic hyperglycemia associated with resulting damages to organs and dysfunctions of metabolic processes. Depending on its etiology, one differentiates between several forms of diabetes, which are either due to an absolute (lacking or decreased insulin secretion) or to a relative lack of insulin. Diabetes mellitus Type I (IDDM, insulin-dependent diabetes mellitus) generally occurs in adolescents under 20 years of age. It is assumed to be of auto-immune etiology, leading to an insulitis with the subsequent destruction of the beta cells of the islets of Langerhans which are responsible for the insulin synthesis. In addition, in latent autoimmune diabetes in adults (LADA; Diabetes Care. 8: 1460-1467, 2001) beta cells are being destroyed due to autoimmune attack. The amount of insulin produced by the remaining pancreatic islet cells is too low, resulting in elevated blood glucose levels (hyperglycemia). Diabetes mellitus Type II generally occurs at an older age. It is above all associated with a resistance to insulin in the liver and the skeletal muscles, but also with a defect of the islets of Langerhans. High blood glucose levels (and also high blood lipid levels) in turn lead to an impairment of beta cell function and to an increase in beta cell apoptosis.

Diabetes is a very disabling disease, because today's common anti-diabetic drugs do not control blood sugar levels well enough to completely prevent the occurrence of high and low blood sugar levels. Out of range blood sugar levels are toxic and cause long-term complications for example retinopathy, renopathy, neuropathy and peripheral vascular disease. There is also a host of related conditions, such as obesity, hypertension, heart disease and hyperlipidemia, for which persons with diabetes are substantially at risk.

Obesity is associated with an increased risk of follow-up diseases such as cardiovascular diseases, hypertension, diabetes, hyperlipidemia and an increased mortality. Diabetes (insulin resistance) and obesity are part of the "metabolic syndrome" which is defined as the linkage between several diseases (also referred to as syndrome X, insulin-resistance syndrome, or deadly quartet). These often occur in the same patients and are major risk factors for development of diabetes type II and cardiovascular disease. It has been suggested that the control of lipid levels and glucose levels is required to treat diabetes type II, heart disease, and other occurrences of metabolic syndrome (see e.g., Diabetes 48: 1836-1841, 1999; JAMA 288: 2209-2716, 2002).

In one embodiment of the present invention the compounds and compositions of the present invention are useful for the treatment and/or prophylaxis of metabolic diseases of the carbohydrate metabolism and their consecutive complications and disorders such as impaired glucose tolerance, diabetes (preferably diabetes type II), diabetic complications such as diabetic gangrene, diabetic arthropathy, diabetic osteopenia, diabetic glomerosclerosis, diabetic nephropathy, diabetic dermopathy, diabetic neuropathy, diabetic cataract and diabetic retinopathy, diabetic maculopathy, diabetic feet syndrome, diabetic coma with or without ketoacidosis, diabetic hyperosmolar coma, hypoglycemic coma, hyperglycemic coma, diabetic acidosis, diabetic ketoacidosis, intracapillary glomerulonephrosis, Kimmelstiel-Wilson syndrome, diabetic amyotrophy, diabetic autonomic neuropathy, diabetic mononeuropathy, diabetic polyneuropathy, diabetic angiopathies, diabetic peripheral angiopathy, diabetic ulcer, diabetic arthropathy, or obesity in diabetes.

In a further embodiment the compounds and compositions of the present invention are useful for the treatment and/or prophylaxis of metabolic diseases of the lipid metabolism (i.e. lipid disorders) and their consecutive complications and disorders such as hypercholesterolemia, familial hypercholesterolemia, Fredrickson's hyperlipoproteinemia, hyperbetalipoproteinemia, hyperlipidemia, low-densitylipoprotein-type [LDL] hyperlipoproteinemia, pure hyperglyceridemia, endogenous hyperglyceridemia, isolated hypercholesterolemia, isolated hypertroglyceridemia, cardiovascular diseases such as hypertension, ischemia, varicose veins, retinal vein occlusion, atherosclerosis, angina pectoris, myocardial infarction, stenocardia, pulmonary hypertension, congestive heart failure, glomerulopaty, tubulointestitial disorders, renal failure, angiostenosis, or cerebrovascular disorders, such as cerebral apoplexy.

In a further embodiment of the present invention the compounds and compositions of the present invention are useful for the treatment and/or prophylaxis of hematopoetic disorders and their consecutive complications and disorders such as acute myeloid leukemia (AML), Morbus Hodgkin, Non-Hodgkin's lymphoma; hematopoetic disease, acute non-lymphocytic leukemia (ANLL), myeloproliferative disease acute promyelocytic leukemia (APL), acute myelomonocytic leukemia (AMMol.), multiple myeloma, polycythemia vera, lymphoma, acute lymphocytic leukemia (ALL), chronic lymphocytic leukemia (CCL), Wilm's tumor, or Ewing's Sarcoma.

In a further embodiment of the present invention the compounds and compositions of the present invention are useful for the treatment and/or prophylaxis of cancer and consecutive complications and disorders such as cancer of the upper gastrointestinal tract, pancreatic carcinoma, breast cancer, colon cancer, ovarian carcinoma, cervix carcinoma, endometrial cancer, brain tumor, testicular cancer, laryngeal carcinoma, osteocarcinoma, prostatic cancer, retinoblastoma, liver carcinoma, lung cancer, neuroblastoma, renal carcinoma, thyroid carcinoma, esophageal cancer, soft tissue sarcoma, skin cancer, osteosarcoma, rhabdomyosarcoma, bladder cancer, metastatic cancer, cachexia, or pain.

Certain anti-cancer drugs such as cisplatin are linked to serious side effects such as nephrotoxicity or ototoxicity, which can be dose limiting. Activation of Mnks has been linked to these side effects. In a further embodiment of the present invention, the compounds and compositions of the present invention are useful for the treatment and/or prophylaxis of ear or kidney damage, in particular for the prevention or treatment of ear and kidney drug induced damage Furthermore, the present invention relates to the use of thienopyrimidine compounds for the production of pharmaceutical compositions for the prophylaxis and/or therapy of cytokine related diseases.

Such diseases are i.a. inflammatory diseases, autoimmune diseases, destructive bone disorders, proliferative disorders, infectious diseases, neurodegenerative diseases, allergies, or other conditions associated with proinflammatory cytokines.

Allergic and inflammatory diseases such as acute or chronic inflammation, chronic inflammatory arthritis, rheumatoid arthritis, psoriasis, COPD, inflammatory bowel disease, asthma and septic shock and their consecutive complications and disorders associated therewith.

Inflammatory diseases like rheumatoid arthritis, inflammatory lung diseases like COPD, inflammatory bowel disease and psoriasis afflict one in three people in the course of their lives. Not only do those diseases impose immense health care costs, but also they are often crippling and debilitating.

Although inflammation is the unifying pathogenic process of these inflammatory diseases below, the current treatment approach is complex and is generally specific for any one disease. Many of the current therapies available today only treat the symptoms of the disease and not the underlying cause of inflammation.

The compositions of the present invention are useful for the treatment and/or prophylaxis of inflammatory diseases and consecutive complications and disorders. such as chronic or acute inflammation, inflammation of the joints such as chronic inflammatory arthritis, rheumatoid arthritis, psoriatic arthritis, osteoarthritis, juvenile rheumatoid arthritis, Reiter's syndrome, rheumatoid traumatic arthritis, rubella arthritis, acute synovitis and gouty arthritis; inflammatory skin diseases such as sunburn, psoriasis, erythrodermic psoriasis, pustular psoriasis, eczema, dermatitis, acute or chronic graft formation, atopic dermatitis, contact dermatitis, urticaria and scleroderma; inflammation of the gastrointestinal tract such as inflammatory bowel disease, Crohn's disease and related conditions, ulcerative colitis, colitis, and diverticulitis; nephritis, urethritis, salpingitis, oophoritis, endomyometritis, spondylitis, systemic lupus erythematosus and related disorders, multiple sclerosis, asthma, meningitis, myelitis, encephalomyelitis, encephalitis, phlebitis, thrombophlebitis, respiratory diseases such as asthma, bronchitis, chronic obstructive pulmonary disease (COPD), inflammatory lung disease and adult respiratory distress syndrome, and allergic rhinitis; endocarditis, osteomyelitis, rheumatic fever, rheumatic pericarditis, rheumatic endocarditis, rheumatic myocarditis, rheumatic mitral valve disease, rheumatic aortic valve disease, prostatitis, prostatocystitis, spondoarthropathies ankylosing spondylitis, synovitis, tenosynovotis, myositis, pharyngitis, polymyalgia rheumatica, shoulder tendonitis or bursitis, gout, pseudo gout, vasculitides, inflammatory diseases of the thyroid selected from granulomatous thyroiditis, lymphocytic thyroiditis, invasive fibrous thyroiditis, acute thyroiditis; Hashimoto's thyroiditis, Kawasaki's disease, Raynaud's phenomenon, Sjogren's syndrome, neuroinflammatory disease, sepsis, conjunctivitis, keratitis, iridocyclitis, optic neuritis, otitis, lymphoadenitis, nasopaharingitis, sinusitis, pharyngitis, tonsillitis, laryngitis, epiglottitis, bronchitis, pneumonitis, stomatitis, gingivitis, oesophagitis, gastritis, peritonitis, hepatitis, cholelithiasis, cholecystitis, glomerulonephritis, goodpasture's disease, crescentic glomerulonephritis, pancreatitis, endomyometritis, myometritis, metritis, cervicitis, endocervicitis, exocervicitis, parametritis, tuberculosis, vaginitis, vulvitis, silicosis, sarcoidosis, pneumoconiosis, pyresis, inflammatory polyarthropathies, psoriatric arthropathies, intestinal fibrosis, bronchiectasis and enteropathic arthropathies.

Moreover, cytokines are also believed to be implicated in the production and development of various cardiovascular and cerebrovascular disorders such as congestive heart disease, myocardial infarction, the formation of atherosclerotic plaques, hypertension, platelet aggregation, angina, stroke, Alzheimer's disease, reperfusion injury, vascular injury including restenosis and peripheral vascular disease, and, for example, various disorders of bone metabolism such as osteoporosis (including senile and postmenopausal osteoporosis), Paget's disease, bone metastases, hypercalcaemia, hyperparathyroidism, osteosclerosis, osteoporosis and periodontitis, and the abnormal changes in bone metabolism which may accompany rheumatoid arthritis and osteoarthritis.

Excessive cytokine production has also been implicated in mediating certain complications of bacterial, fungal and/or viral infections such as endotoxic shock, septic shock and toxic shock syndrome and in mediating certain complications of CNS surgery or injury such as neurotrauma and ischaemic stroke.

Excessive cytokine production has, moreover, been implicated in mediating or exacerbating the development of diseases involving cartilage or muscle resorption, pulmonary fibrosis, cirrhosis, renal fibrosis, the cachexia found in certain chronic diseases such as malignant disease and acquired immune deficiency syndrome (AIDS), tumour invasiveness and tumour metastasis and multiple sclerosis. The treatment and/or prophylaxis of these diseases are also contemplated by the present invention Additionally, the inventive compositions may be used to treat inflammation associated with autoimmune diseases including, but not limited to, systemic lupus erythematosis, Addison's disease, autoimmune polyglandular disease (also known as autoimmune polyglandular syndrome), glomerulonephritis, rheumatoid arthritis scleroderma, chronic thyroiditis, Graves' disease, autoimmune gastritis, diabetes, autoimmune hemolytic anemia, glomerulonephritis, rheumatoid arthritis autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, and graft vs. host disease.

In a further embodiment the compositions of the present invention may be used for the treatment and prevention of infectious diseases such as sepsis, septic shock, Shigellosis, and *Helicobacter pylori* and viral diseases including herpes simplex type 1 (HSV-1), herpes simplex type 2 (HSV-2), cytomegalovirus, Epstein-Barr, human immunodeficiency virus (HIV), acute hepatitis infection (including hepatitis A, hepatits B, and hepatitis C), HIV infection and CMV retinitis, AIDS or malignancy, malaria, mycobacterial infection and meningitis. These also include viral infections, by influenza virus, varicella-zoster virus (VZV), Epstein-Barr virus, human herpesvirus-6 (HHV-6), human herpesvirus-7 (HHV-7), human herpesvirus-8 (HHV-8), Poxvirus, Vacciniavirus, Monkeypoxvirus, pseudorabies and rhinotracheitis.

The compositions of the present invention may also be used topically in the treatment or prophylaxis of topical disease states mediated by or exacerbated by excessive cytokine production, such as inflamed joints, eczema, psoriasis and other inflammatory skin conditions such as sunburn; inflammatory eye conditions including conjunctivitis; pyresis, pain and other conditions associated with inflammation.

Periodontal disease has also been implemented in cytokine production, both topically and systemically. Hence, use of compositions of the present invention to control the inflammation associated with cytokine production in such peroral diseases such as gingivitis and periodontitis is another aspect of the present invention.

Finally, the compositions of the present invention may also be used to treat or prevent neurodegenerative disease selected from Alzheimer's disease, Parkinson's disease, amyotrophic lateral sclerosis, Huntington's disease, frontotemporal lobar dementia, spinocerebellar ataxia, dementia with Lewy bodies, cerebral ischemia or neurodegenerative disease caused by traumatic injury, glutamate neurotoxicity or hypoxia.

In a preferred embodiment the compositions of the present invention may be used to treat or prevent a disease selected from chronic or acute inflammation, chronic inflammatory arthritis, rheumatoid arthritis, psoriasis, COPD, inflammatory bowel disease, septic shock, Crohn's disease, ulcerative colitis, multiple sclerosis and asthma.

Protein kinases are important enzymes involved in the regulation of many cellular functions. The LK6-serine/threonine-kinase gene of Drosophila melanogaster was described as a short-lived kinase which can associate with microtubules (J. Cell Sci. 1997, 110(2): 209-219). Genetic analysis in the development of the compound eye of Drosophila suggested a role in the modulation of the RAS signal pathway (Genetics 2000 156(3): 1219-1230). The closest human homologues of Drosophila LK6-kinase are the MAP-kinase interacting kinase 2 (Mnk2, e.g. the variants Mnk2a and Mnk2b) and MAP-kinase interacting kinase 1 (Mnk1) and variants thereof. These kinases are mostly localized in the cytoplasm. Mnks are phosphorylated by the p42 MAP kinases Erk1 and Erk2 and the p38-MAP kinases. This phosphorylation is triggered in a response to growth factors, phorbol esters and oncogenes such as Ras and Mos, and by stress signaling molecules and cytokines. The phosphorylation of Mnk proteins stimulates their kinase activity towards eukaryotic initiation factor 4E (eIF4E) (EMBO J. 16: 1909-1920, 1997; Mol Cell Biol 19, 1871-1880, 1990; Mol Cell Biol 21, 743-754, 2001). Simultaneous disruption of both, the Mnk1 and Mnk2 gene in mice diminishes basal and stimulated eIF4E phosphorylation (Mol Cell Biol 24, 6539-6549, 2004). Phosphorylation of eIF4E results in a regulation of the protein translation (Mol Cell Biol 22: 5500-5511, 2001).

There are different hypotheses describing the mode of the stimulation of the protein translation by Mnk proteins. Most publications describe a positive stimulatory effect on the cap-dependent protein translation upon activation of MAP kinase-interacting kinases. Thus, the activation of Mnk proteins can lead to an indirect stimulation or regulation of the protein translation, e.g. by the effect on the cytosolic phospholipase 2 alpha (BBA 1488:124-138, 2000).

WO 03/037362 discloses a link between human Mnk genes, particularly the variants of the human Mnk2 genes, and diseases which are associated with the regulation of body weight or thermogenesis. It is postulated that human Mnk genes, particularly the Mnk2 variants are involved in diseases such as e.g. metabolic diseases including obesity, eating disorders, cachexia, diabetes mellitus, hypertension, coronary heart disease, hypercholesterolemia, dyslipidemia, osteoarthritis, biliary stones, cancer of the genitals and sleep apnea, and in diseases connected with the ROS defense, such as e.g. diabetes mellitus and cancer. WO 03/03762 moreover discloses the use of nucleic acid sequences of the MAP kinase-interacting kinase (Mnk) gene family and amino acid sequences encoding these and the use of these sequences or of effectors of Mnk nucleic acids or polypeptides, particularly Mnk inhibitors and activators in the diagnosis, prophylaxis or therapy of diseases associated with the regulation of body weight or thermogenesis.

WO 02/103361 describes the use of kinases 2a and 2b (Mnk2a and Mnk2b) interacting with the human MAP kinase in assays for the identification of pharmacologically active ingredients, particularly useful for the treatment of diabetes mellitus type 2. Moreover, WO 02/103361 discloses also the prophylaxis and/or therapy of diseases associated with insulin resistance, by modulation of the expression or the activity of Mnk2a or Mnk2b. Apart from peptides, peptidomimetics, amino acids, amino acid analogues, polynucleotides, polynucleotide analogues, nucleotides and nucleotide analogues, 4-hydroxybenzoic acid methyl ester are described as a substance which binds the human Mnk2 protein.

First evidence for a role of Mnks in inflammation was provided by studies demonstrating activation of Mnk1 by proinflammatory stimuli. The cytokines TNFα and IL-1β trigger the activation of Mnk1 in vitro (Fukunaga and Hunter, EMBO J. 16(8): 1921-1933, 1997) and induce the phosphorylation of the Mnk-specific substrate eIF4E in vivo (Ueda et al., Mol Cell Biol 24(15): 6539-6549, 2004). In addition, administration of lipopolysaccharide (LPS), a potent stimulant of the inflammatory response, induces activation of Mnk1 and Mnk2 in mice, concomitant with a phosphorylation of their substrate eIF4E (Ueda et al., Mol Cell Biol 24(15): 6539-6549, 2004).

Furthermore, Mnk1 has been shown to be involved in regulating the production of proinflammatory cytokines. Mnk1 enhances expression of the chemokine RANTES (Nikolcheva et al., J Clin Invest 110, 119-126, 2002). RANTES is a potent chemotractant of monocytes, eosinophils, basophiles and, natural killer cells. It activates and induces proliferation of T lymphocytes, mediates degranulation of basophils and induces the respiratory burst in eosinophils (Conti and DiGioacchino, Allergy Asthma Proc 22(3):133-7, 2001)

WO 2005/00385 and Buxade et al., Immunity 23: 177-189, August 2005 both disclose a link between Mnks and the control of TNFα biosynthesis. The proposed mechanism is mediated by a regulatory AU-rich element (ARE) in the TNFα mRNA. Buxade et al. demonstrate proteins binding and controlling ARE function to be phosphorylated by Mnk1 and Mnk2. Specifically Mnk-mediated phosphorylation of the ARE-binding protein hnRNP A1 has been suggested to enhance translation of the TNFα mRNA.

TNFα is not the only cytokine regulated by an ARE. Functional AREs are also found in the transcripts of several interleukins, interferones and chemokines (Khabar, J Interf Cytokine Res 25:1-10, 2005). The Mnk-mediated phosphorylation of ARE-binding proteins has thus the potential to control biosynthesis of cytokines in addition to that of TNFα.

Current evidence demonstrates Mnks as down stream targets of inflammatory signalling as well as mediators of the inflammatory response. Their involvement in the production of TNFα, RANTES, and potentially additional cytokines suggests inhibition of Mnks as strategy for anti-inflammatory therapeutic intervention.

Mnk1 and Mnk2 (including all splice forms) phosphorylate the translation factor eIF4E on Serine 209. Mnk1/2 double knockout mice completely lack phosphorylation on Serine 209, indicating that Mnk kinase are the only kinases able to phosphorylate this site in vivo (Ueda et al., Mol Cell Biol. 2004; 24(15):6539-49). eIF4E is overexpressed in a wide range of human malignancies, and high eIF4E expression is frequently associated with more aggressive disease and poor prognosis. Furthermore, eIF4E can act as an oncogene when assayed in standard assays for oncogenic activity (e.g. Ruggero et al., Nat. Med. 2004 May; 10(5):484-6). eIF4E excerts its oncogenic activity by stimulating the translation of oncogenes such as c-myc and cyclinD1 (Culjkovic et al., J Cell Biol. 2006; 175(3):415-26), by increasing the expression of pro-survival factors such as MCP-1 (Wendel et al., Genes Dev. 2007; 21(24):3232-7) and by positively regulating pathways of drug resistance (Wendel et al., Nature 2004; 428(6980):332-7; Graff et al., Cancer Res. 2008; 68(3): 631-4; De Benedetti and Graff, Oncogene 2004; 23(18):3189-99; Barnhart and Simon, J Clin Invest. 2007; 117(9):2385-8). Suppression of eIF4E expression by antisense oligonucleotides has shown promise in preclinical experiments with human tumor cells (Graff et al., J Clin Invest. 2007; 117(9):2638-48). It has been shown that phosphorylation on Ser209 is strictly required for the oncogenic activity of eIF4E in vitro and in vivo (Topisirovic et al., Cancer Res. 2004; 64(23):8639-42; Wendel et al., Genes Dev. 2007; 21(24):3232-7). Thus, inhibition of Mnk1 and Mnk2 is expected to have beneficial effects in human malignancies.

Inhibitors of Mnk (referred to as CGP57380 and CGP052088) have been described (cf. Mol. Cell. Biol. 21, 5500, 2001; Mol Cell Biol Res Comm 3, 205, 2000; Genomics 69, 63, 2000). CGP052088 is a staurosporine derivative having an $IC_{50}$ of 70 nM for inhibition of in vitro kinase activity of Mnk1. CGP57380 is a low molecular weight selective, non-cytotoxic inhibitor of Mnk2 (Mnk2a or Mnk2b) or of Mnk1: The addition of CGP57380 to cell culture cells, transfected with Mnk2 (Mnk2a or Mnk2b) or Mnk1 showed a strong reduction of phosphorylated eIF4E.

Further inhibitors of Mnk have been described. See for example Applicants patent applications WO 06/066937, describing pyrazolopyrimidine compounds, WO 06/136402 describing certain thienopyrimidine compounds, WO 07/115822 describing further thienopyrimidine compounds with modified core ring, and WO 08/006547 describing pyrrolopyrimidines as inhibitors of Mnk kinases.

The problem underlying the present invention is to provide potent and selective Mnk1 and/or Mnk2 inhibitors which may effectively and safely be used for the treatment of metabolic diseases, inflammatory diseases, cancer, neurodegenerative diseases and their consecutive complication and disorders.

It has now been surprisingly found that certain thienopyrimidine compounds are potent inhibitors of the kinase enzymes Mnk1 and/or Mnk2 and/or variants thereof and as such may be useful in the prophylaxis and/or therapy of diseases which can be influenced by the inhibition of the kinase activity of Mnk1 and/or Mnk2 (Mnk2a or Mnk2b) and/or variants thereof.

In contrast to the thienopyrimidine compounds known in the art, for example, the compounds disclosed in the Applicants patent applications WO 06/136402 and WO 2007/115822, the thienopyrimidine compounds of the present invention provide several advantages, namely, enhanced solubility, the possibility to form stable salts, improved metabolic stability, enhanced or retained activity in biochemical or cellular Mnk activity assays and enhanced or retained selectivity against other kinases.

The thienopyrimidine compounds disclosed in WO 06/136402 and WO 07/115822 exhibit high activity in Mnk enzyme assays and extremely high selectivity, however they show a very low solubility and are in most cases metabolic unstable resulting in undesired pharmacokinetic properties.

It has been surprisingly found that by the introduction of a polar group at the $R^4$-position in the compounds of general formula (I) below leads to surprising substantial metabolic stabilization, rendering the thienopyrimidines of the present invention useful for in vivo pharmacological applications.

Moreover, compounds described in this application also show improved solubility, have strong inhibitory potency in biochemical and cellular assays and are highly selective, resulting in overall greatly improved pharmacological properties.

If not specified otherwise, any alkyl moiety mentioned in this application may be straight-chained or branched.

Thienopyrimidine compounds of the present invention are compounds of the general formula (I):

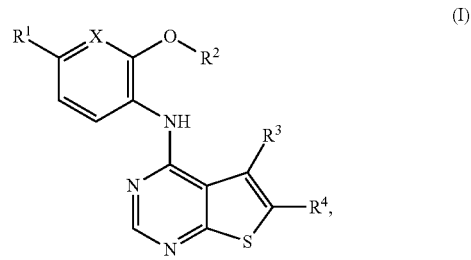

wherein
X is CH or N,
$R^1$ is a hydrogen or halogen atom,
$R^2$ is $C_{3-7}$ cycloalkyl group that is substituted with one or two substituents selected from oxo, halogen, $C_{1-3}$ alkyl, hydroxy, $C_{1-3}$ alkoxy, $C_{1-4}$ alkoxy-carbonyl, amino and morpholinyl,
   wherein the hydrogen atoms of the amino group may optionally be independently replaced by a $C_{1-3}$ alkyl, $C_{1-3}$ alkoxy-$(CH_2)_m$—, $C_{1-4}$ alkoxy-carbonyl, $C_{1-3}$ alkylsulfonyl, $C_{1-3}$ alkyl-carbonyl, $C_{3-6}$-cycloalkyl-carbonyl or piperidinyl group, wherein m is 2 or 3 and wherein the piperidinyl group may optionally be substituted by a methyl group,
   wherein two substituents, which are attached to the same carbon atom, together may form a —O—$(CH_2)_2$—O— group, and
   wherein two substituents, which are attached to two adjacent carbon atoms, together may form a —O—$CH_2$—O— or —O—$C(CH_3)_2$—O— group,
$R^3$ is a $C_{1-2}$ alkyl group and
$R^4$ is a carboxy, $C_{1-3}$ alkoxy-carbonyl, aminocarbonyl, N—$(C_{1-4}$ alkyl)-aminocarbonyl or N,N-[di-$(C_{1-4}$ alkyl)]-aminocarbonyl group,
   wherein the aminocarbonyl group may be substituted with a $C_{1-3}$ alkylsulfonyl, CN, OH, $C_{1-3}$ alkoxy, $C_{3-6}$ cycloalkyl, —CH$_2$—C≡C—CH$_2$—NH$_2$, —CH$_2$—C≡C—CH$_2$—NH(C$_{1-3}$ alkyl) or —CH$_2$—C≡C—CH$_2$—N(C$_{1-3}$ alkyl)$_2$ group or with a piperidinyl or pyrrolidinyl group bound via a carbon atom, and wherein the alkyl moieties of the above-mentioned N—(C$_{1-4}$ alkyl)-aminocarbonyl and N,N-[di-(C$_{1-4}$ alkyl)]-aminocarbonyl groups may optionally be substituted with an aminocarbonyl, N—(C$_{1-3}$ alkyl)-aminocarbonyl or N,N-[di(C$_{1-3}$ alkyl)]-aminocarbonyl group or with a pyrrolidinyl, oxazolyl, imidazolyl, piperidinyl or morpholinyl group, each bound via a carbon atom, or, from position 2 of an ethyl, propyl or butyl moiety onwards, with a OH, CN, C$_{1-3}$ alkoxy, amino, N—(C$_{1-3}$ alkyl)-amino, N,N-[di-(C$_{1-3}$ alkyl)]-amino, C$_{1-5}$ alkyloxycarbonyl-amino, morpholino, piperidino, piperazino or imidazolyl group, wherein each of the above-mentioned cycloalkyl, pyrrolidinyl, oxazolyl, piperidinyl, morpholinyl, piperazinyl and imidazolyl groups may be substituted with a methyl, amino, hydroxy group or C$_{1-3}$ alkoxy, or a tautomer, enantiomer, diastereomer or salt thereof.

Preferred compounds of formula (I) are those, wherein

X, R$^1$, R$^2$ and R$^4$ are as defined above and

R$^3$ is methyl, or a tautomer, enantiomer, diastereomer or salt thereof.

One aspect of the invention concerns those compounds of formula (I), wherein

R$^2$ to R$^4$ are as defined above and

X is CH and

R$^1$ is a fluorine atom, or a tautomer, enantiomer, diastereomer or salt thereof.

Another aspect of the invention concerns those compounds of formula (I), wherein R$^2$ to R$^4$ are as defined above and X is N and R$^1$ is a hydrogen atom, or a tautomer, enantiomer, diastereomer or salt thereof.

More preferred compounds of formula (I) are those, wherein

X and R$^1$ to R$^3$ are as defined above, and

R$^4$ is carboxy, C$_{1-3}$ alkoxy-carbonyl, aminocarbonyl or N—(C$_{1-3}$ alkyl)-aminocarbonyl group, wherein the methyl moiety of the above-mentioned N-(methyl)-aminocarbonyl group may optionally be substituted with a piperidinyl, N-methyl-piperidinyl or morphoinyl group, each bound via a carbon atom, and wherein the ethyl resp. propyl moiety of the above-mentioned N—(C$_{2-3}$ alkyl)-aminocarbonyl group may optionally be terminally substituted with hydroxy, methoxy, amino, N-methylamino, N,N-dimethyl-amino, morpholino, imidazolyl, 4-methyl-piperazinyl, 1-methyl-pyrrolidinyl, piperidinyl, pyrrolidinyl or 4-hydroxy-piperidino group, or a tautomer, enantiomer, diastereomer or salt thereof.

Even more preferred compounds of formula (I) are those, wherein

X and R$^1$ to R$^3$ are as defined as above, and

R$^4$ is aminocarbonyl or N—(C$_{1-3}$alkyl)-aminocarbonyl group, wherein the methyl moiety of the above-mentioned N-(methyl)-aminocarbonyl group may optionally be substituted with a piperidinyl, N-methyl-piperidinyl or morpholinyl group, each bound via a carbon atom, and wherein the ethyl resp. propyl moiety of the above-mentioned N—(C$_{2-3}$alkyl)-aminocarbonyl group may optionally be terminally substituted with hydroxy, methoxy, amino, N-methylamino, N,N-dimethyl-amino, morpholino, imidazolyl, 4-methyl-piperazinyl, 1-methyl-pyrrolidinyl, piperidinyl, pyrrolidinyl or 4-hydroxy-piperidino group, or a tautomer, enantiomer, diastereomer or salt thereof.

Another set of more preferred compounds of formula (I) are those, wherein

X, R$^1$, R$^3$ and R$^4$ are as defined above, and

R$^2$ is cyclopentyl substituted with one or two hydroxy or methoxy groups or with an amino, methylcarbonyl-amino, N-methyl-N-methylcarbonyl-amino group or wherein two adjacent carbon atoms are linked to each other via a —O—CH$_2$—O— or —O—C(CH$_3$)$_2$—O— group, or cyclohexyl substituted with one or two fluorine atoms or one or two hydroxy or methoxy groups or an oxo, C$_{1-3}$ alkoxycarbonyl, morpholino, methyl-piperidinyl or an amino group, wherein the hydrogen atoms of the amino group my optionally independently be replaced with a methyl, methylcarbonyl, 2-methoxy-ethyl or methylsulfonyl group, or wherein two adjacent carbon atoms are linked to each other via-O—C(CH$_3$)$_2$—O— group or wherein two hydrogen atoms attached to the same carbon atom are replaced by a —O—(CH$_2$)$_2$—O— group, or a tautomer, enantiomer, diastereomer or salt thereof, particularly those compounds of formula (I), wherein X, R$^1$, R$^3$ and R$^4$ are as defined as above, and R$^2$ is cyclohexyl substituted with one hydroxy or methoxy group, cyclopentyl substituted with one hydroxy, methoxy, methylcarbonyl-amino or N-methyl-N-methylcarbonyl-amino group or cyclopentyl, wherein two adjacent carbon atoms are linked to each other via a —O—CH$_2$—O— group, or cyclobutyl substituted with a methylcarbonyl-amino or methylcarbonyl-N(methyl)amino group, or a tautomer, enantiomer, diastereomer or salt thereof.

Particularly preferred are the following compounds of formula (I)

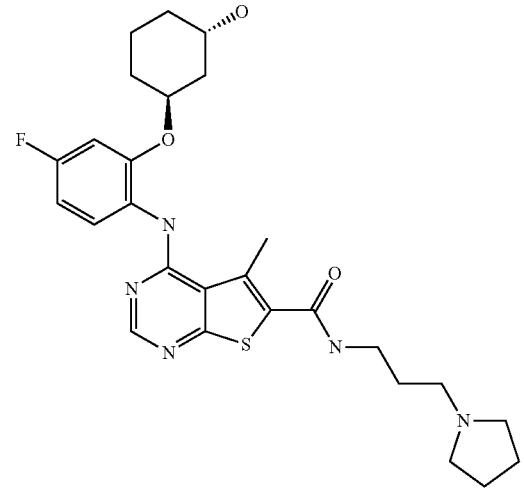

racemic

11
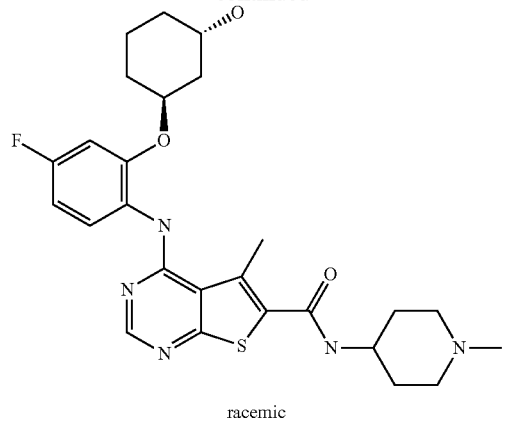
racemic
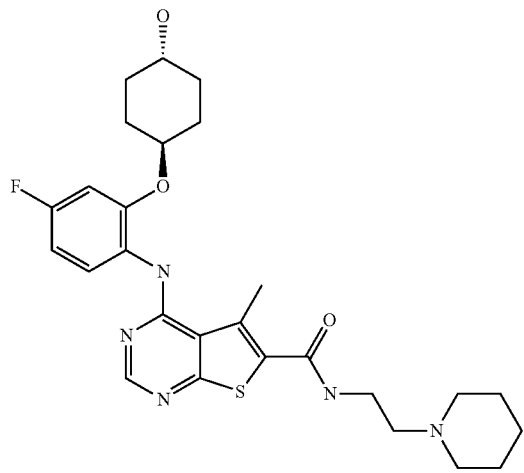
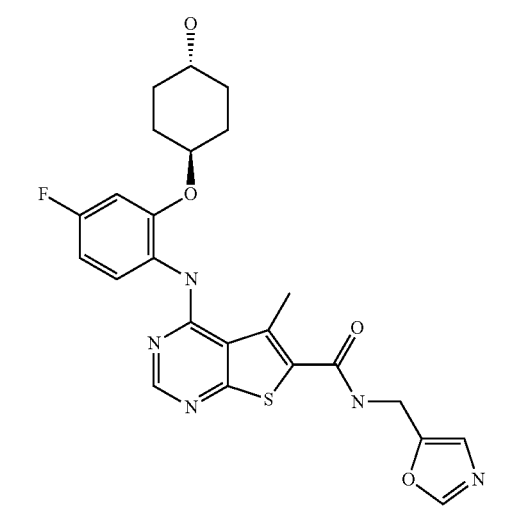
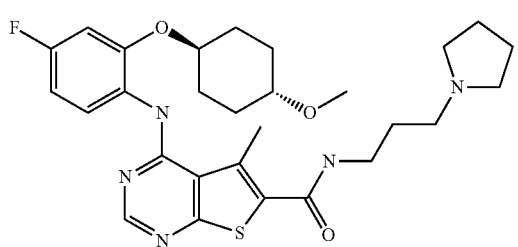
12
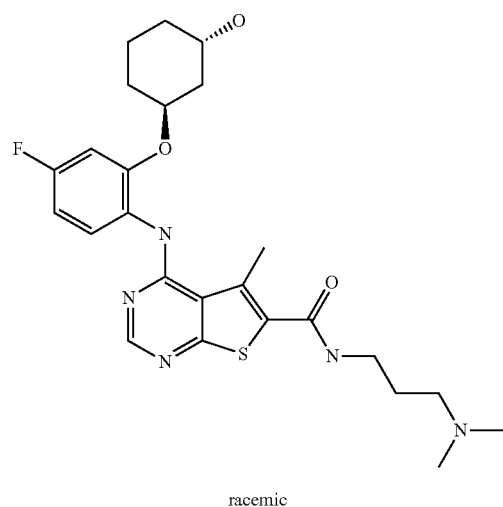
racemic
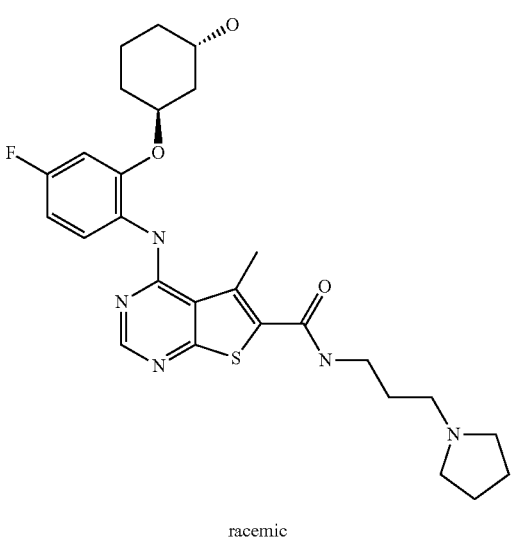
racemic
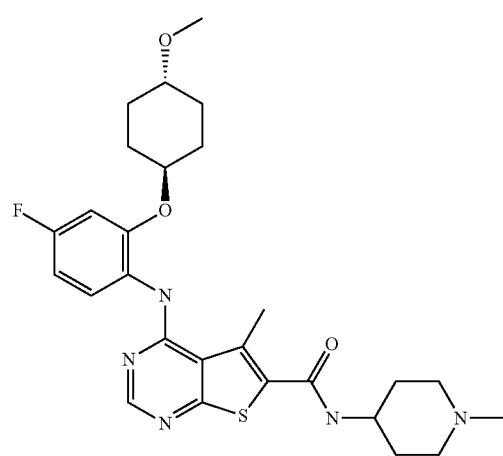

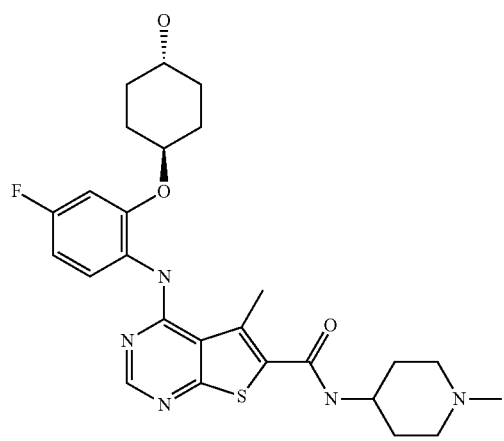
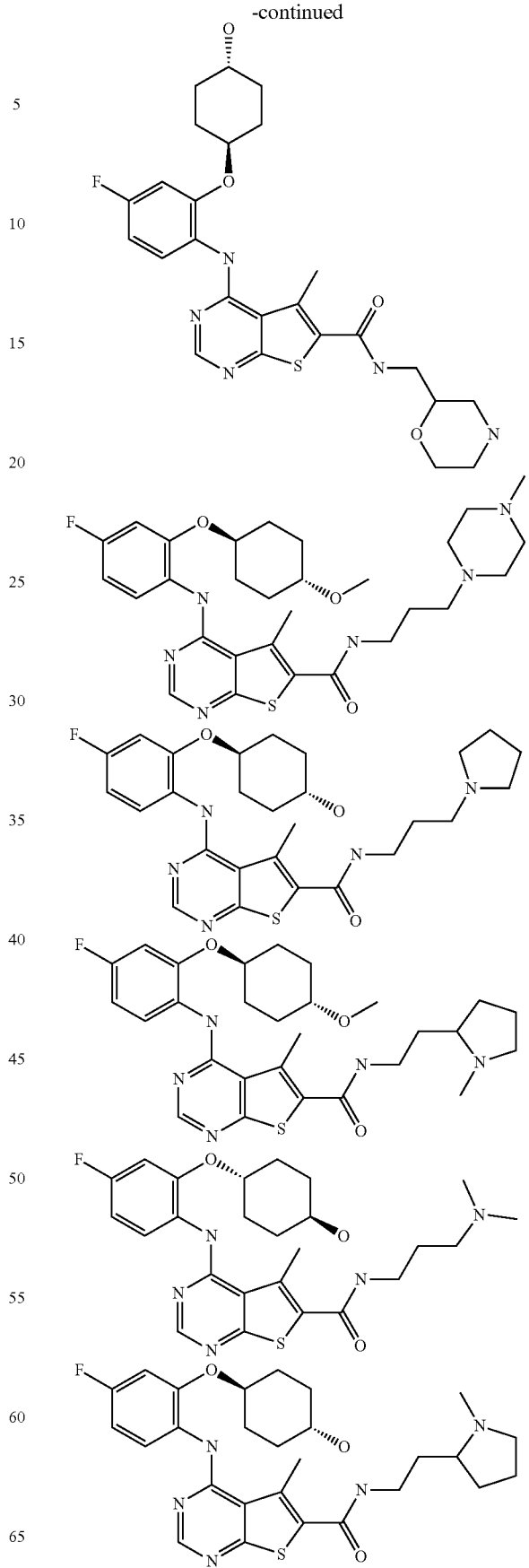

15
-continued

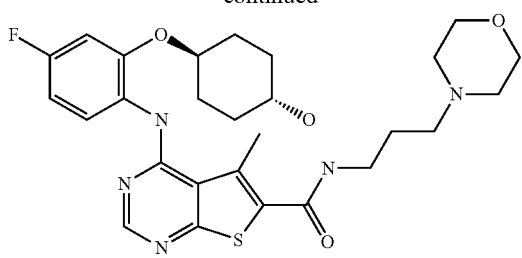

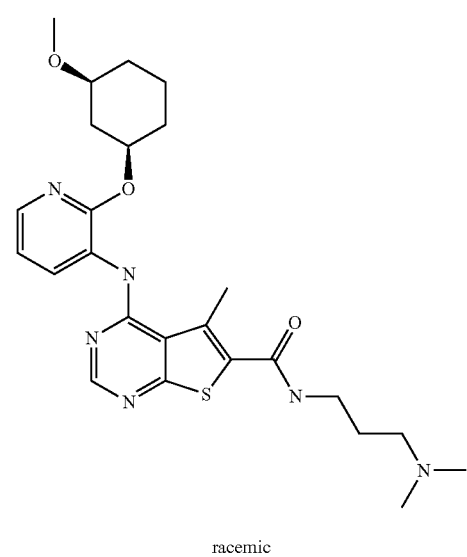

racemic

16
-continued

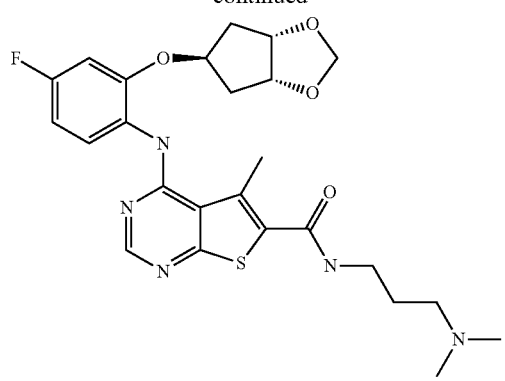

or a salt thereof.

Typical methods of preparing the compounds of the invention are described below in the experimental section.

The potent inhibitory effect of the compounds of the invention may be determined by in vitro enzyme assays as described below in more detail.

The compounds of the present invention can be synthesized according to the following synthesis schemes:

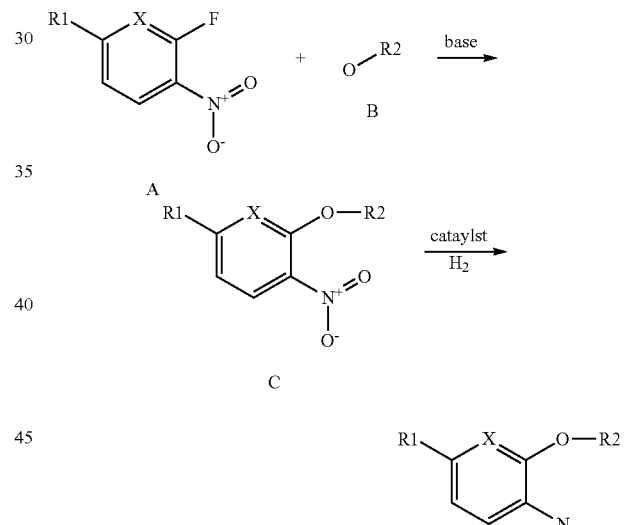

X = CH, N

Compounds of the general formula C can be synthesized by reaction of a compound A with the deprotonated alcohol B in appropriate solvents such as THF or DMF at a temperature between 0° C. and 150° C. The deprotonated form of B can be obtained by deprotonation with a base such as sodium hydride or lithium hexamethyldisilazane at a preferred temperature of 0° C. Hydrogenation of compound C in order to obtain a compound of the general formula D can be achieved by reacting C in the presence of hydrogen and a catalyst such as palladium or Raney nickel. The hydrogen can be introduced as a gas or stem from a hydrogen source such as ammonium formate.

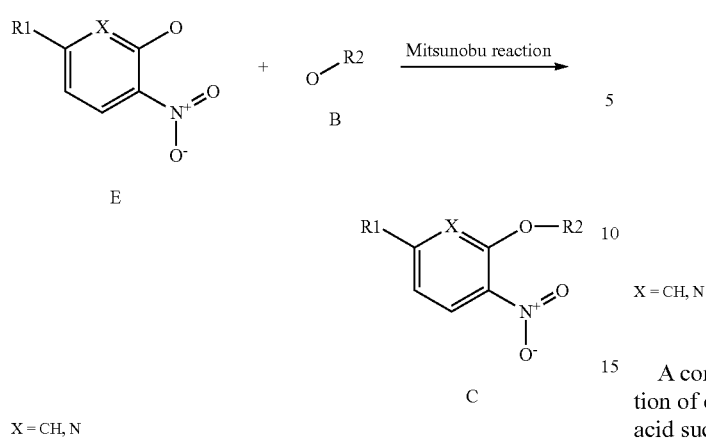

X = CH, N

Compounds of the general formula C can be also obtained by Mitsunobu reaction of a compound with the general formula E with an alcohol B in the presence of triphenylphosphine and an dialkylazodicarboxylate such as diethylazodicarboxylate, diisopropylazodicarboxylate or di-tert.butylazodiacarboxylate in a solvent such as THF at temperatures between −10° C. and 80° C., preferably between 0° C. and 30° C.

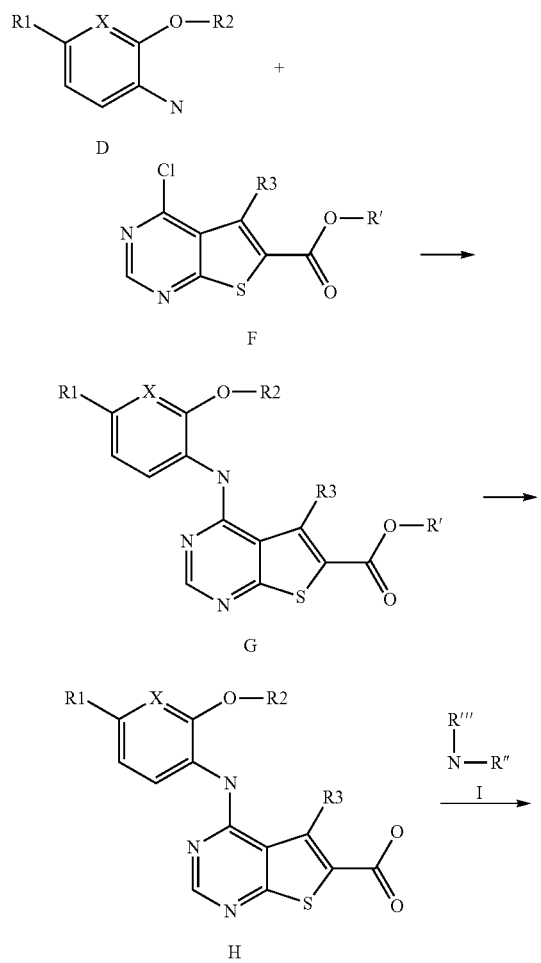

X = CH, N

A compound of the formula G can be synthesized by reaction of compound D with F preferably in the presence of an acid such as p-toluene sulfonic acid or hydrochloric acid in solvents such as dioxan at temperatures between 10° C. and 150° C. Synthesis of a compound with the general formula H can be achieved by reaction of compound G with a base such as sodium hydroxide or lithium hydroxide in solvents such as methanol, ethanol, THF and water or mixtures thereof, preferably in ethanol/THF or THF/water at temperatures between 10° C. and 100° C. A compound of the general formula J can be obtained by reaction of compound H with amines of the general formula I using amide coupling procedures employing reagents such as TBTU, HATU or EDC/N-Hydroxysuccinimide in the presence or absence of bases such as diisopropylethylamine in solvents such as DMF or THF at temperatures between 0° C. and 120° C. preferably between 0° C. and 30° C.

Pharmaceutically acceptable salts of the compounds of the invention of formula (I) can be formed with numerous organic and inorganic acids and bases. Exemplary acid addition salts including acetate, adipate, alginate, ascorbate, aspartate, benzoate, benzenesulfonate, bisulfate, borate, butyrate, citrate, camphorate, camphersulfonate, cyclopentanepropionate, digluconate, dodecyl sulfate, ethane sulfonate, fumarate, glucoheptanoate, glycerophosphate, hemisulfate, heptanoate, hexanoate, hydrochloride, hydrobromide, hydroiodide, 2-hydroxyethane sulfonate, lactate, maleate, methane sulfonate, 2-naphthalene sulfonate, nicotinate, nitrate, oxalate, pamoate, pectinate, persulfate, 3-phenyl sulfonate, 3-phenylpropionate, phosphate, picrate, pivalate, propionate, salicylate, succinate, sulfate, sulfonate, tartrate, thiocyanate, toluene sulfonate such as tosylate, undecanoate, or the like.

Basic nitrogen-containing moieties can be quaternized with such agents as lower alkyl halides, such as methyl, ethyl, propyl, and butyl chloride, bromide and iodide; dialkyl sulfates like dimethyl, diethyl, dibutyl, and diamyl sulfates, long-chain alkyl halides such as decyl, lauryl, myristyl and stearyl chloride, bromide and iodide, or aralkyl halides like benzyl and phenethyl bromides, or others. Water soluble or dispersible products are thereby obtained.

Pharmaceutically acceptable basic addition salts include but are not limited to cations based on the alkaline and alkaline earth metals such as sodium, lithium, potassium, calcium, magnesium, aluminum salts and the like, as well as non toxic ammonium quarternary ammonium, and amine cations, including but not limited to ammonium, tetramethylammonium, tetraethylammonium, methylamine, dimethylamine, trimethylamine, triethylamine, ethylamine and the like. Other representative amines useful for the formation of base addition salts include benzazethine, dicyclohexyl amine, hydrabine, N-methyl-D-glucamine, N-methyl-D-glucamide, t-butyl amine, diethylamine, ethylendiamine, ethanolamine, diethanolamine, piperazine and the like and salts with amino acids such as arginine, lysine, or the like.

Unless specifically indicated, throughout the specification and the appended claims, a given chemical formula or name shall encompass tautomers and all stereo, optical and geometrical isomers (e.g. enantiomers, diastereomers, E/Z isomers etc. . . . ) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

As used herein the term "metabolite" refers to (i) a product of metabolism, including intermediate and products, (ii) any substance involved in metabolism (either as a product of metabolism or as necessary for metabolism), or (iii) any substance produced or used during metabolism. In particular it refers to the end product that remains after metabolism.

As used herein the term "prodrug" refers to (i) an inactive form of a drug that exerts its effects after metabolic processes within the body convert it to a usable or active form, or (ii) a substance that gives rise to a pharmacologically active metabolite, although not itself active (i.e. an inactive precursor).

The terms "prodrug" or "prodrug derivative" mean a covalently-bonded derivative or carrier of the parent compound or active drug substance which undergoes at least some biotransformation prior to exhibiting its pharmacological effect(s). In general, such prodrugs have metabolically cleavable groups and are rapidly transformed in vivo to yield the parent compound, for example, by hydrolysis in blood, and generally include esters and amide analogs of the parent compounds. The prodrug is formulated with the objectives of improved chemical stability, improved patient acceptance and compliance, improved bioavailability, prolonged duration of action, improved organ selectivity, improved formulation (e.g., increased hydrosolubility), and/or decreased side effects (e.g., toxicity). In general, prodrugs themselves have weak or no biological activity and are stable under ordinary conditions. Prodrugs can be readily prepared from the parent compounds using methods known in the art, such as those described in *A Textbook of Drug Design and Development*, Krogsgaard-Larsen and H. Bundgaard (eds.), Gordon & Breach, 1991, particularly Chapter 5: "Design and Applications of Prodrugs"; *Design of Prodrugs*, H. Bundgaard (ed.), Elsevier, 1985; *Prodrugs: Topical and Ocular Drug Delivery*, K. B. Sloan (ed.), Marcel Dekker, 1998; *Methods in Enzymology*, K. Widder et al. (eds.), Vol. 42, Academic Press, 1985, particularly pp. 309-396; *Burger's Medicinal Chemistry and Drug Discovery*, 5th Ed., M. Wolff (ed.), John Wiley & Sons, 1995, particularly Vol. 1 and pp. 172-178 and pp. 949-982; *Pro-Drugs as Novel Delivery Systems*, T. Higuchi and V. Stella (eds.), Am. Chem. Soc., 1975; *Bioreversible Carriers in Drug Design*, E. B. Roche (ed.), Elsevier, 1987, each of which is incorporated herein by reference in their entireties.

The term "pharmaceutically acceptable prodrug" as used herein means a prodrug of a compound of the invention which is, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible.

As used herein the term "$C_{3-10}$ cycloalkyl" or "$C_{3-8}$ cycloalkyl" refers to mono- or polycyclic carbocyclic alkyl substituent or group having 3 to 10 or 3 to 8 ring atoms respectively, such as cyclopropyl, cyclobutyl, cyclopentyl, cyclohexyl, cycloheptyl, cyclobutenyl, cyclopentenyl, cyclopentadienyl, cyclohexenyl, cyclohexadienyl, cycloheptenyl, cycloheptadienyl, cycloheptatrienyl perhydrated naphthalene or indene, adamantyl or norbonanyl and the like.

The term "$C_{1-8}$ alkyl" as used herein alone or in combination with other terms such as in alkoxy refers to a $C_{1-8}$, preferably $C_{1-4}$ straight or branched alkyl/alkoxy group such as methyl, ethyl, propyl (iso-, n-), butyl (iso-, n-, sec-, tert-), pentyl, hexyl, methoxy, ethoxy, propoxy (iso-, n-), butoxy (iso-, n-, sec-, tert-), pentoxy, hexoxy; moreover, the term "$C_{1-8}$ alkyl" also includes an alkyl group which may contain oxygen in the chain and may be substituted with halogen to form an ether or halogenated ether group.

Any hydrogen atom, particularly in an alkyl, alkoxy or alkenyl group may be replaced by a fluorine atom.

The term "$C_{2-8}$ alkenyl" by itself or as part of another group refers to a straight or branched alkenyl group of 2 to 8 carbons, preferably 2 to 6 carbons, in the normal chain, which include one or more double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl.

The term "heterocyclyl" refers to monocyclic saturated or unsaturated heterocyclyl groups with 1 to 4 hetero atoms selected from N, S and O, with the remainder of the ring atoms being carbon atoms and having preferably a total number of ring atoms of 3 to 10, such as morpholino, piperazinyl, piperidinyl, pyridyl, pyrimidinyl, thiazolyl, indolyl, imidazolyl, oxadiazolyl, tetrazolyl, pyrazinyl, triazolyl, thiophenyl or furanyl.

The term "heteroaryl" refers to a mono- or bicyclic aromatic group with 1 to 4 hetero atoms selected from N, S and O, with the remainder of the ring atoms being carbon atoms and having preferably a total number of ring atoms of 5 to 10. Examples without limitation of heteroaryl groups are such as benzofuranyl, furyl, thienyl, benzothienyl, thiazolyl, imidazolyl, oxazolyl, oxadiazolyl, thiadiazolyl, benzothiazolyl, triazolyl, tetrazolyl, isoxazolyl, isothiazolyl, pyrrolyl, pyranyl, tetrahydropyranyl, pyrazolyl, pyridyl, quinolinyl, isoquinolinyl, purinyl, carbazolyl, benzoxazolyl, benzamidazolyl, indolyl, isoindolyl, pyrazinyl, diazinyl, pyrazine, triazinyltriazine, tetrazinyl, tetrazolyl, benzothiophenyl, benzopyridyl and benzimidazolyl.

In a further aspect the present invention provides pharmaceutical compositions comprising a thienopyrimidine compound of the present invention and optionally a pharmaceutically acceptable carrier.

The pharmaceutical composition according to the present invention may further comprise an additional therapeutic agent. Particularly preferred are compositions, wherein the additional therapeutic agent is selected from antidiabetics like insulin, long and short acting insulin analogues, sulfonylureas, biguanides, DPP-IV inhibitors, SGLT2 inhibitors, 11β-HSD inhibitors, glucokinase activators, AMPK activators, Glp-1 receptor agonists, GIP receptor agonists, DGAT inhibitors, PPARgamma agonists, PPARdelta agonists, and other antidiabetics derived from thiazolidinediones, lipid lowering agents such as statines, fibrates, ion exchange resins nicotinic acid derivatives, or HMG-CoA reductase inhibitors, cardiovascular therapeutics such as nitrates, antihypertensiva such as β-blockers, ACE inhibitors, Ca-channel blockers, angiotensin II receptor antagonists, diuretics, thrombocyte aggregation inhibitors, or antineoplastic agents such as alkaloids, alkylating agents, antibiotics, or antimetabolites, or anti-obesity agents. Further preferred compositions are compositions wherein the additional therapeutic agent is selected from a histamine antagonist, a bradikinin antagonist, serotonin antagonist, leukotriene, an antiasthmatic, an NSAID, an antipyretic, a corticosteroid, an antibiotic, an analgetic, a uricosuric agent, chemotherapeutic agent, an anti gout agent, a bronchodilator, a cyclooxygenase-2 inhibitor, a steroid, a 5-lipoxygenase inhibitor, an immunosuppressive agent, a leukotriene antagonist, a cytostatic agent, an antineoplastic agent, a mTor inhibitor, a Tyrosine kinase inhibitor, antibodies or fragments thereof against cytokines and soluble parts (fragments) of cytokine receptors.

More particularly preferred are compounds such as human NPH insulin, human lente or ultralente insulin, insulin Lispro, insulin Aspart, insulin Glulisine, insulin detemir or insulin Glargine, metformin, phenformin, acarbose, miglitol, voglibose, pioglitazone, rosiglizatone, rivoglitazone, aleglitazar, alogliptin, saxagliptin, sitagliptin, vildagliptin, exenatide, liraglutide, albiglutide, pramlintide, carbutamide, chlorpropamide, glibenclamide (glyburide), gliclazide, glimepiride, glipizide, gliquidone, tolazamide, tolbutamide, atenolol, bisoprolol, metoprolol, esmolol, celiprolol, talinolol, oxprenolol, pindolol, propanolol, bupropanolol, penbutolol, mepindolol, sotalol, certeolol, nadolol, carvedilol, nifedipin, nitrendipin, amlodipin, nicardipin, nisoldipin, diltiazem, enalapril, verapamil, gallopamil, quinapril, captopril, lisinopril, benazepril, ramipril, peridopril, fosinopril, trandolapril, irbesatan, losartan, valsartan, telmisartan, eprosartan, olmesartan, hydrochlorothiazide, piretanid, chlorotalidone, mefruside, furosemide, bendroflumethiazid, triamterene, dehydralazine, acetylsalicylic acid, tirofiban-HCl, dipyramidol, triclopidin, iloprost-trometanol, eptifibatide, clopidogrel, piratecam, abciximab, trapidil, simvastatine, bezafibrate, fenofibrate, gemfibrozil, etofyllin, clofibrate, etofibrate, fluvastatine, lovastatine, pravastatin, colestyramide, colestipol-HCl, xantinol nicotinat, inositol nicotinat, acipimox, nebivolol, glycerolnitrate, isosorbide mononitrate, isosorbide dinitrate, pentaerythrityl tetranitrate, indapamide, cilazepril, urapidil, eprosartan, nilvadipin, metoprolol, doxazosin, molsidormin, moxaverin, acebutolol, prazosine, trapidil, clonidine, vinca alkaloids and analogues such as vinblastin, vincristin, vindesin, vinorelbin, podophyllotoxine derivatives, etoposid, teniposid, alkylating agents, nitroso ureas, N-lost analogues, cycloplonphamid, estamustin, melphalan, ifosfamid, mitoxantron, idarubicin, doxorubicin, bleomycin, mitomycin, dactinomycin, daptomycin, docetaxel, paclitaxel, carboplatin, cisplatin, oxaliplatin, BBR3464, satraplatin, busulfan, treosulfan, procarbazine, dacarbazine, temozolomide, chlorambucil, chlormethine, cyclophosphamide, ifosfamide, melphalan, bendamustine, uramustine, ThioTEPA, camptothecin, topotecan, irinotecan, rubitecan, etoposide, teniposide, cetuximab, panitumumab, trastuzumab, rituximab, tositumomab, alemtuzumab, bevacizumab, gemtuzumab, aminolevulinic acid, methyl aminolevulinate, porfimer sodium, verteporfin, axitinib, bosutinib, cediranib, dasatinib, erlotinib, gefitinib, imatinib, lapatinib, lestaurtinib, nilotinib, semaxanib, sorafenib, sunitinib, vandetanib, retinoids (alitretinoin, tretinoin), altretamine, amsacrine, anagrelide, arsenic trioxide, asparaginase (pegaspargase), bexarotene, bortezomib, denileukin diftitox, estramustine, ixabepilone, masoprocol, mitotane, testolactone, tipifarnib, abetimus, deforolimus, everolimus, gusperimus, pimecrolimus, sirolimus, tacrolimus, temsirolimus, antimetabolites such as cytarabin, fluorouracil, fluoroarabin, gemcitabin, tioguanin, capecitabin, combinations such as adriamycin/daunorubicin, cytosine arabinosid/cytarabine, 4-HC, or other phosphamides.

Other particularly preferred compounds are compounds such as clemastine, diphenhydramine, dimenhydrinate, promethazine, cetirizine, astemizole, levocabastine, loratidine, terfenadine, acetylsalicylic acid, sodoum salicylate, salsalate, diflunisal, salicylsalicylic acid, mesalazine, sulfasalazine, osalazine, acetaminophen, indomethacin, sulindac, etodolac, tolmetin, ketorolac, bethamethason, budesonide, chromoglycinic acid, dimeticone, simeticone, domperidone, metoclopramid, acemetacine, oxaceprol, ibuprofen, naproxen, ketoprofen, flubriprofen, fenoprofen, oxaprozin, mefenamic acid, meclofenamic acid, pheylbutazone, oxyphenbutazone, azapropazone, nimesulide, metamizole, leflunamide, eforicoxib, lonazolac, misoprostol, paracetamol, aceclofenac, valdecoxib, parecoxib, celecoxib, propyphenazon, codein, oxapozin, dapson, prednisone, prednisolon, triamcinolone, dexibuprofen, dexamethasone, flunisolide, albuterol, salmeterol, terbutalin, theophylline, caffeine, naproxen, glucosamine sulfate, etanercept, ketoprofen, adalimumab, hyaluronic acid, indometacine, proglumetacine dimaleate, hydroxychloroquine, chloroquine, infliximab, etofenamate, auranofin, gold, [$^{224}$Ra]radium chloride, tiaprofenic acid, dexketoprofen (trometamol), cloprednol, sodium aurothiomalate aurothioglucose, colchicine, allopurinol, probenecid, sulfinpyrazone, benzbromarone, carbamazepine, lornoxicam, fluorcortolon, diclofenac, efalizumab, idarubicin, doxorubicin, bleomycin, mitomycin, dactinomycin, daptomycin, cytarabin, fluorouracil, fluoroarabin, gemcitabin, tioguanin, capecitabin, adriamydin/daunorubicin, cytosine arabinosid/cytarabine, 4-HC, or other phosphamides, penicillamine, a hyaluronic acid preparation, arteparon, glucosamine, MTX, soluble fragments of the TNF-receptor (such as etanercept (Enbrel)) and antibodies against TNF (such as infliximab (Remicade), natalizumab (Tysabri) and adalimumab (Humira)).

It will be appreciated by the person of ordinary skill in the art that the compounds of the invention and the additional therapeutic agent may be formulated in one single dosage form, or may be present in separate dosage forms and may be either administered concomitantly (i.e. at the same time) or sequentially.

The pharmaceutical compositions of the present invention may be in any form suitable for the intended method of administration.

The compounds of the present invention may be administered orally, parenterally, such as bronchopulmonary, subcutaneously, intravenously, intramuscularly, intraperitoneally, intrathecally, transdermally, transmucosally, subdurally, locally or topically via iontopheresis, sublingually, by inhalation spray, aerosol or rectally and the like in dosage unit formulations optionally comprising conventional pharmaceutically acceptable excipients.

Excipients that may be used in the formulation of the pharmaceutical compositions of the present invention comprise carriers, vehicles, diluents, solvents such as monohydric alcohols such as ethanol, isopropanol and polyhydric alcohols such as glycols and edible oils such as soybean oil, coconut oil, olive oil, safflower oil cottonseed oil, oily esters such as ethyl oleate, isopropyl myristate; binders, adjuvants, solubilizers, thickening agents, stabilizers, disintergrants, glidants, lubricating agents, buffering agents, emulsifiers, wetting agents, suspending agents, sweetening agents, colorants, flavors, coating agents, preservatives, antioxidants, processing agents, drug delivery modifiers and enhancers such as calcium phosphate, magnesium state, talc, monosaccharides, disaccharides, starch, gelatine, cellulose, methyl-cellulose, sodium carboxymethyl cellulose, dextrose, hydroxypropyl-β-cyclodextrin, polyvinylpyrrolidone, low melting waxes, ion exchange resins.

Other suitable pharmaceutically acceptable excipients are described in Remington's Pharmaceutical Sciences, 15$^{th}$ Ed., Mack Publishing Co., New Jersey (1991).

Dosage forms for oral administration include tablets, capsules, lozenges, pills, wafers, granules, oral liquids such as syrups, suspensions, solutions, emulsions, powder for reconstitution.

Dosage forms for parenteral administration include aqueous or olageous solutions or emulsions for infusion, aqueous or olageous solutions, suspensions or emulsions for injection pre-filled syringes, and/or powders for reconstitution.

Dosage forms for local/topical administration comprise insufflations, aerosols, metered aerosols, transdermal therapeutic systems, medicated patches, rectal suppositories, and/or ovula.

The amount of the compound of the present invention that may be combined with the excipients to formulate a single dosage form will vary upon the host treated and the particular mode of administration.

The pharmaceutical compositions of the invention can be produced in a manner known per se to the skilled person as described, for example, in Remington's Pharmaceutical Sciences, 15$^{th}$ Ed., Mack Publishing Co., New Jersey (1991).

In a further aspect of the invention the use of a thienopyrimidine compound of the present invention for the production of a pharmaceutical composition for inhibiting the activity of the kinase activity of Mnk1 or Mnk2 (Mnk2a, Mnk2b) or further variants thereof is provided, in particular for the prophylaxis or therapy of metabolic diseases, hematopoietic disorders, cancer and their consecutive complications and disorders. Whereby the prophylaxis and therapy of metabolic diseases of the carbohydrate and/or lipid metabolism is preferred.

Diseases of the invention that are influenced by the inhibition of the kinase activity of Mnk1 and/or Mnk2 (Mnk2a or Mnk2b) and/or further variants thereof include diseases related to the regulation of metabolic diseases, such as obesity, eating disorders, cachexia, diabetes mellitus, metabolic syndrome, hypertension, coronary heart diseases, hypercholesterolemia, dyslipidemia, osteoarthritis, biliary stones and/or sleep apnea and diseases related to reactive oxygen compounds (ROS defense) such as diabetes mellitus, neurodegenerative diseases and cancer.

The pharmaceutical compositions of the invention are particularly useful for prophylaxis and treatment of obesity, diabetes mellitus and other metabolic diseases of the carbohydrate and lipid metabolism as stated above, in particular diabetes mellitus and obesity.

Thus in a more preferred embodiment of this invention the use of a thienopyrimidine compound for the production of a pharmaceutical composition for the prophylaxis or therapy of metabolic diseases is provided.

In yet a further aspect of the invention the use of a thienopyrimidine compound of the invention for the production of a pharmaceutical composition for treating or preventing a cytokine mediated disorder such as an inflammatory disease is provided.

The pharmaceutical compositions of the invention are thus useful for the prophylaxis or therapy of inflammatory diseases, in particular chronic or acute inflammation, chronic inflammatory arthritis, rheumatoid arthritis, psoriatic arthritis, osteoarthritis, juvenile rheumatoid arthritis, gouty arthritis; psoriasis, erythrodermic psoriasis, pustular psoriasis, inflammatory bowel disease, Crohn's disease and related conditions, ulcerative colitis, colitis, diverticulitis, nephritis, urethritis, salpingitis, oophoritis, endomyometritis, spondylitis, systemic lupus erythematosus and related disorders, multiple sclerosis, asthma, meningitis, myelitis, encephalomyelitis, encephalitis, phlebitis, thrombophlebitis, chronic obstructive disease (COPD), inflammatory lung disease, allergic rhinitis, endocarditis, osteomyelitis, rheumatic fever, rheumatic pericarditis, rheumatic endocarditis, rheumatic myocarditis, rheumatic mitral valve disease, rheumatic aortic valve disease, prostatitis, prostatocystitis, spondoarthropathies ankylosing spondylitis, synovitis, tenosynovotis, myositis, pharyngitis, polymyalgia rheumatica, shoulder tendonitis or bursitis, gout, pseudo gout, vasculitides, inflammatory diseases of the thyroid selected from granulomatous thyroiditis, lymphocytic thyroiditis, invasive fibrous thyroiditis, acute thyroiditis; Hashimoto's thyroiditis, Kawasaki's disease, Raynaud's phenomenon, Sjogren's syndrome, neuroinflammatory disease, sepsis, conjubctivitis, keratitis, iridocyclitis, optic neuritis, otitis, lymphoadenitis, nasopaharingitis, sinusitis, pharyngitis, tonsillitis, laryngitis, epiglottitis, bronchitis, pneumonitis, stomatitis, gingivitis, oesophagitis, gastritis, peritonitis, hepatitis, cholelithiasis, cholecystitis, glomerulonephritis, goodpasture's disease, crescentic glomerulonephritis, pancreatitis, dermatitis, endomyometritis, myometritis, metritis, cervicitis, endocervicitis, exocervicitis, parametritis, tuberculosis, vaginitis, vulvitis, silicosis, sarcoidosis, pneumoconiosis, inflammatory polyarthropathies, psoriatric arthropathies, intestinal fibrosis, bronchiectasis and enteropathic arthropathies.

As already stated above, the compositions of the present invention are particularly useful for treating or preventing a disease selected from chronic or acute inflammation, chronic inflammatory arthritis, rheumatoid arthritis, psoriasis, COPD, inflammatory bowel disease, septic shock, Crohn's disease, ulcerative colitis, multiple sclerosis and asthma.

Thus, in a more preferred embodiment of this invention the use of a thienopyrimidine compound for the production of a pharmaceutical composition for the prophylaxis or therapy of inflammatory diseases selected from chronic or acute inflammation, chronic inflammatory arthritis, rheumatoid arthritis, psoriasis, COPD, inflammatory bowel disease, septic shock Crohn's disease, ulcerative colitis, multiple sclerosis and asthma is provided.

In yet a further aspect of the invention the use of a thienopyrimidine compound of the invention for the production of a pharmaceutical composition for treating or preventing cancer, viral diseases or neurodegenerative diseases is provided.

For the purpose of the present invention, a therapeutically effective dosage will generally be from about 1 to 2000 mg/day, preferably from about 10 to about 1000 mg/day, and most preferably from about 10 to about 500 mg/day, which may be administered in one or multiple doses.

It will be appreciated, however, that specific dose level of the compounds of the invention for any particular patient will depend on a variety of factors such as age, sex, body weight, general health condition, diet, individual response of the patient to be treated time of administration, severity of the disease to be treated, the activity of particular compound applied, dosage form, mode of application and concomitant medication. The therapeutically effective amount for a given situation will readily be determined by routine experimentation and is within the skills and judgment of the ordinary clinician or physician.

Kinase Fluorescence Polarization Assays

Assay Principle:

Inhibitory potency of compounds against Mnk1, Mnk2a and other kinases was assessed with assays based on a format known to those skilled in the art as the indirect (competitive)

fluorescence polarization. The assay detection system comprises a small fluorophore-labeled phospho-peptide (termed ligand) bound to a phospho-specific antibody. The product generated by the kinase reaction competes with the ligand for antibody binding. Based on the larger molecular volume of the bound ligand, which results in a lower rotation rate in solution, its emitted light has a higher degree of polarization than the one from the free ligand.

Description of the Specific Homogenous Kinase Assay
Example 2a. Mnk1 and Mnk2a in vitro kinase assay As a source of enzyme, human Mnk1 and human Mnk2a were expressed as GST fusion proteins in *E. coli*, purified to >80% homogeneity by glutathione affinity chromatography and activated in vitro with pre-activated ERK2. In brief, the open reading frames of human Mnk1 and Mnk2a were amplified from cDNA using the forward/reverse primer pairs

```
SEQ ID NO: 1    5'TTTAGGATCCGTATCTTCTCAAAAGTTGG/

SEQ ID NO: 2    5'CTGGGTCGACTCAGAGTGCTGTGGGCGG
and

SEQ ID NO: 3    5'ACAGGGATCCGTGCAGAAGAAACCAGCC/

SEQ ID NO: 4    5'GATGGTCGACTCAGGCGTGGTCTCCCACC
```

(utilized restriction sites underlined), respectively, and cloned into the BamHI and SalI sites of the vector pGEX-4T1 (Amersham, Sweden, cat. no. 27-4580-01). These constructs allow prokaryotic expression of Mnk1 or Mnk2a as fusion protein with a N-terminal glutathione S-transferase (GST) tag, referred to as GST-Mnk1 or GSTMnk2a. The following expression and purification procedure was identical for GST-Mnk1 and GST-Mnk2a, referring in general to GST-Mnk, when not distinguishing between the two isoforms. Expression of GST-Mnk was in *E. coli* BL21 (Merck Biosciences, Germany, cat. no. 69449). Cells were grown in LB-Bouillon (Merck, Germany, cat. no. 1.10285) supplemented with 100 μg/ml ampicillin (Sigma, Germany, cat. no. A9518) at 37° C. When the culture had reached a density corresponding to an $A_{600}$ of 0.8, an equal volume of ice cold LB/ampicillin was added, the culture transferred to 25° C. and induced for 4 h with 1 mM isopropyl thiogalactoside (IPTG, Roth, Germany, cat. no. 2316.4). Cells harvested by centrifugation were resuspended in 10 ml lysis buffer (50 mM tris(hydroxymethyl)aminomethane hydrochloride (Tris/HCl, Sigma, Germany, cat. no. T5941) pH 7.5, 300 mM sodium chloride (NaCl, Sigma, Germany, cat. no. S7653), 5% (w/v) glycerol (Sigma, Germany, cat. no. G5516), 3 mM DTT dithiothreitol (DTT, Sigma, Germany, cat. no. D9779)) per gram wet weight cell pellet. Lysates were prepared by disruption of cells with a sonifier and subsequent clearing by centrifugation at 38000 g for 45 min at 4° C.

The lysate was applied to a GSTPrep FF 16/10 column (Amersham, Sweden, cat. no. 17-5234-01) equilibrated with lysis buffer. Removal of unbound material was with 3 column volumes (CV) lysis buffer. Elution was with 2 CV of elution buffer (50 mM Tris/HCl pH 7.5, 300 mM NaCl, 5% (w/v) glycerol, 20 mM glutathione (Sigma, Germany, cat. no. G4251)). Peak fractions were pooled and the protein transferred into storage buffer (50 mM Tris/HCl pH 7.5, 200 mM NaCl, 0.1 mM ethylene glycolbis(2-aminoethylether)-N,N,N',N'-tetraacetic acid (EGTA, Aldrich, Germany, cat. no. 23, 453-2), 1 mM DTT, 10% (w/v) glycerol, 0.5 M sucrose (Sigma, Germany, cat. no. S0389) by gel filtration on a PD10 desalting column (Amersham, Sweden, cat. no. 17-0851-01). Aliquots were shock frozen in liquid nitrogen and stored at −80° C.

Activation of Mnk1 and Mnk2a was at a concentration of 2.5 μM of either purified GST-Mnk1 or GST-Mnk2a by incubation with 150 nM pre-activated NHis-ERK2 (see ERK2 assay for preparation) and 50 μM adenosine triphosphate (ATP, Sigma, cat. no. A2699) in a buffer comprising 20 mM N-(2-hydroxyethyl)piperazine-N'-(2-ethanesulfonic acid) (HEPES, Fluka, Germany, cat. no 54459)/potassium hydroxide (KOH, Roth, Germany, cat. no 6751.1) pH 7.4, 10 mM magnesium chloride ($MgCl_2$, Sigma, Germany, cat. no. M2670), 0.25 mM DTT, 0.05% (w/v) polyoxyethylene 20 stearylether (Brij 78, Sigma, Germany, cat. no. P4019) (HMDB buffer) for 45 min at 30° C. After the incubation, the preparation was aliquoted into single-use samples, shock frozen in liquid nitrogen, stored at −80° C. and utilized for Mnk1 or Mnk2a kinase assays as detailed below. The presence of activating kinase has been tested to not interfere with the Mnk activity assay.

SUBSTRATE: A carboxy-terminal amidated 12mer peptide with the sequence SEQ ID NO: 5 TATKSGSTTKNR, derived from the amino acid sequence around serine 209 of the eukaryotic translation initiation factor 4E (eIF4E) has been synthesized and purified by high performance liquid chromatography (HPLC) to >95% (Thermo, Germany). The serine residue phosphorylated by Mnk kinases is underlined.

LIGAND: The peptide TATKSG-pS-TTKNR (SEQ ID NO: 6), containing an amidated carboxy-terminus and conjugated at the amino-terminus with the oxazine derived fluorophore depicted below was synthesized and used as ligand.

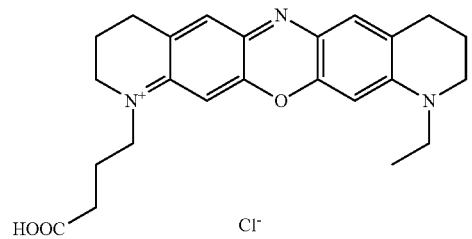 [SMILES: CCN1CCCc2cc3c(cc21)Oc1cc2c(cc1=N3)CCC[N+]=2CCCC(=O)O ; [Cl-]]

ANTIBODY: SPF New Zealand White Rabbits have been immunized according to standard protocols with the peptide NH2-CTATKSG-pS-TTKNR-CONH2 (SEQ ID NO: 7), coupled to keyhole limpet hemocyanin (KLH). The immune globulin G (IgG) fraction was purified from serum of boosted animals by techniques known in the art. In brief, serum was subjected to protein A affinity chromatography. Eluted material was precipitated at 50% cold saturated ammonium sulfate, pellets dissolved and desalted. The resulting material was appropriate for use in below described assay without further antigen-specific purification.

ASSAY SETUP: Inhibition of kinase activity of Mnk1 and Mnk2a was assessed with the same assay system, using pre-activated GST-Mnk1 or GST-Mnk2a, respectively. The kinase reaction contains 30 μM substrate peptide, 20 μM ATP, 60 nM ligand and one of either 25 nM pre-activated Mnk1 or 2.5 nM pre-activated Mnk2a. The reaction buffer conditions are 16 mM HEPES/KOH pH 7.4, 8 mM $MgCl_2$, 0.4 mM DTT, 0.08 (w/v) bovine serum albumin (BSA, Sigma, Germany, cat. no. A3059), 0.008% (w/v) Pluronic F127 (Sigma, Germany, cat. no. P2443), 3% (v/v) DMSO (Applichem, Germany, cat. no. A3006). The kinase reaction is at 30° C. for 40 min. The kinase reaction is terminated by addition of 0.67 reaction volumes of 1 μM antibody in 20 mM HEPES/KOH pH 7.4, 50 mM ethylenediaminetetraacetic acid, disodium salt (EDTA, Sigma, Germany, cat. no. E5134), 0.5 mM DTT, 0.05% (w/v) polyoxyethylene-sorbitan monolaureate (Tween 20, Sigma, Germany, cat. no. P7949). After 1 h equilibration time at room temperature, samples are subjected to fluorescence polarization measurement. The fluorescence polarization readout was generated on an Analyst AD multimode reader (Molecular Devices, Sunnyvale, Calif., USA) equipped with a DLRP650 dichroic mirror (Omega Opticals, Brattleboro, Vt., USA, cat. no. XF2035), a 630AF50 band pass filter (Omega Opticals, Brattleboro, Vt., USA, cat. no. XF1069) on the excitation and a 695AF55 band pass filter on the emission side (Omega Opticals, Brattleboro, Vt., USA, cat. no. XF3076).

The activity of Mnk proteins can be assayed also by other in vitro kinase assay formats. For example, suitable kinase assays have been described in the literature in Knauf et al., Mol Cell Biol. 2001 August; 21(16):5500-11 or in Scheper et al., Mol Cell Biol. 2001 February; 21(3):743-54. In general, Mnk kinase assays can be performed such that a Mnk substrate such as a protein or a peptide, which may or may not include modifications as further described below, or others are phosphorylated by Mnk proteins having enzymatic activity in vitro. The activity of a candidate agent can then be determined via its ability to decrease the enzymatic activity of the Mnk protein. The kinase activity may be detected by change of the chemical, physical or immunological properties of the substrate due to phosphorylation.

In one example, the kinase substrate may have features, designed or endogenous, to facilitate its binding or detection in order to generate a signal that is suitable for the analysis of the substrates phosphorylation status. These features may be, but are not limited to, a biotin molecule or derivative thereof, a glutathione-5-transferase moiety, a moiety of six or more consecutive histidine residues, an amino acid sequence or hapten to function as an epitope tag, a fluorochrome, an enzyme or enzyme fragment. The kinase substrate may be linked to these or other features with a molecular spacer arm to avoid steric hindrance.

In another example the kinase substrate may be labelled with a fluorophore. The binding of the reagent to the labelled substrate in solution may be followed by the technique of fluorescence polarization as it is described in the literature. In a variation of this example, a fluorescent tracer molecule may compete with the substrate for the analyte to detect kinase activity by a technique which is know to those skilled in the art as indirect fluorescence polarization.

In yet another example, radioactive gamma-ATP is used in the kinase reaction, and the effect of the test agent on the incorporation of radioactive phosphate in the test substrate is determined relative to control conditions.

It has been shown that the compounds of the invention exhibit low $IC_{50}$ values in in vitro biological screening assays as described in example 2a for inhibition of Mnk 1 and/or Mnk 2 kinase activity. The following table contains the test results for exemplary compounds.

| Example | MNK2 $IC_{50}$ [nM] |
|---|---|
| 1 | 13 |
| 2 | 21 |
| 3 | 10 |
| 4 | 23 |
| 5 | 3 |
| 6 | 7 |
| 7 | 7 |
| 8 | 12 |
| 9 | 5900 |
| 10 | 2500 |
| 11 | 7 |
| 12 | 7 |
| 13 | 440 |
| 14 | 1600 |
| 15 | — |
| 16 | 13 |
| 17 | 28 |
| 18 | 36 |
| 19 | 31 |
| 20 | 360 |
| 21 | 31 |
| 22 | 65 |
| 23 | 920 |
| 24 | 14 |
| 25 | 300 |
| 26 | 82 |
| 27 | 9700 |
| 28.1 | 158 |
| 29 | 90 |
| 30.1 | 9 |
| 31.1 | 37 |
| 32 | 36 |
| 33 | 7 |
| 34 | 28 |
| 35.2 | 23 |
| 35.3 | 23 |
| 36 | 66 |
| 37 | 69 |
| 38 | 70 |
| 39 | 61 |
| 40 | 40 |
| 41 | 152 |
| 42 | 140 |
| 43 | 360 |
| 44 | 440 |
| 45 | 480 |
| 46 | 460 |
| 47 | 260 |
| 48 | 410 |
| 49 | 380 |
| 50 | 10 |
| 51 | 13 |
| 52 | 30 |
| 53 | 54 |
| 54 | 62 |
| 55 | 59 |
| 56 | 33 |
| 57 | 7 |
| 58 | 6 |
| 59 | 34 |
| 60 | 14 |
| 61 | 26 |
| 62 | 17 |
| 63 | 14 |
| 64 | 21 |
| 65 | 16 |
| 66 | 26 |
| 67 | 18 |
| 68 | 31 |
| 69 | 34 |
| 70 | 17 |
| 71 | 28 |
| 72 | 23 |
| 73 | 43 |
| 74 | 22 |
| 75 | 18 |
| 76 | 13 |
| 77 | 18 |
| 78 | 25 |
| 79 | 15 |
| 80 | 31 |
| 81 | 98 |
| 82 | 44 |
| 83 | 53 |
| 84 | 91 |
| 85 | 46 |
| 86 | 93 |

-continued

| Example | MNK2 IC$_{50}$ [nM] |
|---|---|
| 87 | 38 |
| 88 | 61 |
| 89 | 8 |
| 90 | 34 |
| 91 | 16 |
| 92 | 36 |
| 93 | 16 |
| 94 | 21 |
| 95 | 28 |
| 96 | 14 |
| 97 | 24 |
| 98 | 17 |
| 99 | 36 |
| 100 | 34 |
| 101 | 21 |
| 102 | 34 |
| 103 | 50 |
| 104 | 43 |
| 105 | 24 |
| 106 | 22 |
| 107 | 18 |
| 108 | 19 |
| 109 | 24 |
| 110.1 | 9 |
| 111 | 36 |
| 112 | 13 |
| 113 | 23 |
| 114 | 19 |
| 115 | 19 |
| 116 | 33 |
| 117 | 12 |
| 118 | 22 |
| 119 | 11 |
| 120 | 33 |
| 121 | 41 |
| 122 | 18 |
| 123 | 26 |
| 124 | 36 |
| 125 | 44 |
| 126 | 23 |
| 127 | 16 |
| 128 | 19 |
| 129 | 17 |
| 130 | 24 |
| 131 | 18 |
| 132 | 96 |
| 133 | 53 |
| 134 | 86 |
| 135 | 65 |
| 136 | 44 |
| 137 | 105 |
| 138 | 48 |
| 139 | 84 |
| 140 | 49 |
| 141 | 89 |
| 142 | 125 |
| 143 | 77 |
| 144 | 89 |
| 145 | 68 |
| 146 | 105 |
| 147 | 83 |
| 148 | 49 |
| 149 | 65 |
| 150 | 11 |
| 151 | 36 |
| 152 | 11 |
| 153 | 9 |
| 154 | 12 |
| 155 | 9 |
| 156 | 13 |
| 157 | 9 |
| 158 | 4 |
| 159 | 16 |
| 160 | 6 |
| 161 | 17 |
| 162 | 10 |
| 163 | 9 |
| 164 | 16 |

-continued

| Example | MNK2 IC$_{50}$ [nM] |
|---|---|
| 165 | 8 |
| 166 | 11 |
| 167 | 21 |
| 168 | 20 |
| 169 | 17 |
| 170 | 19 |
| 171 | 43 |
| 172 | 16 |
| 173 | 14 |
| 174 | 10 |
| 175 | 9 |
| 176 | 21 |
| 177 | 18 |
| 178 | 16 |
| 179 | 30 |
| 180 | 16 |
| 181 | 21 |
| 182 | 15 |
| 183 | 23 |
| 184 | 38 |
| 185 | 17 |
| 186 | 20 |
| 187 | 21 |
| 188 | 20 |
| 189 | 28 |
| 190 | 30 |
| 191 | 25 |
| 192 | 21 |
| 193 | 43 |
| 194 | 14 |
| 195 | 19 |
| 196 | 17 |
| 197 | 1 |
| 198 | 10 |
| 199 | 15 |
| 200 | 17 |
| 201 | 16 |
| 202 | 46 |
| 203 | 62 |
| 204 | 5 |
| 205 | 10 |
| 206 | 13 |
| 207 | 9 |
| 208 | 14 |
| 209 | 20 |
| 210 | 22 |
| 211 | 8 |
| 212 | 8 |
| 213 | 74 |
| 214 | 9 |
| 215 | 49 |
| 216 | 53 |
| 217 | 130 |
| 218 | 38 |
| 219 | 12 |
| 220 | 390 |
| 221 | 10 |
| 222 | 41 |
| 223 | 18 |
| 224 | 8 |
| 225 | 6 |
| 226 | 10 |
| 227 | 12 |
| 228 | 1139 |
| 229 | 7 |
| 230 | 4 |
| 231 | 14 |
| 232 | 6 |
| 233 | 19 |
| 234 | 32 |
| 235 | 6 |
| 236 | 16 |
| 237 | 25 |
| 238 | 31 |
| 239 | 15 |
| 240 | 13 |
| 241 | 49 |
| 242 | 5 |

| Example | MNK2 IC$_{50}$ [nM] |
|---|---|
| 242 | 4 |
| 243 | 9 |
| 244 | 2 |
| 245 | 39 |
| 246 | 65 |
| 247 | 139 |
| 248 | 10 |
| 249 | 6 |
| 250 | 19 |
| 251 | 20 |
| 252 | 18 |
| 253 | 19 |
| 254 | 11 |
| 255 | 14 |
| 256 | 1286 |
| 257 | 141 |
| 258 | 110 |
| 259 | 346 |
| 260 | 255 |
| 261 | 175 |
| 262 | 23 |
| 263 | 175 |
| 264 | 42 |
| 265 | 54 |
| 266 | 15 |
| 267 | 10 |
| 268 | 14 |
| 269 | 24 |
| 270 | 58 |
| 271 | 12 |
| 272 | 33 |
| 273 | 4 |
| 274 | 5 |
| 275 | 10 |
| 276 | 12 |
| 277 | 13 |
| 278 | 7 |
| 279 | 11 |
| 280 | 9 |
| 281 | 66 |
| 282 | 11 |
| 283 | 6 |
| 284 | 10 |
| 285 | 9 |
| 286 | 4 |
| 287 | 5 |
| 288 | 19 |
| 289 | 2 |
| 290 | 8 |
| 291 | 19 |
| 292 | 46 |
| 293 | 377 |
| 294 | 183 |
| 295 | 95 |

EXAMPLES

The HPLC data provided in the examples described below were obtained as follows:

Method A:
Waters ZQ2000; Waters 1515 Pumpe, Waters PDA 996 Detektor, Waters 2747 Injektor
Mobile Phase: A Wasser+0.1% formic acid
  B Acetonitrile+0.1% formic acid
Gradient:

| time in min | % A | % B | Flow rate in mL/min |
|---|---|---|---|
| 0.00 | 95.0 | 5.0 | 1.00 |
| 0.10 | 95.0 | 5.0 | 1.00 |
| 3.10 | 2.00 | 98.00 | 1.00 |
| 4.50 | 2.00 | 98.00 | 1.00 |
| 5.00 | 95.0 | 5.0 | 1.00 | stationary phase: X-Terra™ MS C18 2.5 μm 4.6 mm×30 mm
column temperature approximately 25° C.
Diode array detection wavelength: 210-420 nm
Mass m/z 80 bis 800
Mode of ionisation: ESI positive Method B
Waters ZQ2000; Waters 1515 Pumpe, Waters PDA 996 Detektor, Waters 2747 Injektor
Mobile Phase: A Wasser+0.1% formic acid
  B acetonitrile+0.1% formic acid
Gradient:

| time in min | % A | % B | Flow rate in mL/min |
|---|---|---|---|
| 0.00 | 95.0 | 5.0 | 1.00 |
| 0.10 | 95.0 | 5.0 | 1.00 |
| 3.10 | 2.00 | 98.00 | 1.00 |
| 4.50 | 2.00 | 98.00 | 1.00 |
| 5.00 | 95.0 | 5.0 | 1.00 | stationary phase: X-Terra™ MS C18 2.5 μm 4.6 mm×30 mm
column temperature approximately 25° C.
Diode array detection wavelength: 210-420 nm
Mass: m/z 80 bis 800
Mode of ionisationt: ESI positiv and negativ im Switchmodus Method C
Merck Cromolith Speed ROD; RP18e; 4.6×50 mm
Flow Rate: 1.5 mL/min
Solvent A: H$_2$O 0.1% HCOOH; Solvent B: Acetonitrile 0.1% HCOOH
Gradient:
time
0.00: 10% B;
4.50: 90% B;
5.00: 90% B;
5.50: 10% B Method D:
Column: Merck Cromolith Speed ROD, RP18e, 4.6×50 mm
Flow Rate: 1.5 ml/min
Solvents: water with 0.1% formic acid (A) and acetonitrile with 0.1% formic acid (B)

| Gradient: | | |
|---|---|---|
| Time (min) | A (%) | B (%) |
| 0.00 | 90 | 10 |
| 4.50 | 10 | 90 |
| 5.00 | 10 | 90 |
| 5.50 | 90 | 10 |

Agilent 1100, MS G1956, quaternary pump, DAD 190-400 nm
Fragmentor 70, Gain EMV 1.0, mass range 100-1000

Method E
Column: Waters Sunfire C18, 4.6×50 mm, 3.5 μm
Flow rate: 2 ml/min
Solvents: A=H$_2$O, 0.1% TFA; B=methanol Gradient:
Time:
0.00: 80% A;
1.70: 0% A;
2.50: 0% A;
2.60: 80% A
column temperature 60° C.
Method F
Column: Waters Sunfire C18, 4.6×50 mm, 3.5 μm
Flow rate: 1.5 ml/min
Solvents: A=$H_2O$, 0.1% TFA; B=methanol
Gradient:
Time:
0.00: 95% A;
1.30: 0% A;
2.50: 0% A;
2.60: 95% A
column temperature 40° C.
Method G
Column: XBridge C18
Flow rate: 1 ml/min
Solvents: A=$H_2O$, 0.032% NH4OH; B=methanol
Gradient:
time
0.00: 95% A;
2.00: 0% A;
2.50: 0% A;
2.60: 95% A
column temperature 60° C.
Method H
Column: Waters XBridge C18; 3.0×30 mm 2.5 μm
Flow Rate: 1.50
Solvent: $H_2O$ 0.1% NH3
Gradient:
0.00: 10% B;
2.20: 100% B;
2.40: 100% B; 2.60:10% B; 2.80:10% B;
column temperature 40° C.
Method I
Column: Waters Sunfire C18; 4.6×50 mm, 3.5 μm
Flow rate: 2 ml/min
Solvent: A: $H_2O$, 0.1% TFA; B: methanol
Gradient:
0.00: 80% A;
1.70: 0% A;
2.50: 0% A;
2.60: 80% A
column temperature 60° C.
Method J
Column: Waters XBridge C18; 4.6×30 mm 2.5 μm
Flow Rate: 3.1
Solvent: $H_2O$ 0.1% trifluoroacetic acid
Gradient:
0.00: 10% B;
1.50: 100% B;
1.70: 100% B; 1.85: 10% B; 2.00: 10% B;
column temperature approximately 50° C.
Method K
Column: Waters ZQ2000; Waters 1515 Pumpe, Waters PDA 996 Detektor, Waters 2747 Injektor
Mobile phase: A Water+0.1% formic acid
B acetonitrile+0.1% formic acid
Gradient:

| Time in min | % A | % B | Flow rate in mL/min |
|---|---|---|---|
| 0.00 | 95.0 | 5.0 | 1.5 |
| 2.00 | 0.0 | 100 | 1.5 |
| 2.50 | 0.0 | 100 | 1.5 |
| 2.60 | 95.0 | 5.0 | 1.5 |

Stationary Phase: X-Terra™ MS C18 2.5 μm 4.6 mm×30 mm
column temperature approximately 25° C.
Diode array detection wavelength: 200-420 nm
Mass: m/z 80 bis 800
Mode of ionisation: ESI positiv
Method L
Waters ZQ2000; Waters 1515 Pumpe, Waters PDA 996 Detektor, Waters 2747 Injektor
Column: X-Terra™ MS C18 2.5 μm 4.6 mm×30 mm
Mobile Phase: A Water+0.1% formic acid
B Acetonitril+0.1% formic acid
Gradient:

| timet in min | % A | % B | Flow rate in mL/min |
|---|---|---|---|
| 0.00 | 95.0 | 5.0 | 1.5 |
| 2.00 | 0.0 | 100 | 1.5 |
| 2.50 | 0.0 | 100 | 1.5 |
| 2.60 | 95.0 | 5.0 | 1.5 |

Column temperature approximately. 25° C.
Diode array detection wavelength: 200-420 nm
Mass: m/z 80 bis 800
Mode of ionisation: ESI positiv/negativ
Method M
Column: XBridge C18; 3×30 mm, 2.5 μm
Flow Rate: 2.2 ml/min
Solvent: A: H O, 0.1% TFA B: methanol, 0.1% TFA
Gradient:
0.0: 95% A
0.30: 95% A
1.50: 0% A
1.55: 0% A
1.65: 0% A
column temperature 60° C.
Method N
Column: XBridge C18; 4.6×30 mm, 2.5 μm
Flow Rate: 4-3 ml/min
Solvent: A: H O, 0.1% TFA B: methanol, 0.1% TFA
Gradient:
0.0: 95% A Flow: 4 ml/min
0.05: 95% A Flow: 3 ml/min
2.05: 0% A Flow: 3 ml/min
2.10: 0% A Flow: 4 ml/min
2.35: 0% A Flow: 4 ml/min
column temperature 60° C.
Method X:
Column: Ascentis Express, C18, 2.1×50 mm, 2.7 μm
Solvents: A % $H_2O$ containing 0.1% TFA; B % acetonitrile containing 0.1% TFA Gradient:

| Time | A % | B % | Flow in ml/min |
|------|-----|-----|----------------|
| 0.00 | 95.0 | 5.0 | 1.050 |
| 1.00 | 5.0 | 95.0 | 1.050 |
| 1.25 | 5.0 | 95.0 | 1.050 |
| 1.30 | 95.0 | 5.0 | 1.050 |

Column Temperature (° C.) 65.0

ABBREVIATIONS

HATU: (2-(7-aza-1H-benzotriazole-1-yl)-1,1,3,3-tetramethyluronium hexafluorophosphate)
TBTU: 2-(1H-Benzotriazol-1-yl)-1,1,3,3-tetramethyluroniumtetrafluorborat
THF: tetrahydrofuran
EtOH: ethanol
MeOH: methanol
DCM: methylene chloride
DMF: N,N-dimethylformamide
EtOAc: ethyl acetate
HCl: hydrochloric acid
t-BuOH: tert.butanol
DTAD: Di-ter-butyl azodicarboxylate
DEAD: diethyl azodicarboxylate
DIAD: diisopropyl azodicarboxylate
LiHMDS: lithium hexymethyldisilazane
DIPEA: diisopropylethyl amine
EDC: 1-ethyl-3-(3-dimethylaminopropyl)carbodiimid
TFA: trifluoro acetic acid
TEA: triethylamine
brine: saturated sodium chloride solution in water
rt: room temperature
min: minute Intermediate I

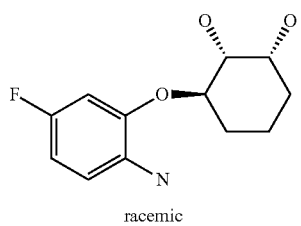 [SMILES: Nc1ccc(F)cc1O[C@@H]1CCC[C@@H](O)[C@H]1O]

racemic

I.1.
2-(Cyclohex-2-enyloxy)-4-fluoro-1-nitro-benzene

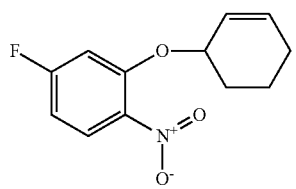 [SMILES: O=[N+]([O-])c1ccc(F)cc1OC1C=CCCC1]

1.89 ml DEAD were added to an ice-cooled solution of the 1.57 g 5-Fluoro-2-nitrophenol, 1.18 ml 2-cyclohexenol and 3.15 g triphenylphosphin in methylene chloride. The reaction mixture was stirred and allowed to warm to rt overnight. The solvent was removed in vacuo. Purification is achieved by silica gel column chromatography with iso-hexane/EtOAc (gradient: 100% i-hexane→10:1 i-hexane/EtOAc).
Yield: 1.9 g

I.2

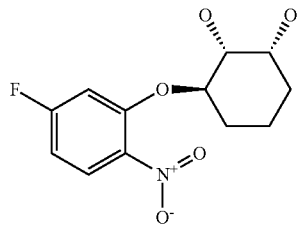

relative stereochemistry

A solution of 1.85 g 2-(Cyclohex-2-enyloxy)-4-fluoro-1-nitro-benzene in 5 ml t-butanol was added to an ice-cooled, pre-mixed solution of 10.9 g AD-mix-alpha in 80 ml tBuOH/water (1:1). The reaction mixture was stirred at this temperature for 1 hour and at rt overnight. The reaction mixture was cooled in ice-water and sodium metabisulfite (11.7 g) was added. After 10 minutes the coolant was removed and the mixture stirred at rt for 1 hour. After that the mixture was extracted with EtOAc. The organic phase was washed with brine and evaporated.
Yield: 2.15 g

I.3

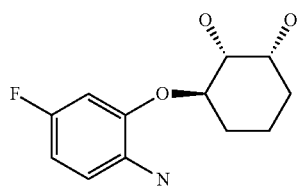

relative stereochemistry

Prepared analogously to example III.2 from 2.11 g compound I.2.
Yield: 1.59 g

Intermediate II racemic
trans-3-(2-Amino-5-fluoro-phenoxy)-cyclohexanol

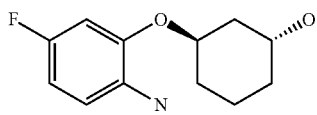

II.1. (3-Benzyloxy-phenoxy)-tert-butyl-dimethyl-silane

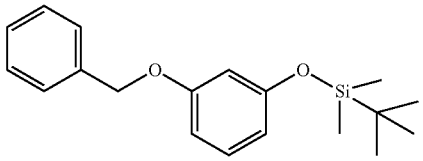 [SMILES: CC(C)(C)[Si](C)(C)Oc1cccc(OCc2ccccc2)c1]

43.459 ml tert-butyl-chloro-dimethyl-silane were added at rt to a solution of 17 g imidazole and 25 g 3-benzyloxy-phenol in 400 ml THF. After 3 hours water was added to the reaction mixture and the mixture was then extracted with methylene chloride. The organic phase was extracted three times with water, dried over sodium sulfate and concentrated in vacuo. The residue was solved in methylene chloride and filtered over Alox (neutral) and concentrated.

Yield: 37 g
retention time (HPLC): 4.15 min (method A)
ESI mass spectrum: m/z=315 (M+H)$^+$

II.2. 3-(tert-Butyl-dimethyl-silanyloxy)-cyclohexanol

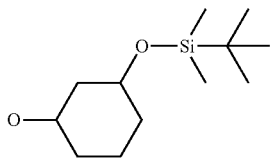

A mixture of 37.6 g (3-benzyloxy-phenoxy)-tert-butyl-dimethyl-silane and 3.8 g of Nishimura's catalyst in 200 ml of ethanol was hydrogenated at rt under 50 psi for 6 hours. The reaction mixture was filtered and the filtrate concentrated.

Yield: 26.48 g
ESI mass spectrum: m/z=231 (M+H)$^+$

II.3. racemic tert-Butyl-[cis-3-(5-fluoro-2-nitro-phenoxy)-cyclohexyloxy]-dimethyl-silane and racemic tert-Butyl-[trans-3-(5-fluoro-2-nitro-phenoxy)cyclohexyloxy]-dimethyl-silane

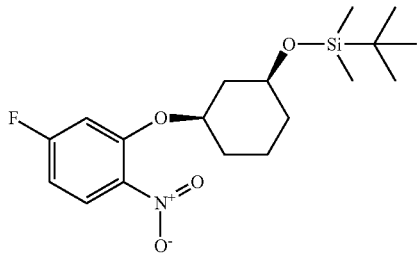

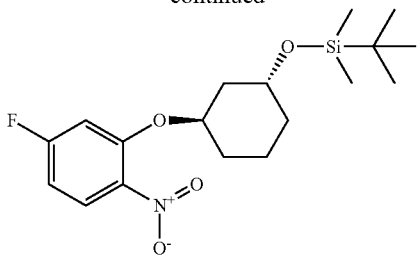

15.211 ml DIAD were added to a solution of 20.118 g triphenylphosphine in 300 ml THF and stirred for 30 min at rt. 9.272 g 5-fluoro-2-nitrophenol were added portionwise and the resulting reaction mixture was stirred for 30 minutes. After that time 17 g 3-(tert-butyl-dimethyl-silanyloxy)-cyclohexanol were added and the mixture was stirred for 18 hours. An additional solution from triphenylphosphine and DIAD in THF was added to the mixture and the mixture was stirred for 2 hours. The reaction mixture was poured in water and then extracted with methylene chloride. The organic phase was extracted three times with water, dried over sodium sulfate and concentrated in vacuo. Petrolether was added the residue and the mixture was filtered. The filtrate was concentrated. Purification is achieved by silica gel column chromatography with cyclohexane/methylene chloride (gradient: 90:10 to 75:25).

racemic tert-Butyl-[cis-3-(5-fluoro-2-nitro-phenoxy)-cyclohexyloxy]-dimethyl-silane Yield: 2.6 g
retention time (HPLC): 4.10 min (method B)
ESI mass spectrum: m/z=370 (M+H)$^+$ racemic tert-Butyl-[trans-3-(5-fluoro-2-nitro-phenoxy)-cyclohexyloxy]-dimethyl-silane Yield: 5.7 g
retention time (HPLC): 4.17 min (method B)
ESI mass spectrum: m/z=370 (M+H)$^+$

II.4. 2-[trans-3-(tert-Butyl-dimethyl-silanyloxy)-cyclohexyloxy]-4-fluoro-phenylamine

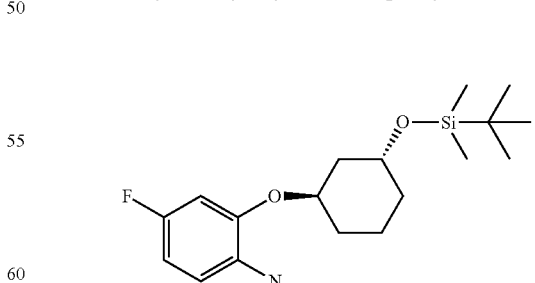

A mixture of 9.2 g racemic tert-Butyl-[trans-3-(5-fluoro-2-nitro-phenoxy)cyclohexyloxy]-dimethyl-silane and 0.92 g of Raney Nickel in 200 ml of methanol was hydrogenated at rt under 50 psi for 6 hours. The reaction mixture was filtered and the filtrate concentrated.

II.5. racemic trans-3-(2-Amino-5-fluoro-phenoxy)-cyclohexanol

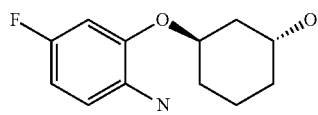

A solution of 8.1 g 2-[trans-3-(tert-butyl-dimethyl-silanyloxy)-cyclohexyloxy]-4-fluoro-phenylamine in 50 ml of HCl in ethanol (1.25 M) was stirred for 1 hour at rt. Sodium hydroxide solution (1 N) was then added to the reaction mixture resulting in a basic pH. This mixture was extracted with methylene chloride. The organic phase was dried over sodium sulfate, filtered and concentrated.

Yield: 5.2 g
ESI mass spectrum: m/z=226 (M+H)$^+$

Intermediate III 2-(1,4-Dioxa-spiro[4.5]dec-8-yloxy)-4-fluoro-phenylamine

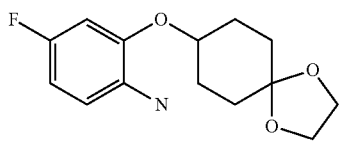 [SMILES: Nc1ccc(F)cc1OC1CCC2(CC1)OCCO2]

III.1. (8-(5-Fluoro-2-nitro-phenoxy)-1,4-dioxa-spiro[4.5]decane

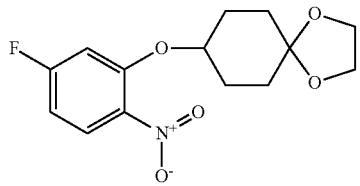 [SMILES: O=[N+]([O-])c1ccc(F)cc1OC1CCC2(CC1)OCCO2]

63 ml LiHMDS (1 M in THF) were added dropwise to a stirred solution of 10 g 1,4-dioxa-spiro[4.5]decan-8-ol in THF (60 ml) at 0° C. and the reaction stirred for 30 min. A solution of 2,4-difluor-1-nitro-benzene in THF (20 ml) was than added over 5 min and the reaction warmed to rt and stirred for 16 h. The reaction was quenched with sat. ammonium chloride solution and adjusted to pH 7 with 2N HCl. The solvent was removed under vacuum and the residue portioned between EtOAc (200 ml) and water (100 ml). The organic layer was separated and the aqueous phase washed with EtOAc (2×50 ml). The combined organic phases were washed with brine (50 ml) and separated. The organic phase was evaporated to give a solid that was used without further purification.

Yield: 14.47 g

III.2. 2-(1,4-Dioxa-spiro[4.5]dec-8-yloxy)-4-fluoro-phenylamine

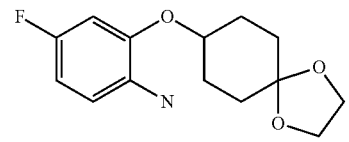 [SMILES: Nc1ccc(F)cc1OC1CCC2(CC1)OCCO2]

0.446 g Pd/C (5%) were added to a mixture of 4.46 g (8-(5-fluoro-2-nitro-phenoxy)-1,4-dioxa-spiro[4.5]decane and 4.03 g ammonium formate in 50 ml anhydrous methanol at rt. The reaction was initiated by gentle warming. The reaction was allowed to cool and stirred for a further 0.5 hours. The suspension was filtered through celite and washed with methanol. The combined organics were concentrated in vacuo and the residue triturated from diethylether. The solids were filtered and the filtrate collected and concentrated in vacuo to yield a solid.

Yield: 3.95 g

Intermediate IV

Trans-N-[4-(2-Amino-5-fluoro-phenoxy)-cyclohexyl]-methanesulfonamide

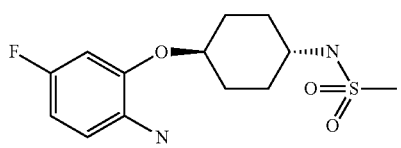 [SMILES: CS(=O)(=O)N[C@H]1CC[C@H](Oc2cc(F)ccc2N)CC1]

IV.1. 4-(5-Fluoro-2-nitro-phenoxy)-cyclohexyl]-carbamic acid tert-butyl ester

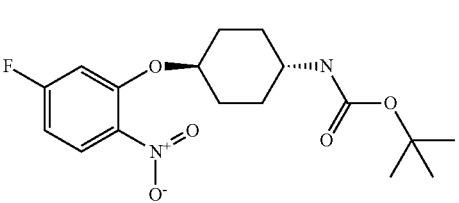 [SMILES: CC(C)(C)OC(=O)N[C@H]1CC[C@H](Oc2cc(F)ccc2[N+](=O)[O-])CC1]

1.2 g sodium hydride were added to an ice cooled solution of 2.15 g trans-(4-hydroxy-cyclohexyl)-carbamic acid tert-butyl ester in 50 ml DMF. After 1 hour 1.64 ml 2,4-difluoronitrobenzene were added and the mixture was stirred at this temperature for 1 hour. The coolant was removed and the reaction mixture was stirred for 4 hours.

The mixture was diluted with EtOAc and washed with water and brine two times. The mixture was dried over magnesium sulfate, filtered and the filtrate was evaporated. Purification is achieved by silica gel column chromatography with iso-hexane/EtOAc (gradient: 100% iso-hexane→5:1 iso-hexane:EtOAc→3:1 iso-hexane:EtOAc). The residue was triturated with diethylether.

Yield: 1.19 g

IV.2.
trans-4-(5-Fluoro-2-nitro-phenoxy)-cyclohexylamine hydrochloride

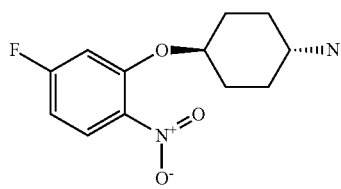 [SMILES: N[C@H]1CC[C@H](Oc2cc(F)ccc2[N+](=O)[O-])CC1]

10 ml of a solution of HCl in dioxane (4 M) were added to 1.19 g trans-[4-(5-fluoro-2-nitro-phenoxy)-cyclohexyl]-carbamic acid tert-butyl ester in methylene chloride. The mixture is stirred for 3 hours and 2 ml of HCl in dioxane (4 M) were added. The reaction mixture was stirred for 1 hour and concentrated in vacuo.

Yield: 1.09 g

IV.3. trans-N-[4-(5-Fluoro-2-nitro-phenoxy)-cyclohexyl]-methanesulfonamide

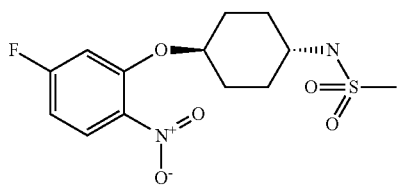 [SMILES: CS(=O)(=O)N[C@H]1CC[C@H](Oc2cc(F)ccc2[N+](=O)[O-])CC1]

120 µl methansulfonyl chloride were added to an ice cooled suspension of 300 mg trans-4-(5-fluoro-2-nitro-phenoxy)-cyclohexylamine hydrochloride and 431 µl triethylamine in 5 ml methylene chloride. The reaction mixture was allowed to warm up slowly to rt over night. Then the mixture was diluted with methylene chloride and washed with 10% potassium hydrogen sulfate. The mixture was filtered through a hydrophobic frit and evaporated. The residue was triturated with ether.

Yield: 0.227 g

IV.4. trans-N-[4-(2-Amino-5-fluoro-phenoxy)-cyclohexyl]-methanesulfonamide

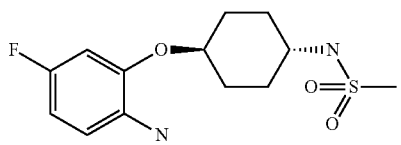 [SMILES: CS(=O)(=O)N[C@H]1CC[C@H](Oc2cc(F)ccc2N)CC1]

Prepared analogously to example III.2 from 0.218 g trans-N-[4-(5-fluoro-2-nitrophenoxy)-cyclohexyl]-methanesulfonamide.

Yield: 0.170 g

Intermediate V trans-N-[4-(2-Amino-5-fluoro-phenoxy)-cyclohexyl]-N-methyl-methanesulfonamide

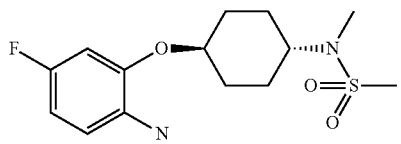

V.1. trans-[4-(5-Fluoro-2-nitro-phenoxy)-cyclohexyl]-methyl-carbamic acid tert-butyl ester

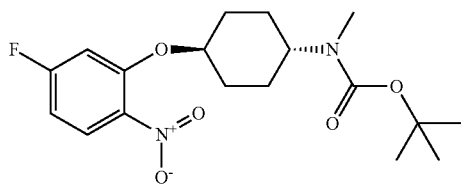 [SMILES: CN(C(=O)OC(C)(C)C)[C@H]1CC[C@H](Oc2cc(F)ccc2[N+](=O)[O-])CC1]

Prepared analogously to example III.1 from 1.11 ml 2,4-difluoronitrobenzene and 1.56 g trans-(4-hydroxy-cyclohexyl)-methyl-carbamic acid tert-butyl ester.

Yield: 2.25 g

V.2. trans-[4-(5-Fluoro-2-nitro-phenoxy)-cyclohexyl]-methyl-amine hydrochloride

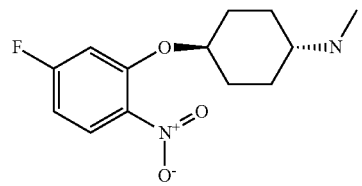 [SMILES: CN[C@H]1CC[C@H](Oc2cc(F)ccc2[N+](=O)[O-])CC1]

Prepared analogously to example IV.2 from 2.2 g trans-[4-(5-Fluoro-2-nitro-phenoxy)cyclohexyl]-methyl-carbamic acid tert-butyl ester.

Yield: 1.41 g

V.3. trans-N-[4-(5-Fluoro-2-nitro-phenoxy)-cyclohexyl]-N-methylmethanesulfonamide

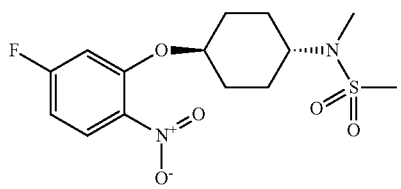 [SMILES: CN([C@H]1CC[C@H](Oc2cc(F)ccc2[N+](=O)[O-])CC1)S(C)(=O)=O]

Prepared analogously to example IV.3 from 0.305 g trans-[4-(5-fluoro-2-nitrophenoxy)-cyclohexyl]-methyl-amine hydrochloride and methanesulfonyl chloride.

Yield: 0.331 g

V.4. trans-N-[4-(2-Amino-5-fluoro-phenoxy)-cyclohexyl]-N-methylmethanesulfonamide

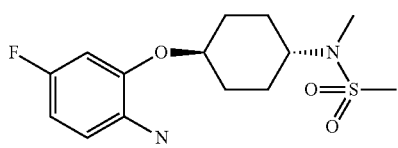

Prepared analogously to example III.2 from 0.329 g trans-N-[4-(5-fluoro-2-nitrophenoxy)-cyclohexyl]-N-methyl-methanesulfonamide.

Yield: 0.083 g

Intermediate VI trans-N-[4-(2-Amino-5-fluoro-phenoxy)-cyclohexyl]-acetamide

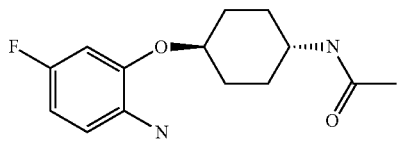 [SMILES: CC(=O)N[C@H]1CC[C@H](Oc2cc(F)ccc2N)CC1]

VI.1. trans-N-[4-(5-Fluoro-2-nitro-phenoxy)-cyclohexyl]-acetamide

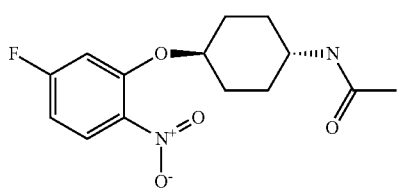 [SMILES: CC(=O)N[C@H]1CC[C@H](Oc2cc(F)ccc2[N+](=O)[O-])CC1]

166 µl acetic anhydride were added to a mixture of 0.341 g trans-4-(5-fluoro-2-nitrophenoxy)-cyclohexylamine hydrochloride and 327 µl triethylamine in 5 ml methylene chloride. The reaction mixture was stirred at rt overnight. The mixture was diluted with methylene chloride and 10% aq. potassium hydrogensulfate and 10% aq. potassium carbonate. Then the mixture was passed through a hydrophobic frit and the solvent was evaporated.

Yield: 0.325 g

VI.1. trans-N-[4-(2-Amino-5-fluoro-phenoxy)-cyclohexyl]-acetamide

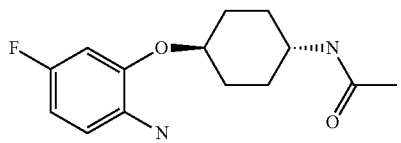 [SMILES: CC(=O)N[C@H]1CC[C@H](Oc2cc(F)ccc2N)CC1]

Prepared analogously to example III.2 from 0.15 g trans-N-[4-(5-fluoro-2-nitrophenoxy)-cyclohexyl]-acetamide.

Yield: 0.14 g

Intermediate VII trans-N-[4-(2-Amino-5-fluoro-phenoxy)-cyclohexyl]-N-methyl-acetamide

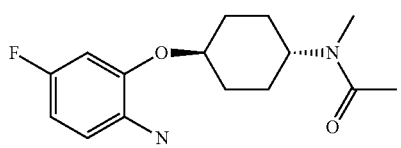 [SMILES: CC(=O)N(C)[C@H]1CC[C@H](Oc2cc(F)ccc2N)CC1]

VII.1. trans-N-[4-(5-Fluoro-2-nitro-phenoxy)-cyclohexyl]-N-methyl-acetamide

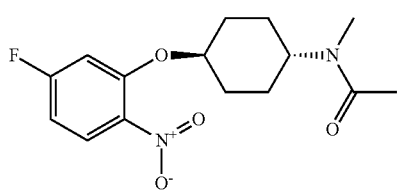 [SMILES: CC(=O)N(C)[C@H]1CC[C@H](Oc2cc(F)ccc2[N+](=O)[O-])CC1]

Prepared analogously to example VI.1 from 0.305 g trans-[4-(5-fluoro-2-nitrophenoxy)-cyclohexyl]-methyl-amine hydrochloride and acetic acid anhydride.

Yield: 0.329 g

VII.2. trans-N-[4-(2-Amino-5-fluoro-phenoxy)-cyclohexyl]-N-methyl-acetamide

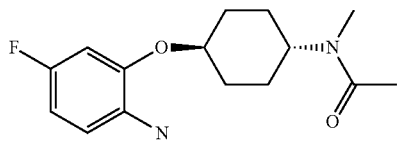

Prepared analogously to example III.2 from 0.305 g trans-N-[4-(5-fluoro-2-nitrophenoxy)-cyclohexyl]-N-methyl-acetamide.

Yield: 0.14 g

Intermediate VIII

Cis-N-[4-(2-Amino-5-fluoro-phenoxy)-cyclohexyl]-N-methyl-methanesulfonamide

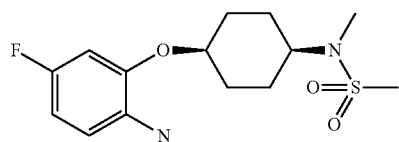 [SMILES: CN([C@H]1CC[C@@H](Oc2cc(F)ccc2N)CC1)S(C)(=O)=O]

VIII.1. Benzoic acid 4-cis-(tert-butoxycarbonyl-methyl-amino)-cyclohexyl ester

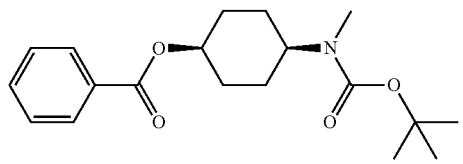 [SMILES: CN(C(=O)OC(C)(C)C)[C@H]1CC[C@@H](OC(=O)c2ccccc2)CC1]

1.74 ml DEAD were added dropwise to a cooled (cold water) solution of 1.69 g trans-(4-hydroxy-cyclohexyl)-methyl-carbamic acid tert-butyl ester, 1.35 g benzoic acid and 2.9 g Triphenylphosphine in 20 ml THF. After 10 mins the coolant was removed and the reaction mixture was stirred for 2 hours. Then the mixture was diluted with methylene chloride and washed with 10% aq. potassium carbonate solution. The organic was passed through a hydrophobic frit and evaporated. Purification is achieved by silica gel column chromatography with iso-hexane/EtOAc (gradient: 100% iso-hexane→5:1 iso-hexane).

Yield: 1.32 g

VIII.2. cis-(4-Hydroxy-cyclohexyl)-methyl-carbamic acid tert-butyl ester

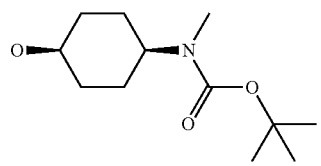 [SMILES: CN(C(=O)OC(C)(C)C)[C@H]1CC[C@@H](O)CC1]

0.807 g potassium carbonate were added to a solution of 1.3 g cis-benzoic acid 4-(tert-butoxycarbonyl-methyl-amino)-cyclohexyl ester in 10 ml methanol. The reaction mixture was stirred at rt overnight. 2 ml sodium hydroxide solution (2M) were added and the mixture was stirred for 4 hours. After that time the mixture was diluted with EtOAc and washed with water and brine. The organic phase was passed through a hydrophobic frit and the solvent was evaporated. Purification was achieved by silica gel column chromatography (gradient: 100% i-hex.→100% methylene chloride→20:1 methylene chloride/methanol).

Yield: 0.876 g

VIII.3. [cis-4-5-Fluoro-2-nitro-phenoxy)-cyclohexyl]-methyl-carbamic acid tert-butyl ester

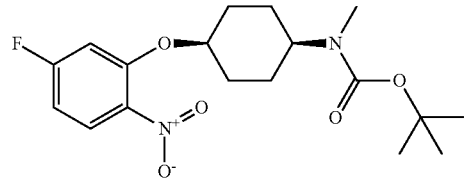 [SMILES: CN(C(=O)OC(C)(C)C)[C@H]1CC[C@@H](Oc2cc(F)ccc2[N+](=O)[O-])CC1]

Prepared analogously to example III.1 from 500 μl 2,4-difluoronitrobenzene and 0.876 g cis-(4-hydroxy-cyclohexyl)-methyl-carbamic acid tert-butyl ester.

Yield: 0.709 g

VIII.4. cis-4-(5-Fluoro-2-nitro-phenoxy)-cyclohexyl]-methyl-amine hydrochloride

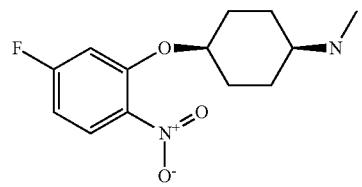 [SMILES: CN[C@H]1CC[C@@H](Oc2cc(F)ccc2[N+](=O)[O-])CC1]

Prepared analogously to example IV.2 from 0.698 g [cis-4-(5-fluoro-2-nitro-phenoxy)cyclohexyl]-methyl-carbamic acid tert-butyl ester.

Yield: 0.511 g

VIII.5. N-[cis-4-(5-Fluoro-2-nitro-phenoxy)-cyclohexyl]-N-methylmethanesulfonamide

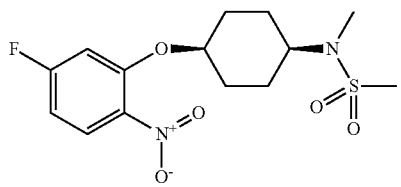 [SMILES: CN([C@H]1CC[C@@H](Oc2cc(F)ccc2[N+](=O)[O-])CC1)S(C)(=O)=O]

Prepared analogously to example IV.3 from 0.252 g [cis-4-(5-fluoro-2-nitro-phenoxy)cyclohexyl]-methyl-amine hydrochloride and methanesulfonyl chloride.

Yield: 0.296 g

V.4. cis-N-[4-(2-Amino-5-fluoro-phenoxy)-cyclohexyl]-N-methylmethanesulfonamide

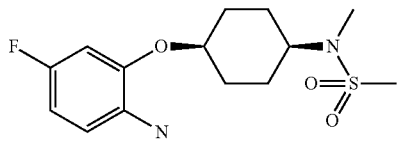 [SMILES: CN([C@H]1CC[C@@H](Oc2cc(F)ccc2N)CC1)S(C)(=O)=O]

Prepared analogously to example III.2 from 0.259 g N-[cis-4-(5-fluoro-2-nitrophenoxy)-cyclohexyl]-N-methyl-methanesulfonamide.

Yield: 0.226 g

Intermediate IX

N-[cis-4-(2-Amino-5-fluoro-phenoxy)-cyclohexyl]-N-methyl-acetamide

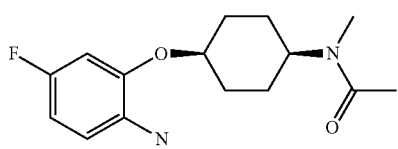 [SMILES: CC(=O)N(C)[C@H]1CC[C@@H](Oc2cc(F)ccc2N)CC1]

IX.1. N-[cis-4-(5-Fluoro-2-nitro-phenoxy)-cyclohexyl]-N-methyl-acetamide

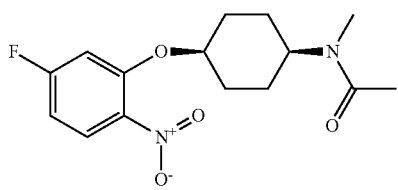 [SMILES: CC(=O)N(C)[C@H]1CC[C@@H](Oc2cc(F)ccc2[N+](=O)[O-])CC1]

Prepared analogously to example VI.1 from 0.252 g [cis-4-(5-fluoro-2-nitro-phenoxy)cyclohexyl]-methyl-amine hydrochloride and acetic acid anhydride.

Yield: 0.259 g

IX.2. N-[cis-4-(2-Amino-5-fluoro-phenoxy)-cyclohexyl]-N-methyl-acetamide

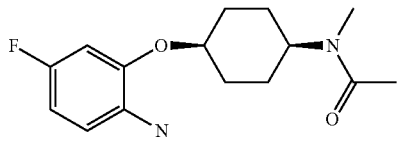 [SMILES: CC(=O)N(C)[C@H]1CC[C@@H](Oc2cc(F)ccc2N)CC1]

Prepared analogously to example III.2 from 0.259 g N-[cis-4-(5-fluoro-2-nitrophenoxy)-cyclohexyl]-N-methyl-acetamide.

Yield: 0.226 g

Intermediate X

[trans-4-(2-Amino-5-fluoro-phenoxy)-cyclohexyl]-methyl-carbamic acid methyl ester X.1. [trans-4-(2-Nitro-5-fluoro-phenoxy)-cyclohexyl]-methyl-carbamic acid methyl ester

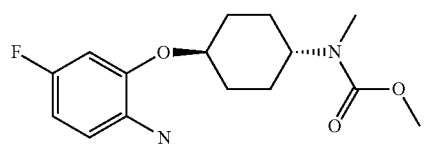 [SMILES: COC(=O)N(C)[C@H]1CC[C@H](Oc2cc(F)ccc2N)CC1]

129 µl methyl chloroformate were added to an ice-cooled mixture of 0.305 g [trans-4-(5-fluoro-2-nitro-phenoxy)-cyclohexyl]-methyl-amine hydrochloride and 417 µl triethylamine in 5 ml methylene chloride. After 10 minutes the coolant was removed and the mixture was stirred at rt overnight. Then the reaction mixture was diluted with methylene chloride and washed with 10% aq. potassium hydrogen sulfate solution and 10% aq.potassium carbonate solution. The organic phase was passed through a hydrophobic frit.

Yield: 0.295 g

X.2. [trans-4-(2-Amino-5-fluoro-phenoxy)-cyclohexyl]-methyl-carbamic acid methyl ester

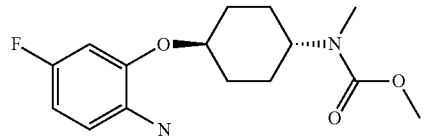 [SMILES: COC(=O)N(C)[C@H]1CC[C@H](Oc2cc(F)ccc2N)CC1]

Prepared analogously to example III.2 from 0.292 g trans-4-(2-Nitro-5-fluorophenoxy)-cyclohexyl]-methyl-carbamic acid methyl ester Yield: 0.248 g

Intermediate XI

XI.1. [trans-4-(2-Amino-5-fluoro-phenoxy)-cyclohexyl]-methyl-carbamic acid tert-butyl ester

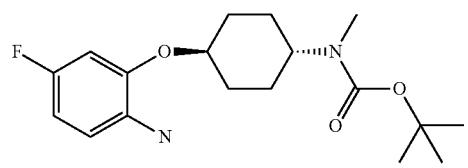 [SMILES: CN(C(=O)OC(C)(C)C)[C@H]1CC[C@H](Oc2cc(F)ccc2N)CC1]

Prepared analogously to example III.2 from 1.42 g [trans-4-(5-fluoro-2-nitrophenoxy)-cyclohexyl]-methyl-carbamic acid tert-butyl ester Yield: 1.4 g Intermediate XII Racemic N-[trans-2-(2-Amino-5-fluoro-phenoxy)-cyclohexyl]-N-methylmethanesulfonamide

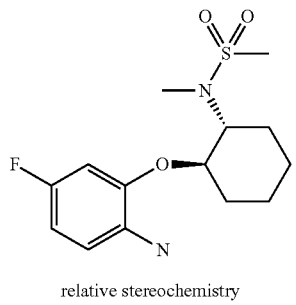 [SMILES: CN([C@@H]1CCCC[C@H]1Oc1cc(F)ccc1N)S(C)(=O)=O]

relative stereochemistry

XII.1. racemic (trans-2-Hydroxy-cyclohexyl)-carbamic acid tert-butyl ester

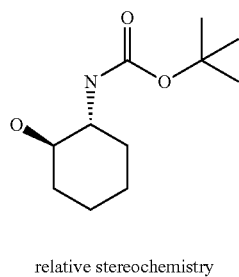

relative stereochemistry

A solution of 3.64 g di-tert-butyldicarbonate in 5 ml methylene chloride was added to a solution of 3.02 g racemic trans-2-aminocyclohexanol and 4.2 ml triethylamine in 40 ml methylene chloride. After completion of the reaction methylene chloride was added and the mixture was washed with 10% au potassium hydrogensulfate solution. The organic phase was passed through a hydrophobic frit and concentrated.

Yield: 3.62 g

XII.2. racemic trans-2-Methylamino-cyclohexanol

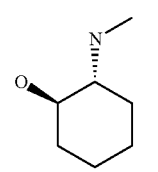

relative stereochemistry 3.51 g racemic trans-(2-hydroxy-cyclohexyl)-carbamic acid tert-butyl ester were added to a suspension of 3.09 g lithium aluminium hydride in THF. The reaction mixture was heated at reflux over night. After that time subsequently 3.1 ml water, 3.1 ml sodium hydroxide solution (2M) and 3.1 ml water were added. The mixture was then stirred for 45 minutes and then filtered through celite. The celite was washed with EtOAc. The solvent was evaporated.

Yield: 1.9 g

XII.3. racemic trans-(2-Hydroxy-cyclohexyl)-methyl-carbamic acid tert-butyl ester

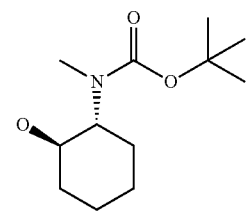

relative stereochemistry

Prepared analogously to XII.1 from 1.9 g racemic trans-2-Methylamino-cyclohexanol.

Yield: 3.49 g

XII.4. racemic [trans-2-(5-Fluoro-2-nitro-phenoxy)-cyclohexyl]-methyl-carbamic acid tert-butyl ester

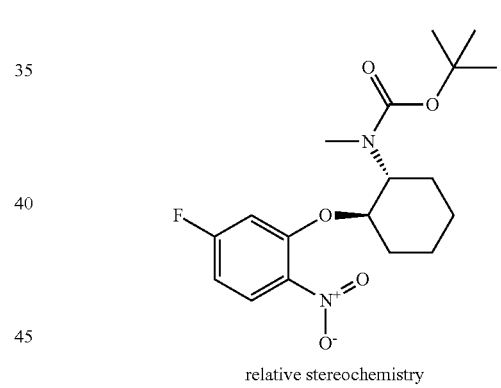

relative stereochemistry

Prepared analogously to III.1 from 0.33 ml 2,4-difluoro-nitrobenzene and 0.687 g racemic trans-(2-hydroxy-cyclohexyl)-methyl-carbamic acid tert-butyl ester.

Yield: 0.844 g

XII.5. racemic [[trans-2-(5-Fluoro-2-nitro-phenoxy)-cyclohexyl]-methyl-amine hydrochloride

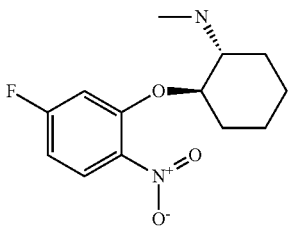

relative stereochemistry

Prepared analogously to IV.2 from 0.84 g racemic [trans-2-(5-fluoro-2-nitro-phenoxy)cyclohexyl]-methyl-carbamic acid tert-butyl ester.

Yield: 0.621 g

XII.6. racemic N-[trans-2-(5-Fluoro-2-nitro-phenoxy)-cyclohexyl]-N-methylmethanesulfonamide

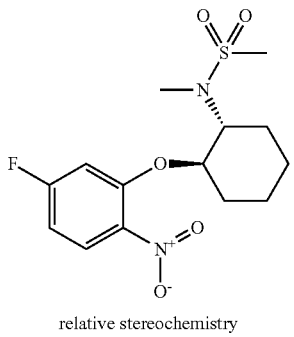 [SMILES: CN([C@@H]1CCCC[C@H]1Oc1cc(F)ccc1[N+](=O)[O-])S(C)(=O)=O]

relative stereochemistry

Prepared analogously to IV.3 from 0.29 g racemic trans-[[trans-2-(5-fluoro-2-nitrophenoxy)-cyclohexyl]-methyl-amine hydrochloride.

Yield: 0.283 g

XII.7. racemic N-[trans-2-(5-fluoro-2-amino-phenoxy)-cyclohexyl]-N-methylmethanesulfonamide

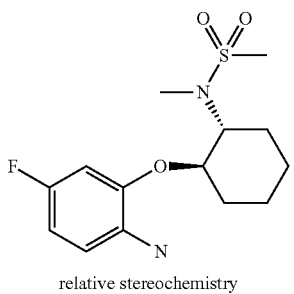 [SMILES: CN([C@@H]1CCCC[C@H]1Oc1cc(F)ccc1N)S(C)(=O)=O]

relative stereochemistry

Prepared analogously to III.2 from 0.274 g racemic N-[trans-2-(5-fluoro-2-nitrophenoxy)-cyclohexyl]-N-methyl-methanesulfonamide.

Yield: 0.265 g

Intermediate XIII

Racemic N-[trans-2-(2-Amino-5-fluoro-phenoxy)-cyclohexyl]-N-methyl-acetamide

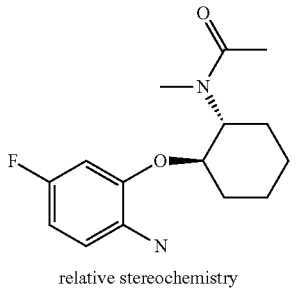 [SMILES: CC(=O)N(C)[C@@H]1CCCC[C@H]1Oc1cc(F)ccc1N]

relative stereochemistry

XIII.1 racemic N-[trans-2-(2-nitro-5-fluoro-phenoxy)-cyclohexyl]-N-methylacetamide

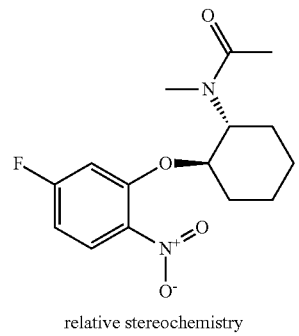 [SMILES: CC(=O)N(C)[C@@H]1CCCC[C@H]1Oc1cc(F)ccc1[N+](=O)[O-]]

relative stereochemistry

Prepared analogously to VI.1 from 0.29 g racemic [[trans-2-(5-fluoro-2-nitrophenoxy)-cyclohexyl]-methyl-amine hydrochloride and acetic acid anhydride.

Yield: 0.289 g

XIII.2. racemic Trans-N-[2-(2-Amino-5-fluoro-phenoxy)-cyclohexyl]-N-methylmethanesulfonamide

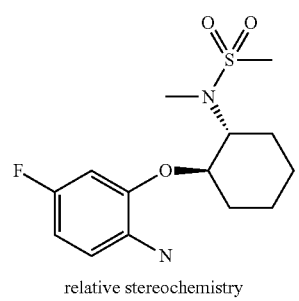 [SMILES: CN([C@@H]1CCCC[C@H]1Oc1cc(F)ccc1N)S(C)(=O)=O]

relative stereochemistry

Prepared analogously to III.2 from 0.285 g racemic N-[trans-2-(2-nitro-5-fluorophenoxy)-cyclohexyl]-N-methyl-methanesulfonamide Yield: 0.25 g Intermediate XIV N-[trans-4-(2-Amino-5-fluoro-phenoxy)-cyclohexyl]-2,2,2-trifluoro-acetamide

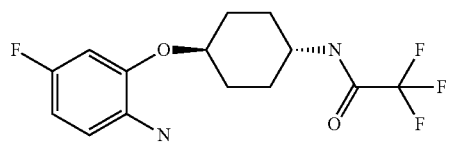 [SMILES: Nc1ccc(F)cc1O[C@H]1CC[C@H](NC(=O)C(F)(F)F)CC1]

XIV.1 N-[trans-4-(2-Nitro-5-fluoro-phenoxy)-cyclohexyl]-2,2,2-trifluoro-acetamide

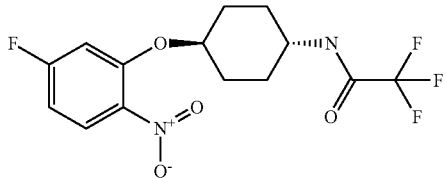 [SMILES: O=C(N[C@H]1CC[C@H](Oc2cc(F)ccc2[N+](=O)[O-])CC1)C(F)(F)F]

A reaction mixture of 0.071 g trans-4-(5-fluoro-2-nitro-phenoxy)-cyclohexylamine hydrochlorid, 0.05 g ethyltrifluoroacetate and 0.075 g triethylamine in 2 ml methanol was stirred overnight. The mixture was concentrated and partitioned between 5 ml EtOAc and 5 ml water. The organic phase was washed with water, HCl solution (2M) and water. The organic phase was dried and the solvent evaporated.

Yield: 0.079 g

XIV.2 N-[trans-4-(2-Nitro-5-fluoro-phenoxy)-cyclohexyl]-2,2,2-trifluoro-acetamide

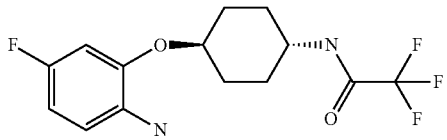 [SMILES: Nc1ccc(F)cc1O[C@H]1CC[C@H](NC(=O)C(F)(F)F)CC1]

Prepared analogously to III.2 from 0.075 g N—[trans-4-(2-nitro-5-fluoro-phenoxy)cyclohexyl]-2,2,2-trifluoro-acetamide.

Yield: 0.05 g

Intermediate XV

[3-(2-Amino-5-fluoro-phenoxy)-cyclohexyl]-methyl-carbamic acid tert-butyl ester

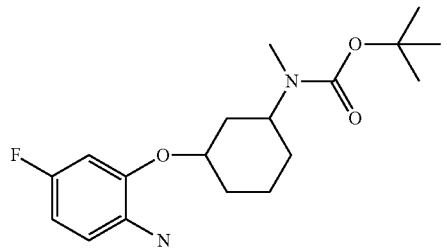 [SMILES: CN(C(=O)OC(C)(C)C)C1CCCC(Oc2cc(F)ccc2N)C1]

XV.1 (3-Hydroxy-cyclohexyl)-carbamic acid tert-butyl ester

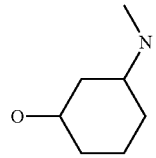

Prepared analogously to XII.1 from 1.357 g 3-amino-cyclohexanol.

Yield: 0.933 g

XV.2 3-Methylamino-cyclohexanol

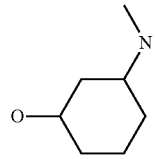

Prepared analogously to XII.2 from 0.933 g (3-hydroxy-cyclohexyl)-carbamic acid tert-butyl ester.

Yield: 0.203 g

XV.3 (3-Hydroxy-cyclohexyl)-methyl-carbamic acid tert-butyl ester

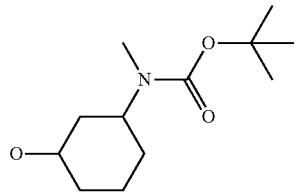 [SMILES: CN(C(=O)OC(C)(C)C)C1CCCC(O)C1]

Prepared analogously to XII.1 from 0.268 g 3-methylamino-cyclohexanol.

Yield: 0.277 g

XV.4 [3-(5-Fluoro-2-nitro-phenoxy)-cyclohexyl]-methyl-carbamic acid tert-butyl ester

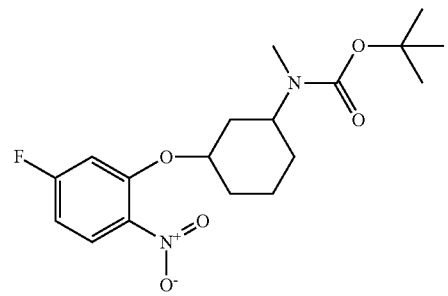 [SMILES: CN(C(=O)OC(C)(C)C)C1CCCC(Oc2cc(F)ccc2[N+](=O)[O-])C1]

Prepared analogously to III.1 from 81 μl 2,4-difluoronitrobenzene and 0.17 g (3-hydroxy-cyclohexyl)-methyl-carbamic acid tert-butyl ester.

Yield: 0.14 g

XV.5 [3-(2-Amino-5-fluoro-phenoxy)-cyclohexyl]-methyl-carbamic acid tert-butyl ester

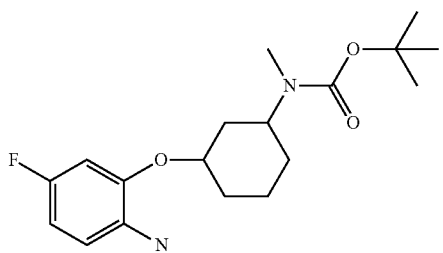 [SMILES: CN(C(=O)OC(C)(C)C)C1CCCC(Oc2cc(F)ccc2N)C1]

Prepared analogously to III.2 from 0.175 g [3-(5-fluoro-2-nitro-phenoxy)-cyclohexyl]-methyl-carbamic acid tert-butyl ester Yield: 0.14 g Intermediate XVI Racemic cis-4-Fluoro-2-(2-methoxy-cyclohexyloxy)-phenylamine

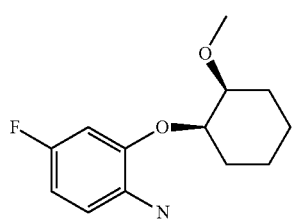

relative stereochemistry

XVI.1 cis-4-Fluoro-2-(2-methoxy-cyclohexyloxy)-1-nitro-benzene

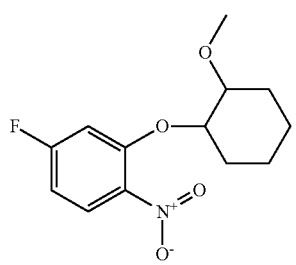 [SMILES: COC1CCCCC1Oc1cc(F)ccc1[N+](=O)[O-]]

2.36 ml DEAD were added to an ice-cooled solution of the 1.57 g 5-fluoro-2-nitrophenol, 1.95 ml 2-methoxycyclohexanol and 3.93 g triphenylphosphine in 30 ml THF. The reaction mixture was allowed to warm to rt overnight. The mixture was stirred additional 48 hours. Then the reaction mixture was diluted with methylene chloride and washed with 10% aq. potassium carbonate solution. The organic phase was passed through a hydrophobic frit and evaporated. Purification was achieved by silica gel column chromatography (solvent:10:1 iso-hexane: EtOAc).

Top spot: 186 mg, racemic trans-4-Fluoro-2-(2-methoxy-cyclohexyloxy)-1-nitro-benzene 1H-NMR: 7.89-7.85 (1H, m); 6.94-6.91 (1H, m); 6.71-6.66 (1H, m); 4.24-4.19 (1H, m); 3.40-3.34 (4H, m); 2.14-1.26 (8H, m)

Mixed spot: 380 mg 1.7:1 mixture of isomers

Bottom spot: 474 mg: racemic cis-4-Fluoro-2-(2-methoxy-cyclohexyloxy)-1-nitro-benzene 1H-NMR: 7.92-7.88 (1H, m); 6.91-6.87 (1H, m); 6.69-6.66 (1H, m); 4.66-4.65 (1H, m); 3.44-3.38 (4H, m); 2.10-1.31 (8H, m)

XVI.2 racemic cis-4-Fluoro-2-(2-methoxy-cyclohexyloxy)-phenylamine

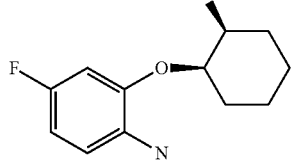

Prepared analogously to III.2 from 0.47 g cis-4-fluoro-2-(2-methoxy-cyclohexyloxy)-1-nitro-benzene.

Yield: 0.373 g

Intermediate XVII

Racemic trans-4-Fluoro-2-(2-methoxy-cyclohexyloxy)-phenylamine

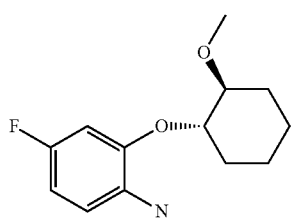 [SMILES: CO[C@H]1CCCC[C@@H]1Oc1cc(F)ccc1N]

Prepared analogously to III.2 from 1.25 g trans-4-fluoro-2-(2-methoxy-cyclohexyloxy)-1-nitro-benzene.

Yield: 1.09 g

Intermediate XVIII (R,R)-4-Fluoro-2-(2-Methoxycyclohexyloxy)-anilin

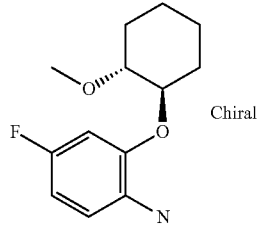 [SMILES: CO[C@@H]1CCCC[C@H]1Oc1cc(F)ccc1N]

XVIII.1 (R,R)-4-Fluoro-2-(2-Methoxycyclohexyloxy)-nitrobenzene

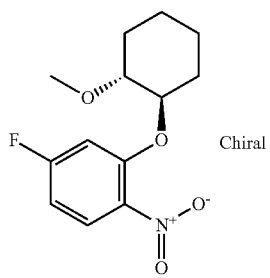 [SMILES: CO[C@@H]1CCCC[C@H]1Oc1cc(F)ccc1[N+](=O)[O-]]

To (R,R)-4-fluoro-2-(2-hydroxycyclohexyloxy)-nitrobenzene (0.200 g) dissolved in methylene chloride (10.0 ml) was added trimethyloxonium tetrafluoroborate (0.348 g). The mixture was stirred overnight at rt. Water was added; the organic phase was separated and evaporated to dryness to yield a brownish oil.

Yield: 207 mg
ESI mass spectrum: m/z=270 (M+H)$^+$

XVIII.2 (R,R)-4-Fluoro-2-(2-Methoxycyclohexyloxy)-anilin

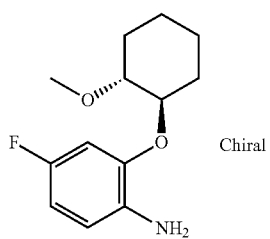 [SMILES: CO[C@@H]1CCCC[C@H]1Oc1cc(F)ccc1N]

(R,R)-4-fluoro-2-(2-methoxycyclohexyloxy)-nitrobenzene (0.18 g) in methanol (20.0 ml) was hydrogenated under 50 psi hydrogen for 20 h at rt using palladium on charcoal (5%) (40 mg) as catalyst. The catalyst was filtered off; the resulting solution was evaporated to dryness to yield an oil.

Yield: 300 mg
ESI mass spectrum: m/z=240 (M+H)$^+$

Intermediate XIX (S,S)-4-Fluoro-2-(2-Methoxycyclohexyloxy)-anilin

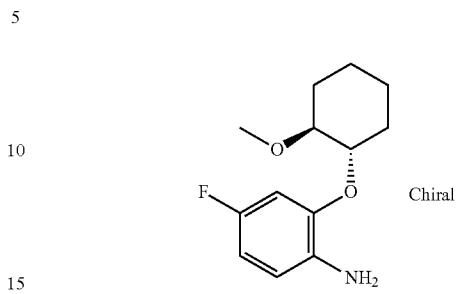

The compound can be prepared analogously to XVIII, starting from (S,S)-4-fluoro-2-(2-Hydroxycyclohexyloxy)-anilin.

Intermediate XX (R,R)-4-Fluoro-2-(2-Hydroxycyclohexyloxy)-anilin

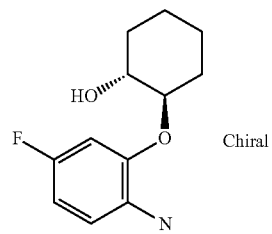 [SMILES: Nc1ccc(F)cc1O[C@@H]1CCCC[C@H]1O]

XX.1 (R,R)-4-Fluoro-2-(2-Hydroxycyclohexyloxy)-nitrobenzene

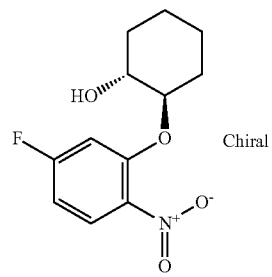 [SMILES: O=[N+]([O-])c1ccc(F)cc1O[C@@H]1CCCC[C@H]1O]

2,4-Difluoronitrobenzene (1.89 ml), (1R,2R)-1,2-cyclohexanediol (2.00 g), and lithium bis(trimethylsilyl)amide (1 mol/l solution in THF; 17.2 ml) in THF (20.0 ml) were stirred overnight at rt. The solvent was removed in vacuo; the residue was taken up in ethyl acetate. The solution was extracted once with hydrochloric acid (1 mol/l) and twice with NaOH solution (1 mol/l), dried with magnesium sulphate, filtered and evaporated to dryness. The residue was purified by column chromatography (silica; methylene chloride/methanol 100:0=>97:3) to yield yellowish oil which crystallized upon storage.

Yield: 2.00 g
ESI mass spectrum: m/z=256 (M+H)$^+$

XX.2
(R,R)-4-Fluoro-2-(2-Hydroxycyclohexyloxy)-anilin

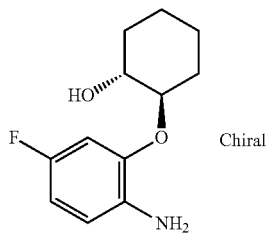 [SMILES: Nc1ccc(F)cc1O[C@@H]1CCCC[C@H]1O]

(R,R)-4-Fluoro-2-(2-hydroxycyclohexyloxy)-nitrobenzene (1.99 g) in methanol (20.0 ml) was hydrogenated under 50 psi hydrogen for 5 h at rt using palladium on charcoal (5%) (200 mg) as catalyst. The catalyst was filtered off; the resulting solution was evaporated to dryness to yield an oil.
Yield: 1.70 g
ESI mass spectrum: m/z=226 (M+H)$^+$ Intermediate XXI (S,S)-4-Fluoro-2-(2-Hydroxycyclohexyloxy)-anilin

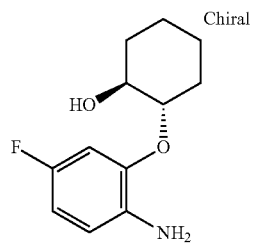 [SMILES: Nc1ccc(F)cc1O[C@H]1CCCC[C@@H]1O]

The compound was prepared analogously to XX, starting from (S,S)-1,2-Cyclohexanediol.
ESI mass spectrum: m/z=226 (M+H)$^+$ Intermediates XXII Pure enantiomers of cis-4-Fluoro-2-(2-Hydroxycyclohexyloxy)-nitrobenzene XXII.1 racemic cis-4-Fluoro-2-(2-Hydroxycyclohexyloxy)-nitrobenzene

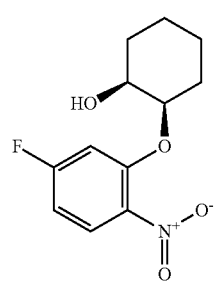

To 2,4-Difluoronitrobenzene (0.549 ml) and cis-1,2-cyclohexanediol (0.581 g) in THF (10.0 ml), cooled with an ice-bath, was added lithium bis(trimethylsilyl)amide (1 mol/l solution in THF; 5.00 ml). The mixture was stirred overnight at rt, and then evaporated to dryness. The residue was taken up in ethyl acetate, extracted once with hydrochloric acid (1 mol/l) and twice with NaOH solution (1 mol/l), dried with magnesium sulphate, filtered and evaporated to dryness. The residue was purified by column chromatography (silica; methylene chloride/methanol 100:0=>97:3) to yield a yellowish oil.
Yield: 455 mg
ESI mass spectrum: m/z=256 (M+H)$^+$ XXII.2 Pure enantiomers of cis-4-Fluoro-2-(2-Hydroxycyclohexyloxy)-nitrobenzene

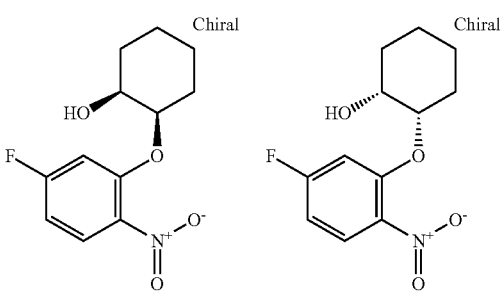 [SMILES: O=[N+]([O-])c1ccc(F)cc1O[C@@H]1CCCC[C@@H]1O ; O=[N+]([O-])c1ccc(F)cc1O[C@H]1CCCC[C@H]1O]

The racemic mixture of XXII.1 was separated into the enantiomers by chiral SFC chromatography:
Column: Daicel ADH; 250 mm×4.6 mm
Mobile phase: CO$_2$/2-Propanol 75:25 (with addition of 0.2% Diethyl amine)

XXII-A

ESI mass spectrum: m/z=522 (M+H)$^+$
R$_t$ (HPLC): 2 min

XXII-B

ESI mass spectrum: m/z=522 (M+H)$^+$
R$_t$ (HPLC): 3.04 min
Absolute stereochemistry of the isomers was not determined and therefore cannot be assigned.

XXII.3 Pure enantiomere of cis-4-fluoro-2-(2-hydroxycyclohexyloxy)-anilin from the XXII-A intermediate (2 min retention time)

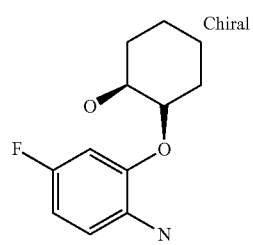

Prepared analogously to XX.2 from 0.5 g cis-4-fluoro-2-(2-hydroxycyclohexyloxy)nitrobenzene (cpd. XXII-A, 2 min retention time).

XXII.4 Pure enantiomere of cis-4-fluoro-2-(2-hydroxycyclohexyloxy)-anilin from the XXII-B intermediate (3.04 min retention time)

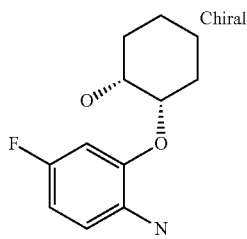 [SMILES: Nc1ccc(F)cc1O[C@H]1CCCC[C@H]1O]

Prepared analogously to XX.2 from 0.5 g cis-4-fluoro-2-(2-hydroxycyclohexyloxy)nitrobenzene (cpd. XXII-B, 3.04 min retention time).

Intermediate XXIV trans-4-(3-Amino-pyridin-2-yloxy)-cyclohexanol

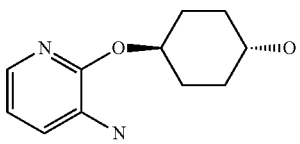 [SMILES: Nc1cccnc1O[C@H]1CC[C@H](O)CC1]

XXIV.1
trans-4-(3-nitro-pyridin-2-yloxy)-cyclohexanol

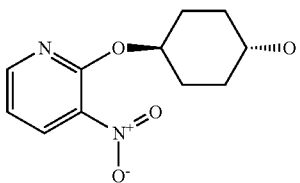 [SMILES: O=[N+]([O-])c1cccnc1O[C@H]1CC[C@H](O)CC1]

Prepared analogously to III.1 from 4.054 g 2-fluoro-3-nitropyridine and 2.26 g trans-1,4-cyclohexanediol.
Yield: 0.29 g

XXIV.2
trans-4-(3-Amino-pyridin-2-yloxy)-cyclohexanol

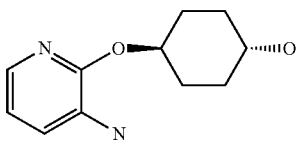 [SMILES: Nc1cccnc1O[C@H]1CC[C@H](O)CC1]

A mixture of 0.29 g trans-4-(3-nitro-pyridin-2-yloxy)-cyclohexanol and 0.05 g Raney nickel in 50 ml methanol was hydrogenated at 5 bar and rt for 4.5 hours. The reaction mixture was filtered and the filtrate concentrated.
Yield: 0.203 g
ESI mass spectrum: m/z=209 (M+H)$^+$

Intermediates XXV

4-Fluoro-2-(trans-4-methoxycyclohexyloxy)-anilin and 4-Fluoro-2-(cis-4-methoxycyclohexyloxy)-anilin

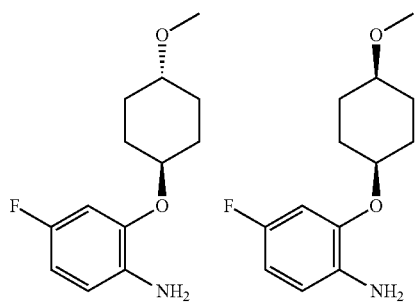 [SMILES: CO[C@H]1CC[C@H](Oc2cc(F)ccc2N)CC1 ; CO[C@H]1CC[C@@H](Oc2cc(F)ccc2N)CC1]

XXV.1. 4-Methoxycyclohexanol (mixture of cis and trans isomers)

4-Methoxyphenol (100 g) in ethanol (759 ml) was hydrogenated under 50 psi hydrogen using Nishimura catalyst (10.0 g) at rt for 4.5 h. The catalyst was filtered off; the solvent was removed in vacuo to yield the desired product as 95% pure yellowish liquid.
Yield: 114 g
EXI mass spectrum: m/z=131 (M+H)$^+$

XXV.2 4-Fluoro-2-(trans-4-methoxycyclohexyloxy)-anilin and 4-Fluoro-2-(cis-4-methoxycyclohexyloxy)-anilin

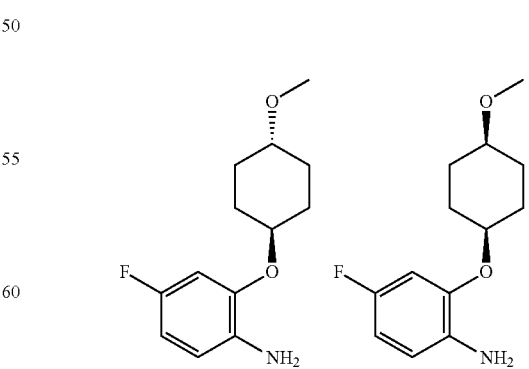

To a cooled (water bath, approx. 10° C.) solution of 5-fluoro-2-nitrophenol (18.9 g) and 4-methoxycylohexanol (19.0 g) in THF (250 ml) were simultaneously added under magnetic stirring di-tert-butyl azodicarboxylate (41.0 g) and triphenyl phosphine (47.0 g). The mixture was stirred for further 2 h at rt and palladium on charcoal 10% (1.90 g) was added. The mixture was hydrogenated at rt under 50 psi Hydrogen for 20 h. The catalyst was filtered off. The resulting solution was diluted with DCM and extracted twice with hydrochloric acid (1 mol/l). The combined aqueous phases were alkalified with NaOH solution (4 mol/l) and extracted twice with methylene chloride. The combined organic layers were dried with sodium sulphate, filtered and concentrated in vacuo. The resulting mixture was subjected to column chromatography (silica; methylene chloride/ethyl acetate 9:1) yielding both isomers as separate fractions.

4-fluoro-2-(trans-4-methoxycyclohexyloxy)-anilin

Yield: 3.10 g
ESI mass spectrum: m/z=240 (M+H)+

4-Fluoro-2-(cis-4-methoxycyclohexyloxy)-anilin

Yield: 2.00 g
ESI mass spectrum: m/z=240 (M+H)+

Intermediates XXVI

4-Fluoro-2-(cis-4-Hydroxycyclohexyloxy)-anilin and trans-4-Fluoro-2-(trans-4-Hydroxycyclohexyloxy)-anilin

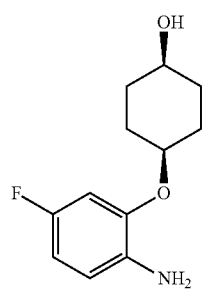 [SMILES: Nc1ccc(F)cc1O[C@H]1CC[C@@H](O)CC1]

XXVI.1 4-Fluoro-2-(cis/trans-4-Hydroxycyclohexyloxy)-nitrobenzene

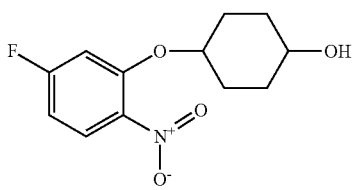 [SMILES: O=[N+]([O-])c1ccc(F)cc1OC1CCC(O)CC1]

To a solution of 1,4-cyclohexanediol (100 g) in THF (1000 ml) was added NaH (60% in mineral oil; 38.5 g). The mixture was refluxed for 1 h. 2,4-difluoronitrobenzene (48.0 ml) was added drop wise during 1 h. The mixture was refluxed for further 2 d, concentrated in vacuo, taken up in water and extracted several times with methylene chloride. The combined organic layers were washed with brine, dried with magnesium sulphate, filtered and concentrated in vacuo. The residue was subject to column chromatography (silica; methylene chloride/methanol 100:0=>98:2; UV detection at 220 nm) furnishing the mixture of isomers as a brownish oil.

Yield: 49.2 g
ESI mass spectrum: m/z=273 (M+NH4)+

Separation into 4-fluoro-2-(cis-4-Hydroxycyclohexyloxy)-nitrobenzene and 4-Fluoro-2-(trans-4-Hydroxycyclohexyloxy)-nitrobenzene

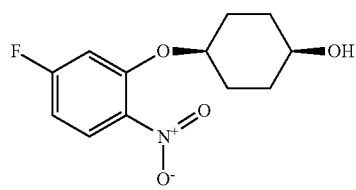

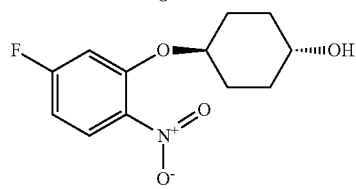

The cis/trans mixture from XXVI.1 was separated into the isomers by SFC chromatography:

Column: Daicel OJH 250 mm×4.6 mm

Mobile phase: CO$_2$/Methanol 85:15 (with addition of 0.2% Diethyl amine)

Eluting first: cis isomer; eluting second: trans isomer

XXVI.2
4-Fluoro-2-(cis-4-Hydroxycyclohexyloxy)-anilin

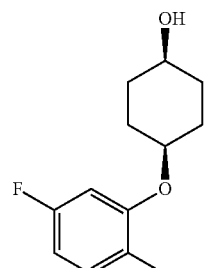

4-Fluoro-2-(cis-4-hydroxycyclohexyloxy)-nitrobenzene (2.00 g) in methanol (15.0 ml) was hydrogenated under 50 psi hydrogen using palladium on charcoal (5%) as catalyst (300 mg) at RT for 2 h. The catalyst was filtered off; the solvent was removed in vacuo to yield the desired product as 95% pure oil.

Yield: 1.96 g
ESI mass spectrum: m/z=226 (M+H)+

Intermediate XXVII
4-Fluoro-2-(trans-4-hydroxycyclohexyloxy)-anilin

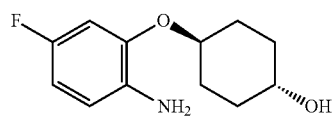 [SMILES: Nc1ccc(F)cc1O[C@H]1CC[C@H](O)CC1]

Prepared analogously to XXVI.3 from 2.26 g 4-Fluoro-2-(trans-4-hydroxycyclohexyloxy)-nitrobenzene.
Yield: 2 g
ESI mass spectrum: m/z=226 (M+H)$^+$

Intermediate XXVIII

All cis-5-(2-Amino-5-fluoro-phenoxy)-cyclohexane-1,3-diol

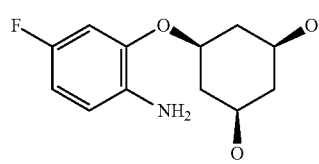

XXVIII.1

Isomer XXVIII A

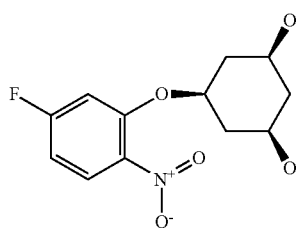

Isomer XXVIII B

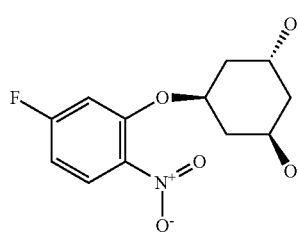

Prepared analogously to III.1 from 1 ml 2,4-difluoro-nitrobenzene and 3.965 g cyclohexane-1,3,5-triol
IsomerXXVIIIA: 0.6 g
ESI mass spectrum: m/z=272 (M+H)$^+$
Rf (silica gel): methylene chloride/methanol=9:1:0.41
IsomerXXVIII B: 0.43 g
ESI mass spectrum: m/z=272 (M+H)$^+$
Rf (silica gel), (methylene chloride/methanol=9:1):0.42

XXVIII.2 All cis-5-(2-Amino-5-fluoro-phenoxy)-cyclohexane-1,3-diol

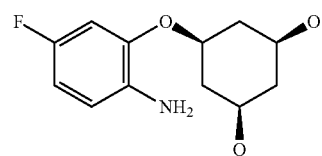 [SMILES: Nc1ccc(F)cc1O[C@@H]1C[C@H](O)C[C@H](O)C1]

Prepared analogously to XXIV.2 from 0.6 g Isomer XXVIII A.
Yield: 0.58 g

Intermediate XXIX

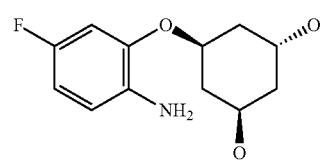

Prepared analogously to XXIV.2 from 0.43 g Isomer XXVIII B.
Yield: 0.4 g

Intermediate XXX

All cis-2-(3,5-Dimethoxy-cyclohexyloxy)-4-fluoro-phenylamine

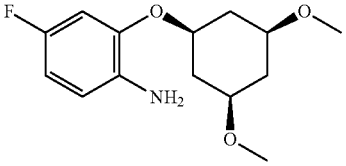 [SMILES: CO[C@@H]1C[C@H](OC)C[C@H](Oc2cc(F)ccc2N)C1]

XXX.1 all cis-2-(3,5-Dimethoxy-cyclohexyloxy)-4-fluoro-1-nitro-benzene

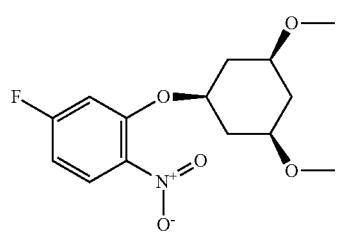 [SMILES: CO[C@@H]1C[C@H](OC)C[C@H](Oc2cc(F)ccc2[N+](=O)[O-])C1]

Prepared analogously to III.1 from 2.193 ml 2,4-difluoro-nitrobenzene and 3.2 g all cis-1,3,5-trimethoxy-cyclohexane.
Yield: 2.8 g
ESI mass spectrum: m/z=300 (M+H)$^+$

XXX.2 All cis-2-(3,5-Dimethoxy-cyclohexyloxy)-4-fluoro-phenylamine

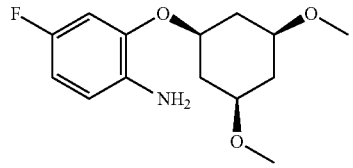 [SMILES: CO[C@@H]1C[C@H](OC)C[C@H](Oc2cc(F)ccc2N)C1]

Prepared analogously to XXIV.2 from 2 g all cis-2-(3,5-Dimethoxy-cyclohexyloxy)-4-fluoro-1-nitro-benzene.
Yield: 1.8 g

Intermediate XXXI 2-(4,4-Dimethyl-cyclohexyloxy)-4-fluoro-phenylamine

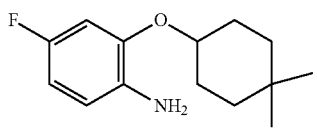 [SMILES: CC1(C)CCC(Oc2cc(F)ccc2N)CC1]

XXXI.1 2-(4,4-Dimethyl-cyclohexyloxy)-4-fluoro-1-nitro-benzene

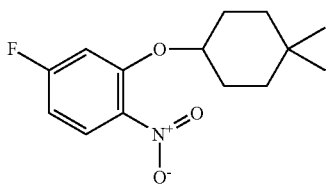 [SMILES: CC1(C)CCC(Oc2cc(F)ccc2[N+](=O)[O-])CC1]

Prepared analogously to III.1 from 2 ml 2,4-difluoro-nitrobenzene and 2.339 g 4,4-dimethyl-cyclohexanol.
Yield: 4.1 g
ESI mass spectrum: m/z=285 (M+NH$_4$)$^+$

XXXI.2 2-(4,4-Dimethyl-cyclohexyloxy)-4-fluoro-phenylamine

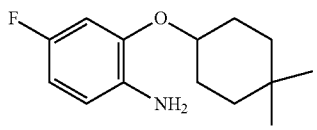 [SMILES: CC1(C)CCC(Oc2cc(F)ccc2N)CC1]

Prepared analogously to XXIV.2 from 4.1 g 2-(4,4-Dimethyl-cyclohexyloxy)-4-fluoro-1-nitro-benzene
Yield: 3.2 g
ESI mass spectrum: m/z=238 (M+H)$^+$
Rf (silica gel), (methylene chloride/methanol=30:1): 0.42

Intermediate XXXII 2-(4,4-Difluoro-cyclohexyloxy)-4-fluoro-phenylamine

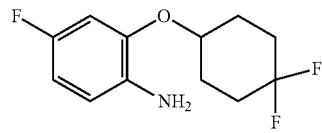 [SMILES: Nc1ccc(F)cc1OC1CCC(F)(F)CC1]

XXXII.1 4,4-difluoro-cyclohexanecarboxylic acid methoxy-methyl-amide

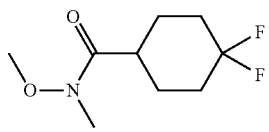

2.78 g HATU were added to a solution of 1 g 4,4-difluoro-cyclohexanecarboxylic acid and 1.3 ml diisopropylethylamine in 10 ml anhydrous DMF at 0° C. The reaction was stirred at 0° C. for 0.5 hours when 0.891 g O,N-Dimethyl-hydroxylamine hydrochloride were added. The reaction was allowed to warm to rt overnight. The solution was concentrated in vacuo by co-evaporation with toluene (3×) and filtered. The filtrate was concentrated in vacuo. Purification was achieved by silica gel column chromatography (solvent: 5:1→3:1 petroleum ether/EtOAc).
Yield: 0.582 g

XXXII.2 1-(4,4-difluoro-cyclohexyl)-ethanone

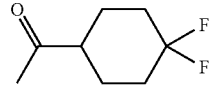

2 ml methyl lithium (1 M in diethylether) were added into a solution of 0.593 g 4,4-difluoro-cyclohexanecarboxylic acid methoxy-methyl-amide in anhydrous 5 ml THF at 0° C. The reaction was allowed to warm to rt overnight. The reaction was quenched with sat. ammonium chloride solution (~50 ml) and diluted with sat. sodium hydrogencarbonate solution (25 ml). The aqueous layer was extracted with diethylether (3×50 ml) and the combined organic phases were dried over sodium sulfate, filtered and concentrated in vacuo. Purification was achieved by silica gel column chromatography (solvent: 5:1→1:1 petroleum/ether (40-60).
Yield: 0.262 g

XXXII.3 4,4-difluorocyclohexanol

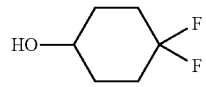

0.361 g meta-chloro-perbenzoic acid were added into a solution of 0.262 g 1-(4,4-difluoro-cyclohexyl)-ethanone in 5 ml chloroform. The reaction was stirred at rt for 2 hours when TLC indicated consumption of the 1-(4,4-difluoro-cyclohexyl)-ethanone. The solution was poured into saturated sodium hydrogencarbonate solution and extracted with chloroform (3×50 ml). The combined organic phases were passed through a phase separator concentrated in vacuo. The crude product was resuspended in methanol (5 ml) and 10% aq. potassium carbonate solution. (5 ml) and stirred at rt over a weekend. The solution was diluted with chloroform (25 ml) and sat. sodium hydrogencarbonate solution. The organic phases were separated and the aqueous phase was extracted with methylene chloride (3×25 ml). The combined organic phases were passed through a phase-separator, concentrated in vacuo. Purification was achieved by silica gel column chromatography (solvent: 100%→1:1 petroleum ether/diethylether).

Yield: 0.105 g

XXXII.4 2-(4,4-Difluoro-cyclohexyloxy)-4-fluoro-1-nitro-benzene

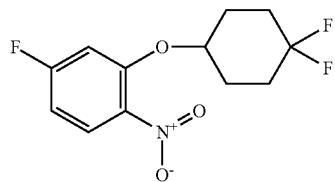 [SMILES: O=[N+]([O-])c1ccc(F)cc1OC1CCC(F)(F)CC1]

0.213 g DTAD was added into a solution of 5-fluoro-2-nitro-phenol, 0.105 g 4,4-difluorocyclohexanol, 0.25 g triphenylphospine in 2 ml of anhydrous methylene chloride at rt. The reaction mixture was stirred at rt overnight when TLC analysis indicated the consumption of the 5-Fluoro-2-nitrophenol. The reaction mixture was diluted with methylene chloride (50 ml) and washed with 10% potassium carbonate solution. The aqueous layer was extracted with methylene chloride (2×25 ml) and the combined organics washed with sodium hydrogecarbonate solution (25 ml). The organic layer was passed through a phase separator and concentrated in vacuo. Purification was achieved by silica gel column chromatography (solvent: 100%→1:1 iso-hexane/EtOAc).

Yield: 0.141 g

XXXII.5 2-(4,4-Difluoro-cyclohexyloxy)-4-fluoro-phenylamine

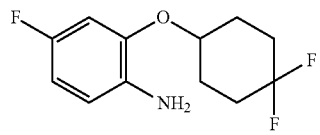 [SMILES: Nc1ccc(F)cc1OC1CCC(F)(F)CC1]

Prepared analogously to III.2 from 0.141 g 2-(4,4-difluoro-cyclohexyloxy)-4-fluoro-1-nitro-benzene.

Yield: 0.08 g

Intermediate XXXIII

Racemic 2-(trans-3-Methoxy-cyclohexyloxy)-pyridin-3-ylamine

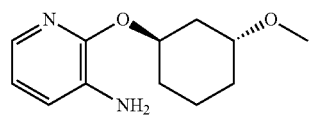 [SMILES: CO[C@@H]1CCC[C@@H](Oc2ncccc2N)C1]

XXXIII.1 3-Methoxycyclohexanol

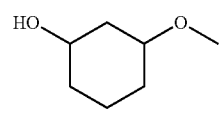

Prepared analogously to 11.2 from 25 g 3-methoxyphenol.

Yield: 25.5 g

ESI mass spectrum: m/z=131 (M+H)$^+$

XXXIII.2 racemic 2-(cis-3-Methoxy-cyclohexyloxy)-3-nitro-pyridine and racemic 2-(trans-3-Methoxy-cyclohexyloxy)-3-nitro-pyridine

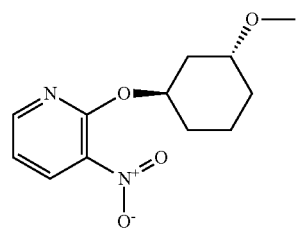

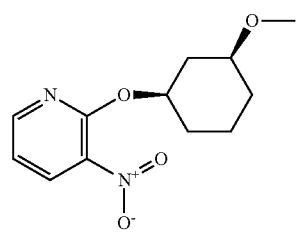

Prepared analogously to III.1 from 5.1 g 2-fluoro-3-nitro-pyridine and 5 g 3-methoxycyclohexanol. Purification was achieved by silica gel column chromatography (solvent: petrolether/EtOAc=70:30 for 20 minutes and within 20 minutes to 50:50).

Racemic
2-(trans-3-Methoxy-cyclohexyloxy)-3-nitro-pyridine
eluding first

Yield: 1.6 g
retention time (HPLC): 3.77 min (method C)
ESI mass spectrum: m/z=253 (M+H)$^+$ Racemic
2-(cis-3-Methoxy-cyclohexyloxy)-3-nitro-pyridine
eluding second Yield: 5.82 g
retention time (HPLC): 3.65 min (method C)
ESI mass spectrum: m/z=253 (M+H)$^+$ XXXIII.3 Racemic 2-(trans-3-Methoxy-cyclohexyloxy)-pyridin-3-ylamine

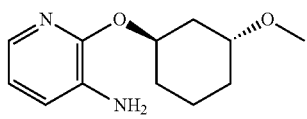 [SMILES: CO[C@@H]1CCC[C@@H](Oc2ncccc2N)C1]

Prepared analogously to III.2 from 1.59 g racemic 2-(trans-3-methoxy-cyclohexyloxy)-3-nitro-pyridine
Yield: 1.11 g Intermediate XXXIV Racemic
2-(cis-3-Methoxy-cyclohexyloxy)-pyridin-3-ylamine

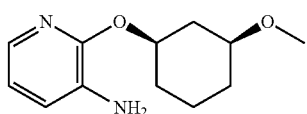

Prepared analogously to III.2 from 5.8 g racemic 2-(cis-3-Methoxy-cyclohexyloxy)-3-nitro-pyridine
Yield: 4.32 g Intermediate XXXV N-[trans-3-(2-Amino-5-fluoro-phenoxy)-cyclobutyl]-acetamide

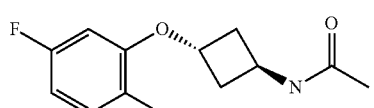

XXXV.1. [trans-3-(5-fluoro-2-nitro-phenoxy)-cyclobutyl]-carbamic acid tert-butyl ester

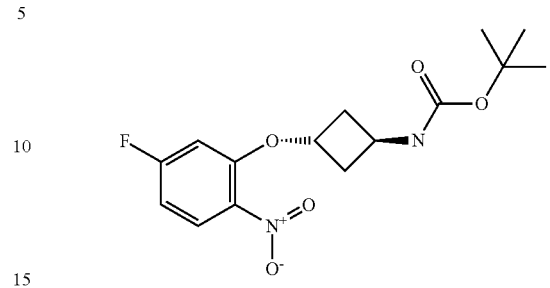

Prepared analogously to XVI.1 from 2.3 g trans-(3-Hydroxy-cyclobutyl)-carbamic acid tert-butyl ester, 1.6 g 5-fluoro-2-nitrophenol and 2.423 mlDIAD.
Yield: 2.8 g
ESI mass spectrum: m/z=327 (M+H)$^+$ XXXV.2
trans-3-(5-Fluoro-2-nitro-phenoxy)-cyclobutylamine trifluoroacetate

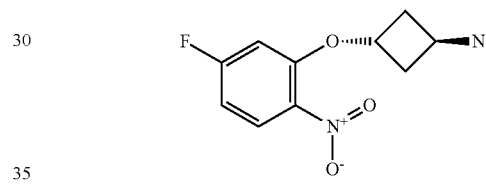

14 ml trifluoroacetic acid were added to a mixture of 2.8 g [trans-3-(5-fluoro-2-nitrophenoxy)-cyclobutyl]-carbamic acid tert-butyl ester in 100 ml methylene chloride at 0° C. The mixture was stirred then for 2 hours at rt and afterwards concentrated. The residue was stirred with diisopropylether and filtered.
Yield: 2.85 g
ESI mass spectrum: m/z=227 (M+H)$^+$ XXXV.3 N-(trans-3-(5-Fluoro-2-nitro-phenoxy)-cyclobutyl]-acetamide trifluoroacetate

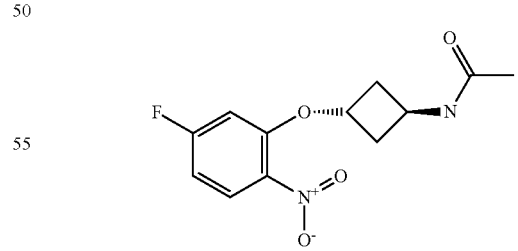

450 μl Acetylchloride were added to a mixture of 1.8 g trans-3-(5-fluoro-2-nitrophenoxy)-cyclobutylamine trifluoroacetate and 3.7 ml triethylamine in 30 ml methylene chloride and stirred for 2 hours at rt. The mixture was extracted two times with water. The organic phase was dried and concentrated. The residue was stirred with diethylether and filtrated. The residue was dried in a drying cabinet.

Yield: 1.4 g
ESI mass spectrum: m/z=269 (M+H)+

XXXV.4 N-[trans-3-(2-Amino-5-fluoro-phenoxy)-cyclobutyl]-acetamide

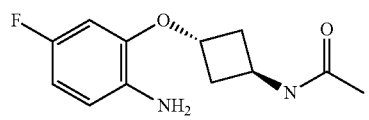 [SMILES: CC(=O)N[C@H]1C[C@H](Oc2cc(F)ccc2N)C1]

Prepared analogously to XXIV.2 from 1.4 g N-[trans-3-(5-Fluoro-2-nitro-phenoxy)cyclobutyl]-acetamide
Yield: 1.55 g
ESI mass spectrum: m/z=239 (M+H)+

Intermediate XXXVI

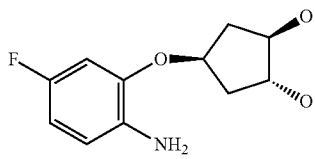

relative stereochemistry

XXXVI.1.
2-(Cyclopent-3-enyloxy)-4-fluoro-1-nitro-benzene

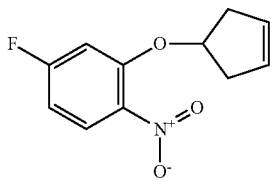 [SMILES: O=[N+]([O-])c1ccc(F)cc1OC1CC=CC1]

Prepared analogously to XVI.1 from 1 g cyclopentenol, 1.57 g 5-fluoro-2-nitro-phenol and 1.89 ml DEAD.
Yield: 2.11 g

XXXVI.2 3-(5-Fluoro-2-nitro-phenoxy)-6-oxa-bicyclo[3.1.0]hexane

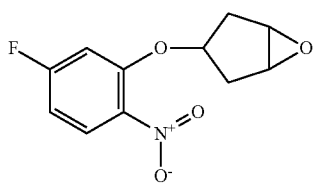 [SMILES: O=[N+]([O-])c1ccc(F)cc1OC1CC2OC2C1]

2.95 g meta chloroperbenzoic acid were added to an ice-cooled solution of 2.05 g 2-(cyclopent-3-enyloxy)-4-fluoro-1-nitro-benzene in 45 ml methylene chloride. The reaction mixture was allowed to warm to rt overnight. Then the reaction mixture was diluted with methylene chloride and washed with 10% aq. potassium carbonate solution (2×). The organic phases were passed through a hydrophobic frit and the solvent was evaporated.

33:1 ratio of epoxide isomers.
Yield: 2.31 g

XXXVI.3

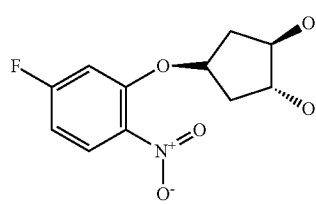

relative stereochemistry 2.2 g 3-(5-Fluoro-2-nitro-phenoxy)-6-oxa-bicyclo[3.1.0]hexane were heated at reflux in 0.2M $H_2SO_4$/THF for 5 hours and then stirred overnight. The solvent was then removed in vacuo and the residue extracted with methylene chloride (2×). The combined organic phases were washed with 10% aq. potassium carbonate solution and evaporated. Purification was achieved by silica gel column chromatography (solvent: 100% iso-hexane→100% methylene chloride→25:1 methylene chloride/MeOH).
Yield: 1.61 g

XXXVI.4

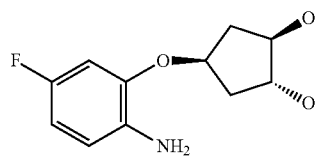

relative stereochemistry

Prepared analogously to III.2 from 1.6 g XXXVI.3.
Yield: 1.04 g

Intermediate XXXVII

[(1S,3S)-3-(2-Amino-5-fluoro-phenoxy)-cyclopentyl]-carbamic acid tea-butyl ester

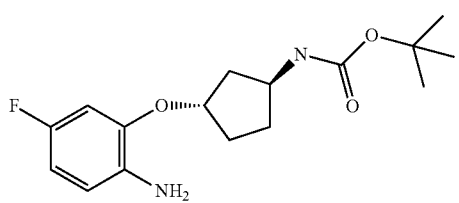 [SMILES: CC(C)(C)OC(=O)N[C@H]1CC[C@H](Oc2cc(F)ccc2N)C1]

XXXVII.1 (1S,3S)-3-(5-fluoro-2-nitro-phenoxy)-cyclopentyl]-carbamic acid tert-butyl ester

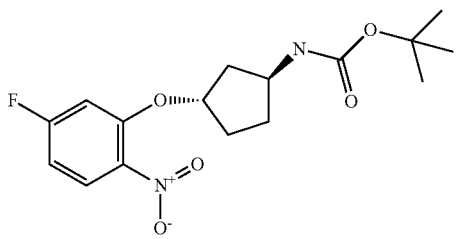 [SMILES: CC(C)(C)OC(=O)N[C@H]1CC[C@H](Oc2cc(F)ccc2[N+](=O)[O-])C1]

2.57 g sodium hydride (55%) were added to mixture of 9.862 g ((1S,3S)-3-hydroxycyclopentyl)-carbamic acid tert-butyl ester in 100 ml THF at 0° C. and stirred at rt for 30 minutes. 5.372 ml 2,4-difluoro-nitrobenzene were added and the reaction mixture was refluxed for 6 hours. After cooling to rt the reaction mixture was extracted with water and methylene chloride. The organic phase was dried and concentrated. Purification was achieved by silica gel column chromatography (solvent: methylene chloride).

Yield: 6.79 g
ESI mass spectrum: m/z=341 (M+H)$^+$

XXXVII.2 [(1S,3S)-3-(2-Amino-5-fluoro-phenoxy)-cyclopentyl]-carbamic acid tert-butyl ester

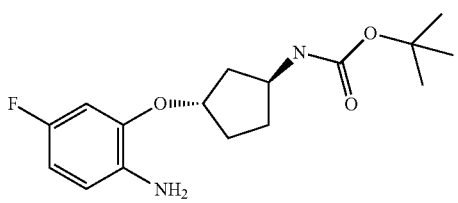 [SMILES: CC(C)(C)OC(=O)N[C@H]1CC[C@H](Oc2cc(F)ccc2N)C1]

Prepared analogously to XXIV.2 from 1.64 g [(1S,3S)-3-(5-fluoro-2-nitro-phenoxy)cyclopentyl]-carbamic acid tert-butyl ester.

Yield: 1.49 g
ESI mass spectrum: m/z=311 (M+H)$^+$

Intermediate XXXVIII

N-[(1S,3S)-3-(2-Amino-5-fluoro-phenoxy)-cyclopentyl]-N-methyl-acetamide

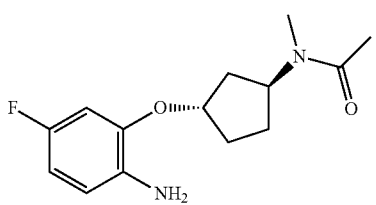 [SMILES: CC(=O)N(C)[C@H]1CC[C@H](Oc2cc(F)ccc2N)C1]

XXXVIII.1 [(1S,3S)-3-(5-fluoro-2-nitro-phenoxy)-cyclopentyl]-methyl-carbamic acid tert-butyl ester

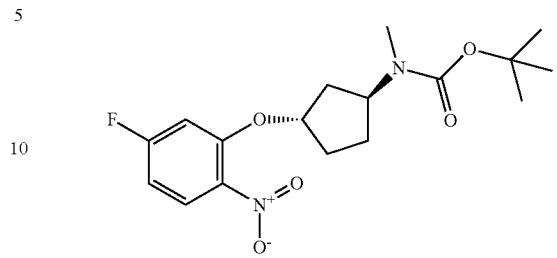

7.1 ml (1 M in THF) LiHMDS were added at 0° C. to a mixture of 2 g (1S,3S)-3-(5-fluoro-2-nitro-phenoxy)-cyclopentyl]-carbamic acid tert-butyl ester in 60 ml THF. The reaction mixture was stirred for 30 minutes at rt. Then 398 µl methyl iodide were added and the reaction mixture was stirred at rt overnight. Then the mixture was concentrated and extracted with water/methylene chloride. The organic phase was dried and concentrated. Purification was achieved by silica gel column chromatography (solvent: methylene chloride/methanol/aq. ammonia solution=90:10:1).

Yield: 1.34 g
ESI mass spectrum: m/z=355 (M+H)$^+$

XXXVIII.1 [(1S,3S)-3-(5-Fluoro-2-nitro-phenoxy)-cyclopentyl]-methyl-amine

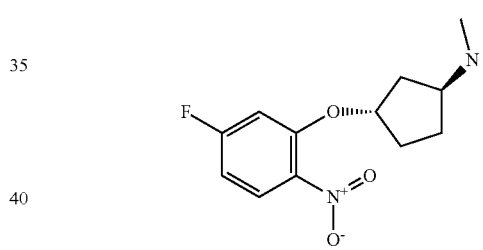

Prepared analogously to XXXV.2 from 1.34 g [(1S,3S)-3-(5-fluoro-2-nitro-phenoxy)cyclopentyl]-methyl-carbamic acid tert-butyl ester.

Yield: 1.203 g
ESI mass spectrum: m/z=255 (M+H)$^+$

XXXVIII.3 N-[(1S,3S)-3-(5-Fluoro-2-nitro-phenoxy)-cyclopentyl]-N-methylacetamide

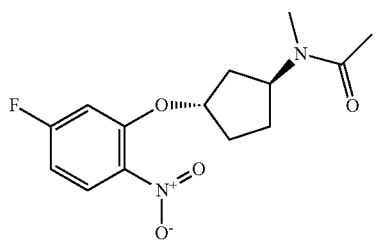 [SMILES: CC(=O)N(C)[C@H]1CC[C@H](Oc2cc(F)ccc2[N+](=O)[O-])C1]

Prepared analogously to XXXV.3 from 0.703 g [(1S,3S)-3-(5-fluoro-2-nitro-phenoxy)cyclopentyl]-methyl-amine trifluoroacetate and acetyl chloride.

Yield: 0.588 g
ESI mass spectrum: m/z=297 (M+H)+

XXXVIII.4 N-[(1S,3S)-3-(2-Amino-5-fluoro-phenoxy)-cyclopentyl]-N-methylacetamide

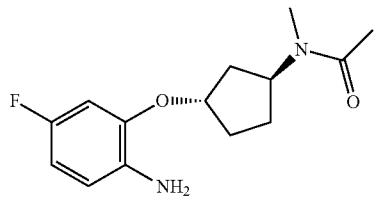 [SMILES: CC(=O)N(C)[C@H]1CC[C@H](Oc2cc(F)ccc2N)C1]

Prepared analogously to XXIV.2 from 0.58 g [(1S,3S)-3-(5-fluoro-2-nitro-phenoxy)cyclopentyl]-methyl-carbamic acid tert-butyl ester.
Yield: 0.52 g
ESI mass spectrum: m/z=267 (M+H)+

Intermediate XXXIX

Cis/trans-4-(3-Amino-pyridin-2-yloxy)-cyclohexanol

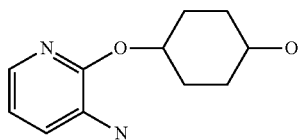 [SMILES: Nc1cccnc1OC1CCC(O)CC1]

XXXIX.1
Cis/trans-4-(3-nitro-pyridin-2-yloxy)-cyclohexanol

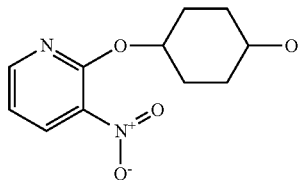

Prepared analogously to III.1 from 3.6 g 2-fluoro-3-nitro-pyridine and 2.9 g 1,4-cyclohexanediol.
Yield: 1.6 g XXXIX.2
Cis/trans-4-(3-Amino-pyridin-2-yloxy)-cyclohexanol

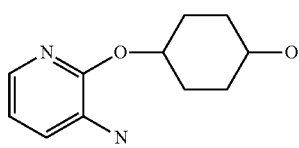 [SMILES: Nc1cccnc1OC1CCC(O)CC1]

Prepared analogously to III.2 from 1.6 g cis/trans-4-(3-nitro-pyridin-2-yloxy)cyclohexanol.
Yield: 1.53 g Intermediate XXXX cis-4-Fluoro-2-(3-methoxy-cyclohexyloxy)-phenylamine

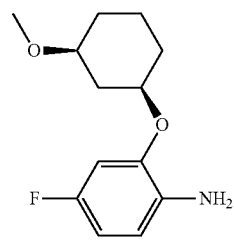 [SMILES: CO[C@H]1CCC[C@@H](Oc2cc(F)ccc2N)C1]

XXXX.1. cis/trans-3-Methoxy-cyclohexanol

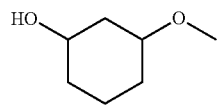

A mixture of cis- and trans-4-methoxy-cyclohexanol (7:3) was prepared by hydrogenation of 3-methoxy-phenol in methanol at room temperature in the presence of Nishimuras catalyst.

XXXX.2. 4-Fluoro-2-(cis-3-methoxy-cyclohexyloxy)-1-nitro-benzene

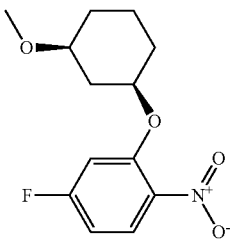 [SMILES: CO[C@H]1CCC[C@@H](Oc2cc(F)ccc2[N+](=O)[O-])C1]

LiHMDS (1 M solution in THF; 5.0 ml) was added slowly to an ice/ethanol-cooled solution of 3-methoxy-cyclohexanol (7:3 mixture of cis- and trans-isomers; 601 mg) in THF (8 ml). Cooling was suspended after 5 minutes and the mixture was stirred for 15 minutes at room temperature before addition of 2,4-difluoro-1-nitro-benzene (482 µl). After 4 h another 1.5 ml of LiHMDS (1 M solution in THF) was added and the reaction mixture was stirred over night at room temperature. The reaction mixture was quenched by addition of hydrochloric acid (0.1 M), diluted with ethyl acetate, and filtered through celite. The organic layer was washed with brine, dried over MgSO$_4$ and concentrated in vacuo. The residue was submitted to column chromatography (silica gel, cyclohexane/ethyl acetate 85:15) to give the cis-isomer (650 mg) and the trans-isomer (230 mg).

Yield: 650 mg (55%)
MS (ESI⁺): 270 (M+H⁺)
HPLC (Method D): Rt 3.89 min

XXXX.3. 4-Fluoro-2-(cis-3-methoxy-cyclohexyloxy)-phenylamine

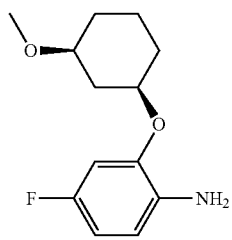 [SMILES: CO[C@H]1CCC[C@@H](Oc2cc(F)ccc2N)C1]

Ammonium formate (738 mg) was added to a suspension of 4-fluoro-2-(cis-3-methoxy-cyclohexyloxy)-1-nitro-benzene (630 mg) and 10% palladium on charcoal (70 mg) in methanol (10 ml) at room temperature and the mixture was heated to reflux for 30 min until LCMS indicated complete conversion of the starting material. The mixture was diluted with dichloromethane (50 ml) and water (20 ml), filtered through celite, and the filtercake was washed with dichloromethane (20 ml). The organic layer was dried over MgSO₄ and concentrated in vacuo. The residue was submitted to column chromatography (silica gel, cyclohexane/ethyl acetate 70:30) to give the desired product.
Yield: 440 mg (79%)
MS (ESI⁺): 240 (M+H⁺)
HPLC (Method D): Rt 2.21 min Intermediate XXXXI trans-4-Fluoro-2-(3-methoxy-cyclohexyloxy)-phenylamine

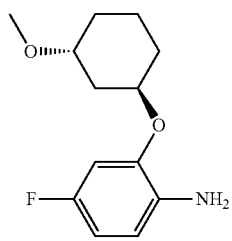 [SMILES: CO[C@@H]1CCC[C@@H](Oc2cc(F)ccc2N)C1]

XXXXI.1. 4-Fluoro-2-(trans-3-methoxy-cyclohexyloxy)-1-nitro-benzene

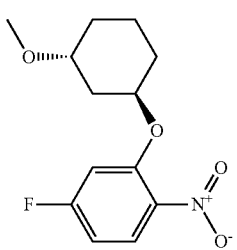 [SMILES: CO[C@@H]1CCC[C@@H](Oc2cc(F)ccc2[N+](=O)[O-])C1]

The compound was prepared as described under XXXX.2.
Yield: 230 mg (19%)
MS (ESI⁺): 270 (M+H⁺)
HPLC (Method D): Rt 3.99 min XXXXI.2. 4-Fluoro-2-(trans-3-methoxy-cyclohexyloxy)-phenylamine

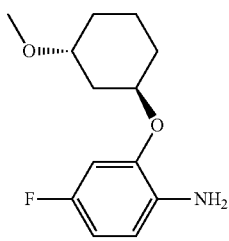 [SMILES: CO[C@@H]1CCC[C@@H](Oc2cc(F)ccc2N)C1]

The compound was prepared from 4-fluoro-2-(trans-3-methoxy-cyclohexyloxy)-1-nitro-benzene (2.07 g) as described for the cis-isomer under XXXX.3.
Yield: 1.94 g (96%)
MS (ESI⁺): 240 (M+H⁺)
HPLC (Method D): Rt 2.24 min Intermediate XXXXII cis-2-(3-methoxy-cyclohexyloxy)-pyridin-3-ylamine

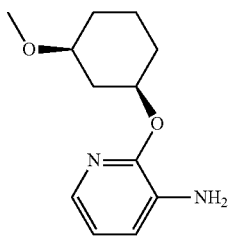 [SMILES: CO[C@H]1CCC[C@@H](Oc2ncccc2N)C1]

XXXXII.1. 2-(cis-3-methoxy-cyclohexyloxy)-3-nitro-pyridine

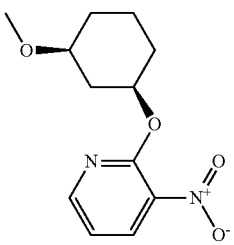 [SMILES: CO[C@H]1CCC[C@@H](Oc2ncccc2[N+](=O)[O-])C1]

LiHMDS (1 M solution in THF; 40.0 ml) was added slowly to an ice/ethanol-cooled solution of cis/trans-4-methoxy-cyclohexanol (5.00 g) in THF (10 ml). Cooling was suspended after the addition was complete and the mixture was stirred for 15 minutes at room temperature. A solution of 2-fluoro-3-nitro-pyridine (5.10 g) in THF (10 ml) was added slowly while the temperature was maintained below 24° C. The reaction mixture was stirred for 2 h at room temperature, neutralized by addition of hydrochloric acid (1M), and extracted with ethyl acetate. The combined organic extracts were washed with brine, dried over MgSO₄ and concentrated in vacuo. The residue was submitted to column chromatography (silica gel, petrol ether/ethyl acetate 70:30 50:50) to give the cis-isomer (5.82 g) and the trans-isomer (1.60 g).

Yield: 5.82 g (64%)

MS (ESI⁺): 253 (M+H⁺)

HPLC (Method D): Rt 3.65 min

XXXXII.2.
2-(cis-3-methoxy-cyclohexyloxy)-pyridin-3-ylamine


Ammonium formate (7.25 g) was added to a suspension of 2-(cis-3-methoxy-cyclohexyloxy)-3-nitro-pyridine (5.80 g) and 10% palladium on charcoal (400 mg) in methanol (40 ml) at room temperature and the mixture was heated to reflux for 30 min until LCMS indicated complete conversion of the starting material. The mixture was diluted with dichloromethane (100 ml) and water (40 ml), filtered through celite, and the filtercake was washed with dichloromethane (30 ml). The organic layer was dried over MgSO₄ and concentrated in vacuo. The residue was submitted to column chromatography (silica gel, petrol ether/ethyl acetate 70:30) to give the desired product.

Yield: 4.32 g (85%)

MS (ESI⁺): 223 (M+H⁺)

HPLC (Method D): Rt 2.36 min

Intermediate XXXXIII 2-(trans-3-methoxy-cyclohexyloxy)-pyridin-3-ylamine

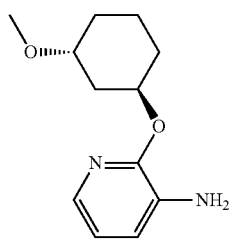 [SMILES: CO[C@@H]1CCC[C@@H](Oc2ncccc2N)C1]

XXXXIII.1.
2-(trans-3-methoxy-cyclohexyloxy)-3-nitro-pyridine

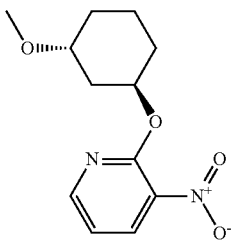 [SMILES: CO[C@@H]1CCC[C@@H](Oc2ncccc2[N+](=O)[O-])C1]

The compound was prepared as described under III.1.

Yield: 1.60 g (18%)

MS (ESI⁺): 253 (M+H⁺)

HPLC (Method D): Rt 3.77 min

XXXXIII.2. trans-2-(3-methoxy-cyclohexyloxy)-pyridin-3-ylamine

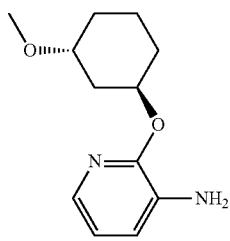 [SMILES: CO[C@@H]1CCC[C@@H](Oc2ncccc2N)C1]

The compound was prepared from 2-(trans-3-methoxy-cyclohexyloxy)-3-nitropyridine (1.59 g) as described for the cis-isomer under III.2.

Yield: 1.11 g (79%)

MS (ESI⁺): 223 (M+H⁺)

HPLC (Method D): Rt 2.36 min

Intermediate XXXXIV

4-Fluoro-2-((1S,2S)-2-methoxy-cyclohexyloxy)-phenylamine

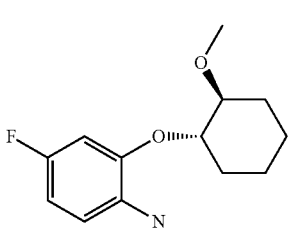 [SMILES: CO[C@H]1CCCC[C@@H]1Oc1cc(F)ccc1N]

XXXXIV.1. 4-Fluoro-2-((1S,2S)-2-methoxy-cyclohexyloxy)-1-nitro-benzene

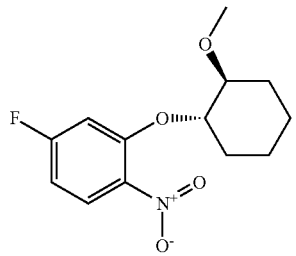 [SMILES: CO[C@H]1CCCC[C@@H]1Oc1cc(F)ccc1[N+](=O)[O-]]

Prepared analogously to III.1 from 926 μl 2,4-difluor-nitrobenzene and 1 g (1S,2S)-2-methoxycyclohexanol.

Yield: 1.34 g

XXXXIV.2. 4-Fluoro-2-((1S,2S)-2-methoxy-cyclohexyloxy)-phenylamine

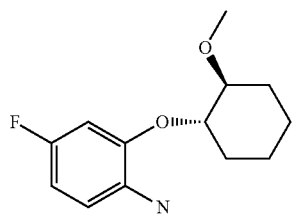 [SMILES: CO[C@H]1CCCC[C@@H]1Oc1cc(F)ccc1N]

Prepared analogously to III.2 from 0.142 g trans-4-Fluoro-2-(2-methoxy-cyclohexyloxy)-1-nitro-benzene.

Yield: 0.115 g

Intermediate XXXXV

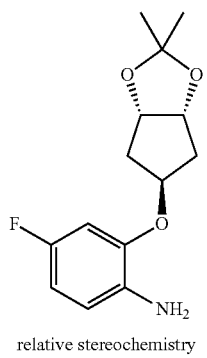 [SMILES: CC1(C)O[C@H]2C[C@H](Oc3cc(F)ccc3N)C[C@H]2O1]

relative stereochemistry

XXXXV.1

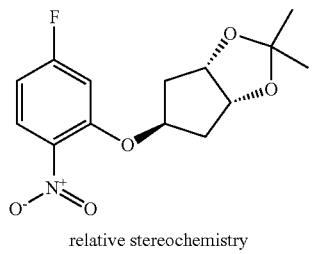 [SMILES: CC1(C)O[C@H]2C[C@H](Oc3cc(F)ccc3[N+](=O)[O-])C[C@H]2O1]

relative stereochemistry

AD-mix-alpha (19.60 g) was added to t-butanol (70.0 ml) and water (70.0 ml). The mixture was cooled to 0° C. and 2-(cyclopent-3-enyloxy)-4-fluoro-1-nitrobenzene (3.14 g) was added. After 2 h the mixture was allowed to warm to room temperature overnight then recooled at 0° C. and sodium metabisulfite (22 g) was added. After 15 min the reaction mixture was stirred at room temperature for 1 h and extracted with EtOAc. The combined organic extracts were concentrated. To the residue was added 2,2-dimethoxypropane (25.0 ml) and p-toluene sulfonic acid (270 mg) and the mixture was heated at reflux for 1 h. The reaction mixture was diluted with EtOAc and washed with 10% aq. $K_2CO_3$ and brine. The organic layer was passed through a hydrophobic frit and concentrated in vacuo. The residue was purified by chromatography to give the desired product.

Yield: 1.77 g

XXXXV.2

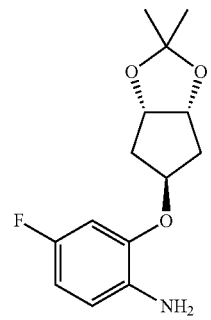

relative stereochemistry

Prepared analogously to III.2 from 0.458 g compound XXXXV.1

Yield: 382 mg

Intermediate XXXXVI

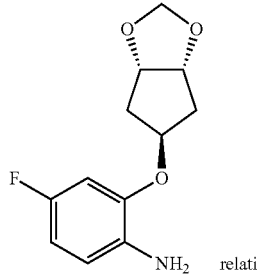

relative stereochemistry

XXXXVI.1

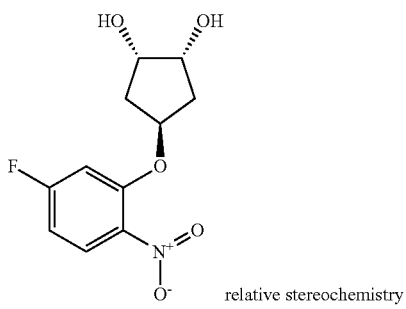 [SMILES: O=[N+]([O-])c1ccc(F)cc1O[C@@H]1C[C@@H](O)[C@@H](O)C1]
relative stereochemistry

To compound XXXXV:1 (521 mg) in THF (5.0 ml) was added 2 M aq. HCl. The reaction mixture was heated to reflux for 1.5 h, then concentrated in vacuo to give the desired product.
Yield: 438 mg

XXXXVI.2

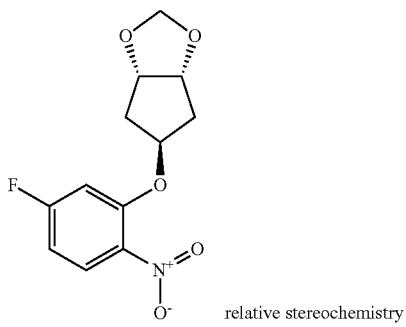 [SMILES: O=[N+]([O-])c1ccc(F)cc1O[C@H]1C[C@@H]2OCO[C@@H]2C1]
relative stereochemistry

Compound XXXXVI.1 (438 mg) and tetra-n-butylammonium bromide (55 mg) in 46/48% aq. sodium hydroxide (7.0 ml) and dibromomethane (7.0 ml) were stirred at 60° C. for 2 h. The reaction mixture was diluted with methylene chloride and water. The layers were separated and the aqueous layer was extracted with methylene chloride. The combined organics were passed through a hydrophobic frit and concentrated in vacuo. The residue was purified by chromatography to yield the desired product.
Yield: 100 mg

XXXXVI.3

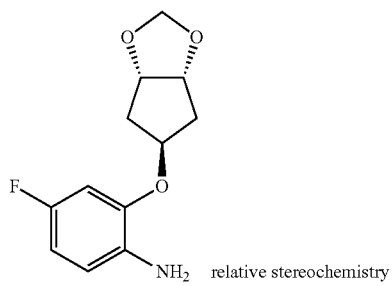 [SMILES: Nc1ccc(F)cc1O[C@H]1C[C@@H]2OCO[C@@H]2C1]
relative stereochemistry

Compound XXXXVI.2 (100 mg), ammonium formate (117 mg) and Pd/C (20 mg) in methanol (2.0 ml) were heated at reflux for 40 min. The reaction mixture was allowed to cool, filtered through a pad of celite and the filtercake was washed with methylene chloride The filtrate was concentrated. The residue was suspended in methylene chloride, passed through a hydrophobic frit and concentrated in vacuo to give the desired product.
Yield: 124 mg Intermediate XXXXVII

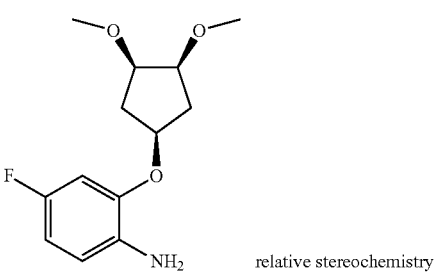 [SMILES: CO[C@H]1C[C@@H](Oc2cc(F)ccc2N)C[C@H]1OC]
relative stereochemistry

XXXXVII.1

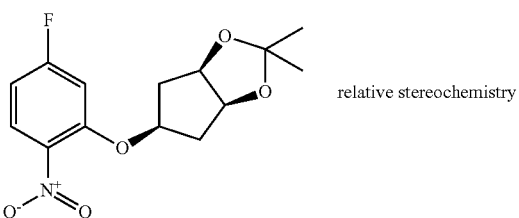 [SMILES: CC1(C)O[C@H]2C[C@@H](Oc3cc(F)ccc3[N+](=O)[O-])C[C@H]2O1]
relative stereochemistry

AD-mix-alpha (19.60 g) was added to t-butanol (70.0 ml) and water (70.0 ml). The mixture was cooled to 0° C. and 2-(cyclopent-3-enyloxy)-4-fluoro-1-nitrobenzene (3.14 g) was added. After 2 h the mixture was allowed to warm to room temperature overnight then recooled at 0° C. and sodium metabisulfite (22 g) was added. After 15 min the reaction mixture was stirred at room temperature for 1 h and extracted with EtOAc. The combined organic extracts were concentrated. To the residue was added 2,2-dimethoxypropane (25.0 ml) and p-toluenesulfonic acid (270 mg) and the mixture was heated at reflux for 1 h. The reaction mixture was diluted with EtOAc and washed with 10% aq. $K_2CO_3$ and brine. The organic layer was passed through a hydrophobic frit and concentrated in vacuo. The residue was purified by chromatography to give the desired product.
Yield: 2.04 g

XXXXVII.2

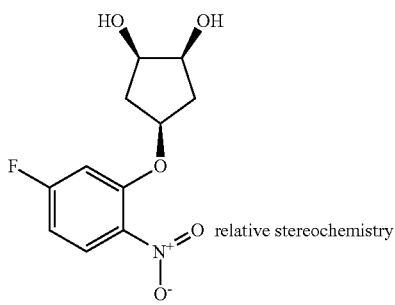 [SMILES: O=[N+]([O-])c1ccc(F)cc1O[C@H]1C[C@@H](O)[C@@H](O)C1]

2 M aq. HCl (7.0 ml) was added to compound XXXXVII.1 (695 mg) in THF (7.0 ml) and the mixture was heated at reflux. After 1.5 h the reaction mixture was concentrated in vacuo. The residue was partitioned between EtOAc and water. The organic layer was passed through a hydrophobic frit and concentrated in vacuo to yield the desired product.
Yield: 521 mg

XXXXVII.3

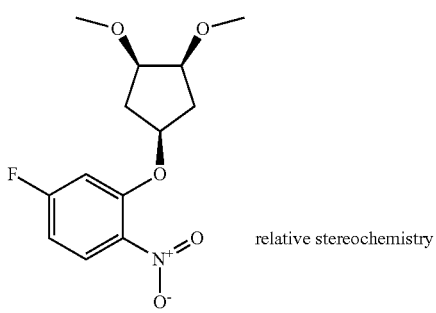 [SMILES: CO[C@H]1C[C@@H](Oc2cc(F)ccc2[N+](=O)[O-])C[C@H]1OC]

Sodium hydride (240 mg, 60%) was added at 0° C. to a mixture of compound XXXXVII.2 (514 mg) and iodomethane (380 IA in DMF (10.0 ml). The reaction mixture was allowed to warm to room temperature overnight, diluted with EtOAc and washed with water and brine. The organic layer was passed through a hydrophobic frit and concentrated in vacuo. The crude was triturated with hexane to yield the desired product.
Yield: 430 mg

XXXXVII.4

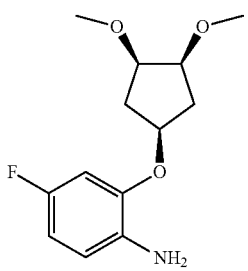 [SMILES: CO[C@H]1C[C@@H](Oc2cc(F)ccc2N)C[C@H]1OC]

Prepared analogously to III.2 from compound XXXXVII.3 (430 mg).
Yield: 365 mg

Intermediate XXXXVIII

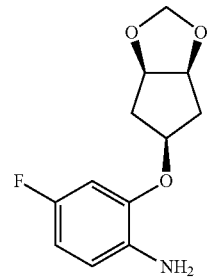 [SMILES: Nc1ccc(F)cc1O[C@@H]1C[C@@H]2OCO[C@@H]2C1]

XXXXVIII.1

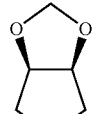

Compound XXXXVII.2 (500 mg) and tetra-n-butylammonium bromide (63 mg) in 46% aq. sodium hydroxide (7.0 ml) and dibromomethane (7.0 ml) were stirred at 60° C. for 2 h. The reaction mixture was allowed to cool and filtered. The filtrate was separated. The organic layer was passed through a hydrophobic frit and concentrated in vacuo. The crude was purified by chromatography to yield the desired product.
Yield: 178 mg

XXXXVIII.2

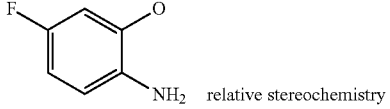

Prepared analogously to III.2 from compound XXXX-VIII.1 (166 mg).

Yield: 141 mg

Intermediate XXXXIX

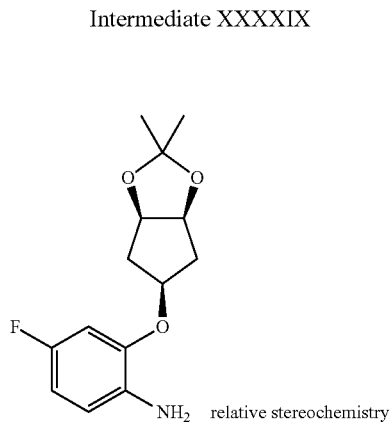

NH₂ relative stereochemistry

Prepared analogously to III.2 from compound XXXXVII.1 (458 mg).

Yield: 391 mg

Intermediate XXXXX

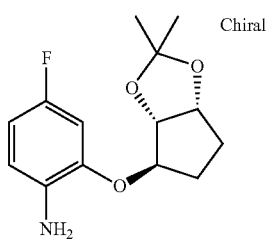 [SMILES: CC1(C)O[C@H]2[C@H](Oc3cc(F)ccc3N)CC[C@H]2O1]

XXXXX.1.
2-(Cyclopent-2-enyloxy)-4-fluoro-1-nitrobenzene

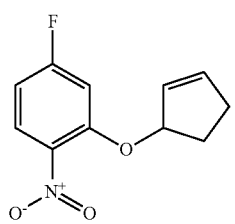 [SMILES: O=[N+]([O-])c1ccc(F)cc1OC1C=CCC1]

To a mixture of 5-fluoro-2-nitrophenol (1.48 g), 2-cyclopenten-1-ol (662 mg) and triphenylphosphine (2.47 g) in THF (25.0 ml) diethylazodicarboxylate (1.48 ml) was added at 0° C. After stirring at room temperature overnight the reaction mixture was diluted with methylene chloride and washed with 10% aq. KHSO₄. The organic layer was passed through a hydrophobic frit and concentrated in vacuo. The residue was purified by chromatography to give the desired product.

Yield: 1.25 g

XXXXX.2.
3-(5-Fluoro-2-nitrophenoxy)cyclopentane-1,2-diol

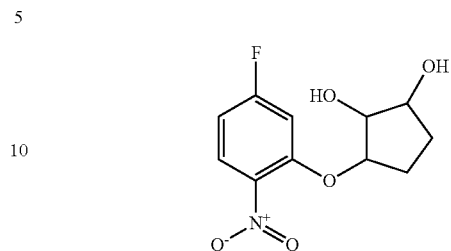

AD-mix-alpha (7.57 g) was added to t-butanol (20.0 ml) and water (25.0 ml) and stirred for 10 min. The mixture was cooled to 0° C. and 2-(cyclopent-2-enyloxy)-4-fluoro-1-nitrobenzene (1.21 g) was added. After stirring at room temperature overnight the mixture was recooled at 0° C. and sodium metabisulfite (8.13 g) was added. After 10 min the reaction mixture was stirred at room temperature for 1 h and extracted with EtOAc. The combined organic extracts were washed with brine passed through a hydrophobic frit and concentrated in vacuo to yield the desired product.

XXXXX.3 compound XXXXX.3.1

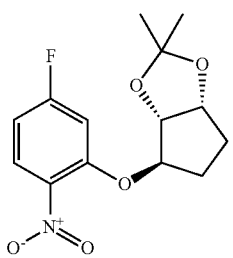

compound XXXXX.3.2

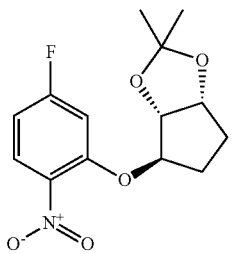

To 3-(5-fluoro-2-nitrophenoxy)cyclopentane-1,2-diol (1.40 g) in 2,2-dimethoxypropane (5.0 ml) was added p-toluenesulfonic acid (103 mg) and the mixture was heated at reflux for 1 h. The reaction mixture was diluted with DCM and 10% aq. K₂CO₃, passed through a hydrophobic frit and concentrated in vacuo. The residue was purified by chromatography (silica gel; solvent: 100% iso-hexane→isohexane/EtOAc (5:1), the compound XXXXX.3.1 eluding first.

Yield: 1.31 g

XXXXX.4

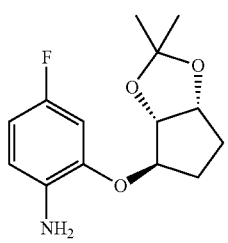 [SMILES: CC1(C)O[C@H]2[C@H](Oc3cc(F)ccc3N)CC[C@H]2O1]

Prepared analogously to III.2. from compound XXXXX.3.1 (595 mg).
Yield: 515 mg

Intermediate XXXXXI

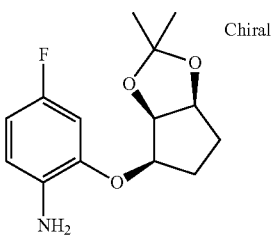 [SMILES: CC1(C)O[C@H]2[C@H](CC[C@H]2Oc2cc(F)ccc2N)O1]

Prepared analogously to III.2 from compound XXXXX.3.2 (106 mg).
Yield: 91 mg

Intermediate XXXXXII racemic
cis-2-(2-amino-5-fluorophenoxy)cyclopentanol

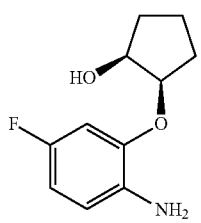 [SMILES: Nc1ccc(F)cc1O[C@@H]1CCC[C@@H]1O]

XXXXXII.1 racemic
cis-2-(5-fluoro-2-nitrophenoxy)cyclopentanol

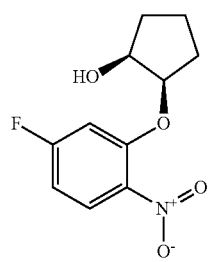 [SMILES: O=[N+]([O-])c1ccc(F)cc1O[C@@H]1CCC[C@@H]1O]

Prepared analogously to III.1 from cis-1,2-cyclopentandiol (1.0 g) and 1.28 ml 2,4-difluoronitrobenzene.
Yield: 1.34 g XXXXXII.2 racemic
cis-2-(2-amino-5-fluorophenoxy)cyclopentanol

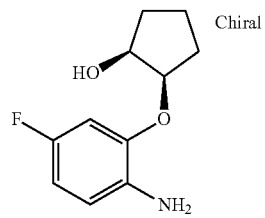 [SMILES: Nc1ccc(F)cc1O[C@@H]1CCC[C@@H]1O]

Prepared analogously to III.2 from racemic cis-2-(5-fluoro-2-nitrophenoxy)cyclopentanol (2.36 g).
Yield: 388 mg Intermediate XXXXXIII 3-(2-amino-5-fluorophenoxy)cyclopentanol XXXXXIII.1.
3-(5-fluoro-2-nitrophenoxy)cyclopentanol

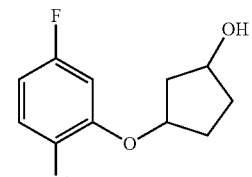

Di-tert-butyl azodicarboxylate was added at 0° C. to a mixture of 1,3-cyclopentandiol (1.02 g), 5-fluoro-2-nitrophenol (0.79 g) and triphenylphosphine (1.97 g) in THF (15.0 ml). After stirring at room temperature over weekend the mixture was treated with 2 M aq. HCl (20.0 ml) and refluxed for 30 min. The reaction mixture was diluted with methylene chloride. The layers were separated. The organic layer was passed through a hydrophobic frit and concentrated in vacuo. The crude was purified by chromatography to yield the desired product.
Yield: 1.10 g XXXXXIII.2.
3-(2-amino-5-fluorophenoxy)cyclopentanol

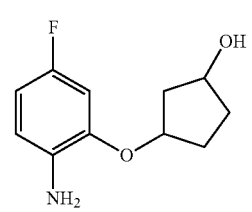 [SMILES: Nc1ccc(F)cc1OC1CCC(O)C1]

Prepared analogously to III.2 from 3-(5-fluoro-2-nitrophenoxy)cyclopentanol (1.09 g).

Yield: 868 mg

Intermediate XXXXXIV racemic
cis-2-(2-Amino-5-fluoro-phenoxy)-cyclohexanol

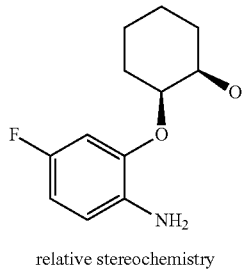

relative stereochemistry

XXXXXIV.1 racemic
cis-2-(5-Fluoro-2-nitro-phenoxy)-cyclohexanol

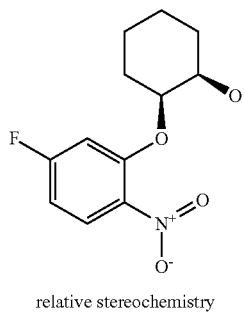

relative stereochemistry

Prepared analogously to III.1 from cis-1,2-cyclohexandiol (1.0 g) and 0.94 ml 2,4-difluoronitrobenzene.

Yield: 1.34 g

XXXXXIV.2 racemic
cis-242-Amino-5-fluoro-phenoxy)-cyclohexanol

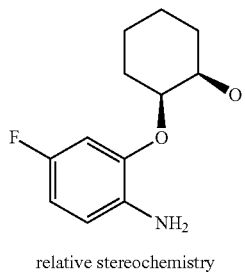

relative stereochemistry

Prepared analogously to III.2 from racemic cis-2-(5-fluoro-2-nitro-phenoxy)cyclohexanol cyclopentanol (2.198 g).

Yield: 627 mg

Intermediate XXXXXVI
3-(2-Amino-5-fluoro-phenoxy)-cyclohexanol

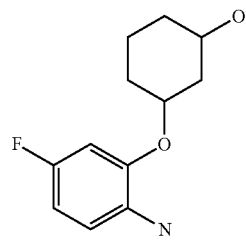 [SMILES: Nc1ccc(F)cc1OC1CCCC(O)C1]

XXXXXVI.1
3-(5-Fluoro-2-nitro-phenoxy)-cyclohexanol

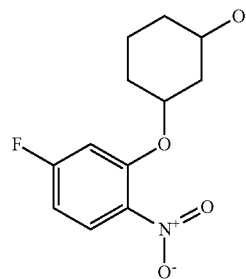 [SMILES: O=[N+]([O-])c1ccc(F)cc1OC1CCCC(O)C1]

Prepared analogously to XVI.1 from −1,3-cyclohexandiol (2.32.0 g) and 1.575-fluoro-2-nitrophenol.

Yield: 0.952 g

XXXXXIV.2
3-(2-Amino-5-fluoro-phenoxy)-cyclohexanol

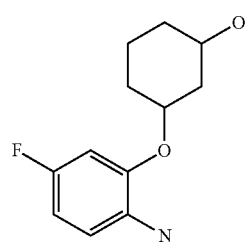 [SMILES: Nc1ccc(F)cc1OC1CCCC(O)C1]

Prepared analogously to III.2 from 3-(5-fluoro-2-nitrophenoxy)-cyclohexanol (0.945 g).
Yield: 487 mg Intermediate XXXXXVII 4-Fluoro-2-(trans-4-methoxy-cyclohexyloxy)-phenylamine

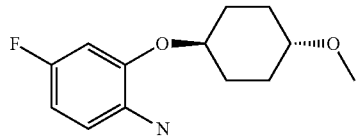 [SMILES: CO[C@H]1CC[C@H](Oc2cc(F)ccc2N)CC1]

XXXXXVII.1 4-Fluoro-2-(trans-4-methoxy-cyclohexyloxy)-1-nitro-benzene

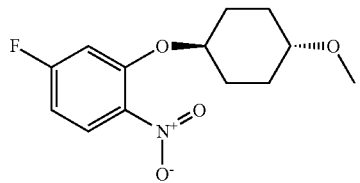 [SMILES: CO[C@H]1CC[C@H](Oc2cc(F)ccc2[N+](=O)[O-])CC1]

0.6 g sodium hydride (60%) were added to a cooled solution (−7° C.) of 2.55 g 4-fluoro-2-(trans-4-hydroxy-cyclohexyloxy)-1-nitro-benzene and iodomethane in 30 ml DMF. The mixture was allowed to warm to rt overnight, diluted with EtOAc and washed with water and brine (3×). The organic phase was dried (MgSO$_4$), passed through a hydrophobic frit and evaporated. The residue was purified by flash column chromatography (silica gel, 100% i-hexane→7:1 i-hexane:EtOAc).

XXXXXVII.2 4-Fluoro-2-(trans-4-methoxy-cyclohexyloxy)-phenylamine

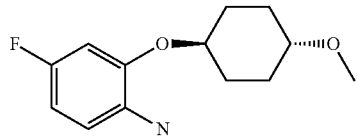 [SMILES: CO[C@H]1CC[C@H](Oc2cc(F)ccc2N)CC1]

Prepared analogously to III.2 from 1.81 g 4-Fluoro-2-(trans-4-methoxy-cyclohexyloxy)-1-nitro-benzene.
Yield: 1.48 g

XXXXXVIII

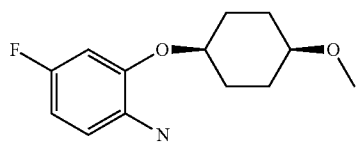 [SMILES: CO[C@H]1CC[C@@H](Oc2cc(F)ccc2N)CC1]

XXXXXVIII.1 4-Methoxycyclohexanol

A mixture of 100 g 4-methoxyphenol and Nishimura's catalyst in 750 ml ethanol were hydrogenated (50 psi hydrogen) at room temperature for 4.5 hours. The mixture was filtered and the filtrate was concentrated.
Yield: 114 g
ESI mass spectrum: m/z=131 (M+H)$^+$ XXXXXVIII.2 4-Fluoro-2-(cis-4-methoxy-cyclohexyloxy)-phenylamine and 4-Fluoro-2-(trans-4-methoxy-cyclohexyloxy)-phenylamine

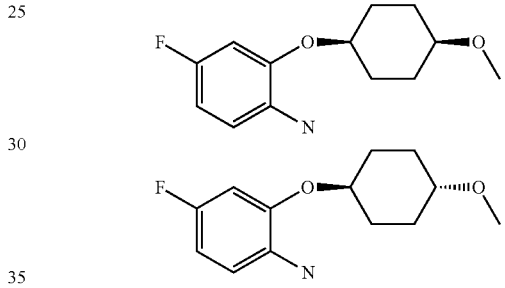

A mixture of 18.9 g 2-nitro-5-fluorophenol and 19 g 4-methoxycyclohexanol in 250 ml THF were placed in a water bath with cold water. 41 g DTAD and 47 g triphenylphosphine were added simultaneously. The reaction mixture was stirred for 2 hours at room temperature. 1.9 g Pd/C (10%) were added and the reaction mixture hydrogenated (50 psi hydrogen) at room temperature for 20 hours. The mixture was filtered and concentrated. Methylene chloride was added to the residue and the mixture was extracted two times with HCl (2M). The water phase were adjusted to basic pH by addition of aq. sodium hydroxide solution (4M) and extracted two times with methylene chloride. The combined organic phases were dried over sodium sulfate, filtered and concentrated. Purification was achieved by column chromatographie on silica (eluent: methylene chloride/EtOAc=9:1).

4-Fluoro-2-(cis-4-methoxy-cyclohexyloxy)-phenylamine

Yield: 2 g
ESI mass spectrum: m/z=240 (M+H)$^+$

4-Fluoro-2-(trans-4-methoxy-cyclohexyloxy)-phenylamine

Yield: 3.8 g
ESI mass spectrum: m/z=240 (M+H)$^+$

Intermediate XXXXXIX 4-(3-Amino-pyridin-2-yloxy)-cyclohexanol

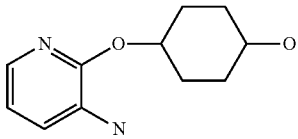 [SMILES: Nc1cccnc1OC1CCC(O)CC1]

XXXXXIX.1
4-(3-Nitro-pyridin-2-yloxy)-cyclohexanol

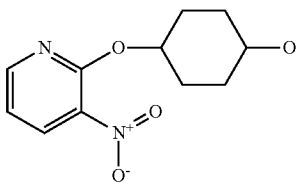 [SMILES: O=[N+]([O-])c1cccnc1OC1CCC(O)CC1]

Prepared analogously to III.1 from 3.6 g 2-fluoro-3-nitro-pyridine and 2.9 g 1,4-cyclohexanediol
Yield: 3 g XXXXXIX.2
4-(3-Amino-pyridin-2-yloxy)-cyclohexanol

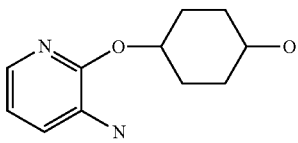 [SMILES: Nc1cccnc1OC1CCC(O)CC1]

Prepared analogously to III.2 from 1.6 g 4-(3-Nitro-pyridin-2-yloxy)-cyclohexanol
Yield: 1.53 g Intermediate XXXXXX
trans-4-(3-Amino-pyridin-2-yloxy)-cyclohexanol

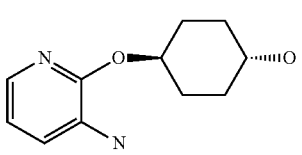 [SMILES: Nc1cccnc1O[C@H]1CC[C@H](O)CC1]

XXXXXX.1
trans-4-(3-Nitro-pyridin-2-yloxy)-cyclohexanol

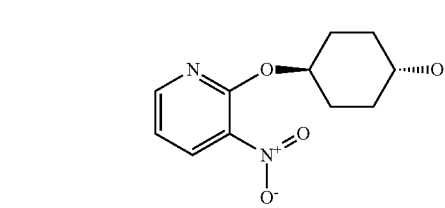

Prepared analogously to III.1 from 4.054 g 2-fluoro-3-nitropyridine and 2.266 g trans-1,4-cyclohexanediol
Yield: 0.298 g XXXXXX.2
trans-4-(3-Amino-pyridin-2-yloxy)-cyclohexanol

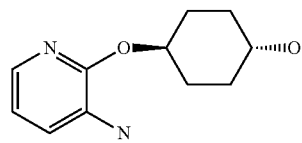 [SMILES: Nc1cccnc1O[C@H]1CC[C@H](O)CC1]

Prepared analogously to XXIV.2 from 0.29 g trans-4-(3-Nitro-pyridin-2-yloxy)cyclohexanol
Yield: 0.203 g
ESI mass spectrum: m/z=209 (M+H)$^+$ Intermediate XXXXXXI

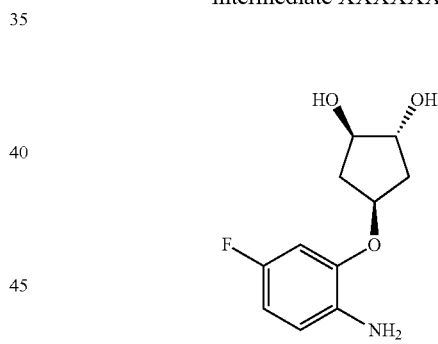

XXXXXXI.1.
2-(cyclopent-3-enyloxy)-4-fluoro-1-nitrobenzene

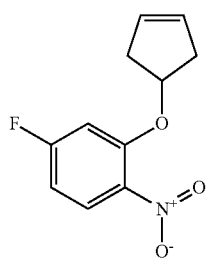 [SMILES: O=[N+]([O-])c1ccc(F)cc1OC1CC=CC1]

To a mixture of 5-fluoro-2-nitrophenol (1.57 g), 2-cyclopentenol (1.00 g) and triphenylphosphine (3.15 g) in methylene chloride (30.0 ml) was added at 0° C. diethylazodicarboxylate (1.89 ml). After stirring at room temperature overnight the reaction mixture was concentrated in vacuo. The residue was purified by chromatography to give the desired product.

Yield: 2.11 g

XXXXXXI.2. 3-(5-fluoro-2-nitrophenoxy)-6-oxabicyclo[3.1.0]hexane

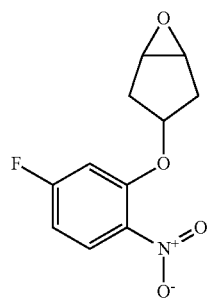 [SMILES: O=[N+]([O-])c1ccc(F)cc1OC1CC2OC2C1]

To 2-(cyclopent-3-enyloxy)-4-fluoro-1-nitrobenzene (2.05 g) in methylene chloride (45.0 ml) at 0° C. was added 3-chloroperoxybenzoic acid (2.95 g) and the mixture was allowed to warm to room temperature overnight. The reaction mixture was diluted with methylene chloride and washed with 10% aq. $K_2CO_3$. The organic layer was passed through a hydrophobic frit and solvent evaporated to give the desired product.

Yield: 2.31 g

XXXXXXI.3

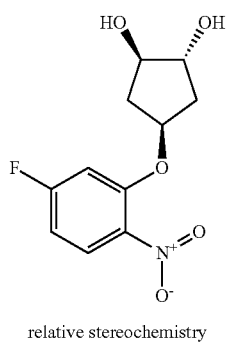

relative stereochemistry 3-(5-fluoro-2-nitrophenoxy)-6-oxabicyclo[3.1.0]hexane (2.20 g) was heated in 0.2 M sulphuric acid (50.0 ml) and THF (50.0 ml) for 5 h. After stirring at room temperature overnight the reaction mixture was concentrated in vacuo. The residue was extracted with methylene chloride. The combined organic extracts were washed with 10% aq. $K_2CO_3$ and concentrated in vacuo. The residue was purified by chromatography to give the desired product.

Yield: 1.61 g

XXXXXXI.4

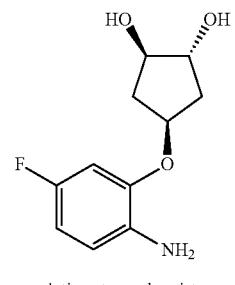

relative stereochemistry

Compound XXXXXXI.3 (1.60 g), ammonium formate (1.96 g) and Pd/C (0.30 g) in methanol (30.0 ml) were heated at reflux for 1 h. The reaction mixture was filtered through a pad of celite and the filtercake was washed with DCM. The filtrate was concentrated in vacuo and the residue was purified by chromatography to give the desired product.

Yield: 1.04 g

Intermediate XXXXXXII

N-[(1S,3S)-3-(2-Amino-5-fluoro-phenoxy)-cyclopentyl]-acetamide

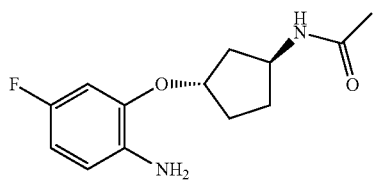 [SMILES: CC(=O)N[C@H]1CC[C@H](Oc2cc(F)ccc2N)C1]

XXXXXXII.1 (1S,3S)-3-(5-Fluoro-2-nitro-phenoxy)-cyclopentylamine trifluoroacetate

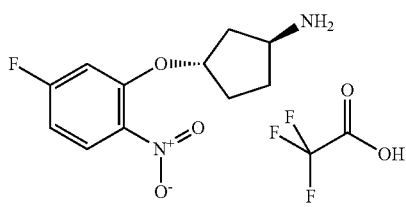

To [(1S,3S)-3-(5-fluoro-2-nitro-phenoxy)-cyclopentyl]-carbamic acid tert-butyl ester, cpd. XXXVII.1 (2.13 g) in DCM (150 ml) was added at 0° C. TFA (10 ml) and stirred at rt overnight. The reaction mixture was concentrated at rt and triturated with diisopropyl ether to give the desired compound.

Yield: 1.80 g

ESI mass spectrum: m/z=241 (M+H)$^+$

XXXXXXII.2 N-[(1S,3S)-3-(5-Fluoro-2-nitro-phenoxy)-cyclopentyl]-acetamide

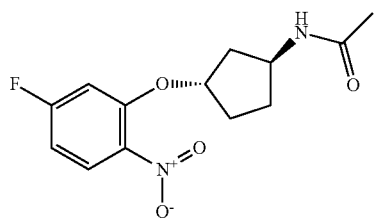 [SMILES: CC(=O)N[C@H]1CC[C@H](Oc2cc(F)ccc2[N+](=O)[O-])C1]

Acetyl chloride (360 µl) was added at 0° C. to a mixture of (1S,3S)-3-(5-fluoro-2-nitrophenoxy)-cyclopentylamine trifluoroacetate (1.80 g) and DIPEA (4.4 ml) in methylene chloride (150 ml) and stirred at rt for 1 hour. The reaction mixture was diluted with water and the organic layer was dried and concentrated. The crude was triturated with diisopropyl ether to give the desired product.

Yield: 1.40 g

ESI mass spectrum: m/z=283 (M+H)$^+$

XXXXXXII.3 N-[(1S,3S)-3-(2-Amino-5-fluorophenoxy)-cyclopentyl]-acetamide

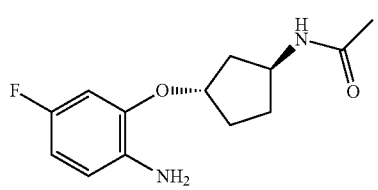 [SMILES: CC(=O)N[C@H]1CC[C@H](Oc2cc(F)ccc2N)C1]

A mixture of N-[(1S,3S)-3-(5-fluoro-2-nitro-phenoxy)-cyclopentyl]-acetamide (1.45 g) and Raney Ni (200 mg) in MeOH (150 ml) was stirred at rt overnight under hydrogen atmosphere (5 bar). The catalyst was removed by filtration and the filtrate was concentrated to give the desired product.

Yield: 1.89 g (65% pure)

ESI mass spectrum: m/z=253 (M+H)$^+$

Intermediate XXXXXXIII

[4-(3-Amino-pyridin-2-yloxy)cyclohexyl]-carbamic acid tert-butyl ester

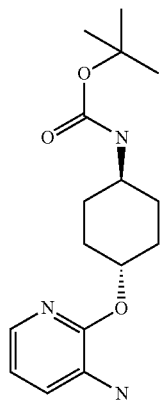 [SMILES: CC(C)(C)OC(=O)N[C@H]1CC[C@H](Oc2ncccc2N)CC1]

A mixture of 7.8 g [4-(3-nitro-pyridin-2-yloxy)cyclohexyl]-carbamic acid tert-butyl ester and 0.8 g raney nickel in 100 ml methanol was hydrogenated at rt under 50 psi overnight. The reaction mixture was filtered and the filtrate concentrated.

Yield: 6.9 g

ESI mass spectrum: m/z=308 (M+H)$^+$

Intermediate XXXXXXIV (1S,2S)[2-(2-Amino-5-fluoro-phenoxy)-cyclopentyl]-carbamic acid tert-butyl ester

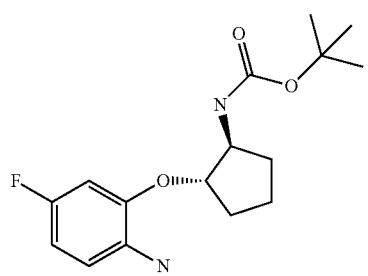

XXXXXXIV.1 (1S,2S)[2-(5-Fluoro-2-nitro-phenoxy)-cyclopentyl]-carbamic acid tert-butyl ester

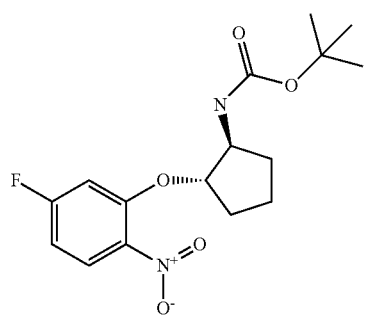

(1S,2S)-trans-N-boc-2-aminocyclopentanol was dissolved in 50 ml THF and cooled to 10° C. To the reaction mixture were added 32.2 ml LiHMDS 1M in THF. After 1 hour 2.72 ml 2,4-difluoronitrobenzol were added and the mixture was stirred at rt overnight. Then the mixture was poured in water and extracted with ethylacetate. The organic layer was washed with water, dried and concentrated in vacuo.

Yield: 9.0 g

ESI mass spectrum: m/z=341 (M+H)$^+$

XXXXXXIV.2 (1S,2S)[2-(2-Amino-5-fluoro-phenoxy)-cyclopentyl]-carbamic acid tert-butyl ester

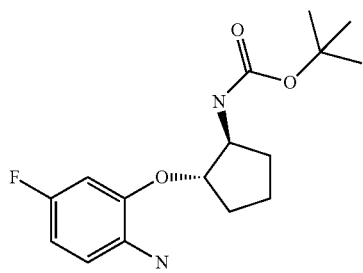

Prepared analogously to example III.2 from 9.0 g (1S,2S) [2-(5-fluoro-2-nitrophenoxy)-cyclopentyl]-carbamic acid tert-butyl ester (compound XXXXXXIV.1)

Yield: 8.0 g
ESI mass spectrum: m/z=311 (M+H)⁺

XXXXXXIV.3 (1S,2S) 4-[2-(2-tert-Butoxycarbonylamino-cyclopentyloxy)-4-fluoro-phenylamino]-5-methyl thieno[2,3-d]yrimidine-6-carboxylic acid methyl ester

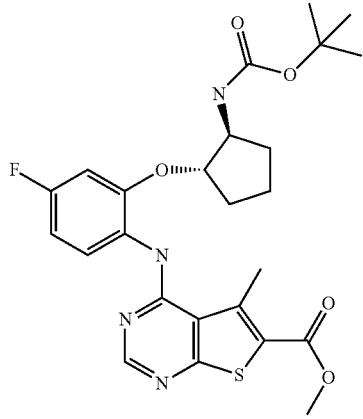

A reaction mixture of 2.0 g 4-chloro-5-methyl-thieno[2,3d]pyrimidine-6-carboxylic acid methyl ester, 2.5 g intermediate XXXXXXIV.2 and 0.283 g p-toluenesulfonic acid in 20 ml Dioxan was heated at 110° C. in the microwave for 1 hour. The reaction mixture was diluted with MeOH and filtered. The filtrate was washed with dioxane/MeOH. The residue was triturated with diisopropylether.

XXXXXXIV.4 (1S,2S) 4-[2-(2-tert-Butoxycarbonylamino-cyclopentyloxy)-4-fluoro-phenylamino]-5-methyl thieno[2,3-d]pyrimidine-6-carboxylic acid A mixture of 2.4 g (1S,2S) 4-[2-(2-tert-butoxycarbonylamino-cyclopentyloxy)-4-fluoro-phenylamino]-5-methyl thieno[2,3-d]pyrimidine-6-carboxylic acid methyl ester and 20 ml 1M sodium hydroxide solution in 50 ml MeOH was stirred at rt overnight. To the reaction mixture was added 20 ml 1M hydrochloric acid until a pH range of 2-3 was reached. The mixture was diluted with water and filtrated. The solid was dried in vacuo at 50° C.

Yield: 2.2 g
ESI mass spectrum: m/z=503 (M+H)⁺

XXXXXXIV.5 (1S,2S) {2-(2-(6-Carbamoyl-5-methyl-thieno[2,3-d]pyrimidin-4-ylamino)-5-fluoro-phenoxy]-cyclopentyl}-carbamic acid ten-butyl ester

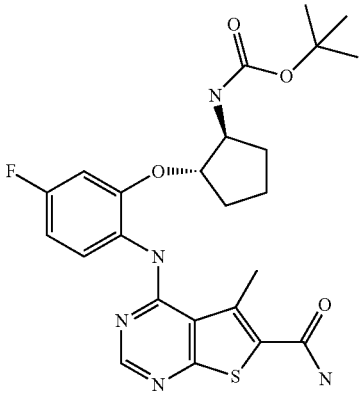

Prepared analogously to example 1.4 from 2.20 g (1S,2S) 4-[2-(2-tert-butoxycarbonylamino-cyclopentyloxy)-4-fluoro-phenylamino]-5-methyl thieno[2,3-d]pyrimidine-6-carboxylic acid (compound XXXXXXIV.4) and ammonia.

Yield: 2.1 g
ESI mass spectrum: m/z=502 (M+H)

XXXXXXIV.6 (1S,2S) 4-[2-(2-Amino-cyclopentyloxy)-4-fluoro-phenylamino]-5-methyl thieno[2,3-d]pyrimidine-6-carboxylic acid amide

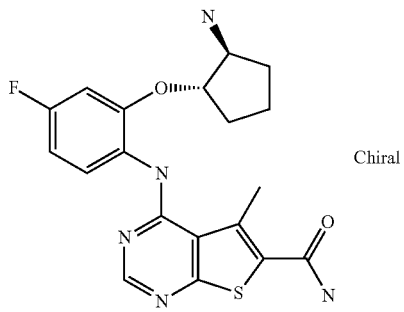 [SMILES: Cc1c(C(N)=O)sc2ncnc(Nc3ccc(F)cc3O[C@H]3CCC[C@@H]3N)c12]

Chiral

A reaction mixture of 2.1 g 1S,2S) {2-(2-(6-carbamoyl-5-methyl-thieno[2,3-d]pyrimidin-4-ylamino)-5-fluoro-phenoxy]-cyclopentyl}-carbamic acid tert-butyl ester, and 1.24 ml trifluoroacetic acid in 50 ml DCM was stirred for 3 days at 46° C. The mixture was concentrated, diluted with toluenel and concentrated. The residue was extracted with DCM and water, whereby the water layer had the pH range of 10. The organic layer was dried and concentrated in vacuo. The residue was purified by chromatography.

Yield: 0.5 g
ESI mass spectrum: m/z=402 (M+H)+

End Compounds

Example 1

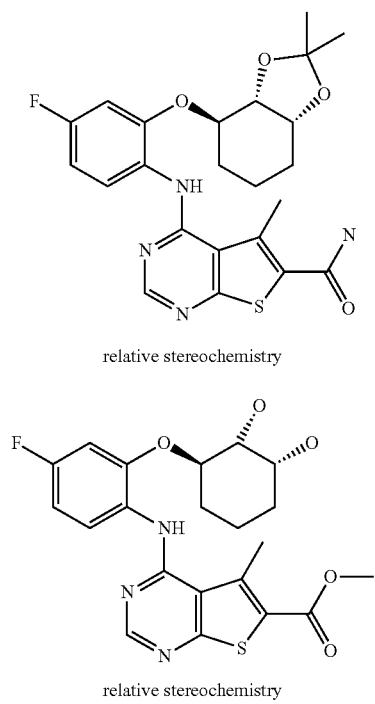

relative stereochemistry relative stereochemistry

A reaction mixture of 0.265 g 4-chloro-5-methyl-thieno[2,3-d]pyrimidine-6-carboxylic acid methyl ester, 0.265 g intermediate 1 and 0.02 g p-toluenesulfonic acid in 3 ml dioxane were heated at 110° C. for 8 hours.

Then aq. ammonium hydroxide solution (3M) was added. The mixture was filtered and the solid washed with water and diethyl ether. The solid was dried in vacuo at 50° C. for 3 h and at rt over weekend.

Yield: 0.385 g 1.2

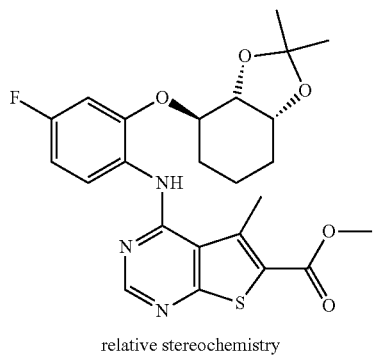

relative stereochemistry 0.385 g compound 1.1, 0.016 g p-toluenesulfonic acid and 1 ml 2,2-dimethoxypropane in 1 ml DMF were heated at 80° C. for 45 minutes. Then the reaction mixture was diluted with EtOAc and washed with 10% aq. potassium carbonate solution and brine (2×). The organic phase was passed through a hydrophobic frit and evaporated. The residue triturated with diethylether.

Yield: 0.306 g 1.3

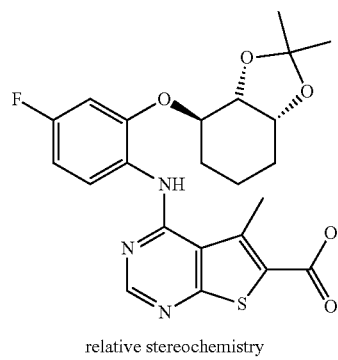

relative stereochemistry 1.6 ml sodium hydroxide solution (2M) were added to a mixture of 0.306 g compound 1.2. in 6 ml EtOH/THF (1:1). The reaction mixture was stirred at rt for 45 minutes and at reflux for 40 minutes. Then the solvent was removed in vacuo and the residue suspended in water. aqu.hydrochloric acid solution (2M) was added. The mixture was filtered and the solid washed with water. The solid was suspended in ethanol and the mixture then concentrated. This was repeated twice.

Yield: 0.274 g 1.4

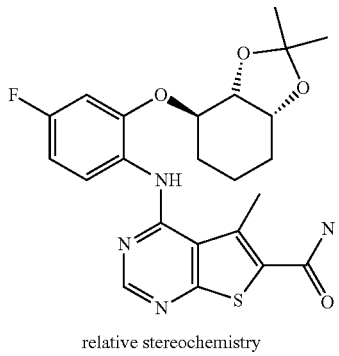

relative stereochemistry 0.256 g HATU were added to an ice-cooled solution of 0.265 g compound 1.3 and 117 μl DIPEA in 3 ml DMF. After 30 minutes at this temperature 1.5 ml of a solution of ammonia in methanol (7 mol/l) were added. The mixture was allowed to warm to rt overnight. DMF was evaporated in vacuo and the residue was evaporated from toluene (3×). The residue was suspended in methanol and heated to reflux. The reaction mixture was filtered, the solid washed with diethyl-ether and dried.

Yield: 0.185 g

ESI mass spectrum: m/z=473 (M+H)$^+$

R$_t$ (HPLC): 1.42 min (method X)

Example 2

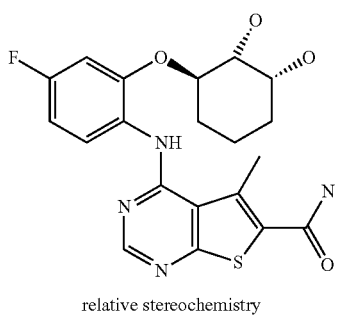

relative stereochemistry

A mixture of 0.155 g compound 1.4 and 2 ml aq. hydrochloric acid solution (2M) in 2 ml THF were heated at reflux for 20 minutes. The reaction mixture was filtered at rt. The solid was washed with water and diethylether and dried in vacuo over phosphorous pentoxide.

Yield: 0.110 g

ESI mass spectrum: m/z=433 (M+H)$^+$

R$_t$ (HPLC): 1.23 min (method X)

Example 3

4-[4-Fluoro-2-(trans-4-methanesulfonylamino-cyclohexyloxy)-phenylamino]-5-methyl-thieno[2,3-d]pyrimidine-6-carboxylic acid amide

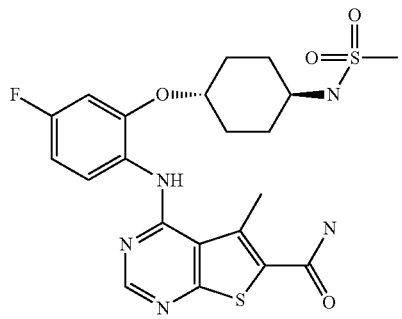 [SMILES: Cc1c(C(N)=O)sc2ncnc(Nc3ccc(F)cc3O[C@H]3CC[C@H](NS(C)(=O)=O)CC3)c12]

3.1. 4-[4-Fluoro-2-(trans-4-methanesulfonylamino-cyclohexyloxy)-phenylamino]-5-methyl-thieno[2,3-d]pyrimidine-6-carboxylic acid methyl ester

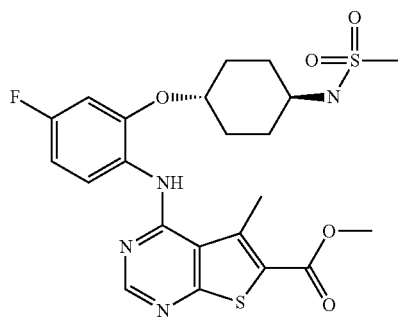 [SMILES: COC(=O)c1sc2ncnc(Nc3ccc(F)cc3O[C@H]3CC[C@H](NS(C)(=O)=O)CC3)c2c1C]

Prepared analogously to 1.1 from intermediate IV (0.16 g) and 4-chloro-5-methyl-thieno[2,3-d]pyrimidine-6-carboxylic acid methyl ester (0.129 g).

Yield: 0.223 g 3.2. 4-[4-Fluoro-2-(trans-4-methanesulfonylamino-cyclohexyloxy)-phenylamino]-5-methyl-thieno[2,3-d]pyrimidine-6-carboxylic acid

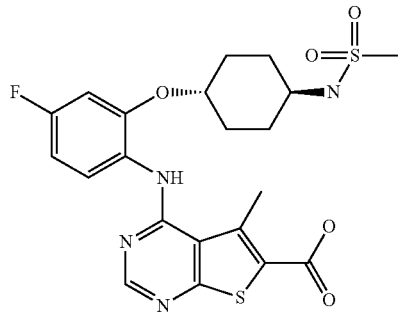 [SMILES: Cc1c(C(=O)O)sc2ncnc(Nc3ccc(F)cc3O[C@H]3CC[C@H](NS(C)(=O)=O)CC3)c12]

Prepared analogously to 1.3 from 0.22 g 4-[4-fluoro-2-(trans-4-methanesulfonylamino-cyclohexyloxy)-phenylamino]-5-methyl-thieno[2,3-d]pyrimidine-6-carboxylic acid methyl ester (cpd.3.1).

Yield: 0.118 g

3.3. 4-[4-Fluoro-2-(trans-4-methanesulfonylamino-cyclohexyloxy)-phenylamino]-5-methyl-thieno[2,3-d]pyrimidine-6-carboxylic acid amide

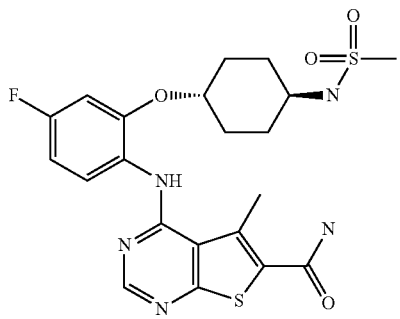 [SMILES: Cc1c(C(N)=O)sc2ncnc(Nc3ccc(F)cc3O[C@H]3CC[C@H](NS(C)(=O)=O)CC3)c12]

Prepared analogously to 1.4 from 0.11 g 4-[4-fluoro-2-(trans-4-methanesulfonylamino-cyclohexyloxy)-phenylamino]-5-methyl-thieno[2,3-d]pyrimidine-6-carboxylic acid (cpd.3.2).
Yield: 0.080 g
ESI mass spectrum: m/z=494 (M+H)$^+$
$R_t$ (HPLC): 1.31 min (method X)

Example 4

4-(4-Fluoro-2-(trans-4-(N-methylmethylsulfonamido)cyclohexyloxy)phenylamino)-5-methylthieno[2,3-d]pyrimidine-6-carboxamide

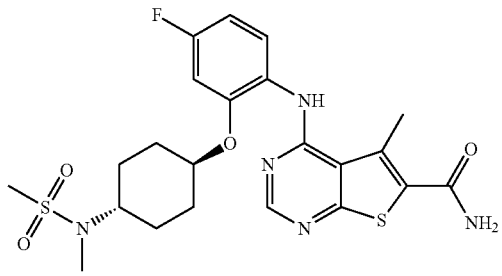 [SMILES: Cc1c(C(N)=O)sc2ncnc(Nc3ccc(F)cc3O[C@H]3CC[C@H](N(C)S(C)(=O)=O)CC3)c12]

4.1 Methyl 4-(4-fluoro-2-(trans-4-(N-methylmethylsulfonamido)cyclohexyloxy)phenylamino)-5-methylthieno[2,3-d]pyrimidine-6-carboxylate

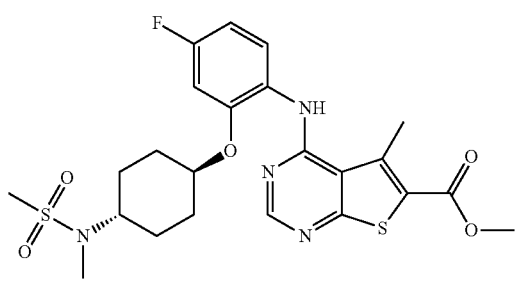

Prepared analogously to 1.1 from intermediate V (0.242 g) and 4-chloro-5-methyl-thieno[2,3-d]pyrimidine-6-carboxylic acid methyl ester (0.155 g).
Yield: 0.272 g

4.2 4-(4-Fluoro-2-(trans-4-(N-methylmethylsulfonamido)cyclohexyloxy)phenylamino)-5-methylthieno[2,3-d]pyrimidine-6-carboxylic acid

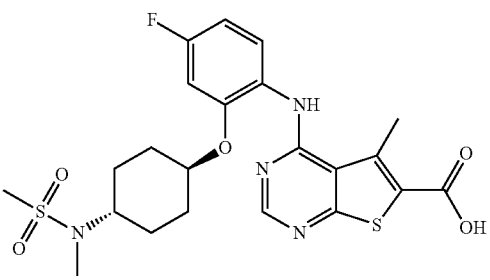 [SMILES: Cc1c(C(=O)O)sc2ncnc(Nc3ccc(F)cc3O[C@H]3CC[C@H](N(C)S(C)(=O)=O)CC3)c12]

Prepared analogously to 1.3 from 0.272 g methyl 4-(4-fluoro-2-(trans-4-(N-methylmethylsulfonamido)cyclohexyloxy)phenylamino)-5-methylthieno[2,3-d]pyrimidine-6-carboxylate (cpd.4.1).
Yield: 0.118 g

4.3 4-(4-Fluoro-2-(trans-4-(N-methylmethylsulfonamido)cyclohexyloxy)phenylamino)-5-methylthieno[2,3-d]pyrimidine-6-carboxamide

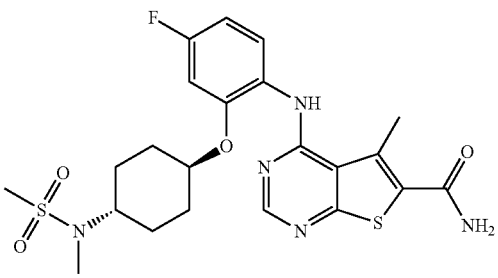 [SMILES: Cc1c(C(N)=O)sc2ncnc(Nc3ccc(F)cc3O[C@H]3CC[C@H](N(C)S(C)(=O)=O)CC3)c12]

Prepared analogously to 1.4 from 0.137 g 4-(4-fluoro-2-(trans-4-(N-methylmethylsulfonamido)cyclohexyloxy)phenylamino)-5-methylthieno[2,3-d]pyrimidine-6-carboxylic acid (cpd.4.2).
Yield: 0.099 g
ESI mass spectrum: m/z=508 (M+H)$^+$
$R_t$ (HPLC): 1.37 min (method X)

Example 5

4-(2-(trans-4-acetamidocyclohexyloxy)-4-fluorophenylamino)-5-methylthieno[2,3-d]pyrimidine-6-carboxamide

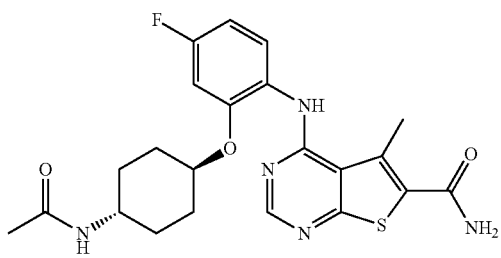 [SMILES: CC(=O)N[C@H]1CC[C@H](Oc2cc(F)ccc2Nc2ncnc3sc(C(N)=O)c(C)c23)CC1]

5.1 Methyl 4-(2-(trans-4-acetamidocyclohexyloxy) 4-fluorophenylamino)-5-methylthieno[2,3-d]pyrimidine-6-carboxylate

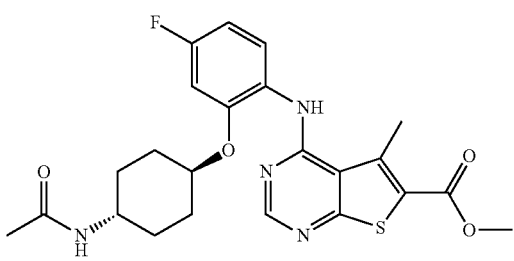 [SMILES: COC(=O)c1sc2ncnc(Nc3ccc(F)cc3O[C@H]3CC[C@H](NC(C)=O)CC3)c2c1C]

Prepared analogously to 1.1 from intermediate VI (0.422 g) and 4-chloro-5-methyl-thieno[2,3-d]pyrimidine-6-carboxylic acid methyl ester (0.243 g).

Yield: 0.301 g

5.2 4-(2-(trans-4-acetamidocyclohexyloxy) 4-fluorophenylamino)-5-methylthieno[2,3-d]pyrimidine-6-carboxylic acid

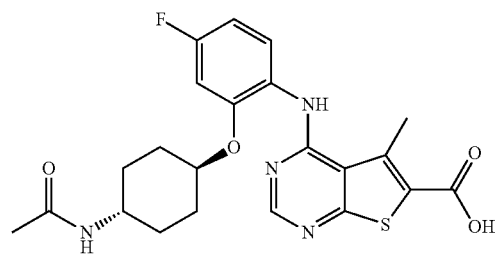 [SMILES: CC(=O)N[C@H]1CC[C@H](Oc2cc(F)ccc2Nc2ncnc3sc(C(=O)O)c(C)c23)CC1]

Prepared analogously to 1.3 from 0.301 g methyl 4-(2-(trans-4-acetamidocyclohexyloxy) 4-fluorophenylamino)-5-methylthieno[2,3-d]pyrimidine-6-carboxylate (cpd.5.1).

Yield: 0.283 g

5.3 4-(2-(trans-4-acetamidocyclohexyloxy)-4-fluorophenylamino)-5-methylthieno[2,3-d]pyrimidine-6-carboxamide

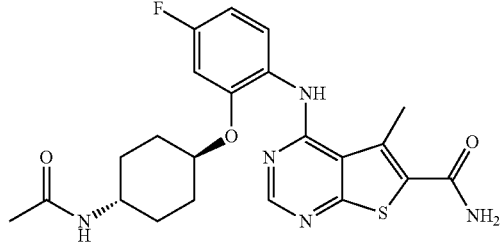 [SMILES: CC(=O)N[C@H]1CC[C@H](Oc2cc(F)ccc2Nc2ncnc3sc(C(N)=O)c(C)c23)CC1]

Prepared analogously to 1.4 from 0.100 g 4-(2-(trans-4-acetamidocyclohexyloxy) 4-fluorophenylamino)-5-methylthieno[2,3-d]pyrimidine-6-carboxylic acid (cpd.5.2).

Yield: 0.073 g

ESI mass spectrum: m/z=458 (M+H)$^+$ $R_t$ (HPLC): 1.29 min (method X)

Example 6

4-(2-(trans-4-acetamidocyclohexyloxy)-4-fluorophenylamino)-N-(3-dimethylamino)propyl)-5-methylthieno[2,3-d]pyrimidine-6-carboxamide

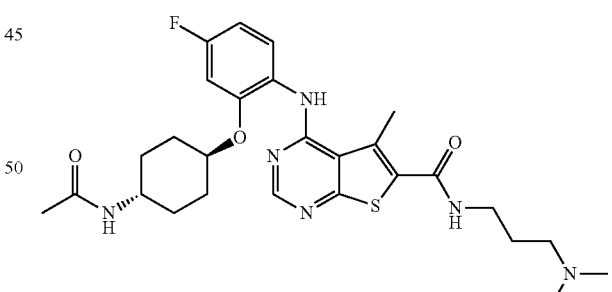

Prepared analogously to 1.4 from 0.092 g 4-(2-(trans-4-acetamidocyclohexyloxy) 4-fluorophenylamino)-5-methylthieno[2,3-d]pyrimidine-6-carboxylic acid (cpd.5.2) and 3-(dimethylamino)propylamine (126 µl).

Yield: 0.050 g

ESI mass spectrum: m/z=543 (M+H)$^+$ $R_t$ (HPLC): 1.24 min (method X)

Example 7

4-(4-fluoro-2-(trans-4-(N-methylacetamidocyclohexyloxy)phenylamino)-5-methylthieno[2,3-d]pyrimidine-6-carboxamide

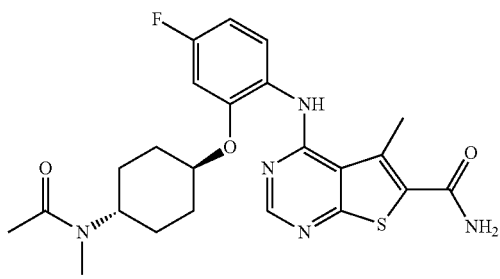 [SMILES: CC(=O)N(C)[C@H]1CC[C@H](Oc2cc(F)ccc2Nc2ncnc3sc(C(N)=O)c(C)c23)CC1]

7.1 Methyl 4-(4-fluoro-2-(trans-4-(N-methylacetamido)cyclohexyloxy)phenylamino)-5-methylthieno[2,3-d]pyrimidine-6-carboxylate

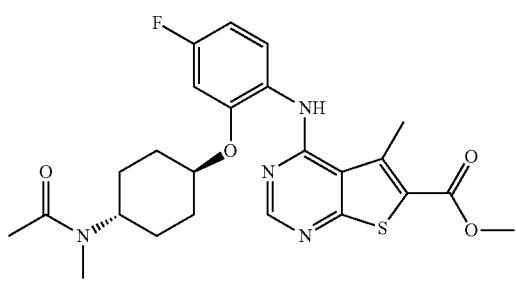 [SMILES: COC(=O)c1sc2ncnc(Nc3ccc(F)cc3O[C@H]3CC[C@H](N(C)C(C)=O)CC3)c2c1C]

Prepared analogously to 1.1 from intermediate VII (0.255 g) and 4-chloro-5-methyl-thieno[2,3-d]pyrimidine-6-carboxylic acid methyl ester (0.184 g).

Yield: 0.225 g

7.2 4-(4-Fluoro-2-(trans-4-(N-methylacetamido)cyclohexyloxy)phenylamino)-5-methylthieno[2,3-d]pyrimidine-6-carboxylic acid

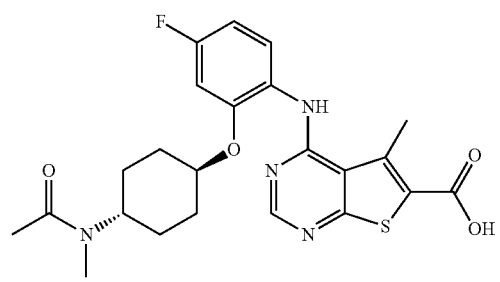 [SMILES: CC(=O)N(C)[C@H]1CC[C@H](Oc2cc(F)ccc2Nc2ncnc3sc(C(=O)O)c(C)c23)CC1]

Prepared analogously to 1.3 from 0.225 g methyl 4-(4-fluoro-2-(trans-4-(N-methylacetamidocyclohexyloxy)phenylamino)-5-methylthieno[2,3-d]pyrimidine-6-carboxylate (cpd.7.1).

Yield: 0.221 g

7.3 4-(4-fluoro-2-(trans-4-(N-methylacetamidocyclohexyloxy)phenylamino)-5-methylthieno[2,3-d]pyrimidine-6-carboxamide

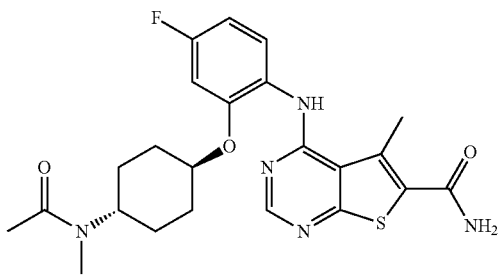 [SMILES: CC(=O)N(C)[C@H]1CC[C@H](Oc2cc(F)ccc2Nc2ncnc3sc(C(N)=O)c(C)c23)CC1]

Prepared analogously to 1.4 from 0.118 g 4-(4-fluoro-2-(trans-4-(N-methylacetamido)cyclohexyloxy)phenylamino)-5-methylthieno[2,3-d]pyrimidine-6-carboxylic acid (cpd.7.2).

Yield: 0.062 g

ESI mass spectrum: m/z=472 (M+H)$^+$ $R_t$ (HPLC): 1.34 min (method X)

Example 8

N-(3-(dimethylamino)propyl)-4-(4-fluoro-2-(trans-4-(N-methylacetamido)cyclohexyloxy)phenylamino)-5-methylthieno[2,3-d]pyrimidine-6-carboxamide

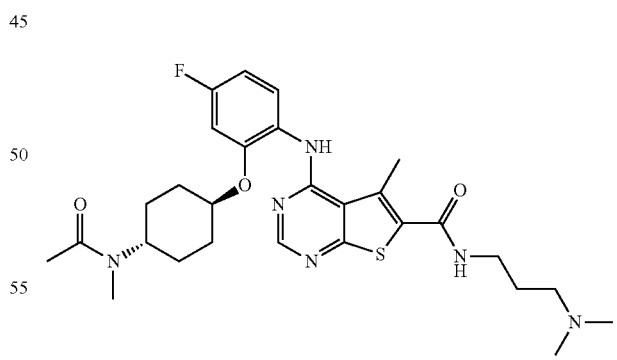

Prepared analogously to 1.4 from 0.094 g 4-(4-Fluoro-2-(trans-4-(N-methylacetamido)cyclohexyloxy)phenylamino)-5-methylthieno[2,3-d]pyrimidine-6-carboxylic acid (cpd.7.2) and 3-(dimethylamino)propylamine (126 µl).

Yield: 0.060 g

ESI mass spectrum: m/z=557 (M+H)$^+$ $R_t$ (HPLC): 1.27 min (method X)

Example 9

4-(4-Fluoro-2-(cis-4-(N-methylmethylsulfonamido)cyclohexyloxy)phenylamino)-5-methylthieno[2,3-d]pyrimidine-6-carboxamide

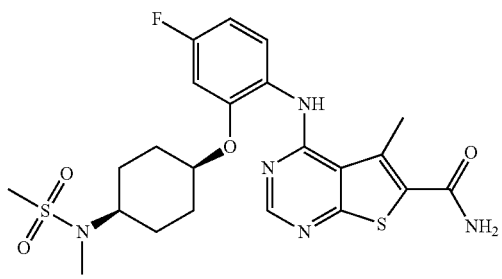 [SMILES: Cc1c(C(N)=O)sc2ncnc(Nc3ccc(F)cc3O[C@H]3CC[C@@H](N(C)S(C)(=O)=O)CC3)c12]

9.1 Methyl 4-(4-fluoro-2-(cis-4-(N-methylmethylsulfonamido)cyclohexyloxy)phenylamino)-5-methylthieno[2,3-d]pyrimidine-6-carboxylate

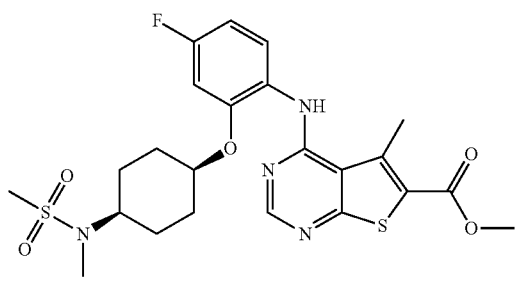

Prepared analogously to 1.1 from intermediate VIII (0.229 g) and 4-chloro-5-methyl-thieno[2,3-d]pyrimidine-6-carboxylic acid methyl ester (0.146 g).
Yield: 0.213 g

9.2 4-(4-Fluoro-2-(cis-4-(N-methylmethylsulfonamido)cyclohexyloxy)phenylamino)-5-methylthieno[2,3-d]pyrimidine-6-carboxylic acid

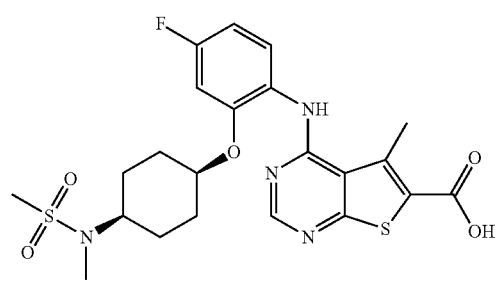 [SMILES: Cc1c(C(=O)O)sc2ncnc(Nc3ccc(F)cc3O[C@H]3CC[C@@H](N(C)S(C)(=O)=O)CC3)c12]

Prepared analogously to 1.3 from 0.213 g methyl 4-(4-fluoro-2-(cis-4-(N-methylmethylsulfonamido)cyclohexyloxy)phenylamino)-5-methylthieno[2,3-d]pyrimidine-6-carboxylate (cpd.9.1).
Yield: 0.205 g

9.3 4-(4-Fluoro-2-(cis-4-(N-methylmethylsulfonamido)cyclohexyloxy)phenylamino)-5-methylthieno[2,3-d]pyrimidine-6-carboxamide

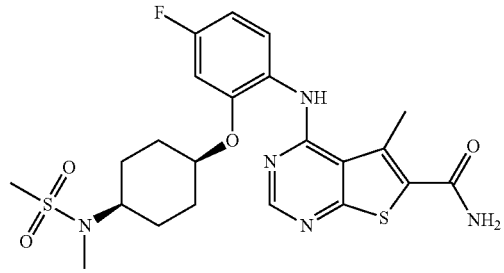 [SMILES: Cc1c(C(N)=O)sc2ncnc(Nc3ccc(F)cc3O[C@H]3CC[C@@H](N(C)S(C)(=O)=O)CC3)c12]

Prepared analogously to 1.4 from 0.193 g 4-(4-fluoro-2-(cis-4-(N-methylmethylsulfonamido)cyclohexyloxy)phenylamino)-5-methylthieno[2,3-d]pyrimidine-6-carboxylic acid (cpd.9.2).
Yield: 0.096 g
ESI mass spectrum: m/z=508 (M+H)$^+$
R$_t$ (HPLC): 1.28 min (method X)

Example 10

4-(4-fluoro-2-(cis-4-(N-methylacetamidocyclohexyloxy)phenylamino)-5-methylthieno[2,3-d]pyrimidine-6-carboxamide

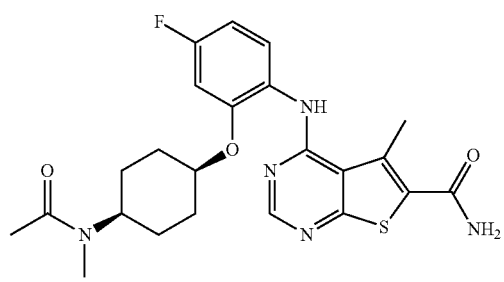 [SMILES: CC(=O)N(C)[C@H]1CC[C@@H](Oc2cc(F)ccc2Nc2ncnc3sc(C(N)=O)c(C)c23)CC1]

10.1 Methyl 4-(4-fluoro-2-(cis-4-(N-methylacetamidocyclohexyloxy)phenylamino)-5-methylthieno[2,3-d]pyrimidine-6-carboxylate

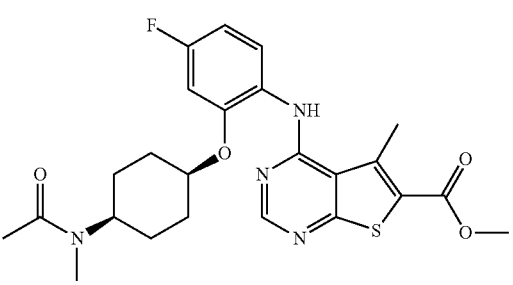 [SMILES: COC(=O)c1sc2ncnc(Nc3ccc(F)cc3O[C@H]3CC[C@@H](N(C)C(C)=O)CC3)c2c1C]

Prepared analogously to 1.1 from intermediate IX (0.217 g) and 4-chloro-5-methyl-thieno[2,3-d]pyrimidine-6-carboxylic acid methyl ester (0.155 g).
Yield: 0.157 g 10.2 4-(4-Fluoro-2-(cis-4-(N-methylacetamido)cyclohexyloxy)phenylamino)-5-methylthieno[2,3-d]pyrimidine-6-carboxylic acid

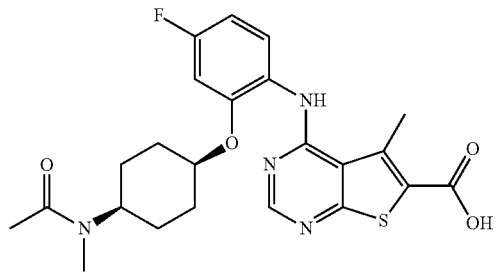 [SMILES: CC(=O)N(C)[C@H]1CC[C@@H](Oc2cc(F)ccc2Nc2ncnc3sc(C(=O)O)c(C)c23)CC1]

Prepared analogously to 1.3 from 0.157 g methyl 4-(4-fluoro-2-(cis-4-(N-methylacetamido)cyclohexyloxy)phenylamino)-5-methylthieno[2,3-d]pyrimidine-6-carboxylate (cpd.10.1).

Yield: 0.118 g 10.3 4-(4-Fluoro-2-(cis-4-(N-methylacetamido)cyclohexyloxy)phenylamino)-5-methylthieno[2,3-d]pyrimidine-6-carboxamide

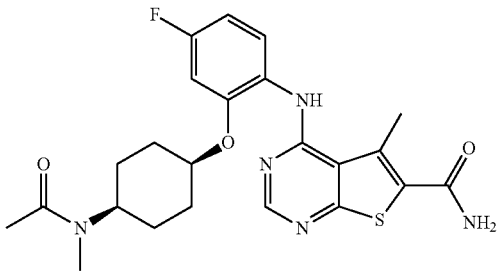 [SMILES: CC(=O)N(C)[C@H]1CC[C@@H](Oc2cc(F)ccc2Nc2ncnc3sc(C(N)=O)c(C)c23)CC1]

Prepared analogously to 1.4 from 0.113 g 4-(4-fluoro-2-(cis-4-(N-methylacetamido)cyclohexyloxy)phenylamino)-5-methylthieno[2,3-d]pyrimidine-6-carboxylic acid (cpd.10.2).

Yield: 0.084 g

ESI mass spectrum: m/z=472 (M+H)$^+$

R$_t$ (HPLC): 1.24 min (method X)

Example 11

Methyl trans-4-(2-(6-carbamoyl-5-methylthieno[2,3-d]pyrimidin-4-ylamino)-5-fluorophenoxy)cyclohexyl(methyl)carbamate

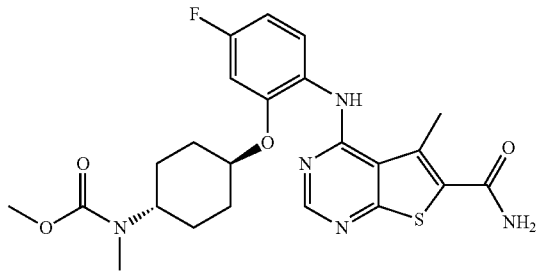 [SMILES: COC(=O)N(C)[C@H]1CC[C@H](Oc2cc(F)ccc2Nc2ncnc3sc(C(N)=O)c(C)c23)CC1]

11.1 Methyl 4-(4-fluoro-2-(trans-4-(methoxycarbonyl(methyl)amino)cyclohexyloxy)phenylamino)-5-methylthieno[2,3-d]pyrimidine-6-carboxylate

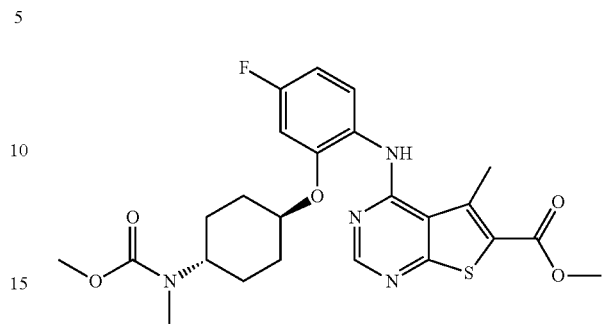

Prepared analogously to 1.1 from intermediate X (0.236 g) and 4-chloro-5-methyl-thieno[2,3-d]pyrimidine-6-carboxylic acid methyl ester (0.166 g).

Yield: 0.311 g 11.2 4-(4-Fluoro-2-(trans-4-(methoxycarbonyl(methyl)amino)cyclohexyloxy)phenylamino)-5-methylthieno[2,3-d]pyrimidine-6-carboxylic acid

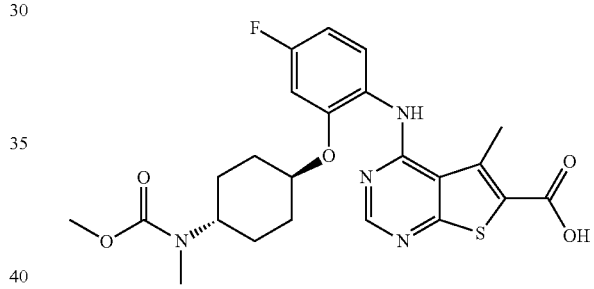

Prepared analogously to 1.3 from 0.311 g methyl 4-(4-fluoro-2-(trans-4-(methoxycarbonyl(methyl)amino)cyclohexyloxy)phenylamino)-5-methylthieno[2,3-d]pyrimidine-6-carboxylate (cpd.11.1).

Yield: 0.249 g 11.3 Methyl trans-4-(2-(6-carbamoyl-5-methylthieno[2,3-d]pyrimidin-4-ylamino)-5-fluorophenoxy)cyclohexyl(methyl)carbamate

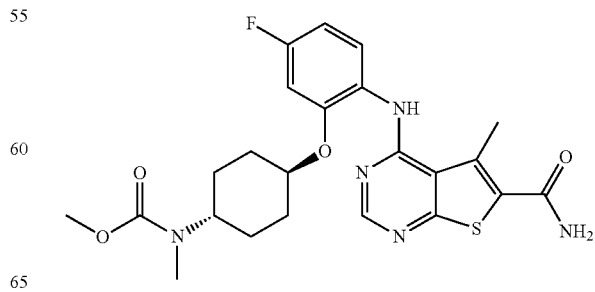

Prepared analogously to 1.4 from 0.098 g 4-(4-fluoro-2-(trans-4-(methoxycarbonyl(methyl)amino)cyclohexyloxy)phenylamino)-5-methylthieno[2,3-d]pyrimidine-6-carboxylic acid (cpd.11.2).

Yield: 0.021 g
ESI mass spectrum: m/z=488 (M+H)+
$R_t$ (HPLC): 1.42 min (method X)

Example 12

4-(4-Fluoro-2-(trans-4-(methylamino)cyclohexyloxy)phenylamino)-5-methylthieno[2,3-d]pyrimidine-6-carboxamide

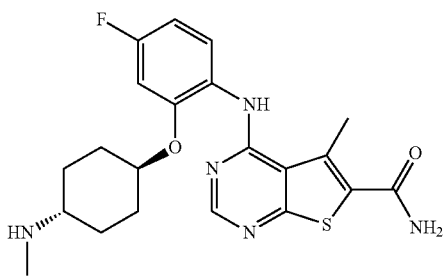 [SMILES: CN[C@H]1CC[C@H](Oc2cc(F)ccc2Nc2ncnc3sc(C(N)=O)c(C)c23)CC1]

12.1 Methyl 4-(2-(trans-4-(tert-butoxycarbonyl(methyl)amino)cyclohexyloxy)-4-fluorophenylamino)-5-methylthieno[2,3-d]pyrimidine-6-carboxylate

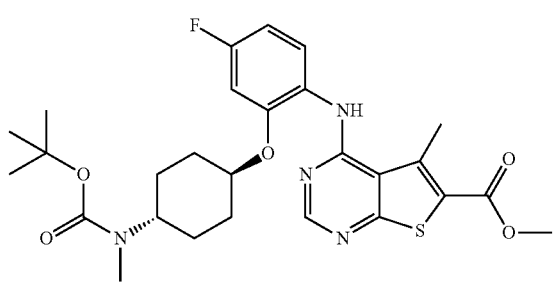 [SMILES: COC(=O)c1sc2ncnc(Nc3ccc(F)cc3O[C@H]3CC[C@H](N(C)C(=O)OC(C)(C)C)CC3)c2c1C]

Prepared analogously to 1.1 from intermediate XI (1.29 g) and 4-chloro-5-methyl-thieno[2,3-d]pyrimidine-6-carboxylic acid methyl ester (0.728 g). Purification by chromatography.

Yield: 0.439 g 12.2 4-(2-(trans-4-(tert-Butoxycarbonyl(methyl)amino)cyclohexyloxy)-4-fluorophenylamino)-5-methylthieno[2,3-d]pyrimidine-6-carboxylic acid

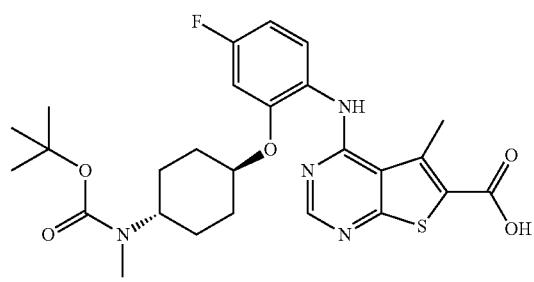 [SMILES: Cc1c(C(=O)O)sc2ncnc(Nc3ccc(F)cc3O[C@H]3CC[C@H](N(C)C(=O)OC(C)(C)C)CC3)c12]

Prepared analogously to 1.3 from 0.747 g methyl 4-(2-(trans-4-(tertbutoxycarbonyl(methyl)amino)cyclohexyloxy)-4-fluorophenylamino)-5-methylthieno[2,3-d]pyrimidine-6-carboxylate (cpd.12.1).

Yield: 0.747 g 12.3 tert-Butyl-trans-4-(-2-(6-carbamoyl-5-methylthieno[2,3-d]pyrimidin-4-ylamino)-5-fluorophenoxy)cyclohexyl(methyl)carbamate

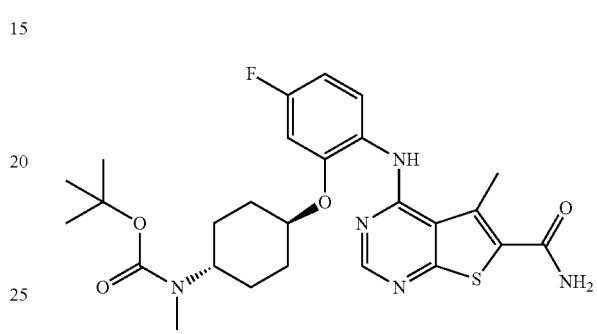

Prepared analogously to 1.4 from 0.747 g 4-(2-(trans-4-(tertbutoxycarbonyl(methyl)amino)cyclohexyloxy)-4-fluorophenylamino)-5-methylthieno[2,3-d]pyrimidine-6-carboxylic acid (cpd.12.2).

Yield: 0.684 g 12.4 4-(4-Fluoro-2-(trans-4-(methylamino)cyclohexyloxy)phenylamino)-5-methylthieno[2,3-d]pyrimidine-6-carboxamide

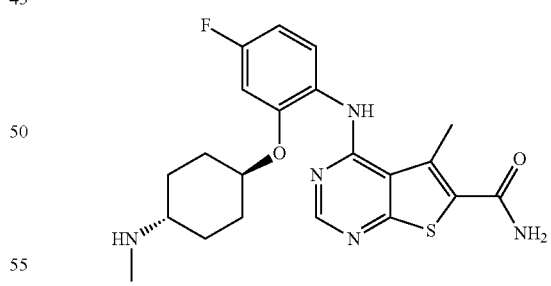

A mixture of 0.684 g tert-butyl-trans-4-(-2-(6-carbamoyl-5-methylthieno[2,3-d]pyrimidin-4-ylamino)-5-fluorophenoxy)cyclohexyl(methyl)carbamate in 5 ml 4 M HCl/dioxane and 5 ml MeOH was stirred at rt for 1.5 h. The reaction mixture was concentrated in vacuo. The crude was purified by chromatography to give the desired product.

Yield: 0.387 g

Example 13

Racemic 4-(4-Fluoro-2-(trans-2-(N-methylmethyl-sulfonamido)cyclohexyloxy)phenylamino)-5-methylthieno[2,3-d]pyrimidine-6-carboxamide

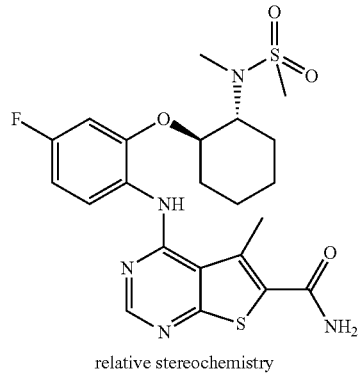 [SMILES: Cc1c(C(N)=O)sc2ncnc(Nc3ccc(F)cc3O[C@@H]3CCCC[C@H]3N(C)S(C)(=O)=O)c12]
relative stereochemistry

13.1 racemic Methyl 4-(4-fluoro-2-(trans-2-(N-methylmethylsulfonamido)cyclohexyloxy)phenylamino)-5-methylthieno[2,3-d]pyrimidine-6-carboxylate

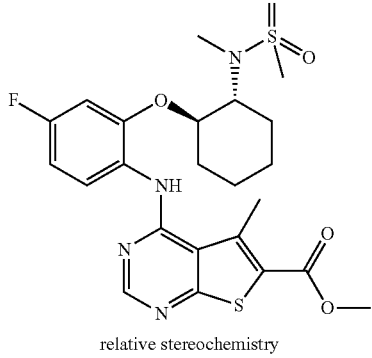
relative stereochemistry

Prepared analogously to 1.1 from intermediate XII (0.231 g) and 4-chloro-5-methyl-thieno[2,3-d]pyrimidine-6-carboxylic acid methyl ester (0.147 g).
Yield: 0.279 g

13.2 racemic 4-(4-Fluoro-2-(trans-2-(N-methylmethylsulfonamido)cyclohexyloxy)phenylamino)-5-methylthieno[2,3-d]pyrimidine-6-carboxylic acid

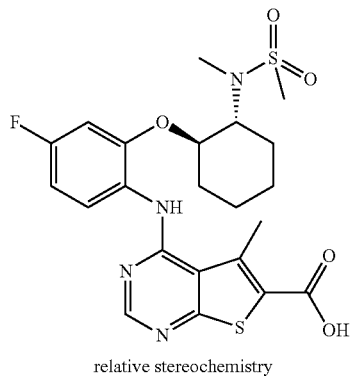 [SMILES: Cc1c(C(=O)O)sc2ncnc(Nc3ccc(F)cc3O[C@@H]3CCCC[C@H]3N(C)S(C)(=O)=O)c12]
relative stereochemistry

Prepared analogously to 1.3 from 0.279 g racemic methyl 4-(4-fluoro-2-(trans-2-(N-methylmethylsulfonamido)cyclohexyloxy)phenylamino)-5-methylthieno[2,3-d]pyrimidine-6-carboxylate (cpd.13.1).
Yield: 0.242 g

13.3 racemic 4-(4-Fluoro-2-(trans-2-(N-methylmethylsulfonamido)cyclohexyloxy)phenylamino)-5-methylthieno[2,3-d]pyrimidine-6-carboxamide

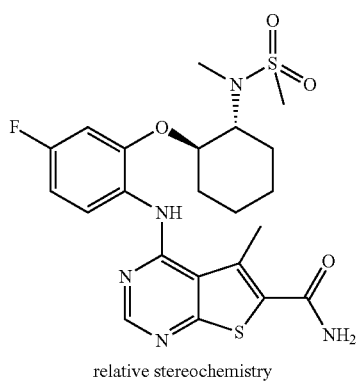 [SMILES: Cc1c(C(N)=O)sc2ncnc(Nc3ccc(F)cc3O[C@@H]3CCCC[C@H]3N(C)S(C)(=O)=O)c12]
relative stereochemistry

Prepared analogously to 1.4 from 0.101 g racemic 4-(4-fluoro-2-(trans-2-(N-methylmethylsulfonamido)cyclohexyloxy)phenylamino)-5-methylthieno[2,3-d]pyrimidine-6-carboxylic acid (cpd.13.2).
Yield: 0.015 g
ESI mass spectrum: m/z=508 (M+H)$^+$
R$_t$ (HPLC): 1.33 min (method X)

Example 14

Racemic 4-(4-fluoro-2-(trans-2-(N-methylacetamido)cyclohexyloxy)phenylamino)-5-methylthieno[2,3-d]pyrimidine-6-carboxamide

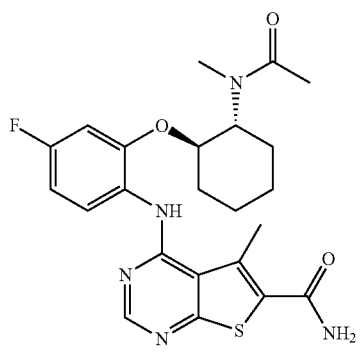
relative stereochemistry

14.1 racemic Methyl 4-(4-fluoro-2-(trans-2-(N-methylacetamido)cyclohexyloxy)phenylamino)-5-methylthieno[2,3-d]pyrimidine-6-carboxylate

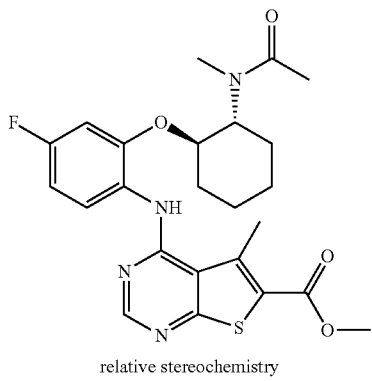 [SMILES: COC(=O)c1sc2ncnc(Nc3ccc(F)cc3O[C@@H]3CCCC[C@H]3N(C)C(C)=O)c2c1C]

relative stereochemistry

Prepared analogously to 1.1 from intermediate XIII (0.225 g) and 4-chloro-5-methyl-thieno[2,3-d]pyrimidine-6-carboxylic acid methyl ester (0.162 g).
Yield: 0.180 g

14.2 racemic 4-(4-Fluoro-2-(trans-2-(N-methylacetamido)cyclohexyloxy)phenylamino)-5-methylthieno[2,3-d]pyrimidine-6-carboxylic acid

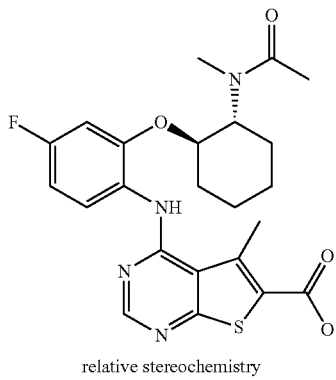 [SMILES: CC(=O)N(C)[C@@H]1CCCC[C@H]1Oc1cc(F)ccc1Nc1ncnc2sc(C(N)=O)c(C)c12]

relative stereochemistry

Prepared analogously to 1.3 from 0.180 g racemic methyl 4-(4-fluoro-2-(trans-2-(N-methylacetamidocyclohexyloxy)phenylamino)-5-methylthieno[2,3-d]pyrimidine-6-carboxylate (cpd.14.1).
Yield: 0.170 g

14.3 4-(4-Fluoro-2-(trans-2-(N-methylacetamido)cyclohexyloxy)phenyl amino)-5-methylthieno[2,3-d]pyrimidine-6-carboxamide

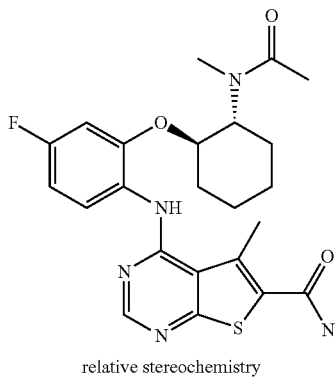

relative stereochemistry

Prepared analogously to 1.4 from 0.095 g 4-(4-fluoro-2-(trans-2-(N-methylacetamido)cyclohexyloxy)phenylamino)-5-methylthieno[2,3-d]pyrimidine-6-carboxylic acid (cpd.14.2). Purification by chromatography.
Yield: 0.040 g
ESI mass spectrum: m/z=472 (M+H)$^+$
$R_t$ (HPLC): 1.34 min (method X)

Example 15

4-(2-(trans-4-aminocyclohexyloxy)-4-fluorophenylamino)-5-methylthieno[2,3-d]pyrimidine-6-carboxamide

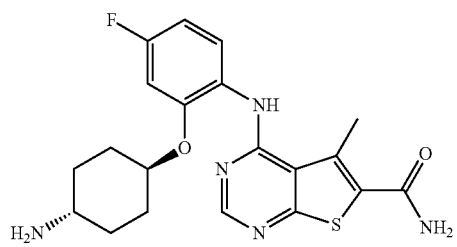 [SMILES: Cc1c(C(N)=O)sc2ncnc(Nc3ccc(F)cc3O[C@H]3CC[C@H](N)CC3)c12]

15.1 Methyl 4-(4-fluoro-2-(trans-4-(2,2,2-trifluoroacetamido)cyclohexyloxy)phenyl amino)-5-methylthieno[2,3-d]pyrimidine-6-carboxylate

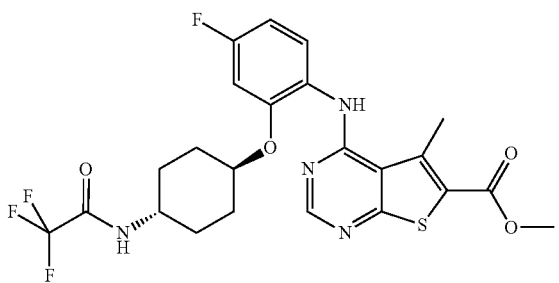 [SMILES: COC(=O)c1sc2ncnc(Nc3ccc(F)cc3O[C@H]3CC[C@H](NC(=O)C(F)(F)F)CC3)c2c1C]

Prepared analogously to 1.1 from intermediate XIV (0.050 g) and 4-chloro-5-methyl-thieno[2,3-d]pyrimidine-6-carboxylic acid methyl ester (0.038 g).
Yield: 0.062 g

15.2 4-(2-(trans-4-Aminocyclohexyloxy)-4-fluorophenylamino)-5-methylthieno[2,3-d]pyrimidine-6-carboxamide

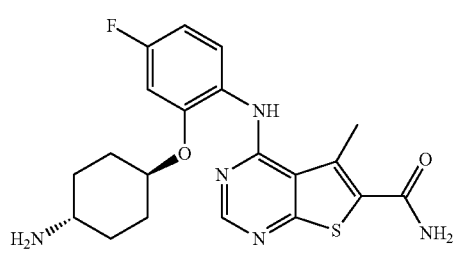 [SMILES: Cc1c(C(N)=O)sc2ncnc(Nc3ccc(F)cc3O[C@H]3CC[C@H](N)CC3)c12]

0.100 g methyl 4-(4-fluoro-2-(trans-4-(2,2,2-trifluoroacetamido)cyclohexyloxy)phenylamino)-5-methylthieno[2,3-d]pyrimidine-6-carboxylate (cpd.15.1) and 2 ml 7 M ammonia in MeOH were stirred in a pressure tube overnight at 70° C. and 8 days at 90° C. The reaction mixture was concentrated in vacuo. The residue was purified by chromatography to give the desired compound.

Yield: 0.067 g

Example 16

4-(4-Fluoro-2-(trans-4-(1-methylpiperidin-4-ylamino)cyclohexyloxy)phenylamino)-5-methylthieno[2,3-d]pyrimidine-6-carboxamide

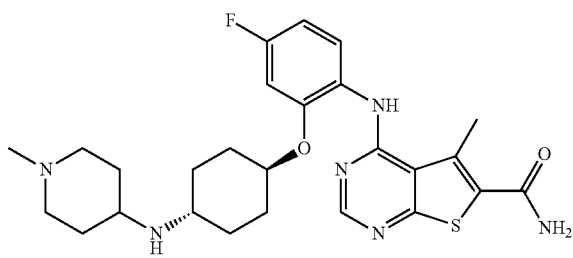 [SMILES: Cc1c(C(N)=O)sc2ncnc(Nc3ccc(F)cc3O[C@H]3CC[C@H](NC4CCN(C)CC4)CC3)c12]

0.019 g 1-methyl-4-piperidone in 1.5 ml MeOH followed by 1 drop acetic acid were added to a mixture of 0.070 g 4-(2-(trans-4-aminocyclohexyloxy)-4-fluorophenylamino)-5-methylthieno[2,3-d]pyrimidine-6-carboxamide (cpd.15.2) in 2 ml methanol. Sodium cyanoborohydride was added when the mixture was stirred at rt for 40 min. After stirring at 50° C. for 3 h further 0.010 g 1-methyl-4-piperidone and 0.010 g sodium cyanoborohydride were added and heating was continued overnight.

The reaction mixture was concentrated in vacuo. The residue was purified by chromatography followed by recrystallisation from MeOH.

Yield: 0.056 g
ESI mass spectrum: m/z=513 (M+H)$^+$
R$_t$ (HPLC): 1.16 min (method X)

Example 17

4-(4-Fluoro-2-(cis-3-(N-methylamino)cyclohexyloxy)phenylamino)-5-methylthieno[2,3-d]pyrimidine-6-carboxamide

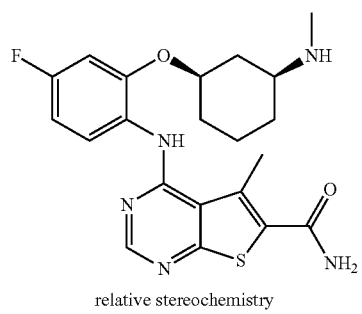 [SMILES: CN[C@H]1CCC[C@@H](Oc2cc(F)ccc2Nc2ncnc3sc(C(N)=O)c(C)c23)C1]

relative stereochemistry 17.1 Methyl 4-(2-(3-(tert-butoxycarbonyl(methyl)amino)cyclohexyloxy-4-fluorophenylamino)-5-methylthieno[2,3-d]pyrimidine-6-carboxylate

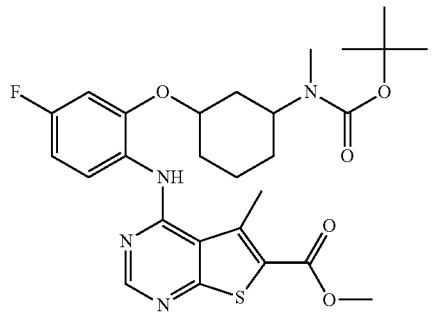 [SMILES: COC(=O)c1sc2ncnc(Nc3ccc(F)cc3OC3CCCC(N(C)C(=O)OC(C)(C)C)C3)c2c1C]

Prepared analogously to 1.1 from intermediate XV (0.170 g) and 4-chloro-5-methyl-thieno[2,3-d]pyrimidine-6-carboxylic acid methyl ester (0.130 g). Purification by chromatography (gradient: CH2Cl2→2% MeOH/CH2Cl2 using the Biotage SP4)

Yield: 0.190 g 17.2 4-(2-(3-(tert-Butoxycarbonyl(methyl)amino)cyclohexyloxy-4-fluorophenylamino)-5-methylthieno[2,3-d]pyrimidine-6-carboxylic acid

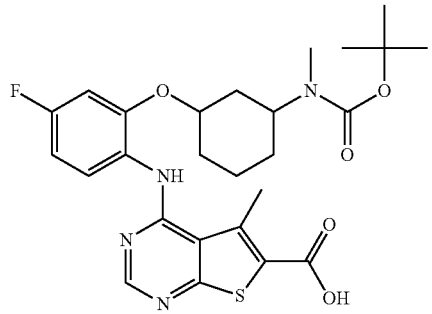 [SMILES: Cc1c(C(=O)O)sc2ncnc(Nc3ccc(F)cc3OC3CCCC(N(C)C(=O)OC(C)(C)C)C3)c12]

Prepared analogously to 1.3 from 0.190 g methyl 4-(2-(3-(tertbutoxycarbonyl(methyl)amino)cyclohexyloxy-4-fluorophenylamino)-5-methylthieno[2,3-d]pyrimidine-6-carboxylate (cpd.17.1). The crude was triturated in hot MeCN.

Yield: 0.120 g 17.3 tert-Butyl 3-(2-(6-carbamoyl-5-methylthieno[2,3-d]pyrimidin-4-ylamino)-5-fluorophenoxy)cyclohexyl(methyl)carbamate

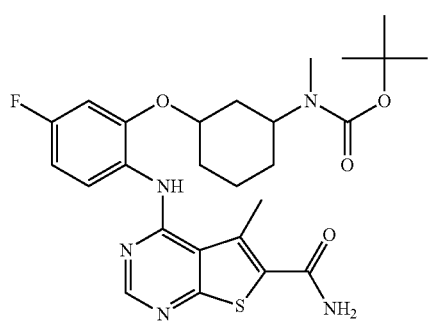 [SMILES: Cc1c(C(N)=O)sc2ncnc(Nc3ccc(F)cc3OC3CCCC(N(C)C(=O)OC(C)(C)C)C3)c12]

Prepared analogously to 1.4 from 0.110 g 4-(2-(3-(tertbutoxycarbonyl(methyl)amino)cyclohexyloxy-4-fluorophenylamino)-5-methylthieno[2,3-d]pyrimidine-6-carboxylic acid (cpd.17.2). Purification by chromatography (gradient: CH2Cl2→20% MeOH/CH2Cl2 using the Biotage SP4)

Yield: 0.090 g

17.4 4-(4-Fluoro-2-(cis-3-(N-methylamino)cyclohexyloxy)phenylamino)-5-methylthieno[2,3-d]pyrimidine-6-carboxamide

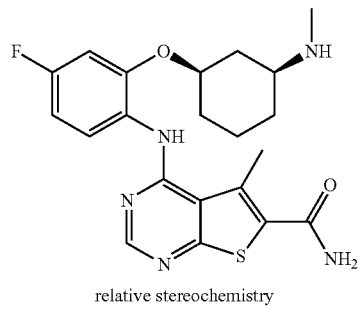 [SMILES: CN[C@H]1CCC[C@@H](Oc2cc(F)ccc2Nc2ncnc3sc(C(N)=O)c(C)c23)C1]

relative stereochemistry

220 μl 4 M HCl in dioxane was added to 0.093 g tert-butyl 3-(2-(6-carbamoyl-5-methylthieno[2,3-d]pyrimidin-4-ylamino)-5-fluorophenoxy)cyclohexyl(methyl)carbamate (cpd. 17.3) in 4 ml dioxane. The reaction mixture was stirred for 1 h at rt when further aliquots of 4 M HCl in dioxane were added. methanol was added and the mixture stirred for 2 days at rt. The mixture was purified by chromatography (gradient: CH2Cl2→20% MeOH/CH2Cl2 using the Biotage SP4).

ESI mass spectrum: m/z=430 (M+H)$^+$

R$_t$ (HPLC): 1.20 min (method X)

Example 18

4-(4-Fluoro-2-(trans-3-(N-methylamino)cyclohexyloxy)phenylamino)-5-methylthieno[2,3-d]pyrimidine-6-carboxamide

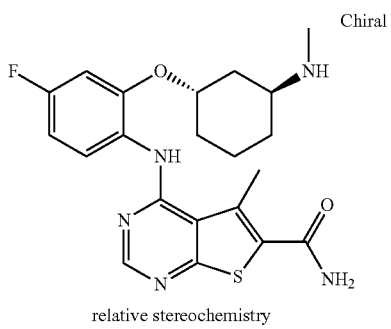 [SMILES: CN[C@H]1CCC[C@H](Oc2cc(F)ccc2Nc2ncnc3sc(C(N)=O)c(C)c23)C1]

relative stereochemistry

Prepared analogously to 17.4 from 0.093 g tert-butyl 3-(2-(6-carbamoyl-5-methylthieno[2,3-d]pyrimidin-4-ylamino)-5-fluorophenoxy)cyclohexyl(methyl)carbamate (cpd.17.3).

ESI mass spectrum: m/z=430 (M+H)$^+$

R$_t$ (HPLC): 1.20 min (method X)

Example 19

4-(2-(1,4-Dioxaspiro[4.5]decan-8-yloxy)-4-fluorophenylamino)-5-methylthieno[2,3-d]pyrimidine-6-carboxamide

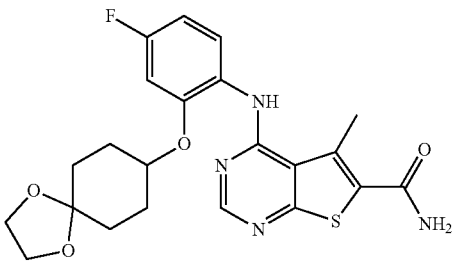 [SMILES: Cc1c(C(N)=O)sc2ncnc(Nc3ccc(F)cc3OC3CCC4(CC3)OCCO4)c12]

19.1 Methyl 4-(2-(1,4-dioxaspiro[4.5]decan-8-yloxy)-4-fluorophenylamino)-5-methylthieno[2,3-d]pyrimidine-6-carboxylate

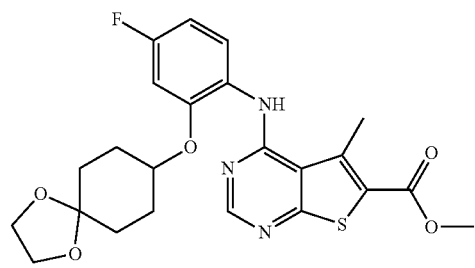 [SMILES: COC(=O)c1sc2ncnc(Nc3ccc(F)cc3OC3CCC4(CC3)OCCO4)c2c1C]

Prepared analogously to 1.1 from intermediate III (2.300 g) and 4-chloro-5-methyl-thieno[2,3-d]pyrimidine-6-carboxylic acid methyl ester (2.080 g) at 80° C.

Yield: 3.600 g

ESI mass spectrum: m/z=474 (M+H)$^+$

R$_t$ (HPLC): 1.65 min (method X)

19.2 4-(2-(1,4-Dioxaspiro[4.5]decan-8-yloxy)-4-fluorophenylamino)-5-methylthieno[2,3-d]pyrimidine-6-carboxylic acid

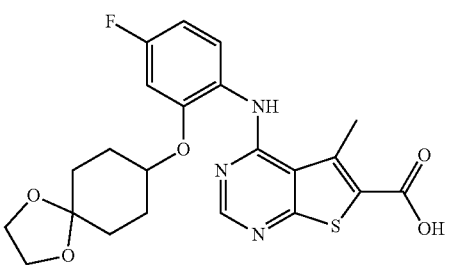 [SMILES: Cc1c(C(=O)O)sc2ncnc(Nc3ccc(F)cc3OC3CCC4(CC3)OCCO4)c12]

1.065 g lithium hydroxide monohydrate was added to 2.003 g methyl 4-(2-(1,4-dioxaspiro[4.5]decan-8-yloxy)-4-fluorophenylamino)-5-methylthieno[2,3-d]pyrimidine-6-carboxylate (cpd.19.1) in 100 ml THF and 60 ml water. After stirring at rt overnight the reaction mixture was quenched by 2 M aq. HCl and concentrated in vacuo. The resulting aq. layer was filtered. The filtercake was dried and triturated with MeOH:Et$_2$O 20:1 to give the desired compound.

Yield: 1.280 g

19.3 4-(2-(1,4-Dioxaspiro[4.5]decan-8-yloxy)-4-fluorophenylamino)-5-methylthieno[2,3-d]pyrimidine-6-carboxamide

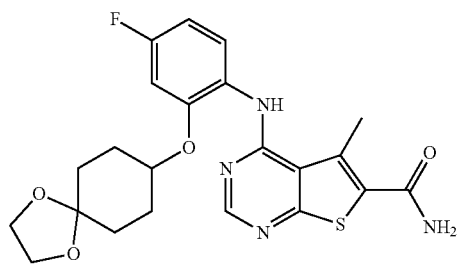 [SMILES: Cc1c(C(N)=O)sc2ncnc(Nc3ccc(F)cc3OC3CCC4(CC3)OCCO4)c12]

Prepared analogously to 1.4 from 1.287 g 4-(2-(1,4-dioxaspiro[4.5]decan-8-yloxy)-4-fluorophenylamino)-5-methylthieno[2,3-d]pyrimidine-6-carboxylic acid (cpd.19.2). Purification by chromatography.

Yield: 1.210 g

Example 20

Methyl 4-(4-fluoro-2-(4-oxocyclohexyloxy)phenylamino)-5-methylthieno[2,3-d]pyrimidine-6-carboxylate

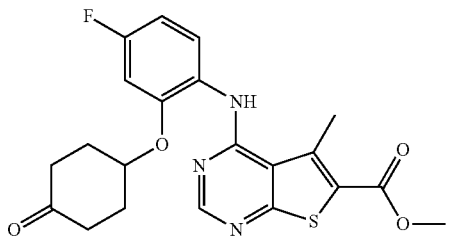 [SMILES: COC(=O)c1sc2ncnc(Nc3ccc(F)cc3OC3CCC(=O)CC3)c2c1C]

1.000 g p-toluenesulfonic acid was added to 0.500 g methyl 4-(2-(1,4-dioxaspiro[4.5]decan-8-yloxy)-4-fluorophenylamino)-5-methylthieno[2,3-d]pyrimidine-6-carboxylate (cpd.19.1) in 10 ml THF and 5 ml water. After refluxing overnight the reaction mixture was adjusted to pH 8 using aq. Na$_2$CO$_3$. The aq. layer was extracted with chloroform. The combined extracts were passed through a hydrophobic frit and concentrated to give the desired compound.

Yield: 0.413 g

ESI mass spectrum: m/z=430 (M+H)$^+$

R$_t$ (HPLC): 1.50 min (method X)

Example 21

4-(4-Fluoro-2-(4-oxocyclohexyloxy)phenylamino)-5-methylthieno[2,3-d]pyrimidine-6-carboxamide

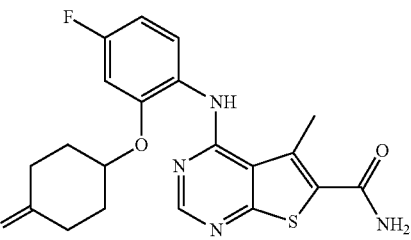

Prepared analogously to Example 20 from 1.211 g 4-(2-(1,4-dioxaspiro[4.5]decan-8-yloxy)-4-fluorophenylamino)-5-methylthieno[2,3-d]pyrimidine-6-carboxamide (cpd.19.3). The crude was triturated with MeOH.

Yield: 0.888 g

ESI mass spectrum: m/z=415 (M+H)$^+$

R$_t$ (HPLC): 1.27 min (method X)

Example 22

4-(4-Fluoro-2-(trans-4-((2-methoxyethyl)(methyl)amino)cyclohexyloxy)phenylamino)-5-methylthieno[2,3-d]pyrimidine-6-carboxamide

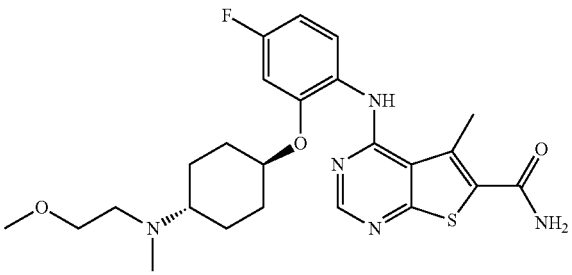 [SMILES: COCCN(C)[C@H]1CC[C@H](Oc2cc(F)ccc2Nc2ncnc3sc(C(N)=O)c(C)c23)CC1]

22.1 Methyl 4-(4-fluoro-2-(4-((2-methoxyethyl)(methyl)amino)cyclohexyloxy)phenylamino)-5-methylthieno[2,3-d]pyrimidine-6-carboxylate

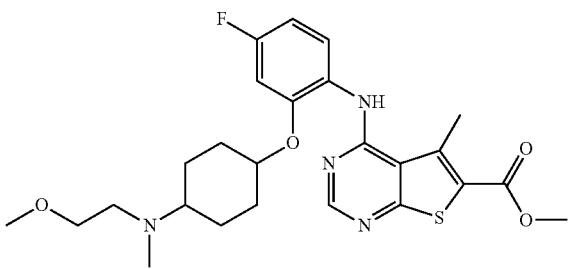

To a stirred mixture of 0.100 g methyl 4-(4-fluoro-2-(4-oxocyclohexyloxy)phenylamino)-5-methylthieno[2,3-d]pyrimidine-6-carboxylate (cpd.20) in 3 ml methylene chloride was added 0.045 g 2-(methoxyethyl)methylamine. After 15 min at rt 0.045 g sodium triacetoxyborohydride was added and stirring was continued overnight. The reaction was quenched by the addition of water. The mixture was passed through a hydrophobic frit and the organic layer was concentrated. The crude was crystallized in 7 M ammonia in MeOH to give the desired compound.

Yield: 0.062 g

22.2 4-(4-Fluoro-2-(trans-4-((2-methoxyethyl)(methyl)amino)cyclohexyloxy)phenylamino)-5-methylthieno[2,3-d]pyrimidine-6-carboxamide

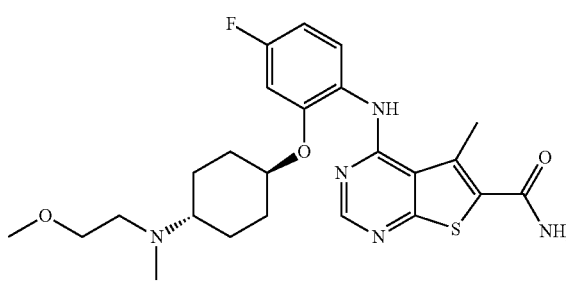

Prepared analogously to 15.2 from 0.060 g methyl 4-(4-fluoro-2-(4-((2-methoxyethyl)(methyl)amino)cyclohexyloxy)phenylamino)-5-methylthieno[2,3-d]pyrimidine-6-carboxylate (cpd.22.1) at 100° C. for 14 h. The title compound was obtained by HPLC separation.

Yield: 0.011 g
ESI mass spectrum: m/z=488 (M+H)$^+$
$R_t$ (HPLC): 1.22 min (method X)

Example 23

4-(4-Fluoro-2-(cis-4-((2-methoxyethyl)(methyl)amino)cyclohexyloxy)phenylamino)-5-methylthieno[2,3-d]pyrimidine-6-carboxamide

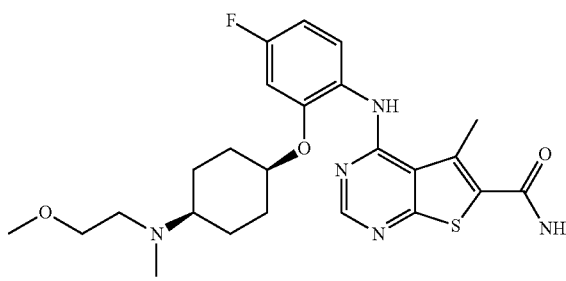

Prepared analogously to 15.2 from 0.060 g methyl 4-(4-fluoro-2-(4-((2-methoxyethyl)(methyl)amino)cyclohexyloxy)phenylamino)-5-methylthieno[2,3-d]pyrimidine-6-carboxylate (cpd.22.1) at 100° C. for 14 h. The title compound was obtained by HPLC separation.

Yield: 0.007 g
ESI mass spectrum: m/z=488 (M+H)$^+$
$R_t$ (HPLC): 1.16 min (method X)

Example 24

4-(4-Fluoro-2-(trans-4-(2-methoxyethylamino)cyclohexyloxy)phenylamino)-5-methylthieno[2,3-d]pyrimidine-6-amide

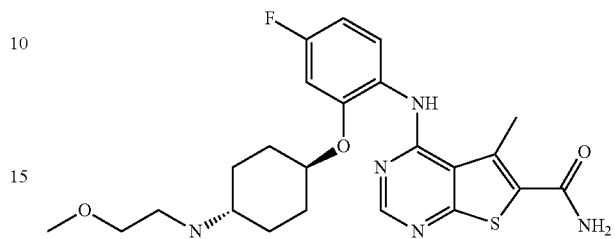

24.1 Methyl 4-(4-fluoro-2-(4-(2-methoxyethylamino)cyclohexyloxy)phenylamino)-5-methylthieno[2,3-d]pyrimidine-6-carboxylate

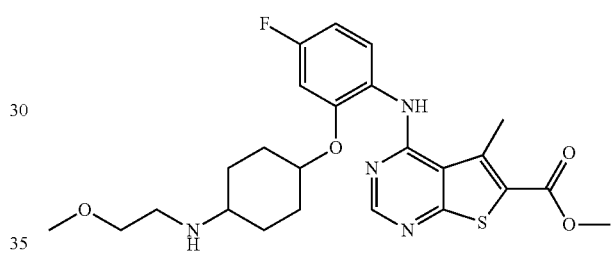

Prepared analogously to 22.1 from 0.249 g methyl 4-(4-fluoro-2-(4-oxocyclohexyloxy)phenylamino)-5-methylthieno[2,3-d]pyrimidine-6-carboxylate (cpd.20). Crystallisation was replaced by purification by chromatography.

Yield: 0.280 g

24.2 4-(4-Fluoro-2-(trans-4-(2-methoxyethylamino)cyclohexyloxy)phenylamino)-5-methylthieno[2,3-d]pyrimidine-6-carboxamide

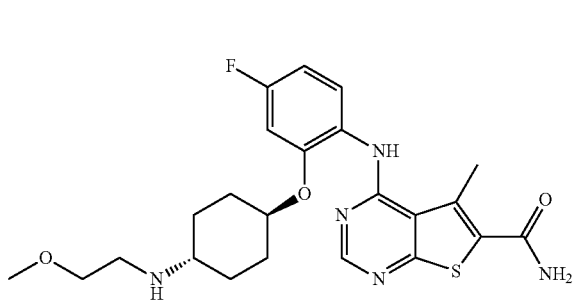 [SMILES: COCCN[C@H]1CC[C@H](Oc2cc(F)ccc2Nc2ncnc3sc(C(N)=O)c(C)c23)CC1]

Prepared analogously to 15.2 from 0.280 g methyl 4-(4-fluoro-2-(4-(2-methoxyethylamino)cyclohexyloxy)phenylamino)-5-methylthieno[2,3-d]pyrimidine-6-carboxylate (cpd.24.1). The title compound was obtained by HPLC separation.

Yield: 0.055 g
ESI mass spectrum: m/z=474 (M+H)$^+$
$R_t$ (HPLC): 1.21 min (method X)

Example 25

4-(4-Fluoro-2-(cis-4-(2-methoxyethylamino)cyclohexyloxy)phenylamino)-5-methylthieno[2,3-d]pyrimidine-6-carboxamide

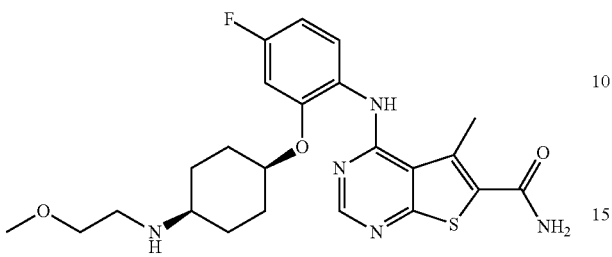

Prepared analogously to 15.2 from 0.280 g methyl 4-(4-fluoro-2-(4-(2-methoxyethylamino)cyclohexyloxy)phenylamino)-5-methylthieno[2,3-d]pyrimidine-6-carboxylate (cpd.24.1). The title compound was obtained by HPLC separation.

Yield: 0.104 g

ESI mass spectrum: m/z=474 (M+H)$^+$ $R_t$ (HPLC): 1.18 min (method X)

Example 26

4-(4-Fluoro-2-(trans-4-morpholinocyclohexyloxy)phenylamino)-5-methylthieno[2,3-d]pyrimidine-6-carboxamide

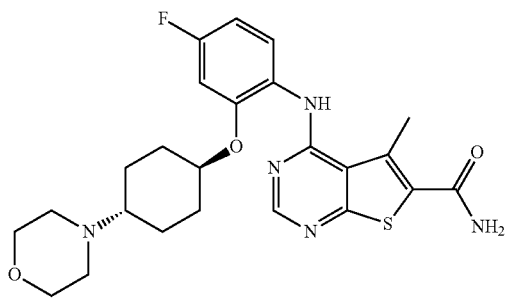 [SMILES: Cc1c(C(N)=O)sc2ncnc(Nc3ccc(F)cc3O[C@H]3CC[C@H](N4CCOCC4)CC3)c12]

26.1 Methyl 4-(4-fluoro-2-(4-morpholinocyclohexyloxy)phenylamino)-5-methylthieno[2,3-d]pyrimidine-6-carboxylate

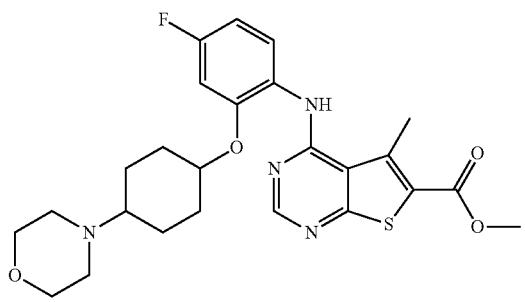 [SMILES: COC(=O)c1sc2ncnc(Nc3ccc(F)cc3OC3CCC(N4CCOCC4)CC3)c2c1C]

Prepared analogously to 22.1 from 0.249 g methyl 4-(4-fluoro-2-(4-oxocyclohexyloxy)phenylamino)-5-methylthieno[2,3-d]pyrimidine-6-carboxylate (cpd.20.). Crystallisation was replaced by purification by chromatography. Yield: 0.275 g 26.2 4-(4-Fluoro-2-(trans-4-morpholinocyclohexyloxy)phenylamino)-5-methylthieno[2,3-d]pyrimidine-6-carboxamide

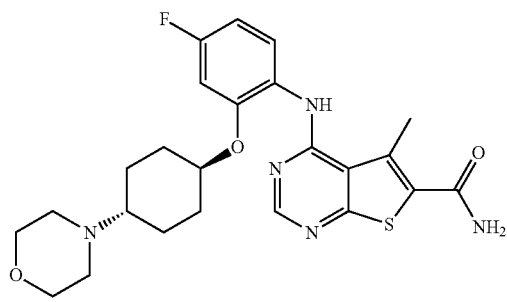 [SMILES: Cc1c(C(N)=O)sc2ncnc(Nc3ccc(F)cc3O[C@H]3CC[C@H](N4CCOCC4)CC3)c12]

Prepared analogously to 15.2 from 0.280 g methyl 4-(4-fluoro-2-(4-morpholinocyclohexyloxy)phenylamino)-5-methylthieno[2,3-d]pyrimidine-6-carboxylate (cpd.26.1). The title compound was obtained by HPLC separation.

Yield: 0.025 g

ESI mass spectrum: m/z=486 (M+H)$^+$ $R_t$ (HPLC): 1.20 min (method X)

Example 27

4-(4-Fluoro-2-(cis-4-morpholinocyclohexyloxy)phenylamino)-5-methylthieno[2,3-d]pyrimidine-6-carboxamide

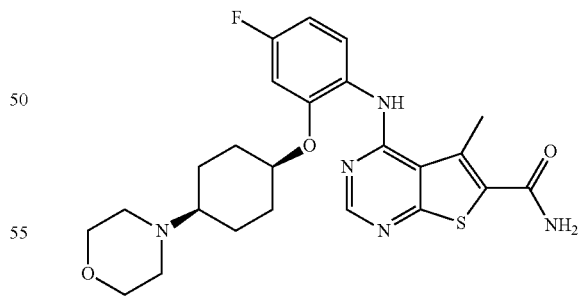

Prepared analogously to 15.2 from 0.280 g methyl 4-(4-fluoro-2-(4-morpholinocyclohexyloxy)phenylamino)-5-methylthieno[2,3-d]pyrimidine-6-carboxylate (cpd.26.1). The title compound was obtained by HPLC separation.

Yield: 0.023 g

ESI mass spectrum: m/z=486 (M+H)$^+$ $R_t$ (HPLC): 1.15 min (method X)

Example 28

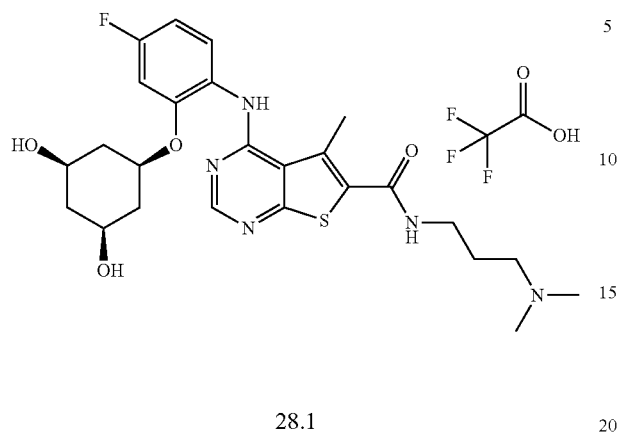

28.1

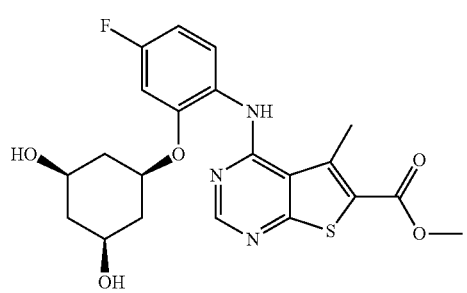 [SMILES: COC(=O)c1sc2ncnc(Nc3ccc(F)cc3O[C@@H]3C[C@H](O)C[C@H](O)C3)c2c1C]

A reaction mixture of 0.503 g 4-chloro-5-methyl-thieno[2,3-d]pyrimidine-6-carboxylic acid methyl ester, 0.500 g intermediate XXVIII and 0.070 g p-toluenesulfonic acid in 8 ml dioxane were heated under microwave radiation at 140° C. for 15 minutes. The mixture was cooled, filtered and purified by chromatography. The crude was triturated with diethyl ether.

Yield: 0.320 g
ESI mass spectrum: m/z=448 (M+H)$^+$
R$_t$ (HPLC): 1.74 min (method K)

28.2

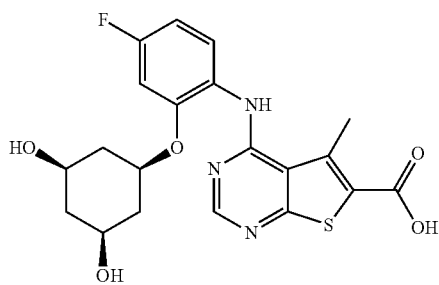 [SMILES: Cc1c(C(=O)O)sc2ncnc(Nc3ccc(F)cc3O[C@@H]3C[C@H](O)C[C@H](O)C3)c12]

A mixture of 3.4 ml sodium hydroxide solution (1M) and 0.300 g cpd. 28.1 in 10 ml MeOH was stirred at 100° C. for 2 hours and at reflux for 40 minutes. Then the mixture was neutralized with aq. HCl, concentrated and filtered. The filtercake was washed with EtOH and diethyl ether and dried.

Yield: 0.230 g
ESI mass spectrum: m/z=434 (M+H)$^+$
R$_t$ (HPLC): 1.47 min (method K 28.3

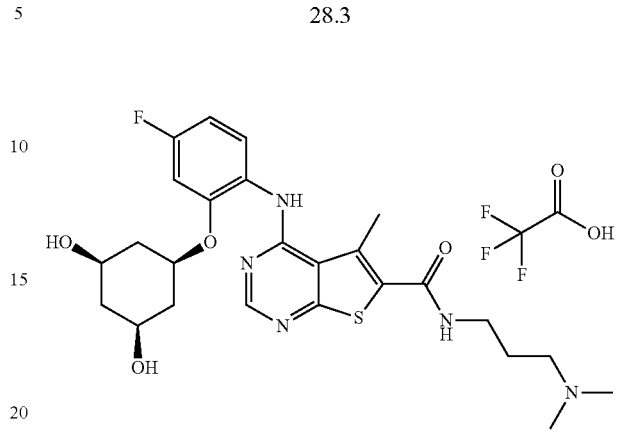

A mixture of 0.060 g cpd. 28.2, 0.018 ml N,N-dimethyl-propane-1,3-diamine, 0.045 g TBTU and 0.049 ml DIPEA in 7.5 ml THF/DMF 2/1 was stirred at rt over the weekend. The mixture was concentrated and the crude was purified by chromatography.

Yield: 0.100 g
ESI mass spectrum: m/z=518 (M+H)$^+$
R$_t$ (HPLC): 1.3 7 min (method K)

Example 29

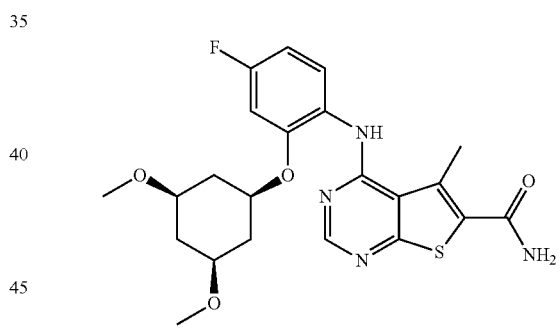

29.1

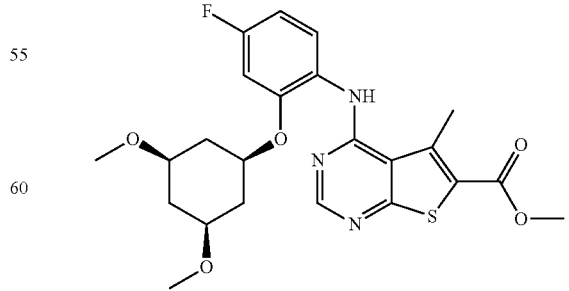

Synthesized analogously to 28.1 from 4-chloro-5-methyl-thieno[2,3-d]pyrimidine-6-carboxylic acid methyl ester (1.532 g) and intermediate XXX (1.700 g). The mixture was filtered and the filtercake was washed with dioxane, MeOH and diethyl ether.

Yield: 2.150 g

ESI mass spectrum: m/z=476 (M+H)+

$R_t$ (HPLC): 2.08 min (method K)

$R_f$ (TLC): 0.79 (silica gel, methylene chloride/methanol 9/1)

29.2

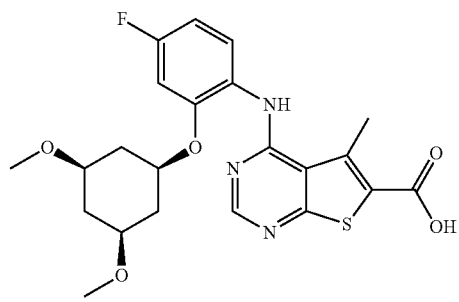 [SMILES: CO[C@@H]1C[C@H](OC)C[C@H](Oc2cc(F)ccc2Nc2ncnc3sc(C(=O)O)c(C)c23)C1]

Prepared analogously to 28.2 from 1.500 g cpd. 28.1.

Yield: 1.200 g

ESI mass spectrum: m/z=462 (M+H)+

$R_t$ (HPLC): 1.77 min (method K)

29.3

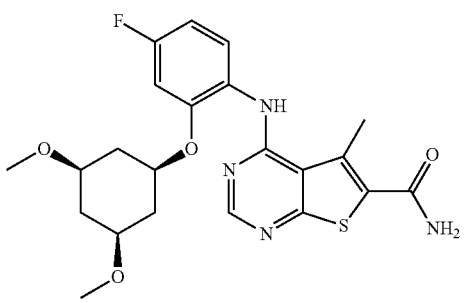 [SMILES: CO[C@@H]1C[C@H](OC)C[C@H](Oc2cc(F)ccc2Nc2ncnc3sc(C(N)=O)c(C)c23)C1]

A mixture of 0.150 g cpd. 29.2, 0.700 ml 0.5 M ammonia in THF, 0.112 g TBTU and 0.122 ml DIPEA in 10 ml THF was stirred at rt over the weekend. The mixture was concentrated. The crude was diluted with DCM, washed with water, dried over Na₂SO₄ and concentrated. The residue was triturated with diethyl ether.

Yield: 0.085 g

ESI mass spectrum: m/z=461 (M+H)+

$R_t$ (HPLC): 1.59 min (method K)

Example 30

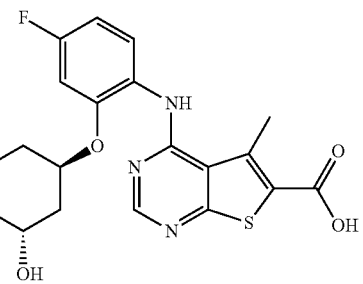

relative stereochemistry 30.1

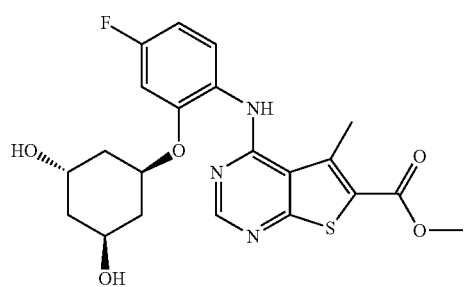

relative stereochemistry

Prepared analogously to 29.1 from 4-chloro-5-methyl-thieno[2,3-d]pyrimidine-6-carboxylic acid methyl ester (0.362 g) and intermediate XXIX (0.360 g).

Yield: 0.290 g

ESI mass spectrum: m/z=448 (M+H)+

$R_t$ (HPLC): 1.65 min (method K)

30.2

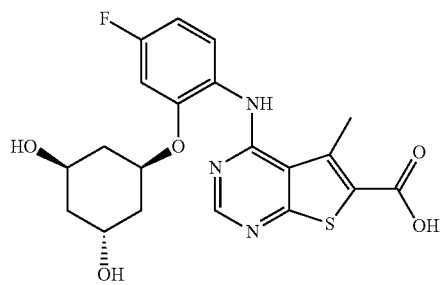

Prepared analogously to 28.2 from 0.280 g cpd. 30.1.

Yield: 0.230 g

ESI mass spectrum: m/z=434 (M+H)+

$R_t$ (HPLC): 1.48 min (method K)

Example 31

4-[2-(4,4-Dimethyl-cyclohexyloxy)-4-fluoro-phenylamino]-5-methyl-thieno[2,3-d]pyrimidine-6-carboxylic acid amide

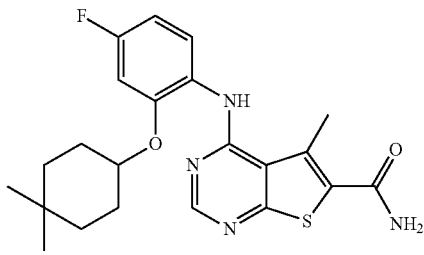 [SMILES: Cc1c(C(N)=O)sc2ncnc(Nc3ccc(F)cc3OC3CCC(C)(C)CC3)c12]

31.1 4-[(2-(4,4-Dimethyl-cyclohexyloxy)-4-fluoro-phenylamino]-5-methyl-thieno[2,3-d]pyrimidine-6-carboxylic acid methyl ester

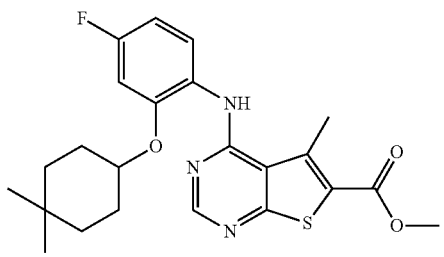

Prepared analogously to 29.1 from 4-chloro-5-methyl-thieno[2,3-d]pyrimidine-6-carboxylic acid methyl ester (1.500 g) and intermediate XXXI (1.467 g).

Yield: 2.000 g

ESI mass spectrum: m/z=444 (M+H)$^+$ $R_t$ (HPLC): 2.15 min (method K)

31.2 4-[2-(4,4-Dimethyl-cyclohexyloxy)-4-fluoro-phenylamino]-5-methyl-thieno[2,3-d]pyrimidine-6-carboxylic acid

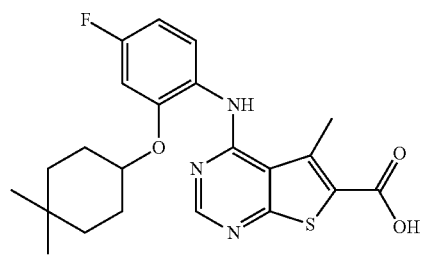 [SMILES: Cc1c(C(=O)O)sc2ncnc(Nc3ccc(F)cc3OC3CCC(C)(C)CC3)c12]

Prepared analogously to 28.2 from 1.000 g 4-[2-(4,4-dimethyl-cyclohexyloxy)-4-fluoro-phenylamino]-5-methyl-thieno[2,3-d]pyrimidine-6-carboxylic acid methyl ester (cpd. 31.1).

Yield: 0.850 g

ESI mass spectrum: m/z=430 (M+H)$^+$ $R_t$ (HPLC): 2.27 min (method K)

31.3 4-[2-(4,4-Dimethyl-cyclohexyloxy)-4-fluoro-phenylamino]-5-methyl-thieno[2,3-d]pyrimidine-6-carboxylic acid amide

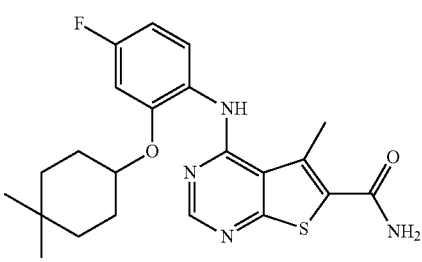 [SMILES: Cc1c(C(N)=O)sc2ncnc(Nc3ccc(F)cc3OC3CCC(C)(C)CC3)c12]

Prepared analogously to 29.3 from 0.150 g 4-[2-(4,4-dimethyl-cyclohexyloxy)-4-fluoro-phenylamino]-5-methyl-thieno[2,3-d]pyrimidine-6-carboxylic acid (cpd. 31.2).

Yield: 0.065 g

ESI mass spectrum: m/z=429 (M+H)$^+$ $R_t$ (HPLC): 2.09 min (method K)

Example 32

4-[2-(4,4-Dimethyl-cyclohexyloxy)-4-fluoro-phenylamino]-5-methyl-thieno[2,3-d]pyrimidine-6-carboxylic acid (3-dimethylamino-propyl)-amide

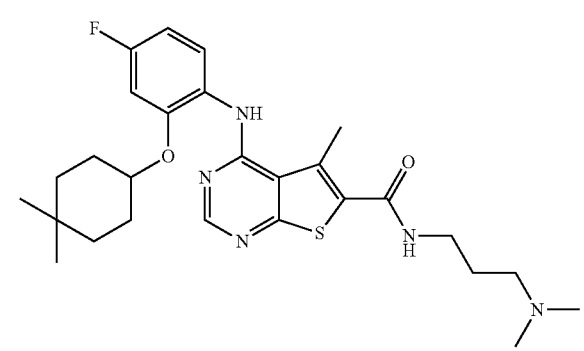

Prepared analogously to 29.3 from 0.150 g 4-[2-(4,4-dimethyl-cyclohexyloxy)-4-fluoro-phenylamino]-5-methyl-thieno[2,3-d]pyrimidine-6-carboxylic acid (cpd. 31.2) and 0.044 ml N,N-dimethyl-propane-1,3-diamine.

Yield: 0.128 g

ESI mass spectrum: m/z=514 (M+H)$^+$ $R_t$ (HPLC): 1.46 min (method K)

Example 33

4-[2-(4,4-Difluoro-cyclohexyloxy)-4-fluoro-phenylamino]-5-methyl-thieno[2,3-d]pyrimidine-6-carboxylic acid amide

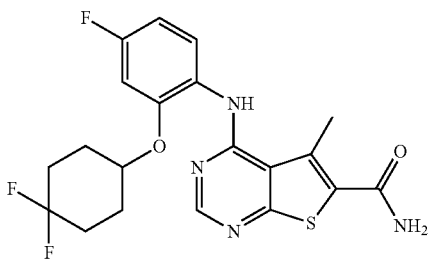 [SMILES: Cc1c(C(N)=O)sc2ncnc(Nc3ccc(F)cc3OC3CCC(F)(F)CC3)c12]

33.1 4-[2-(4,4-Difluoro-cyclohexyloxy)-4-fluoro-phenylamino]-5-methyl-thieno[2,3-d]pyrimidine-6-carboxylic acid methyl ester

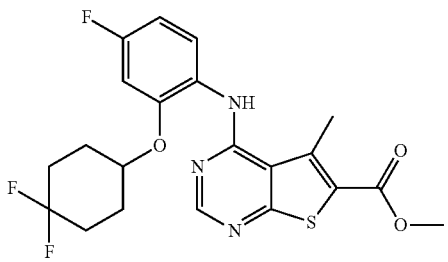 [SMILES: COC(=O)c1sc2ncnc(Nc3ccc(F)cc3OC3CCC(F)(F)CC3)c2c1C]

A mixture of 0.087 g 4-chloro-5-methyl-thieno[2,3-d]pyrimidine-6-carboxylic acid methyl ester, 0.088 g intermediate XXXII and 0.006 g p-toluenesulfonic acid in 2 ml dioxane was heated at 120° C. for 1.5 h. The reaction mixture was cooled, filtered and the filtercake was washed with dioxane and dried.

Yield: 0.115 g

33.2 4-[2-(4,4-Difluoro-cyclohexyloxy)-4-fluoro-phenylamino]-5-methyl-thieno[2,3-d]pyrimidine-6-carboxylic acid

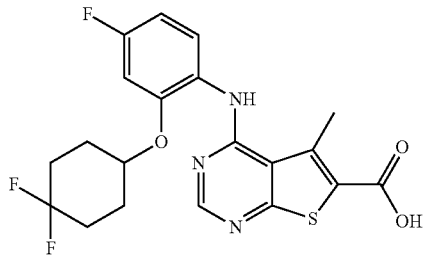 [SMILES: Cc1c(C(=O)O)sc2ncnc(Nc3ccc(F)cc3OC3CCC(F)(F)CC3)c12]

0.620 ml sodium hydroxide solution (2M) was added to 0.110 g 4-[2-(4,4-difluoro-cyclohexyloxy)-4-fluoro-phenylamino]-5-methyl-thieno[2,3-d]pyrimidine-6-carboxylic acid methyl ester (cpd. 33.1) in 4 ml THF/MeOH (1/1). An additional aliquot of sodium hydroxide solution was added when the reaction mixture was stirred at rt overnight. After further 6 hours at rt the mixture was concentrated, the resulting aq. layer was adjusted to pH 4-5 with aq. 2 M aq.HCl and stirred under cooling for 30 minutes. Then the mixture was filtered, the filtercake was washed with water and dried.

Yield: 0.100 g

33.3 4-[2-(4,4-Difluoro-cyclohexyloxy)-4-fluoro-phenylamino]-5-methyl-thieno[2,3-d]pyrimidine-6-carboxylic acid amide

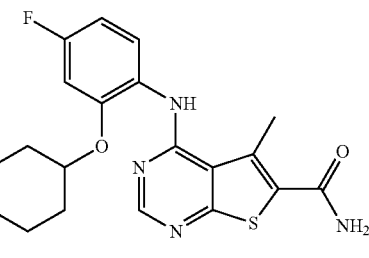

0.029 g EDC was added to a mixture of 0.050 g 4-[2-(4,4-difluoro-cyclohexyloxy)-4-fluoro-phenylamino]-5-methyl-thieno[2,3-d]pyrimidine-6-carboxylic acid (cpd. 33.2) and 0.020 g 1-hydroxy-pyrrolidine-2,5-dione in 1 ml DMF and stirred at rt over the weekend. After the addition of 0.327 ml ammonia (7M) the reaction mixture was stirred at rt for further 1.5 hours. The mixture was concentrated and the residue was recrystallized from hot MeOH.

Yield: 0.041 g

ESI mass spectrum: m/z=437 (M+H)$^+$ $R_t$ (HPLC): 1.38 min (method X)

Example 34

4-[2-(4,4-Difluoro-cyclohexyloxy)-4-fluoro-phenylamino]-5-methyl-thieno[2,3-d]pyrimidine-6-carboxylic acid (3-dimethylamino-propyl)-amide

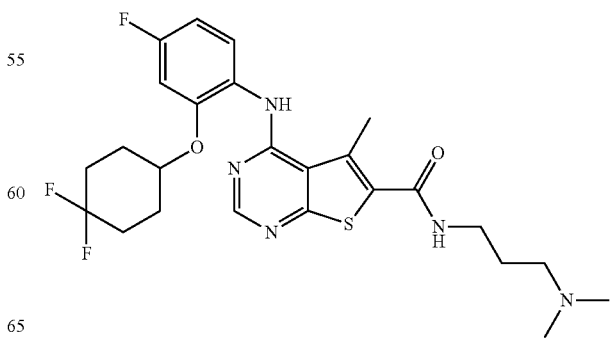

Prepared analogously to 33.3 from 0.050 g 4-[2-(4,4-difluoro-cyclohexyloxy)-4-fluoro-phenylamino]-5-methyl-thieno[2,3-d]pyrimidine-6-carboxylic acid (cpd. 33.2) and 0.126 ml N,N-dimethyl-propane-1,3-diamine.

Yield: 0.023 g

ESI mass spectrum: m/z=522 (M+H)⁺

R$_t$ (HPLC): 1.29 min (method X)

Example 35

4-[2-(trans-3-Acetylamino-cyclobutoxy)-4-fluoro-phenylamino]-5-methyl-thieno[2,3-d]pyrimidine-6-carboxylic acid amide

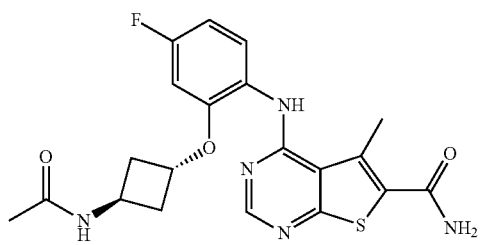 [SMILES: CC(=O)N[C@H]1C[C@H](Oc2cc(F)ccc2Nc2ncnc3sc(C(N)=O)c(C)c23)C1]

35.1 4-[2-(trans-3-Acetylamino-cyclobutoxy)-4-fluoro-phenylamino]-5-methyl-thieno[2,3-d]pyrimidine-6-carboxylic acid methyl ester

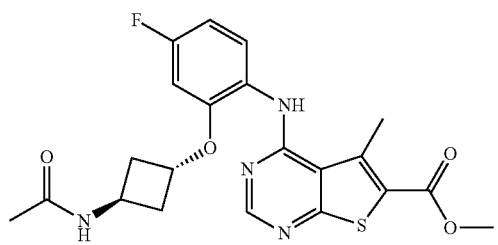 [SMILES: COC(=O)c1sc2ncnc(Nc3ccc(F)cc3O[C@H]3C[C@H](NC(C)=O)C3)c2c1C]

A mixture of 1.700 g 4-chloro-5-methyl-thieno[2,3-d]pyrimidine-6-carboxylic acid methyl ester, 2.000 g intermediate XXXV and 0.255 g p-toluenesulfonic acid in 20 ml dioxane was heated under microwave radiation at 110° C. for 1 h. The reaction mixture was filtered and the filtercake was washed with dioxane and stirred with MeOH. Then water was added and the mixture was filtered.

Yield: 1.700 g

ESI mass spectrum: m/z=445 (M+H)⁺

35.2 4-[2-(trans-3-Acetylamino-cyclobutoxy)-4-fluoro-phenylamino]-5-methyl-thieno[2,3-d]pyrimidine-6-carboxylic acid

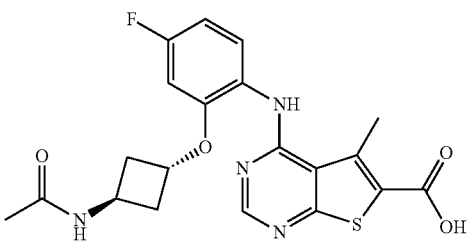 [SMILES: CC(=O)N[C@H]1C[C@H](Oc2cc(F)ccc2Nc2ncnc3sc(C(=O)O)c(C)c23)C1]

A mixture of 1.800 g 4-[2-(trans-3-acetylamino-cyclobutoxy)-4-fluoro-phenylamino]-5-methyl-thieno[2,3-d]pyrimidine-6-carboxylic acid methyl ester (cpd.35.1) in 17 ml sodium hydroxide solution (1M) and 30 ml MeOH was stirred at rt overnight. The reaction mixture was neutralized with aq. HCl (1M) and concentrated. The residue was filtered and the filtercake was washed with diethyl ether.

Yield: 1.680 g

ESI mass spectrum: m/z=431 (M+H)⁺

35.3 4-[2-(trans-3-Acetylamino-cyclobutoxy)-4-fluoro-phenylamino]-5-methyl-thieno[2,3-d]pyrimidine-6-carboxylic acid amide

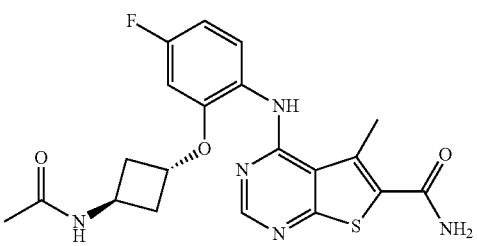 [SMILES: CC(=O)N[C@H]1C[C@H](Oc2cc(F)ccc2Nc2ncnc3sc(C(N)=O)c(C)c23)C1]

0.050 ml DIPEA was added to a mixture of 0.100 g 4-[2-(trans-0.86   3-acetylamino-cyclobutoxy)-4-fluoro-phenylamino]-5-methyl-thieno[2,3-d]pyrimidine-6-carboxylic acid (cpd. 35.2) and 0.095 g HATU in 1.5 ml DMF and stirred at rt for 15 minutes. 2.323 ml ammonia in THF (0.5M) was added and the stirring was continued for further 6 hours. Then the reaction mixture was concentrated and the residue was purified by chromatography.

Yield: 0.015 g

ESI mass spectrum: m/z=430 (M+H)⁺

R$_t$ (HPLC): 0.86 (method A)

The following compounds were prepared analogously to 35.3:
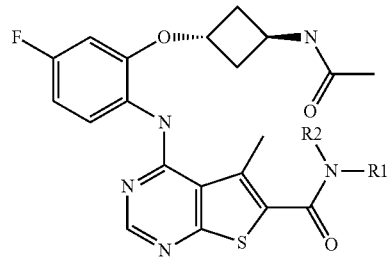
| Example | NR1R2 | educt | Mass spectrum | HPLC (retention time) |
|---|---|---|---|---|
| 36 | 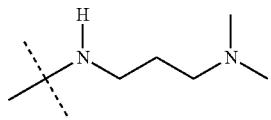 | Cpd. 35.2 | 515 (M + H)+ | 0.89 (Method A) |
| 37 | 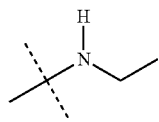 | Cpd. 35.2 | 458 (M + H)+ | 2.35 min (Method B) |
| 38 | 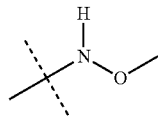 | Cpd. 35.2 | 460 (M + H)+ | 2.23 min (Method B) |
| 39 | 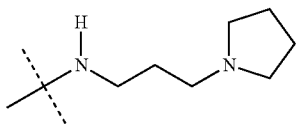 | Cpd. 35.2 | 541 (M + H)+ | 1.86 min (Method B) |
| 40 | 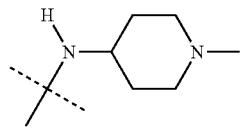 | Cpd. 35.2 | 527 (M + H)+ | 1.85 min (Method B) |
| 41 | 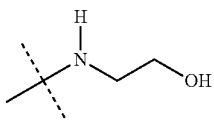 | Cpd. 35.2 | 474 (M + H)+ | 2.11 min (Method B) |

Example 42

4-[4-Fluoro-2-((1S,2S)-2-methoxy-cyclohexyloxy)-phenylamino]-5-methyl-thieno[2,3-d]pyrimidine-6-carboxylic acid amide

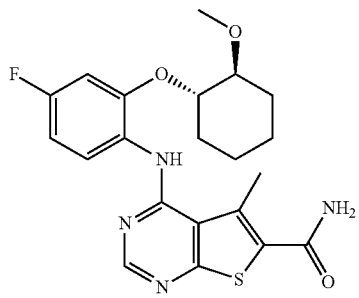 [SMILES: CO[C@H]1CCCC[C@@H]1Oc1cc(F)ccc1Nc1ncnc2sc(C(N)=O)c(C)c12]

42.1 4-[4-Fluoro-2-((1S,2S)-2-methoxy-cyclohexyloxy)-phenylamino]-5-methyl-thieno[2,3-d]pyrimidine-6-carboxylic acid methyl ester

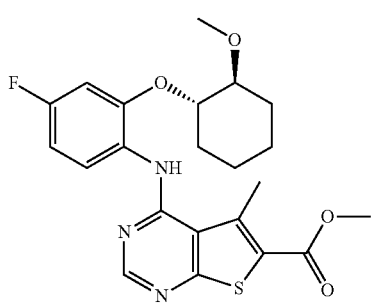 [SMILES: COC(=O)c1sc2ncnc(Nc3ccc(F)cc3O[C@H]3CCCC[C@@H]3OC)c2c1C]

Prepared analogously to 1.1 from 0.846 g 4-chloro-5-methyl-thieno[2,3-d]pyrimidine-6-carboxylic acid methyl ester and 1.000 g Intermediate XXXXIV.

Yield: 1.390 g

42.2 4-[4-Fluoro-2-((1S,2S)-2-methoxy-cyclohexyloxy)-phenylamino]-5-methyl-thieno[2,3-d]pyrimidine-6-carboxylic acid

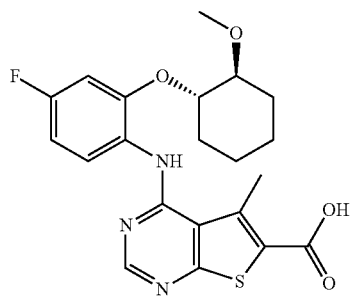 [SMILES: CO[C@H]1CCCC[C@@H]1Oc1cc(F)ccc1Nc1ncnc2sc(C(=O)O)c(C)c12]

7 ml sodium hydroxide solution (2M) were added to a mixture of 1.270 g 4-[4-fluoro-2-((1S,2S)-2-methoxy-cyclohexyloxy)-phenylamino]-5-methyl-thieno[2,3-d]pyrimidine-6-carboxylic acid methyl ester (cpd. 42.1) in 10 ml MeOH/THF (1:1). The reaction mixture was stirred at reflux for 15 minutes, then cooled and acidified with 2 M aq. HCl. The solvent was removed in vacuo, the residue suspended in water, filtered and dried.

42.3 4-[4-Fluoro-2-((1S,2S)-2-methoxy-cyclohexyloxy)-phenylamino]-5-methyl-thieno[2,3-d]pyrimidine-6-carboxylic acid amide

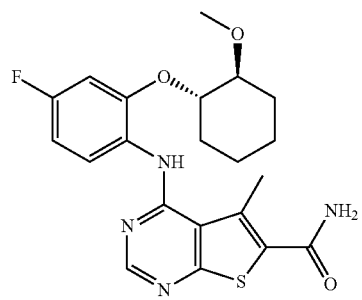 [SMILES: CO[C@H]1CCCC[C@@H]1Oc1cc(F)ccc1Nc1ncnc2sc(C(N)=O)c(C)c12]

Prepared analogously to 1.4 from 0.100 g 4-[4-fluoro-2-((1S,2S)-2-methoxycyclohexyloxy)-phenylamino]-5-methyl-thieno[2,3-d]pyrimidine-6-carboxylic acid.

Yield: 0.074 g

ESI mass spectrum: m/z=431 (M+H)$^+$ $R_t$ (HPLC): 1.41 min (method X)

Example 43

4-[4-Fluoro-2-((1S,2S)-2-methoxy-cyclohexyloxy)-phenylamino]-5-methyl-thieno[2,3-d]pyrimidine-6-carboxylic acid (3-dimethylamino-propyl)-amide

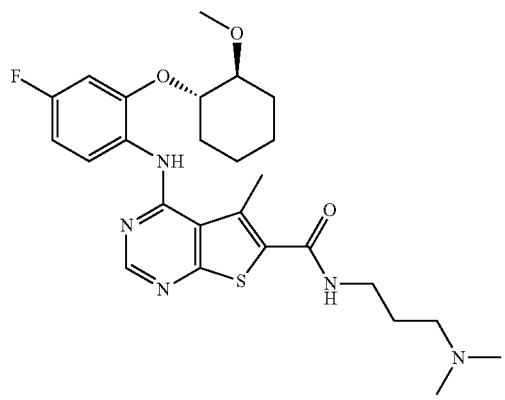 [SMILES: CO[C@H]1CCCC[C@@H]1Oc1cc(F)ccc1Nc1ncnc2sc(C(=O)NCCCN(C)C)c(C)c12]

43.1 4-[4-Fluoro-2-((1S,2S)-2-methoxy-cyclohexyloxy)-phenylamino]-5-methyl-thieno[2,3-d]pyrimidine-6-carboxylic acid 2,5-dioxo-pyrrolidin-1-yl ester

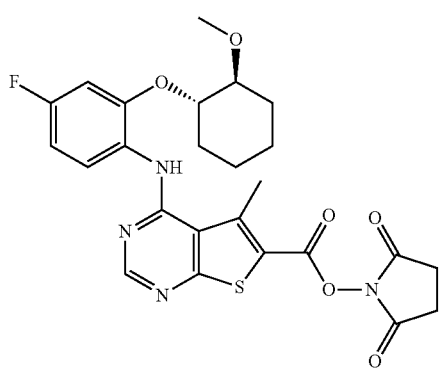 [SMILES: CO[C@H]1CCCC[C@@H]1Oc1cc(F)ccc1Nc1ncnc2sc(C(=O)ON3C(=O)CCC3=O)c(C)c12]

EDC (53 mg, 0.28 mmol) was added to a mixture of 0.100 g 4-[4-fluoro-2-((1S,2S)-2-methoxy-cyclohexyloxy)-phenylamino]-5-methyl-thieno[2,3-d]pyrimidine-6-carboxylic acid (cpd.42.2) and 0.040 g N-hydroxysuccinimide in 1 ml DMF. And stirred at rt overnight. The reaction mixture was diluted with EtOAc and washed with water and brine. The organic layer was passed through a hydrophobic frit and concentrated.

Yield: 0.100 g

43.2 4-[4-Fluoro-2-((1S,2S)-2-methoxy-cyclohexyloxy)-phenylamino]-5-methyl-thieno[2,3-d]pyrimidine-6-carboxylic acid (3-dimethylamino-propyl)-amide

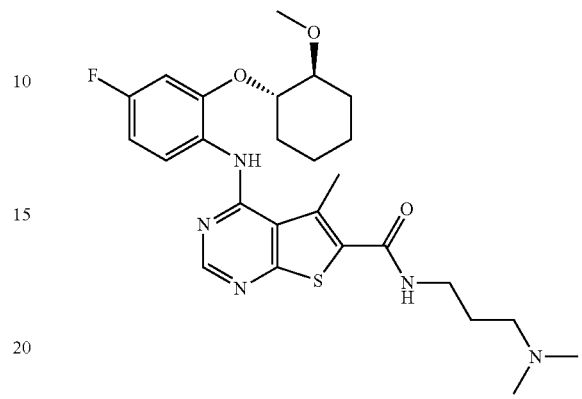

0.129 g 3-dimethylaminopropylamine was added to 0.155 g 4-[4-fluoro-2-((1S,2S)-2-methoxy-cyclohexyloxy)-phenylamino]-5-methyl-thieno[2,3-d]pyrimidine-6-carboxylic acid 2,5-dioxo-pyrrolidin-1-yl ester in 2 ml DMF and stirred at rt for 30 minutes. The reaction mixture was concentrated. The residue was dissolved in EtOAc, washed with water and brine, passed through a hydrophobic frit and concentrated.

Yield: 0.129 g
ESI mass spectrum: m/z=516 (M+H)$^+$
R$_t$ (HPLC): 1.31 min (method X)

The following compounds were prepared analogously to 43.2:

| Example | NR1R2 | educt | Mass spectrum | HPLC (retention time) |
|---|---|---|---|---|
| 44 | H$_2$N-CH$_2$CH$_2$CH$_2$-N(CH$_3$)$_2$ | Cpd. 43.1 | 502 (M + H)$^+$ | 1.30 min (Method X) |
| 45 | H$_2$N-CH$_2$CH$_2$CH$_2$-N(morpholine) | Cpd. 43.1 | 558 (M + H)+ | 1.31 min (Method X) |
| 46 | H$_2$N-CH$_2$CH$_2$CH$_2$-N(imidazole) | Cpd. 43.1 | 539 (M + H)+ | 1.31 min (Method X) |

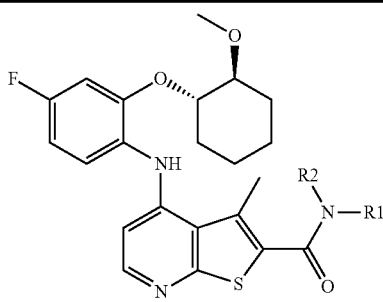

| Example | NR1R2 | educt | Mass spectrum | HPLC (retention time) |
|---|---|---|---|---|
| 47 | H₂N-(CH₂)₃-pyrrolidine | Cpd. 43.1 | 542 (M + H)+ | 1.31 min (Method X) |
| 48 | H₂N-CH₂CH₂-(N-methylpyrrolidin-2-yl) | Cpd. 43.1 | 542 (M + H)+ | 1.32 min (Method X) |
| 49 | H₂N-CH₂CH₂-OH | Cpd. 43.1 | 475 (M + H)+ | 1.38 min (Method X) |

Example 50

Racemic 4-[4-Fluoro-2-(trans-2-methoxy-cyclohexyloxy)-phenylamino]-5-methyl-thieno[2,3-d]pyrimidine-6-carboxylic acid amide

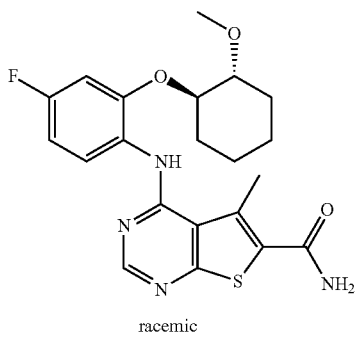 [SMILES: CO[C@@H]1CCCC[C@H]1Oc1cc(F)ccc1Nc1ncnc2sc(C(N)=O)c(C)c12]

racemic 50.1 racemic 4-[4-Fluoro-2-(trans-2-methoxy-cyclohexyloxy)-phenylamino]-5-methyl-thieno[2,3-d]pyrimidine-6-carboxylic acid methyl ester

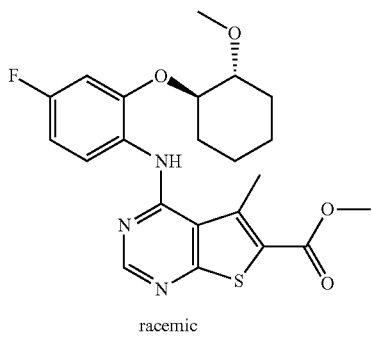 [SMILES: COC(=O)c1sc2ncnc(Nc3ccc(F)cc3O[C@@H]3CCCC[C@H]3OC)c2c1C]

racemic

A reaction mixture of 0.073 g 4-chloro-5-methyl-thieno[2,3-d]pyrimidine-6-carboxylic acid methyl ester, 0.091 g intermediate XVII and 0.003 g p-toluenesulfonic acid in 1 ml dioxane was heated at 110° C. for 10 hours. The reaction mixture was diluted with methylene chloride and 3M ammonia and passed through a hydrophobic frit. The organic layer was concentrated and the residue was recrystallized from MeOH.

Yield: 0.098 g 50.2 racemic 4-[4-Fluoro-2-(trans-2-methoxy-cyclohexyloxy)-phenylamino]-5-methyl-thieno[2,3-d]pyrimidine-6-carboxylic acid

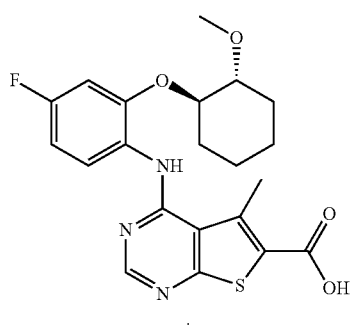

racemic

Prepared analogously to 42.2 from 0.089 g racemic 4-[4-fluoro-2-(trans-2-methoxycyclohexyloxy)-phenylamino]-5-methyl-thieno[2,3-d]pyrimidine-6-carboxylic acid methyl ester (cpd. 50.1).

Yield: 0.075 g

50.3 racemic 4-[4-Fluoro-2-(trans-2-methoxy-cyclohexyloxy)-phenylamino]-5-methyl-thieno[2,3-d]pyrimidine-6-carboxylic acid amide

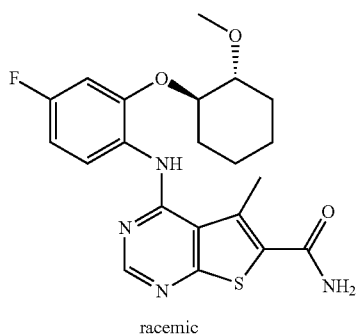 [SMILES: CO[C@@H]1CCCC[C@H]1Oc1cc(F)ccc1Nc1ncnc2sc(C(N)=O)c(C)c12]

racemic

Prepared analogously to 1.4 from 0.073 g 4-[4-fluoro-2-(trans-2-methoxycyclohexyloxy)-phenylamino]-5-methyl-thieno[2,3-d]pyrimidine-6-carboxylic acid (cpd. 50.2).
Yield: 0.041 g
ESI mass spectrum: m/z=431 (M+H)$^+$
R$_t$ (HPLC): 1.41 min (method X)

Example 51

4-[4-Fluoro-2-((1S,2S)-2-hydroxy-cyclohexyloxy)-phenylamino]-5-methyl-thieno[2,3-d]pyrimidine-6-carboxylic acid amide

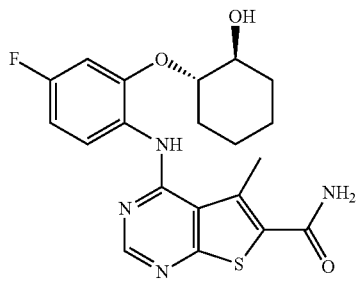 [SMILES: Cc1c(C(N)=O)sc2ncnc(Nc3ccc(F)cc3O[C@H]3CCCC[C@@H]3O)c12]

51.1 4-[4-Fluoro-2-((1S,2S)-2-hydroxy-cyclohexyloxy)-phenylamino]-5-methyl-thieno[2,3-d]pyrimidine-6-carboxylic acid methyl ester

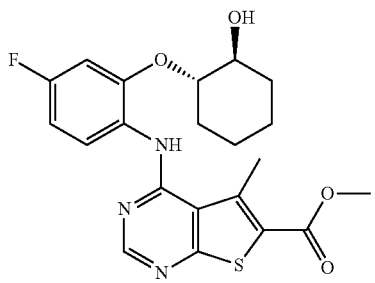 [SMILES: COC(=O)c1sc2ncnc(Nc3ccc(F)cc3O[C@H]3CCCC[C@@H]3O)c2c1C]

A mixture of 1.832 g 4-chloro-5-methyl-thieno[2,3-d]pyrimidine-6-carboxylic acid methyl ester, 1.700 g intermediate XXI and 0.130 g p-toluenesulfonic acid in 30 ml dioxane was stirred at 100° C. for 2 hours. The reaction mixture was cooled, diluted with water and filtered. The filtercake was washed with water and dried.

Yield: 3.020 g
ESI mass spectrum: m/z=432 (M+H)$^+$
R$_t$ (HPLC): 2.04 min (Method L)

51.2 4-[4-Fluoro-2-((1S,2S)-2-hydroxy-cyclohexyloxy)-phenylamino]-5-methyl-thieno[2,3-d]pyrimidine-6-carboxylic acid

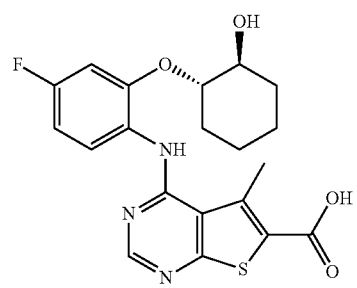 [SMILES: Cc1c(C(=O)O)sc2ncnc(Nc3ccc(F)cc3O[C@H]3CCCC[C@@H]3O)c12]

5 ml sodium hydroxide solution (4M) was added to a mixture of 2.960 g 4-[4-Fluoro-2-((1S,2S)-2-hydroxy-cyclohexyloxy)-phenylamino]-5-methyl-thieno[2,3-d]pyrimidine-6-carboxylic acid methyl ester (cpd. 51.1) in 60 ml methanol/THF (1:1). The reaction mixture was stirred at rt for 3 hours, then acidified with aq. HCl and diluted with water. The mixture was filtered and the filtercake was dried.

Yield: 2.780 g
ESI mass spectrum: m/z=418 (M+H)$^+$
R$_t$ (HPLC): 1.85 min (Method L)

51.3 4-[4-Fluoro-2-((1S,2S)-2-hydroxy-cyclohexyloxy)-phenylamino]-5-methyl-thieno[2,3-d]pyrimidine-6-carboxylic acid amide

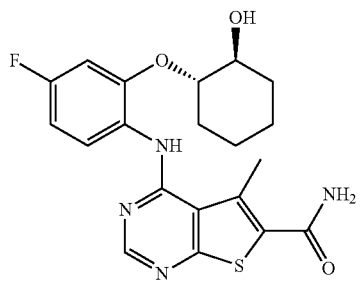 [SMILES: Cc1c(C(N)=O)sc2ncnc(Nc3ccc(F)cc3O[C@H]3CCCC[C@@H]3O)c12]

A mixture of 0.100 g 4-[4-fluoro-2-((1S,2S)-2-hydroxy-cyclohexyloxy)-phenylamino]-5-methyl-thieno[2,3-d]pyrimidine-6-carboxylic acid (cpd. 51.2), 2.5 ml ammonia in dioxane (0.5M), 0.109 g HATU and 0.046 ml DIPEA in 2 ml DMF was stirred at rt overnight. The reaction mixture was diluted with water, stirred and filtered. The filtercake was dried.

Yield: 0.086 g
ESI mass spectrum: m/z=417 (M+H)$^+$
R$_t$ (HPLC): 1.61 min (Method L)

Example 52

4-[4-Fluoro-2-((1R,2R)-2-hydroxy-cyclohexyloxy)-phenylamino]-5-methyl-thieno[2,3-d]pyrimidine-6-carboxylic acid amide

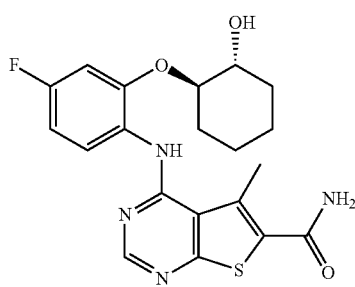 [SMILES: Cc1c(C(N)=O)sc2ncnc(Nc3ccc(F)cc3O[C@@H]3CCCC[C@H]3O)c12]

52.1 4-[4-Fluoro-2-((1R,2R)-2-hydroxy-cyclohexyloxy)-phenylamino]-5-methyl-thieno[2,3-d]pyrimidine-6-carboxylic acid methyl ester

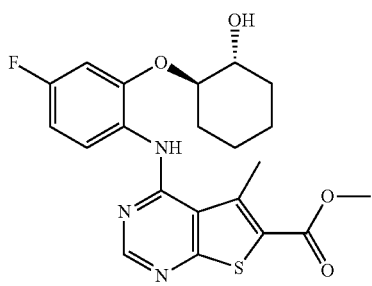 [SMILES: COC(=O)c1sc2ncnc(Nc3ccc(F)cc3O[C@@H]3CCCC[C@H]3O)c2c1C]

Prepared analogously to 51.1 from 1.723 g 4-chloro-5-methyl-thieno[2,3-d]pyrimidine-6-carboxylic acid methyl ester and 1.600 g intermediate XX.

Yield: 2.780 g
ESI mass spectrum: m/z=432 (M+H)$^+$
R$_t$ (HPLC): 2.02 min (Method L)

52.2 4-[4-Fluoro-2-((1R,2R)-2-hydroxy-cyclohexyloxy)-phenylamino]-5-methyl-thieno[2,3-d]pyrimidine-6-carboxylic acid

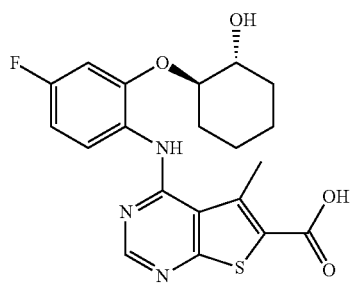 [SMILES: Cc1c(C(=O)O)sc2ncnc(Nc3ccc(F)cc3O[C@@H]3CCCC[C@H]3O)c12]

Prepared analogously to 51.2 from 2.750 g 4-[4-fluoro-2-((1R,2R)-2-hydroxycyclohexyloxy)-phenylamino]-5-methyl-thieno[2,3-d]pyrimidine-6-carboxylic acid methyl ester (cpd. 52.1).

Yield: 2.630 g
ESI mass spectrum: m/z=418 (M+H)$^+$
R$_t$ (HPLC): 1.74 min (Method L)

52.3 4-[4-Fluoro-2-((1R,2R)-2-hydroxy-cyclohexyloxy)-phenylamino]-5-methyl-thieno[2,3-d]pyrimidine-6-carboxylic acid amide

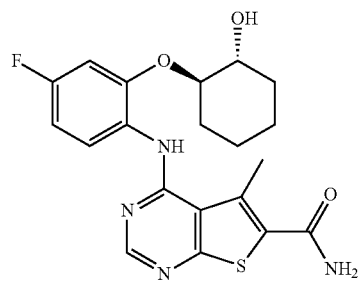 [SMILES: Cc1c(C(N)=O)sc2ncnc(Nc3ccc(F)cc3O[C@@H]3CCCC[C@H]3O)c12]

Prepared analogously to 51.3 from 0.120 g 4-[4-fluoro-2-((1R,2R)-2-hydroxycyclohexyloxy)-phenylamino]-5-methyl-thieno[2,3-d]pyrimidine-6-carboxylic acid (cpd. 52.2).

Yield: 0.095 g
ESI mass spectrum: m/z=417 (M+H)$^+$
R$_t$ (HPLC): 1.74 min (method L)

Example 53

4-[4-Fluoro-2-((1R,2R)-2-hydroxy-cyclohexyloxy)-phenylamino]-5-methyl-thieno[2,3-d]pyrimidine-6-carboxylic acid (3-dimethylamino-propyl)-amide

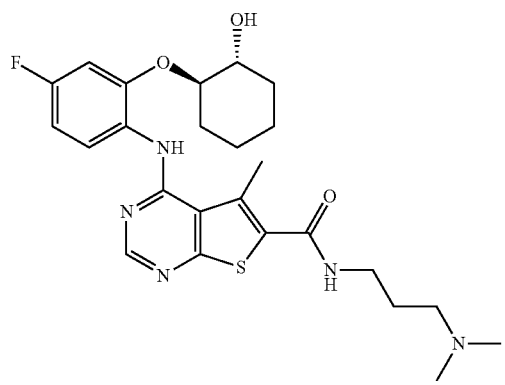 [SMILES: Cc1c(C(=O)NCCCN(C)C)sc2ncnc(Nc3ccc(F)cc3O[C@@H]3CCCC[C@H]3O)c12]

A mixture of 0.096 g 4-[4-fluoro-2-((1R,2R)-2-hydroxycyclohexyloxy)-phenylamino]-5-methyl-thieno[2,3-d]pyrimidine-6-carboxylic acid (cpd. 52.2), 0.081 g TBTU and 0.088 ml DIPEA in 15 ml THF was stirred at rt for 30 minutes. Then 0.028 ml dimethylaminopropylamine was added and stirring was continued overnight. The reaction mixture was concentrated and purified by chromatography.

Yield: 0.072 g
ESI mass spectrum: m/z=502 (M+H)$^+$
R$_t$ (HPLC): 2.18 min (Method L)

Example 54

4-[4-Fluoro-2-((1R,2R)-2-hydroxy-cyclohexyloxy)-phenylamino]-5-methyl-thieno[2,3-d]pyrimidine-6-carboxylic acid (2-methoxy-ethyl)-amide

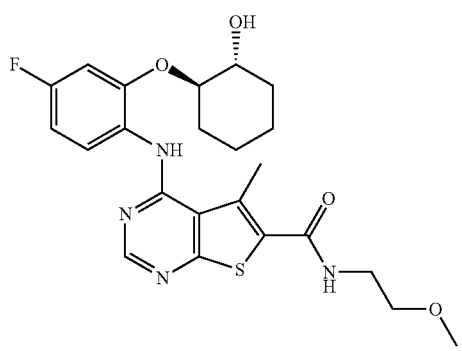 [SMILES: COCCNC(=O)c1sc2ncnc(Nc3ccc(F)cc3O[C@@H]3CCCC[C@H]3O)c2c1C]

Prepared analogously to 53 from 0.091 g 4-[4-fluoro-2-((1R,2R)-2-hydroxycyclohexyloxy)-phenylamino]-5-methyl-thieno[2,3-d]pyrimidine-6-carboxylic acid (cpd. 52.2) and 0.020 ml methoxyethylamine.

Yield: 0.069 g

ESI mass spectrum: m/z=475 (M+H)$^+$ $R_t$ (HPLC): 2.85 min (Method L)

$R_f$ (TLC): 0.43 (silica gel, methylene chloride/methanol/NH$_3$ 90/10/1)

Example 55

Racemic 4-[4-Fluoro-2-(cis-2-methoxy-cyclohexyloxy)-phenylamino]-5-methyl-thieno[2,3-d]pyrimidine-6-carboxylic acid amide

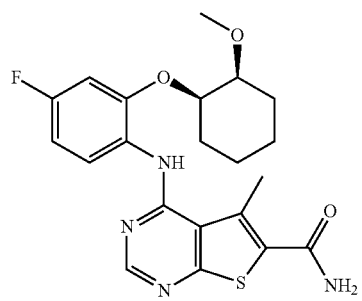
relative stereochemistry 55.1 racemic 4-[4-Fluoro-2-(cis-2-methoxy-cyclohexyloxy)-phenylamino]-5-methyl-thieno[2,3-d]pyrimidine-6-carboxylic acid methyl ester

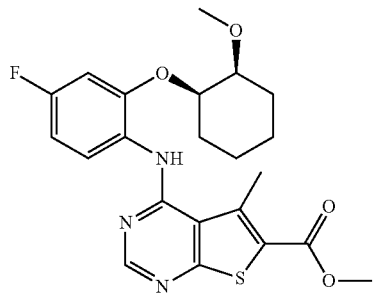
relative stereochemistry

Prepared analogously to 50.1 from 0.136 g 4-chloro-5-methyl-thieno[2,3-d]pyrimidine-6-carboxylic acid methyl ester and 0.147 g intermediate XVI.

Yield: 0.163 g 55.2 racemic 4-[4-Fluoro-2-(cis-2-methoxy-cyclohexyloxy)-phenylamino]-5-methyl-thieno[2,3-d]pyrimidine-6-carboxylic acid

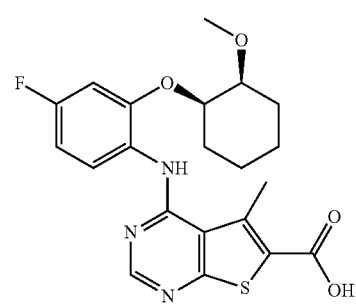
relative stereochemistry

Prepared analogously to 42.2 from 0.163 g racemic 4-[4-fluoro-2-(cis-2-methoxycyclohexyloxy)-phenylamino]-5-methyl-thieno[2,3-d]pyrimidine-6-carboxylic acid methyl ester (cpd. 55.1).

Yield: 0.149 g 55.3 racemic 4-[4-Fluoro-2-(cis-2-methoxy-cyclohexyloxy)-phenylamino]-5-methyl-thieno[2,3-d]pyrimidine-6-carboxylic acid amide

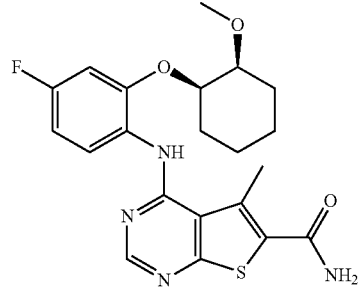
relative stereochemistry

Prepared analogously to 1.4 from 0.141 g racemic 4-[4-Fluoro-2-(cis-2-methoxycyclohexyloxy)-phenylamino]-5-methyl-thieno[2,3-d]pyrimidine-6-carboxylic acid (cpd. 55.2).

Yield: 0.094 g

ESI mass spectrum: m/z=431 (M+H)⁺

$R_t$ (HPLC): 1.40 min (method X)

Example 56

Racemic 4-[4-Fluoro-2-((cis)-2-hydroxy-cyclohexyloxy)-phenylamino]-5-methyl-thieno[2,3-d]pyrimidine-6-carboxylic acid amide

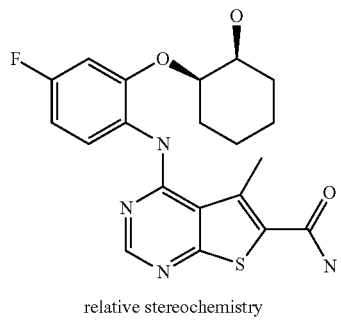 [SMILES: Cc1c(C(N)=O)sc2ncnc(Nc3ccc(F)cc3O[C@@H]3CCCC[C@@H]3O)c12]

relative stereochemistry

56.1 Racemic 4-[4-Fluoro-2-((cis)-2-hydroxy-cyclohexyloxy)-phenylamino]-5-methyl-thieno[2,3-d]pyrimidine-6-carboxylic acid methylester

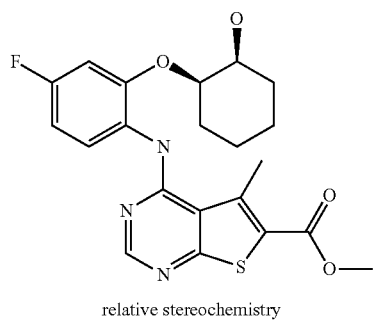 [SMILES: COC(=O)c1sc2ncnc(Nc3ccc(F)cc3O[C@@H]3CCCC[C@@H]3O)c2c1C]

relative stereochemistry

Prepared analogously to example 1.1 from 0.277 g 4-Chloro-5-methyl-thieno[2,3-d]pyrimidine-6-carboxylic acid methyl ester and 0.267 g intermediate XXXXXIV.

Yield: 0.173 g

56.2 Racemic 4-[4-Fluoro-2-((cis)-2-hydroxy-cyclohexyloxy)-phenylamino]-5-methyl-thieno[2,3-d]pyrimidine-6-carboxylic acid

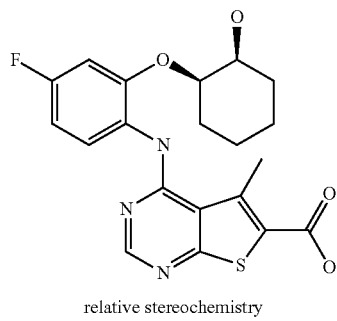 [SMILES: Cc1c(C(N)=O)sc2ncnc(Nc3ccc(F)cc3O[C@@H]3CCCC[C@@H]3O)c12]

relative stereochemistry

Prepared analogously to example 1.3 from 0.173 g racemic 4-[4-Fluoro-2-((cis)-2-hydroxy-cyclohexyloxy)-phenylamino]-5-methyl-thieno[2,3-d]pyrimidine-6-carboxylic acid methylester.

Yield: 0.123 g

56.3 Racemic 4-[4-Fluoro-2-((cis)-2-hydroxy-cyclohexyloxy)-phenylamino]-5-methyl-thieno[2,3-d]pyrimidine-6-carboxylic acid amide

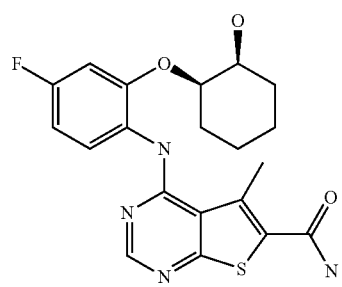

relative stereochemistry

Prepared analogously to example 1.4 from 0.083 g racemic 4-[4-Fluoro-2-((cis)-2-hydroxy-cyclohexyloxy)-phenylamino]-5-methyl-thieno[2,3-d]pyrimidine-6-carboxylic acid and ammonia.

Yield: 0.046 g

ESI mass spectrum: m/z=417 (M+H)⁺

$R_t$ (HPLC): 1.3 (method X)

Example 57

Racemic 4-[4-Fluoro-2-((cis)-3-hydroxy-cyclohexyloxy)-phenylamino]-5-methyl-thieno[2,3-d]pyrimidine-6-carboxylic acid amide

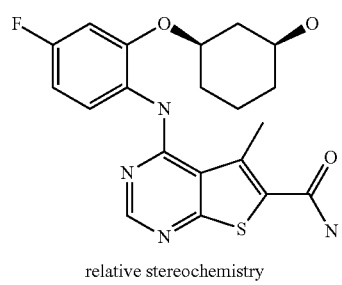 [SMILES: Cc1c(C(N)=O)sc2ncnc(Nc3ccc(F)cc3O[C@@H]3CCC[C@H](O)C3)c12]

relative stereochemistry

57.1 4-[4-Fluoro-2-(3-hydroxy-cyclohexyloxy)-phenylamino]-5-methyl-thieno[2,3-d]pyrimidine-6-carboxylic acid methyl ester

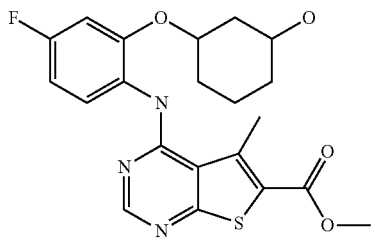 [SMILES: COC(=O)c1sc2ncnc(Nc3ccc(F)cc3OC3CCCC(O)C3)c2c1C]

Prepared analogously to example 1.1 from 0.485 g 4-Chloro-5-methyl-thieno[2,3-d]pyrimidine-6-carboxylic acid methyl ester and 0.491 g intermediate XXXXXVI.
Yield: 0.140 g

57.2 4-[4-Fluoro-2-(3-hydroxy-cyclohexyloxy)-phenylamino]-5-methyl-thieno[2,3-d]pyrimidine-6-carboxylic acid

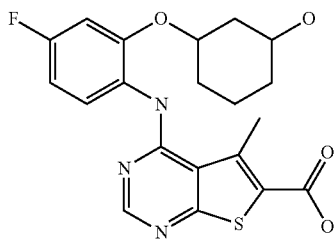 [SMILES: Cc1c(C(=O)O)sc2ncnc(Nc3ccc(F)cc3OC3CCCC(O)C3)c12]

Prepared analogously to example 1.3 from 0.48 g 4-[4-Fluoro-2-(3-hydroxycyclohexyloxy)-phenylamino]-5-methyl-thieno[2,3-d]pyrimidine-6-carboxylic acid methyl ester.
Yield: 0.448 g

57.3 Racemic 4-[4-Fluoro-2-((cis)-3-hydroxy-cyclohexyloxy)-phenylamino]-5-methyl-thieno[2,3-d] pyrimidine-6-carboxylic acid amide

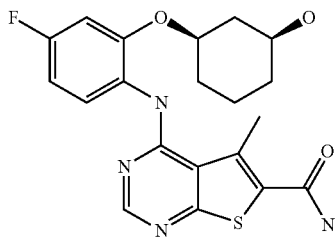

relative stereochemistry

Prepared analogously to example 1.4 from 0.445 g 4-[4-Fluoro-2-(3-hydroxycyclohexyloxy)-phenylamino]-5-methyl-thieno[2,3-d]pyrimidine-6-carboxylic acid ammonia. Separation in racemic cis and trans-isomer was performed by HPLC.
Yield: 0.095 g (title compound, cis.isomer)
ESI mass spectrum: m/z=417 (M+H)$^+$
$R_t$ (HPLC): 1.3 (method X)

Example 58

Racemic 4-[4-Fluoro-2-((trans)-3-hydroxy-cyclohexyloxy)-phenylamino]-5-methyl-thieno[2,3-d] pyrimidine-6-carboxylic acid amide

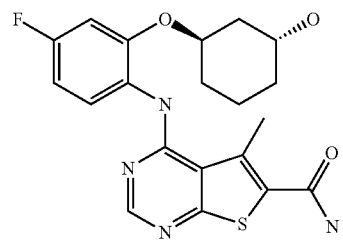

relative stereochemistry

58.1 racemic Racemic 4-[4-Fluoro-2-((trans)-3-hydroxy-cyclohexyloxy)phenylamino]-5-methyl-thieno[2,3-d]pyrimidine-6-carboxylic acid methylester

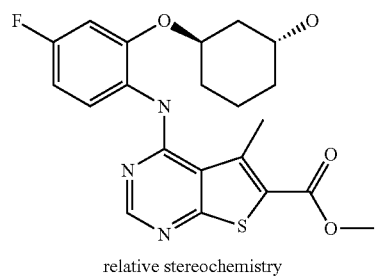 [SMILES: COC(=O)c1sc2ncnc(Nc3ccc(F)cc3O[C@@H]3CCC[C@@H](O)C3)c2c1C]

relative stereochemistry

Prepared analogously to example 1.1 from 4.956 g 4-chloro-5-methyl-thieno[2,3-d]pyrimidine-6-carboxylic acid methyl ester and 4.6 g intermediate II in isopropanol.
Yield: 6.1 g
ESI mass spectrum: m/z=432 (M+H)$^+$

58.2 racemic Racemic 4-[4-Fluoro-2-((trans)-3-hydroxy-cyclohexyloxy)phenylamino]-5-methyl-thieno[2,3-d]pyrimidine-6-carboxylic acid

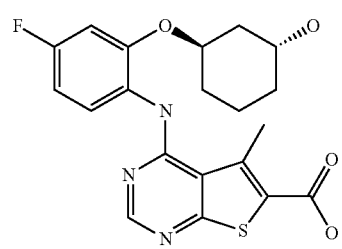

relative stereochemistry 2.665 g lithium hydroxide were added to a mixture of 6.5 g racemic racemic 4-[4-fluoro-2-((trans)-3-hydroxy-cyclohexyloxy)-phenylamino]-5-methyl-thieno[2,3-d]pyrimidine-6-carboxylic acid methylester in 350 ml water and 70 ml water. The mixture was stirred overnight. Then the mixture was acidified by addition of citric acid (10% in water) and concentrated. Water was added and the mixture was filtered. The solid was washed with water and dried.
Yield: 6.15 g
ESI mass spectrum: m/z=418 (M+H)$^+$

58.3 Racemic 4-[4-Fluoro-2-((trans)-3-hydroxy-cyclohexyloxy)-phenylamino]-5-methyl-thieno[2,3-d]pyrimidine-6-carboxylic acid amide

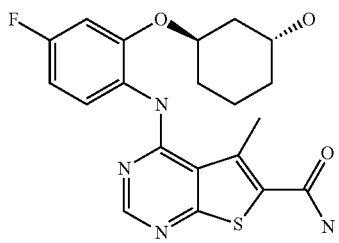

relative stereochemistry

Prepared analogously to example 1.4 from 5.6 g racemic racemic 4-[4-Fluoro-2-((trans)-3-hydroxy-cyclohexyloxy)-phenylamino]-5-methyl-thieno[2,3-d]pyrimidine-6-carboxylic acid and 100 ml ammonia (0.5 M in THF).

Yield: 3.85 g

ESI mass spectrum: m/z=417 (M+H)$^+$

R$_t$ (HPLC): 2.55 (method A)

The following compounds were prepared analogously to 1.4.:

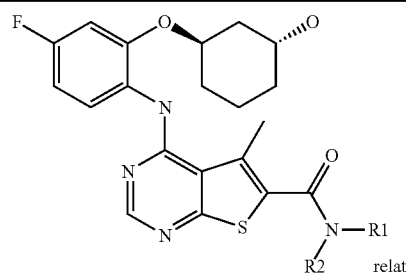

relative stereochemistry

| Example | NR1R2 | educt | Mass spectrum | HPLC (retention time) |
|---|---|---|---|---|
| 59 | | Cpd. 58.2 | 472 (M + H)$^+$ | 1.74 min (Method F) |
| 60 | | Cpd. 58.2 | 484 (M + H)+ | 1.73 min (Method F) |
| 61 | | Cpd. 58.2 | 489 (M + H)+ | 1.77 min (Method E) |
| 62 | | Cpd. 58.2 | 498 (M + H)+ | 2.18 min (Method F) |
| 63 | | Cpd. 58.2 | 456 (M + H)+ | 1.79 min (Method E) |
| 64 | | Cpd. 58.2 | 488 (M + H)+ | 2.05 min (Method F) |

-continued
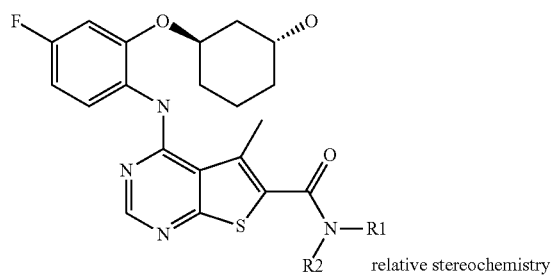
relative stereochemistry
| Example | NR1R2 | educt | Mass spectrum | HPLC (retention time) |
|---|---|---|---|---|
| 65 | 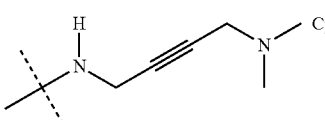 | Cpd. 58.2 | 512 (M + H)+ | 1.91 min (Method F) |
| 66 | 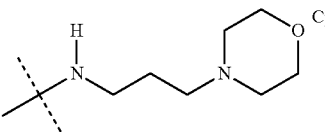 | Cpd. 58.2 | 544 (M + H)+ | 1.9 min (Method F) |
| 67 | 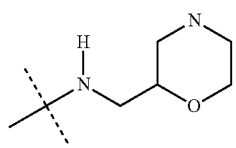 | Cpd. 58.2 | 516 (M + H)+ | 1.74 min (Method F) |
| 68 | 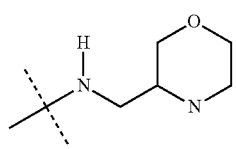 | Cpd. 58.2 | 516 (M + H)+ | 1.72 min (Method F) |
| 69 | 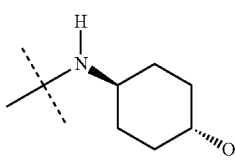 | Cpd. 58.2 | 515 (M + H)+ | 1.8 min (Method E) |
| 70 | 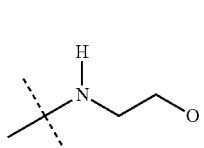 | Cpd. 58.2 | 484 (M + H)+ | 2.14 min (Method F) |
| 71 | 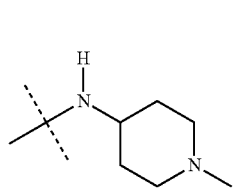 | Cpd. 58.2 | 489 (M + H)+ | 1.4 min (Method E) |

-continued

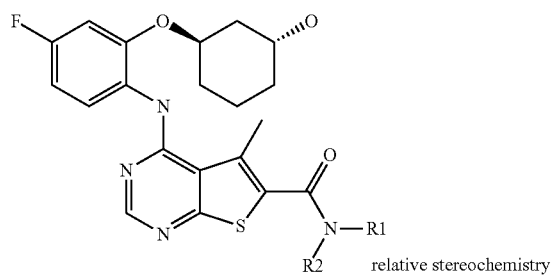

relative stereochemistry

| Example | NR1R2 | educt | Mass spectrum | HPLC (retention time) |
|---|---|---|---|---|
| 72 | [structure: N-CH2CH2-piperidine] | Cpd. 58.2 | 528 (M + H)+ | 1.43 min (Method E) |
| 73 | [structure: N-CH2-CH(CH3)-OH] | Cpd. 58.2 | 475 (M + H)+ | 1.77 min (Method E) |
| 74 | [structure: N-CH2CH2CH2-OH] | Cpd. 58.2 | 475 (M + H)+ | 1.76 min (Method E) |
| 75 | [structure: N-CH2CH2CH2-pyrrolidine] | Cpd. 58.2 | 528 (M + H)+ | 1.41 min (Method E) |
| 76 | [structure: N-CH2-(1-methylimidazole)] | Cpd. 58.2 | 511 (M + H)+ | 1.81 min (Method F) |
| 77 | [structure: N-CH2CH2CH2-N(CH3)2] | Cpd. 58.2 | 502 (M + H)+ | 1.9 min (Method F) |
| 78 | [structure: N-ethyl] | Cpd. 58.2 | 445 (M + H)+ | 2.12 min (Method F) |

Example 79

Racemic 4-[4-Fluoro-2-((trans)-3-methoxy-cyclohexyloxy)-phenylamino]-5-methyl-thieno[2,3-d]pyrimidine-6-carboxylic acid amide

79.1 racemic 4-[4-Fluoro-2-((trans)-3-methoxy-cyclohexyloxy)-phenylamino]-5-methyl-thieno[2,3-d]pyrimidine-6-carboxylic acid ethylester

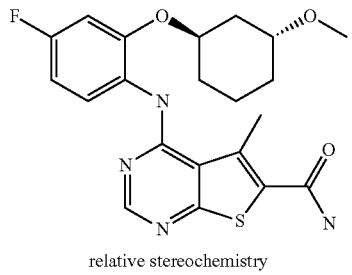 [SMILES: CO[C@@H]1CCC[C@@H](Oc2cc(F)ccc2Nc2ncnc3sc(C(N)=O)c(C)c23)C1]

relative stereochemistry

Prepared analogously to example 1.1 from 0.76 g 4-chloro-5-methyl-thieno[2,3-d]pyrimidine-6-carboxylic acid ethyl ester and 0.7 g intermediate XXXXI in dioxan.

Yield: 1.04 g
ESI mass spectrum: m/z=460 (M+H)$^+$
$R_t$ (HPLC): 5.41 (method C)

79.2 racemic 4-[4-Fluoro-2-((trans)-3-methoxy-cyclohexyloxy)-phenylamino]-5-methyl-thieno[2,3-d]pyrimidine-6-carboxylic acid relative stereochemistry Prepared analogously to 1.3 from 1.02 g racemic 4-[4-fluoro-2-((trans)-3-methoxycyclohexyloxy)-phenylamino]-5-methyl-thieno[2,3-d]pyrimidine-6-carboxylic acid ethylester.

Yield: 0.36 g
ESI mass spectrum: m/z=432 (M+H)$^+$
$R_t$ (HPLC): 4.13 (method C)

79.3 Racemic 4-[4-Fluoro-2-((trans)-3-methoxy-cyclohexyloxy)-phenylamino]-5-methyl-thieno[2,3-d]pyrimidine-6-carboxylic acid amide

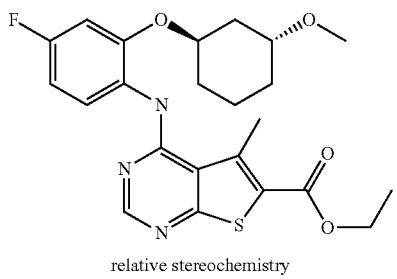 [SMILES: CCOC(=O)c1sc2ncnc(Nc3ccc(F)cc3O[C@@H]3CCC[C@@H](OC)C3)c2c1C]

relative stereochemistry

Prepared analogously to example 1.4 from 0.15 g racemic 4-[4-Fluoro-2-((trans)-3-methoxy-cyclohexyloxy)-phenylamino]-5-methyl-thieno[2,3-d]pyrimidine-6-carboxylic acid and ammonia (7 M in methanol).

Yield: 0.05 g
ESI mass spectrum: m/z=431 (M+H)$^+$
$R_t$ (HPLC): 3.65 (method C)

The following compounds were prepared analogously to 1.4.:

| Example | NR1R2 | educt | Mass spectrum | HPLC (retention time) |
|---|---|---|---|---|
| 80 | ![structure with H-N-CH2-C≡C-CH2-N(CH3)-] | Cpd. 79.2 | 498 (M + H)+ | 1.55 min (Method E) |

-continued

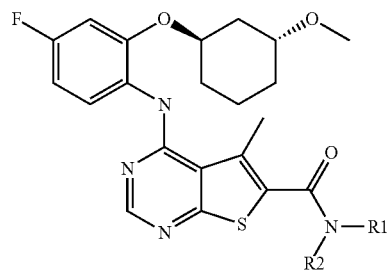

| Example | NR1R2 | educt | Mass spectrum | HPLC (retention time) |
|---|---|---|---|---|
| 81 | -N(H)-CH2CH2CH2CH2-OH | Cpd. 79.2 | 503 (M + H)+ | 1.94 min (Method E) |
| 82 | -N(H)-CH2-(oxazole) | Cpd. 79.2 | 512 (M + H)+ | 1.95 min (Method E) |
| 83 | -N(H)-CH2-(morpholin-2-yl) | Cpd. 79.2 | 530 (M + H)+ | 1.55 min (Method E) |
| 84 | -N(H)-CH2-(morpholin-3-yl) | Cpd. 79.2 | 530 (M + H)+ | 1.55 min (Method E) |
| 85 | -N(H)-CH2CH2-OH | Cpd. 79.2 | 388 (M + H)+ | 1.87 min (Method E) |
| 86 | -N(H)-(1-methylpiperidin-4-yl) | Cpd. 79.2 | 528 (M + H)+ | 1.55 min (Method E) |
| 87 | -N(H)-CH2CH2CH2-(pyrrolidin-1-yl) | Cpd. 79.2 | 542 (M + H)+ | 1.56 min (Method E) |
| 88 | -N(H)-CH2CH2CH2-N(CH3)2 | Cpd. 79.2 | 516 (M + H)+ | 1.54 min (Method E) |

Example 89

Racemic 4-[4-Fluoro-2-((cis)-3-methoxy-cyclohexyloxy)-phenylamino]-5-methyl-thieno[2,3-d]pyrimidine-6-carboxylic acid amide

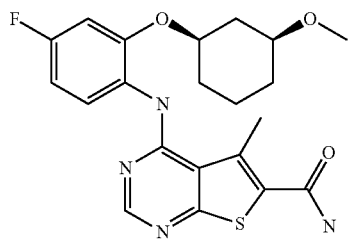

relative stereochemistry

89.1 racemic 4-[4-Fluoro-2-((cis)-3-methoxy-cyclohexyloxy)-phenylamino]-5-methyl-thieno[2,3-d]pyrimidine-6-carboxylic acid ethylester

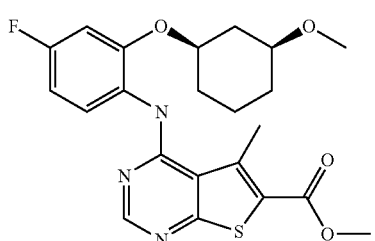

relative stereochemistry

Prepared analogously to example 1.1 from 0.52 g 4-chloro-5-ethyl-thieno[2,3-d]pyrimidine-6-carboxylic acid methyl ester and 0.43 g intermediate XXXX in dioxan.

Yield: 0.82 g
ESI mass spectrum: m/z=460 (M+H)$^+$
R$_t$ (HPLC): 5.34 (method C)

89.2 racemic 4-[4-Fluoro-2-((cis)-3-methoxy-cyclohexyloxy)-phenylamino]-5-methyl-thieno[2,3-d]pyrimidine-6-carboxylic acid

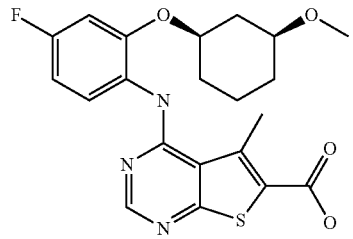

relative stereochemistry

Prepared analogously to 1.3 from 0.8 g racemic 4-[4-fluoro-2-((cis)-3-methoxycyclohexyloxy)-phenylamino]-5-methyl-thieno[2,3-d]pyrimidine-6-carboxylic acid methylester.

Yield: 0.7 g

89.3 Racemic 4-[4-Fluoro-2-((cis)-3-methoxy-cyclohexyloxy)-phenylamino]-5-methyl-thieno[2,3-d]pyrimidine-6-carboxylic acid amide

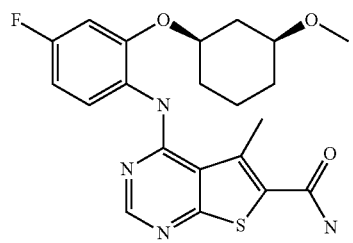

relative stereochemistry

Prepared analogously to example 1.4 from 0.3 g racemic 4-[4-Fluoro-2-((cis)-3-methoxy-cyclohexyloxy)-phenylamino]-5-methyl-thieno[2,3-d]pyrimidine-6-carboxylic acid and ammonia (0.5 M in dioxan).

Yield: 0.25 g
ESI mass spectrum: m/z=431 (M+H)$^+$
R$_t$ (HPLC): 2.13 (method I)

The following compounds were prepared analogously to 1.4.:

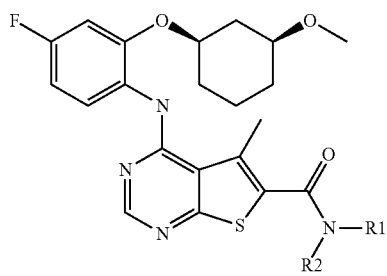

| Example | NR1R2 | educt | Mass spectrum | HPLC (retention time) |
|---|---|---|---|---|
| 90 | 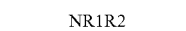 | Cpd. 89.2 | 486 (M + H)$^+$ | 1.55 min (Method E) |

-continued
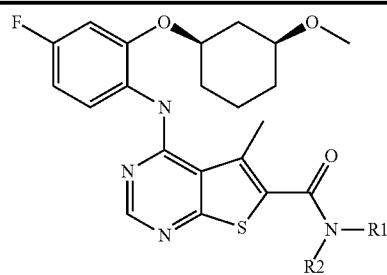
| Example | NR1R2 | educt | Mass spectrum | HPLC (retention time) |
|---|---|---|---|---|
| 91 | | Cpd. 89.2 | 498 (M + H)+ | 1.56 min (Method E) |
| 92 | | Cpd. 89.2 | 503 (M + H)+ | 1.95 min (Method E) |
| 93 | | Cpd. 89.2 | 512 (M + H)+ | 1.96 min (Method E) |
| 94 | | Cpd. 89.2 | 470 (M + H)+ | 1.96 min (Method E) |
| 95 | | Cpd. 89.2 | 502 (M + H)+ | 1.92 min (Method E) |
| 96 | | Cpd. 89.2 | 526 (M + H)+ | 1.58 min (Method E) |
| 97 | | Cpd. 89.2 | 558 (M + H)+ | 1.57 min (Method E) |
| 98 | | Cpd. 89.2 | 530 (M + H)+ | 1.55 min (Method E) |
| 99 | | Cpd. 89.2 | 530 (M + H)+ | 1.56 min (Method E) |

-continued
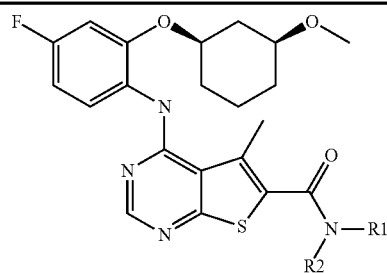
| Example | NR1R2 | educt | Mass spectrum | HPLC (retention time) |
|---|---|---|---|---|
| 100 | | Cpd. 89.2 | 529 (M + H)+ | 1.97 min (Method E) |
| 101 | | Cpd. 89.2 | 475 (M + H)+ | 1.92 min (Method E) |
| 102 | | Cpd. 89.2 | 528 (M + H)+ | 1.56 min (Method E) |
| 103 | | Cpd. 89.2 | 542 (M + H)+ | 1.59 min (Method E) |
| 104 | | Cpd. 89.2 | 498 (M + H)+ | 1.94 min (Method E) |
| 105 | | Cpd. 89.2 | 489 (M + H)+ | 1.94 min (Method E) |
| 106 | | Cpd. 89.2 | 542 (M + H)+ | 1.57 min (Method E) |
| 107 | | Cpd. 89.2 | 525 (M + H)+ | 1.56 min (Method E) |
| 108 | | Cpd. 89.2 | 516 (M + H)+ | 1.31 min (Method X) |

-continued

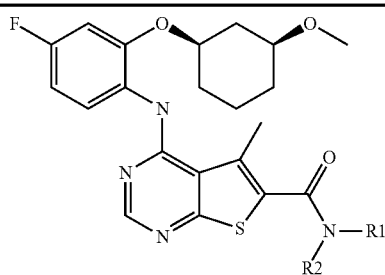

| Example | NR1R2 | educt | Mass spectrum | HPLC (retention time) |
|---|---|---|---|---|
| 109 | [structure] | Cpd. 89.2 | 459 (M + H)+ | 2.0 min (Method E) |

Example 110

Racemic 4-[2-((cis)-3-Methoxy-cyclohexyloxy)-pyridin-3-ylamino]-5-methyl-thieno[2,3-d]pyrimidine-6-carboxylic acid amide

110.1 Racemic 4-[2-((cis)-3-Methoxy-cyclohexyloxy)-pyridin-3-ylamino]-5-methyl-thieno[2,3-d]pyrimidine-6-carboxylic acid methylester

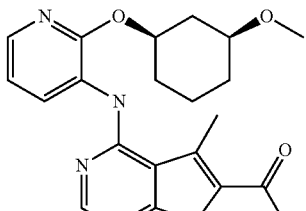
relative stereochemistry

Prepared analogously to example 1.1 from 2.22 g 4-chloro-5-methyl-thieno[2,3-d]pyrimidine-6-carboxylic acid methyl ester and 1.669 g intermediate XXXXII in dioxan.

Yield: 1.82 g
ESI mass spectrum: m/z=429 (M+H)$^+$
R$_t$ (HPLC): 5.08 (method C)

110.2 Racemic 4-[2-((cis)-3-methoxy-cyclohexyloxy)-pyridin-3-ylamino]-5-methyl-thieno[2,3-d]pyrimidine-6-carboxylic acid

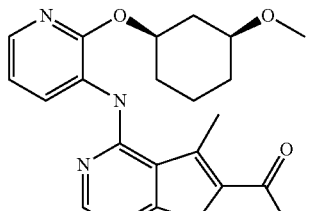
relative stereochemistry

Prepared analogously to 1.3 from 1.82 g racemic 4-[2-((cis)-3-methoxycyclohexyloxy)-pyridin-3-ylamino]-5-methyl-thieno[2,3-d]pyrimidine-6-carboxylic acid methylester.
Yield: 1.75 g
ESI mass spectrum: m/z=415 (M+H)$^+$
R$_t$ (HPLC): 4.06 (method C

110.3 Racemic 4-[2-((cis)-3-Methoxy-cyclohexyloxy)-pyridin-3-ylamino]-5-methyl-thieno[2,3-d]pyrimidine-6-carboxylic acid amide

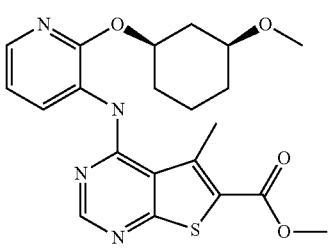
relative stereochemistry

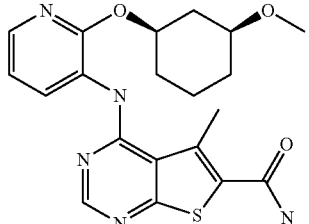
relative stereochemistry

Prepared analogously to example 1.4 from 0.1 g racemic 4-[2-((cis)-3-methoxycyclohexyloxy)-pyridin-3-ylamino]-5-methyl-thieno[2,3-d]pyrimidine-6-carboxylic acid and ammonia (7 M in methanol) using TBTU instead of HATU in DMF as solvent.

Yield: 0.078 g
ESI mass spectrum: m/z=414 (M+H)+
$R_t$ (HPLC): 1.32 (method J)
The following compounds were prepared analogously to 1.4.:

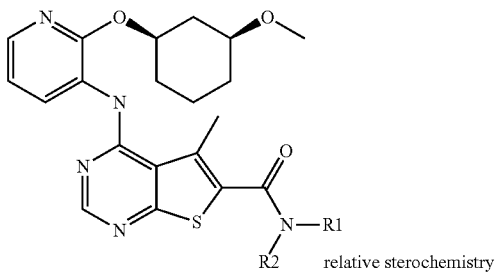

relative sterochemistry

| Example | NR1R2 | educt | Mass spectrum | HPLC (retention time) |
|---|---|---|---|---|
| 111 | | Cpd. 110.2 | 469 (M + H)+ | 1.54 min (Method E) |
| 112 | | Cpd. 110.2 | 481 (M + H)+ | 1.56 min (Method E) |
| 113 | | Cpd. 110.2 | 486 (M + H)+ | 1.95 min (Method E) |
| 114 | | Cpd. 110.2 | 495 (M + H)+ | 1.96 min (Method E) |
| 115 | | Cpd. 110.2 | 453 (M + H)+ | 1.96 min (Method E) |
| 116 | | Cpd. 110.2 | 485 (M + H)+ | 1.91 min (Method E) |
| 117 | | Cpd. 110.2 | 509 (M + H)+ | 1.91 min (Method E) |
| 118 | | Cpd. 110.2 | 541 (M + H)+ | 1.56 min (Method E) |

-continued
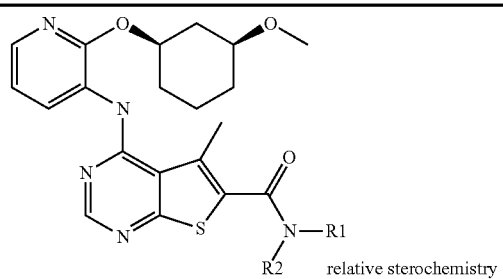
relative sterochemistry
| Example | NR1R2 | educt | Mass spectrum | HPLC (retention time) |
|---|---|---|---|---|
| 119 | | Cpd. 110.2 | 513 (M + H)+ | 1.55 min (Method E) |
| 120 | | Cpd. 110.2 | 513 (M + H)+ | 1.55 min (Method E) |
| 121 | | Cpd. 110.2 | 512 (M + H)+ | 1.92 min (Method E) |
| 122 | | Cpd. 110.2 | 458 (M + H)+ | 1.92 min (Method E) |
| 123 | | Cpd. 110.2 | 511 (M + H)+ | 1.55 min (Method E) |
| 124 | | Cpd. 110.2 | 525 (M + H)+ | 1.57 min (Method E) |
| 125 | | Cpd. 110.2 | 472 (M + H)+ | 2.21 min (Method F) |
| 126 | | Cpd. 110.2 | 472 (M + H)+ | 1.94 min (Method E) |
| 127 | | Cpd. 110.2 | 525 (M + H)+ | 1.56 min (Method E) |

-continued

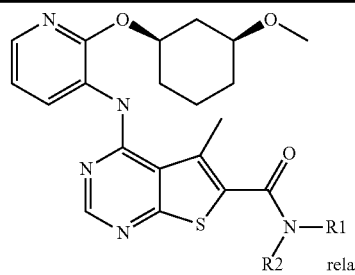
relative sterochemistry

| Example | NR1R2 | educt | Mass spectrum | HPLC (retention time) |
|---|---|---|---|---|
| 128 | | Cpd. 110.2 | 508 (M + H)+ | 1.55 min (Method E) |
| 129 | | Cpd. 110.2 | 499 (M + H)+ | 1.55 min (Method E) |
| 130 | | Cpd. 110.2 | 442 (M + H)+ | 2.01 min (Method E) |

Example 131

Racemic 4-[2-((trans)-3-Methoxy-cyclohexyloxy)-pyridin-3-ylamino]-5-methyl-thieno[2,3-d]pyrimidine-6-carboxylic acid amide

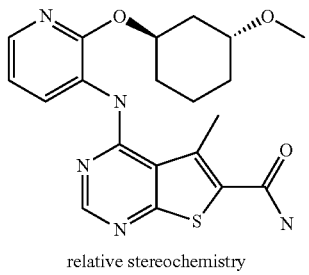 [SMILES: CO[C@@H]1CCC[C@@H](Oc2ncccc2Nc2ncnc3sc(C(N)=O)c(C)c23)C1]
relative stereochemistry 131.1 Racemic 4-[2-((trans)-3-Methoxy-cyclohexyloxy)-pyridin-3-ylamino]-5-methyl-thieno[2,3-d]pyrimidine-6-carboxylic acid methylester

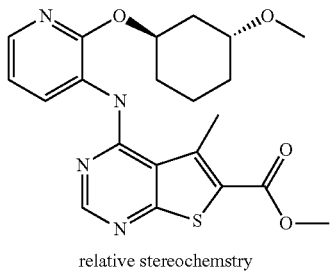 [SMILES: COC(=O)c1sc2ncnc(Nc3cccnc3O[C@@H]3CCC[C@@H](OC)C3)c2c1C]
relative stereochemstry

Prepared analogously to example 1.1 from 1.48 g 4-chloro-5-methyl-thieno[2,3-d]pyrimidine-6-carboxylic acid ethyl ester and 1.1 g intermediate XXXXIII in dioxan.

Yield: 1.14 g

ESI mass spectrum: m/z=443 (M+H)$^+$ $R_t$ (HPLC): 1.76 (method H)

131.2 Racemic 4-[2-((trans)-3-Methoxy-cyclohexyloxy)-pyridin-3-ylamino]-5-methyl-thieno[2,3-d] pyrimidine-6-carboxylic acid

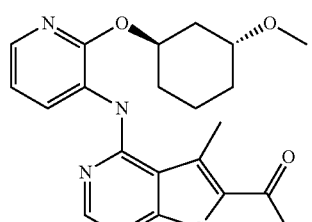
relative stereochemstry

Prepared analogously to 1.3 from 1.1 g racemic 4-[2-((trans)-3-Methoxycyclohexyloxy)-pyridin-3-ylamino]-5-methyl-thieno[2,3-d]pyrimidine-6-carboxylic acid ethylester.

Yield: 0.92 g

ESI mass spectrum: m/z=415 (M+H)$^+$ $R_t$ (HPLC): 4.15 (method C)

131.3 Racemic 4-[2-((trans)-3-Methoxy-cyclohexyloxy)-pyridin-3-ylamino]-5-methyl-thieno[2,3-d]pyrimidine-6-carboxylic acid amide

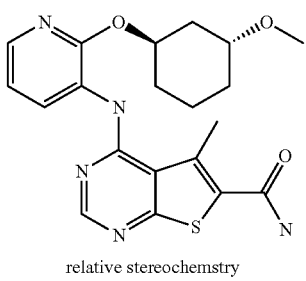 [SMILES: CO[C@@H]1CCC[C@@H](Oc2ncccc2Nc2ncnc3sc(C(N)=O)c(C)c23)C1]

relative stereochemstry

Prepared analogously to example 1.4 from 0.11 g racemic 4-[2-((trans)-3-Methoxycyclohexyloxy)-pyridin-3-ylamino]-5-methyl-thieno[2,3-d]pyrimidine-6-carboxylic acid and ammonia (7 M in methanol) using TBTU instead of HATU in DMF as solvent.

Yield: 0.068 g

ESI mass spectrum: m/z=414 (M+H)$^+$

R$_t$ (HPLC): 3.4 (method C)

The following compounds were prepared analogously to 1.4.:

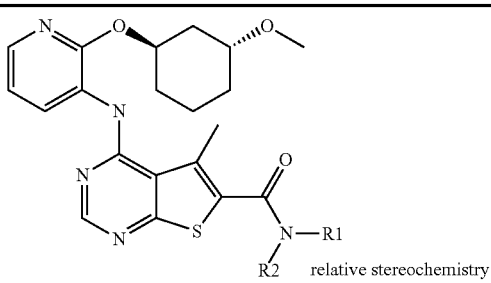

relative stereochemistry

| Example | NR1R2 | educt | Mass spectrum | HPLC (retention time) |
|---|---|---|---|---|
| 132 | | Cpd. 131.2 | 469 (M + H)$^+$ | 1.49 min (Method E) |
| 133 | | Cpd. 131.2 | 481 (M + H)+ | 1.5 min (Method E) |
| 134 | | Cpd. 131.2 | 486 (M + H)+ | 1.94 min (Method E) |
| 135 | | Cpd. 131.2 | 495 (M + H)+ | 1.94 min (Method E) |
| 136 | | Cpd. 131.2 | 453 (M + H)+ | 1.94 min (Method E) |
| 137 | | Cpd. 131.2 | 485 (M + H)+ | 2.26 min (Method F) |

-continued
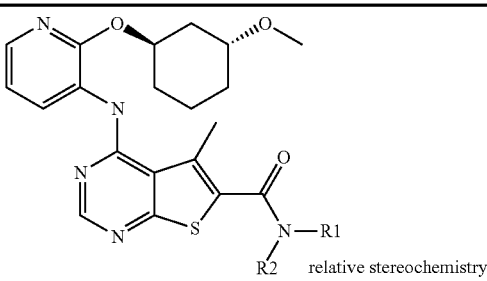
relative stereochemistry
| Example | NR1R2 | educt | Mass spectrum | HPLC (retention time) |
|---|---|---|---|---|
| 138 | | Cpd. 131.2 | 509 (M + H)+ | 1.53 min (Method E) |
| 139 | | Cpd. 131.2 | 541 (M + H)+ | 1.51 min (Method E) |
| 140 | | Cpd. 131.2 | 513 (M + H)+ | 1.5 min (Method E) |
| 141 | | Cpd. 131.2 | 513 (M + H)+ | 1.51 min (Method E) |
| 142 | | Cpd. 131.2 | 512 (M + H)+ | 1.96 min (Method E) |
| 143 | | Cpd. 131.2 | 458 (M + H)+ | 1.89 min (Method E) |
| 144 | | Cpd. 131.2 | 511 (M + H)+ | 1.51 min (Method E) |
| 145 | | Cpd. 131.2 | 525 (M + H)+ | 1.55 min (Method E) |
| 146 | | Cpd. 131.2 | 472 (M + H)+ | 1.93 min (Method E) |

-continued

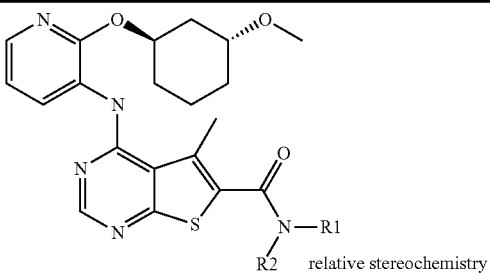

relative stereochemistry

| Example | NR1R2 | educt | Mass spectrum | HPLC (retention time) |
|---|---|---|---|---|
| 147 | | Cpd. 131.2 | 472 (M + H)+ | 1.92 min (Method E) |
| 148 | | Cpd. 131.2 | 525 (M + H)+ | 1.53 min (Method E) |
| 149 | | Cpd. 131.2 | 499 (M + H)+ | 1.5 min (Method E) |

Example 150

4-[4-Fluoro-2-((cis-4-hydroxy-cyclohexyloxy)-phenylamino]-5-methyl-thieno[2,3-d]pyrimidine-6-carboxylic acid amide

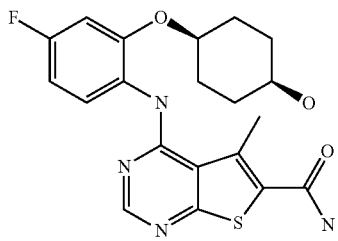 [SMILES: Cc1c(C(N)=O)sc2ncnc(Nc3ccc(F)cc3O[C@H]3CC[C@@H](O)CC3)c12]

0.064 g sodium borohydride were added to a mixture of 0.7 g 4-(4-fluoro-2-(4-oxocyclohexyloxy)phenylamino)-5-methylthieno[2,3-d]pyrimidine-6-carboxamide (example 21) in 20 ml methanol at 0° C. The mixture was allowed to warm up overnight. The reaction mixture was filtered. The solid was recrystallized from hot methanol. The mixture of cis and trans isomer was separated by HPLC.

Cis-Isomer:
Yield: 0.412 g
ESI mass spectrum: m/z=417 (M+H)+
R$_t$ (HPLC): 1.28 (method X)

Example 151

4-[4-Fluoro-2-(cis-4-hydroxy-cyclohexyloxy)-phenylamino]-5-methyl-thieno[2,3-d]pyrimidine-6-carboxylic acid (3-dimethylamino-propyl)-amide

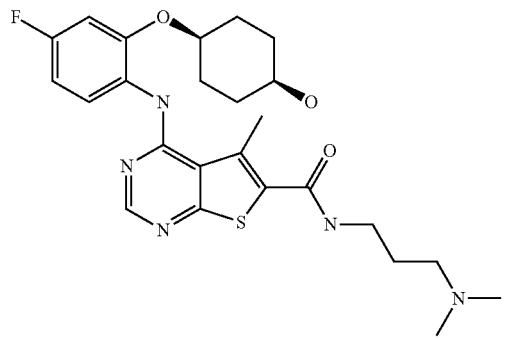 [SMILES: Cc1c(C(=O)NCCCN(C)C)sc2ncnc(Nc3ccc(F)cc3O[C@H]3CC[C@@H](O)CC3)c12]

151.1 4-[4-Fluoro-2-(cis-4-hydroxy-cyclohexyloxy)-phenylamino]-5-methyl-thieno[2,3-d]pyrimidine-6-carboxylic acid methyl ester

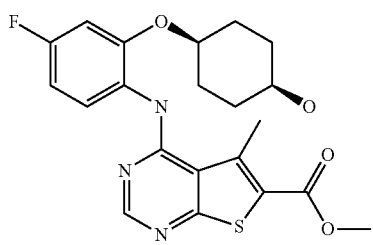 [SMILES: COC(=O)c1sc2ncnc(Nc3ccc(F)cc3O[C@H]3CC[C@@H](O)CC3)c2c1C]

Prepared analogously to example 1.1 from 0.218 g 4-chloro-5-methyl-thieno[2,3-d]pyrimidine-6-carboxylic acid methyl ester and 0.225 g intermediate XXVI in dioxan.
Yield: 0.301 g 151.2 4-[4-Fluoro-2-(cis-4-hydroxy-cyclohexyloxy)-phenylamino]-5-methyl-thieno[2,3-d]pyrimidine-6-carboxylic acid

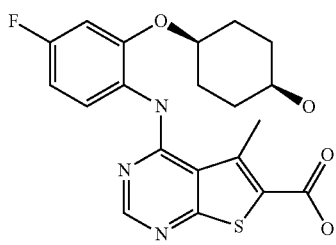

Prepared analogously to 1.3 from 0.301 g 4-[4-fluoro-2-(cis-4-hydroxycyclohexyloxy)-phenylamino]-5-methyl-thieno[2,3-d]pyrimidine-6-carboxylic acid methyl ester.
Yield: 0.262 g 151.3 4-[4-Fluoro-2-(cis-4-hydroxy-cyclohexyloxy)-phenylamino]-5-methyl-thieno[2,3-d]pyrimidine-6-carboxylic acid (3-dimethylamino-propyl)-amide

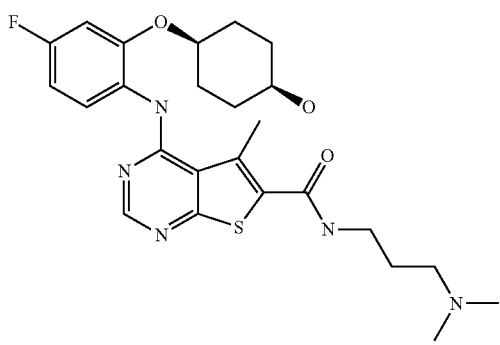

Prepared analogously to example 1.4 from 0.11 g 4-[4-fluoro-2-(cis-4-hydroxycyclohexyloxy)-phenylamino]-5-methyl-thieno[2,3-d]pyrimidine-6-carboxylic acid in DMF.
Yield: 0.113 g
ESI mass spectrum: m/z=502 (M+H)$^+$
R$_t$ (HPLC): 1.23 (method X)

Example 152

4-[4-Fluoro-2-(trans-4-hydroxy-cyclohexyloxy)-phenylamino]-5-methyl-thieno[2,3-d]pyrimidine-6-carboxylic acid (3-dimethylamino-propyl)-amide

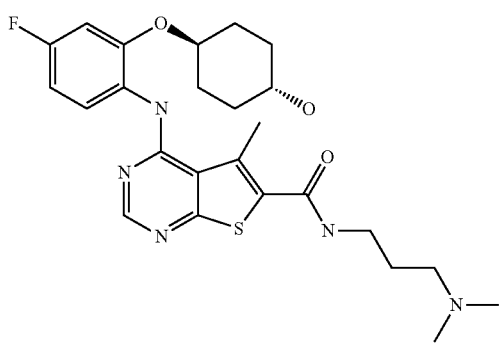

152.1 4-[4-Fluoro-2-(trans-4-hydroxy-cyclohexyloxy)-phenylamino]-5-methyl-thieno[2,3-d]pyrimidine-6-carboxylic acid ethyl ester

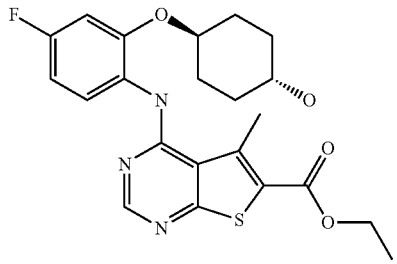 [SMILES: CCOC(=O)c1sc2ncnc(Nc3ccc(F)cc3O[C@H]3CC[C@H](O)CC3)c2c1C]

Prepared analogously to example 1.1 from 2.756 g 4-chloro-5-methyl-thieno[2,3-d]pyrimidine-6-carboxylic acid ethyl ester and 2 g intermediate XXVII in dioxan.
Yield: 2.85 g
ESI mass spectrum: m/z=446 (M+H)$^+$ 152.2 4-[4-Fluoro-2-(trans-4-hydroxy-cyclohexyloxy)-phenylamino]-5-methyl-thieno[2,3-d]pyrimidine-6-carboxylic acid

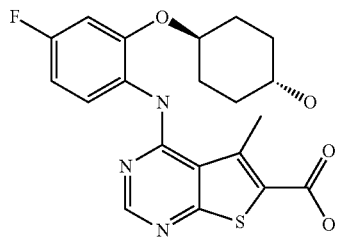

Prepared analogously to 1.3 from 2.8 g 4-[4-fluoro-2-(trans-4-hydroxycyclohexyloxy)-phenylamino]-5-methyl-thieno[2,3-d]pyrimidine-6-carboxylic acid ethyl ester.
Yield: 2.29 g
ESI mass spectrum: m/z=418 (M+H)$^+$
R$_t$ (HPLC): 1.65 (method K)

152.3 4-[4-Fluoro-2-(trans-4-hydroxy-cyclohexyloxy)-phenylamino]-5-methyl-thieno[2,3-d]pyrimidine-6-carboxylic acid (3-dimethylamino-propyl)-amide

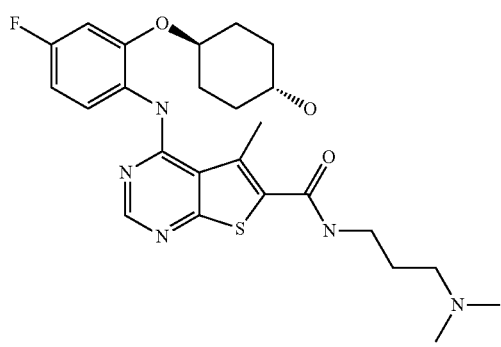

0.072 g EDC were added to a mixture of 0.13 g 4-[4-fluoro-2-(trans-4-hydroxycyclohexyloxy)-phenylamino]-5-methyl-thieno[2,3-d]pyrimidine-6-carboxylic acid and 0.054 g N-Hydroxysuccinimide in DMF (2 ml). The reaction mixture was stirred at rt overnight then diluted with EtOAc and washed with water and brine (2×). The organic phase was passed through a hydrophobic frit and evaporated. The residue was treated with 2 ml DMF and 213 µl 3-dimethylaminopropylamine were added. The mixture was stirred at rt for 40 minutes and then diluted with EtOAc and washed with water and brine (2×). The organic phase was dried with MgSO$_4$ and passed through a hydrophobic frit.

Yield: 0.089 g
ESI mass spectrum: m/z=502 (M+H)$^+$
R$_t$ (HPLC): 1.23 (method X)

Example 153

4-[4-Fluoro-2-(trans-4-hydroxy-cyclohexyloxy)-phenylamino]-5-methyl-thieno[2,3-d]pyrimidine-6-carboxylic acid (3-pyrrolidin-1-yl-propyl)-amide

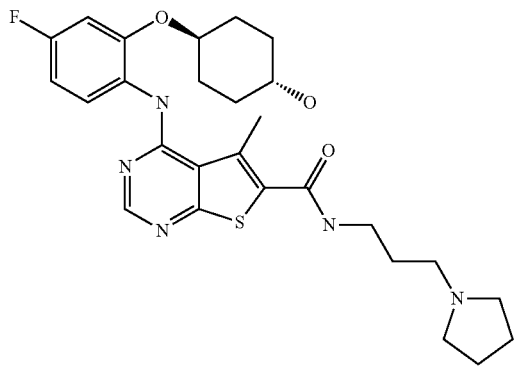 [SMILES: Cc1c(C(=O)NCCCN2CCCC2)sc2ncnc(Nc3ccc(F)cc3O[C@H]3CC[C@H](O)CC3)c12]

153.1

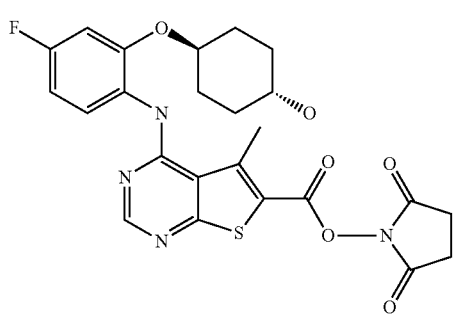 [SMILES: Cc1c(C(=O)ON2C(=O)CCC2=O)sc2ncnc(Nc3ccc(F)cc3O[C@H]3CC[C@H](O)CC3)c12]

0.309 g EDC were added to a suspension of 0.573 g 4-[4-fluoro-2-(trans-4-hydroxycyclohexyloxy)-phenylamino]-5-methyl-thieno[2,3-d]pyrimidine-6-carboxylic acid and 0.231 g N-Hydroxysuccinimide in 5 ml DMF. The reaction mixture was stirred at rt overnight. Then EtOAc and water were added. The suspension was filtered, the filtrate was separated and the aqueous phase was discarded. The organic phase was washed with water and brine (2×) and water. The solvent was evaporated and the residue suspended in ether and filtered. The residues were combined, washed with further ether and air-dried under vacuum.

Yield: 0.707 g 153.2 4-[4-Fluoro-2-(trans-4-hydroxy-cyclohexyloxy)-phenylamino]-5-methyl-thieno[2,3-d]pyrimidine-6-carboxylic acid (3-pyrrolidin-1-yl-propyl)-amide

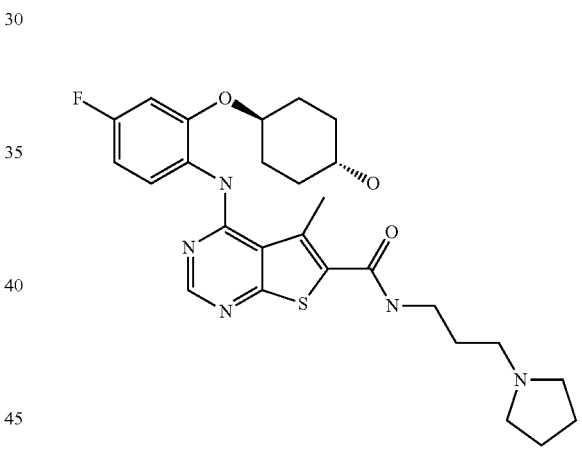

175 µl 3-pyrrolidin-1-yl-propylamine were added to a solution of 0.12 g compound 153.1 in 1 ml DMF. The reaction mixture was stirred for 1 h then diluted with EtOAc/H$_2$O. The mixture was filtered, the solid washed with water and ether. The solid was dissolved in d$_6$-DMSO and evaporated to dryness (Genevac).

Yield: 0.058 g
ESI mass spectrum: m/z=528 (M+H)$^+$
R$_t$ (HPLC): 1.24 (method X)

The following compounds were prepared analogously to 153.2.:

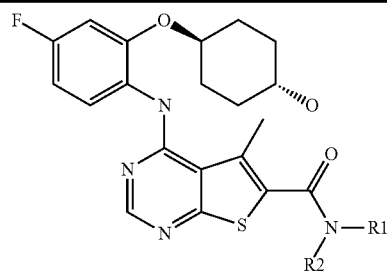

| Example | NR1R2 | educt | Mass spectrum | HPLC (retention time) |
|---|---|---|---|---|
| 154 | 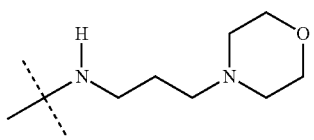 | Cpd. 153.1 | 544 (M + H)$^+$ | 1.23 min (Method X) |
| 155 | 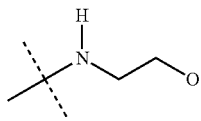 | Cpd. 153.1 | 461 (M + H)$^+$ | 1.25 min (Method X) |
| 156 | 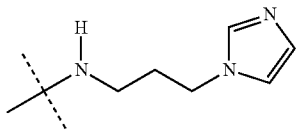 | Cpd. 153.1 | 525 (M + H)$^+$ | 1.23 min (Method X) |
| 157 | 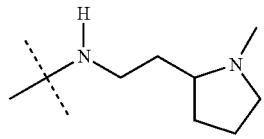 | Cpd. 153.1 | 528 (M + H)$^+$ | 1.24 min (Method X) |

Example 158

4-[4-Fluoro-2-(trans-4-hydroxy-cyclohexyloxy)-phenylamino]-5-methyl-thieno[2,3-d]pyrimidine-6-carboxylic acid amide

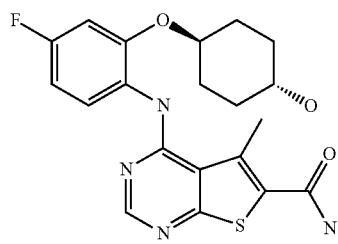

Prepared analogously to example 1.4 from 7 g 4-[4-fluoro-2-(trans-4-hydroxycyclohexyloxy)-phenylamino]-5-methyl-thieno[2,3-d]pyrimidine-6-carboxylic acid in DMF.

Yield: 2.82 g

ESI mass spectrum: m/z=417 (M+H)$^+$ $R_t$ (HPLC): 1.62 (method K)

The following compounds were prepared analogously to 1.4.:

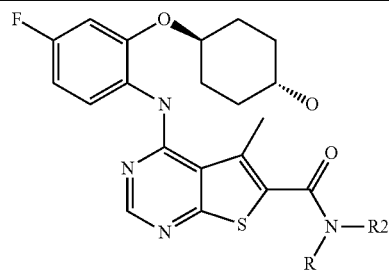
| Example | NR1R2 | educt | Mass spectrum | HPLC (retention time) |
|---|---|---|---|---|
| 159 | | Cpd. 152.2 | 472 (M + H)+ | 1.77 min (Method F) |
| 160 | | Cpd. 152.2 | 484 (M + H)+ | 1.75 min (Method F) |
| 161 | | Cpd. 152.2 | 489 (M + H)+ | 1.82 min (Method E) |
| 162 | | Cpd. 152.2 | 498 (M + H)+ | 1.83 min (Method E) |
| 163 | | Cpd. 152.2 | 456 (M + H)+ | 1.83 min (Method E) |
| 164 | | Cpd. 152.2 | 488 (M + H)+ | 2.09 min (Method F) |
| 165 | | Cpd. 152.2 | 512 (M + H)+ | 1.46 min (Method E) |
| 166 | | Cpd. 152.2 | 516 (M + H)+ | 1.75 min (Method F) |
| 167 | | Cpd. 152.2 | 516 (M + H)+ | 1.77 min (Method F) |

-continued

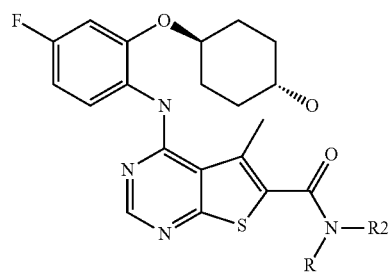

| Example | NR1R2 | educt | Mass spectrum | HPLC (retention time) |
|---|---|---|---|---|
| 168 | (trans-4-hydroxycyclohexyl)amino | Cpd. 152.2 | 515 (M + H)+ | 1.84 min (Method E) |
| 169 | (1-methylpiperidin-4-yl)amino | Cpd. 152.2 | 514 (M + H)+ | 1.46 min (Method E) |
| 170 | (2-piperidin-1-yl-ethyl)amino | Cpd. 152.2 | 528 (M + H)+ | 1.48 min (Method E) |
| 171 | (2-hydroxypropyl)amino | Cpd. 152.2 | 475 (M + H)+ | 1.81 min (Method E) |
| 172 | (3-hydroxypropyl)amino | Cpd. 152.2 | 475 (M + H)+ | 1.8 min (Method E) |
| 173 | ethylamino | Cpd. 152.2 | 445 (M + H)+ | 1.87 min (Method E) |
| 174 | [(1-methyl-1H-imidazol-4-yl)methyl]amino | Cpd. 152.2 | 511 (M + H)+ | 1.45 min (Method E) |

Example 175

4-[4-Fluoro-2-(trans-4-methoxy-cyclohexyloxy)-phenylamino]-5-methyl-thieno[2,3-d]pyrimidine-6-carboxylic acid amide

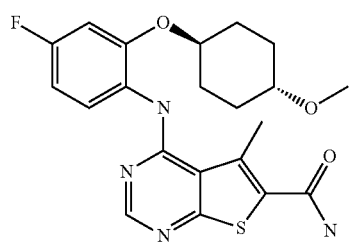 [SMILES: CO[C@H]1CC[C@H](Oc2cc(F)ccc2Nc2ncnc3sc(C(N)=O)c(C)c23)CC1]

175.1 4-[4-Fluoro-2-(trans-4-methoxy-cyclohexyloxy)-phenylamino]-5-methyl-thieno[2,3-d]pyrimidine-6-carboxylic acid ethylester

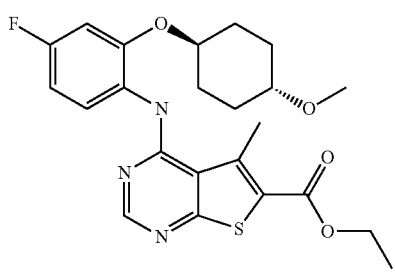 [SMILES: CCOC(=O)c1sc2ncnc(Nc3ccc(F)cc3O[C@H]3CC[C@H](OC)CC3)c2c1C]

Prepared analogously to example 1.1 from 5.842 g 4-chloro-5-methyl-thieno[2,3-d]pyrimidine-6-carboxylic acid ethyl ester and 4.9 g intermediate XXXXXVII in dioxan.
Yield: 2.85 g
ESI mass spectrum: m/z=446 (M+H)$^+$

175.2 4-[4-Fluoro-2-(trans-4-methoxy-cyclohexyloxy)-phenylamino]-5-methyl-thieno[2,3-d]pyrimidine-6-carboxylic acid

Prepared analogously to 58.2 from 9.1 g 4-[4-fluoro-2-(trans-4-methoxycyclohexyloxy)-phenylamino]-5-methyl-thieno[2,3-d]pyrimidine-6-carboxylic acid ethylester.
Yield: 6.8 g
ESI mass spectrum: m/z=432 (M+H)$^+$
R$_t$ (HPLC): 3.17 (method A)

175.3 4-[4-Fluoro-2-(trans-4-methoxy-cyclohexyloxy)-phenylamino]-5-methyl-thieno[2,3-d]pyrimidine-6-carboxylic acid amide

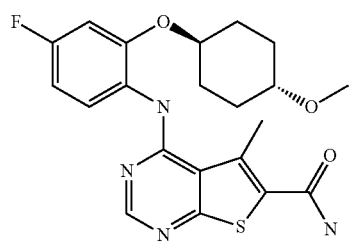 [SMILES: CO[C@H]1CC[C@H](Oc2cc(F)ccc2Nc2ncnc3sc(C(N)=O)c(C)c23)CC1]

Prepared analogously to 1.4 from 0.1 g 4-[4-fluoro-2-(trans-4-methoxycyclohexyloxy)-phenylamino]-5-methyl-thieno[2,3-d]pyrimidine-6-carboxylic acid and ammonia (7M in methanol).
Yield: 0.072 g
ESI mass spectrum: m/z=431 (M+H)$^+$
R$_t$ (HPLC): 1.39 (method X)

The following compound were prepared analogously to 1.4.:

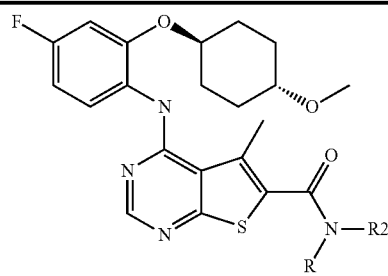
| Example | NR1R2 | educt | Mass spectrum | HPLC (retention time) |
|---|---|---|---|---|
| 176 | H N N | Cpd. 175.2 | 516 (M + H)+ | 1.29 min (Method X) |
| 177 | H N N | Cpd. 175.2 | 542 (M + H)+ | 2.2 min (Method A) |
| 178 | H N N | Cpd. 175.2 | 498 (M + H)+ | 1.54 min (Method E) |
| 179 | H N N O | Cpd. 175.2 | 530 (M + H)+ | 1.54 min (Method E) |
| 180 | H N N O | Cpd. 175.2 | 530 (M + H)+ | 1.54 min (Method E) |
| 181 | H N O | Cpd. 175.2 | 503 (M + H)+ | 1.94 min (Method E) |
| 182 | H N N | Cpd. 175.2 | 470 (M + H)+ | 1.95 min (Method E) |
| 183 | H N O | Cpd. 175.2 | 529 (M + H)+ | 1.96 min (Method E) |
| 184 | H N O | Cpd. 175.2 | 489 (M + H)+ | 1.94 min (Method E) |

-continued
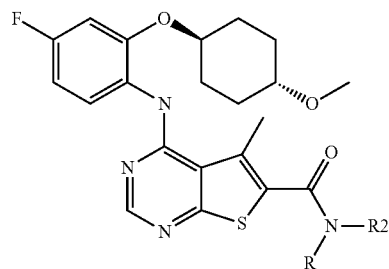
| Example | NR1R2 | educt | Mass spectrum | HPLC (retention time) |
|---------|-------|-------|---------------|------------------------|
| 185 | | Cpd. 175.2 | 512 (M + H)+ | 1.95 min (Method E) |
| 186 | | Cpd. 175.2 | 525 (M + H)+ | 1.54 min (Method E) |
| 187 | | Cpd. 175.2 | 526 (M + H)+ | 1.56 min (Method E) |
| 188 | | Cpd. 175.2 | 502 (M + H)+ | 1.91 min (Method E) |
| 189 | | Cpd. 175.2 | 486 (M + H)+ | 1.54 min (Method E) |
| 190 | | Cpd. 175.2 | 542 (M + H)+ | 1.58 min (Method E) |
| 191 | | Cpd. 175.2 | 528 (M + H)+ | 1.55 min (Method E) |

Example 192

4-[4-Fluoro-2-(trans-4-methoxy-cyclohexyloxy)-phenylamino]-5-methyl-thieno[2,3-d]pyrimidine-6-carboxylic acid (3-morpholin-4-yl-propyl)-amide

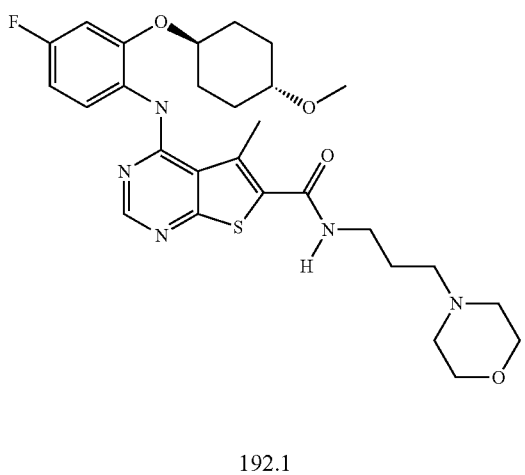

192.1

Prepared analogously to 153.1 from 0.267 g 4-[4-fluoro-2-(trans-4-methoxycyclohexyloxy)-phenylamino]-5-methyl-thieno[2,3-d]pyrimidine-6-carboxylic acid and 0.143 g EDC.

Yield: 0.232 g 192.2 4-[4-Fluoro-2-(trans-4-methoxy-cyclohexyloxy)-phenylamino]-5-methyl-thieno[2,3-d]pyrimidine-6-carboxylic acid (3-morpholin-4-yl-propyl)-amide

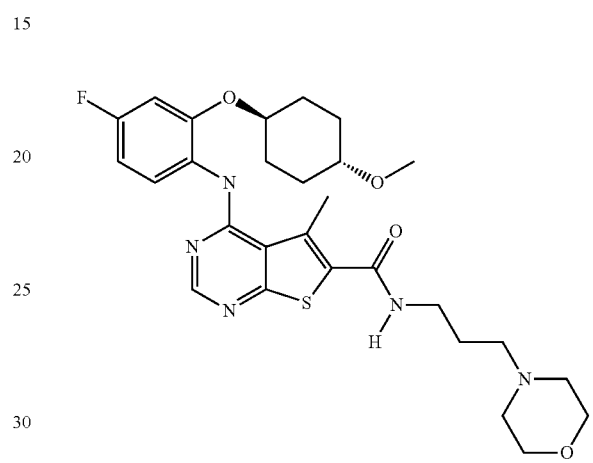

Prepared analogously to 153.2 from 0.161 g compound 192.1 and 222 µl N-(3-aminopropyl)morpholine.

Yield: 0.130 g

ESI mass spectrum: m/z=558 (M+H)$^+$

R$_t$ (HPLC): 1.29 (method X)

The following compound were prepared analogously to 153.2.:

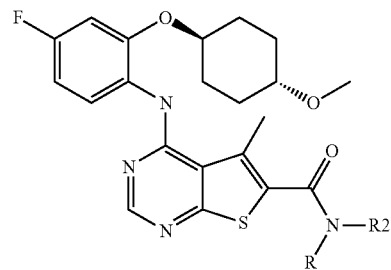

| Example | NR1R2 | educt | Mass spectrum | HPLC (retention time) |
|---|---|---|---|---|
| 193 | ![H-N-CH2CH2-N(CH3)2] | Cpd. 192.1 | 502 (M + H)$^+$ | 1.29 min (Method X) |

-continued

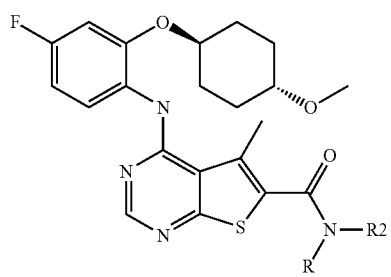

| Example | NR1R2 | educt | Mass spectrum | HPLC (retention time) |
|---|---|---|---|---|
| 194 | ![structure: N-H-CH2CH2-(1-methylpyrrolidin-2-yl)] | Cpd. 192.1 | 542 (M + H)+ | 1.3 min (Method X) |
| 195 | ![structure: N-H-(CH2)3-OH] | Cpd. 192.1 | 489 (M + H)+ | 1.37 min (Method X) |
| 196 | ![structure: N-H-CH2CH2-OH] | Cpd. 192.1 | 475 (M + H)+ | 1.35 min (Method X) |
| 197 | ![structure: N-H-(CH2)3-imidazol-1-yl] | Cpd. 192.1 | 539 (M + H)+ | 1.3 min (Method X) |
| 198 | ![structure: N-H-(CH2)3-(4-methylpiperazin-1-yl)] | Cpd. 192.1 | 571 (M + H)+ | 1.24 min (Method X) |
| 199 | ![structure: N-H-CH2-(4-methylmorpholin-2-yl)] | Cpd. 192.1 | 544 (M + H)+ | 1.28 min (Method X) |

Example 200

4-[4-Fluoro-2-(trans-4-methoxy-cyclohexyloxy)-phenylamino]-5-methyl-thieno[2,3-d]pyrimidine-6-carboxylic acid (piperidin-3-ylmethyl)-amide

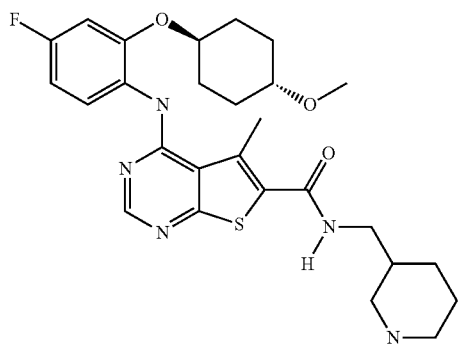 [SMILES: CO[C@H]1CC[C@H](Oc2cc(F)ccc2Nc2ncnc3sc(C(=O)NCC4CCCNC4)c(C)c23)CC1]

200.1 3-[({4-[4-Fluoro-2-(trans-4-methoxy-cyclohexyloxy)-phenylamino]-5-methyl-thieno[2,3-d]pyrimidine-6-carbonyl}-amino)-methyl]-piperidine-1-carboxylic acid tert-butyl ester

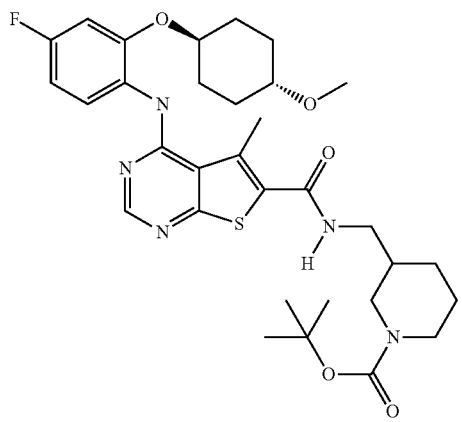 [SMILES: CO[C@H]1CC[C@H](Oc2cc(F)ccc2Nc2ncnc3sc(C(=O)NCC4CCCN(C(=O)OC(C)(C)C)C4)c(C)c23)CC1]

Prepared analogously to 153.2 from 0.1 g compound 192.1 and 0.15 g 3-aminomethyl-piperidine-1-carboxylic acid tert-butyl ester.

Yield: 0.119 g

200.2 4-[4-Fluoro-2-(trans-4-methoxy-cyclohexyloxy)-phenylamino]-5-methyl-thieno[2,3-d]pyrimidine-6-carboxylic acid (piperidin-3-ylmethyl)-amide

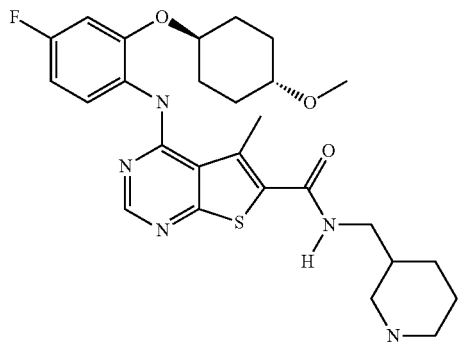 [SMILES: CO[C@H]1CC[C@H](Oc2cc(F)ccc2Nc2ncnc3sc(C(=O)NCC4CCCNC4)c(C)c23)CC1]

Prepared analogously to IV.2 from 0.119 g 3-[({-4-[4-fluoro-2-(trans-4-methoxycyclohexyloxy)-phenylamino]-5-methyl-thieno[2,3-d]pyrimidine-6-carbonyl}-amino)methyl]-piperidine-1-carboxylic acid tert-butyl ester.

Yield: 0.059 g

ESI mass spectrum: m/z=558 (M+H)$^+$

Example 201

4-[4-Fluoro-2-(trans-4-methoxy-cyclohexyloxy)-phenylamino]-5-methyl-thieno[2,3-d]pyrimidine-6-carboxylic acid [3-(3-hydroxy-pyrrolidin-1-yl)-propyl]-amide

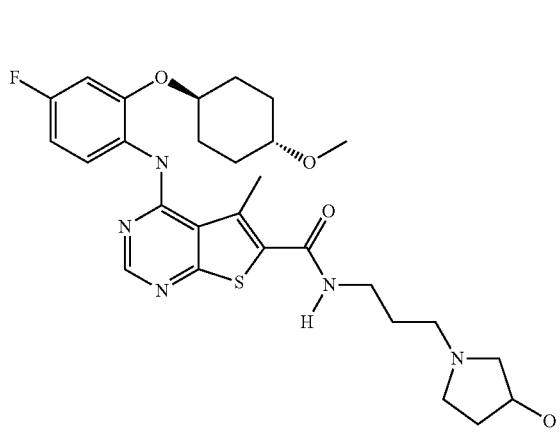 [SMILES: CO[C@H]1CC[C@H](Oc2cc(F)ccc2Nc2ncnc3sc(C(=O)NCCCN4CCC(O)C4)c(C)c23)CC1]

201.1 4-[4-Fluoro-2-(trans-4-methoxy-cyclohexyloxy)-phenylamino]-5-methyl-thieno[2,3-d]pyrimidine-6-carboxylic acid (3,3-diethoxy-propyl)-amide

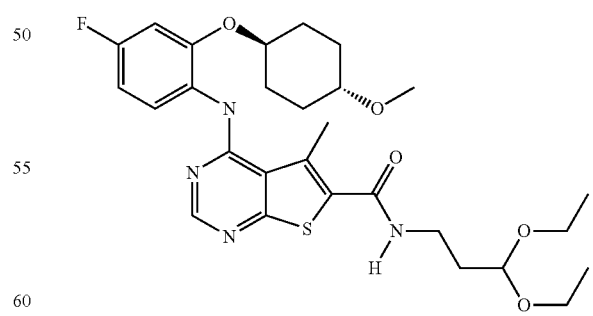

Prepared analogously to 153.2 from 0.287 g compound 192.1 and 437 µl 1-amino-3,3-diethoxypropane.

Yield: 0.266 g

201.2 4-[4-Fluoro-2-(trans-4-methoxy-cyclohexyloxy)-phenylamino]-5-methyl-thieno[2,3-d]pyrimidine-6-carboxylic acid (3-oxo-propyl)-amide

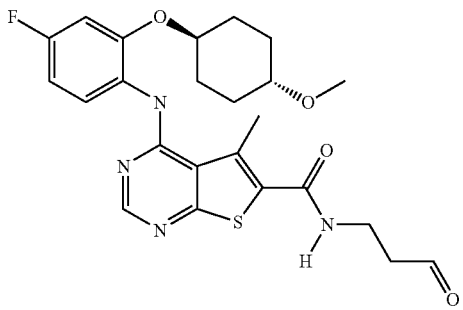 [SMILES: CO[C@H]1CC[C@H](Oc2cc(F)ccc2Nc2ncnc3sc(C(=O)NCCC=O)c(C)c23)CC1]

A mixture of 0.261 g compound 201.1 and p-toluene sulfonic acid in 3 ml acetone were heated at reflux for 30 minutes. Then methylene chloride and aq. potassium carbonate solution (10%) were added and the mixture was shaken. After that the mixture was passed through a hydrophobic frit. The filtrate was evaporated.

Yield: 0.213 g

201.3 4-[4-Fluoro-2-(trans-4-methoxy-cyclohexyloxy)-phenylamino]-5-methyl-thieno[2,3-d]pyrimidine-6-carboxylic acid [3-(3-hydroxy-pyrrolidin-1-yl)-propyl]-amide

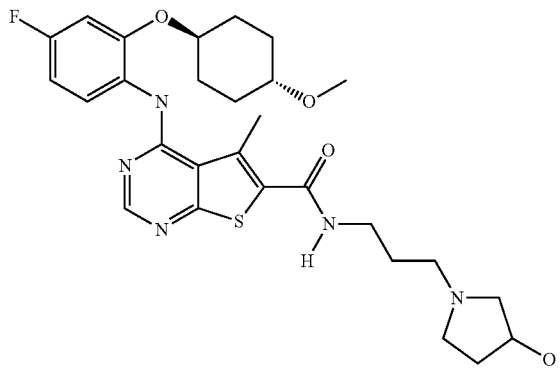 [SMILES: CO[C@H]1CC[C@H](Oc2cc(F)ccc2Nc2ncnc3sc(C(=O)NCCCN4CCC(O)C4)c(C)c23)CC1]

0.155 g sodium triacetoxyborohydride were added to a solution of the 0.21 g 4-[4-fluoro-2-(trans-4-methoxy-cyclohexyloxy)-phenylamino]-5-methyl-thieno[2,3-d]pyrimidine-6-carboxylic acid (3-oxo-propyl)-amide and 43 µl 3-pyrrolidinol in methylene chloride followed by addition of 49 µl acetic acid. The mixture was stirred at rt overnight, diluted with methylene chloride and then washed with 10% aq. K$_2$CO$_3$. The mixture was passed through a hydrophobic frit. The filtrate was evaporated and purified by chromatography.

Yield: 0.15 g

ESI mass spectrum: m/z=558 (M+H)$^+$

R$_t$ (HPLC): 1.28 (method X)

Example 202

4-[4-Fluoro-2-(cis-4-methoxy-cyclohexyloxy)-phenylamino]-5-methyl-thieno[2,3-d]pyrimidine-6-carboxylic acid (3-dimethylamino-propyl)-amide

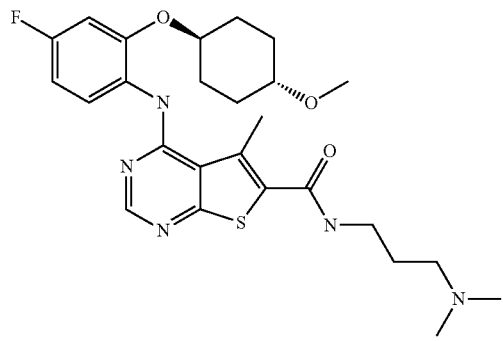 [SMILES: CO[C@H]1CC[C@H](Oc2cc(F)ccc2Nc2ncnc3sc(C(=O)NCCCN(C)C)c(C)c23)CC1]

202.1 4-[4-Fluoro-2-(cis-4-methoxy-cyclohexyloxy)-phenylamino]-5-methyl-thieno[2,3-d]pyrimidine-6-carboxylic acid methylester

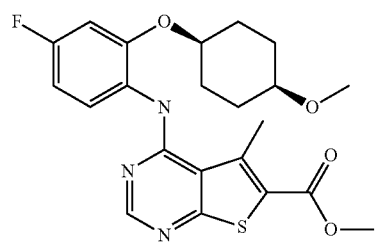 [SMILES: COC(=O)c1sc2ncnc(Nc3ccc(F)cc3O[C@H]3CC[C@@H](OC)CC3)c2c1C]

Prepared analogously to example 1.1 from 0.507 g 4-chloro-5-methyl-thieno[2,3-d]pyrimidine-6-carboxylic acid methyl ester and 0.5 g intermediate XXXXXVIII in dioxan.

Yield: 0.905 g

ESI mass spectrum: m/z=446 (M+H)$^+$

R$_t$ (HPLC): 2.22 (method K)

202.2 4-[4-Fluoro-2-(cis-4-methoxy-cyclohexyloxy)-phenylamino]-5-methyl-thieno[2,3-d]pyrimidine-6-carboxylic acid

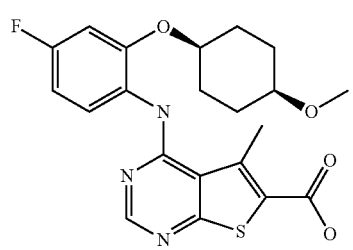 [SMILES: CO[C@H]1CC[C@@H](Oc2cc(F)ccc2Nc2ncnc3sc(C(=O)O)c(C)c23)CC1]

Prepared analogously to 1.3 from 0.85 g 4-[4-fluoro-2-(cis-4-methoxy-cyclohexyloxy)phenylamino]-5-methyl-thieno[2,3-d]pyrimidine-6-carboxylic acid methylester.
Yield: 0.753 g
ESI mass spectrum: m/z=432 (M+H)+
$R_t$ (HPLC): 3.22 (method A)

202.3 4-[4-Fluoro-2-(cis-4-methoxy-cyclohexyloxy)-phenylamino]-5-methyl-thieno[2,3-d]pyrimidine-6-carboxylic acid (3-dimethylamino-propyl)-amide

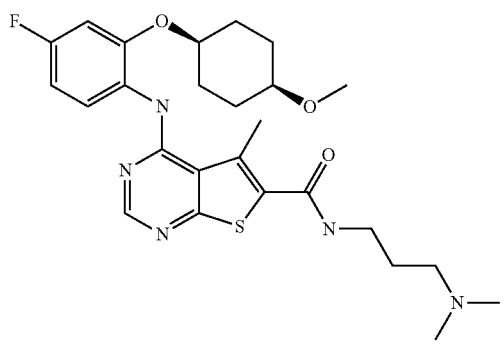 [SMILES: CO[C@H]1CC[C@@H](Oc2cc(F)ccc2Nc2ncnc3sc(C(=O)NCCCN(C)C)c(C)c23)CC1]

Prepared analogously to 1.4 from 0.1 g 4-[4-fluoro-2-(cis-4-methoxy-cyclohexyloxy)phenylamino]-5-methyl-thieno[2,3-d]pyrimidine-6-carboxylic acid and 42 µl N,N-dimethyl-1,3-propanediamine.
Yield: 0.097 g
ESI mass spectrum: m/z=516 (M+H)+
$R_t$ (HPLC): 1.34 (method K)
The following compound was prepared analogously to 1.4.:

Example 204

4-[2-(trans-4-Hydroxy-cyclohexyloxy)-pyridin-3-ylamino]-5-methyl-thieno[2,3-d]pyrimidine-6-carboxylic acid amide

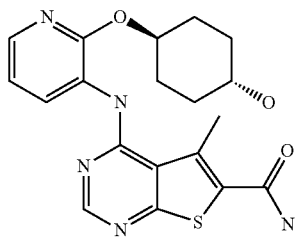 [SMILES: Cc1c(C(N)=O)sc2ncnc(Nc3cccnc3O[C@H]3CC[C@H](O)CC3)c12]

204.1 4-[2-(4-Hydroxy-cyclohexyloxy)-pyridin-3-ylamino]-5-methyl-thieno[2,3-d]pyrimidine-6-carboxylic acid methylester

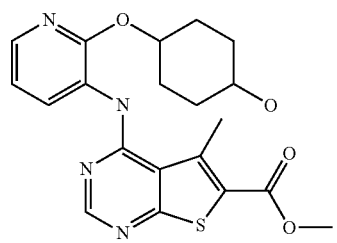 [SMILES: COC(=O)c1sc2ncnc(Nc3cccnc3OC3CCC(O)CC3)c2c1C]

Prepared analogously to example 1.1 from 1.78 g 4-chloro-5-methyl-thieno[2,3-d]pyrimidine-6-carboxylic acid methyl ester and 1.53 g intermediate XXXXXIX in dioxan.
Yield: 1.8 g

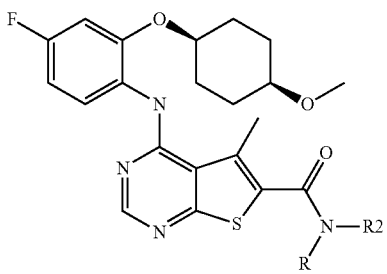

| Example | NR1R2 | educt | Mass spectrum | HPLC (retention time) |
|---|---|---|---|---|
| 203 | 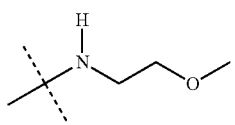 | Cpd. 202.2 | 489 (M + H)+ | 1.83 min (Method K) |

204.2 4-[2-(4-Hydroxy-cyclohexyloxy)-pyridin-3-ylamino]-5-methyl-thieno[2,3-d]pyrimidine-6-carboxylic acid

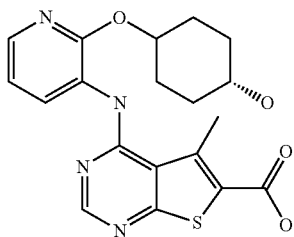

Prepared analogously to 1.3 from 0.363 g 4-[2-(4-hydroxy-cyclohexyloxy)-pyridin-3-ylamino]-5-methyl-thieno[2,3-d]pyrimidine-6-carboxylic acid methylester.
Yield: 0.221 g

204.3 4-[2-(trans-4-Hydroxy-cyclohexyloxy)-pyridin-3-ylamino]-5-methyl-thieno[2,3-d]pyrimidine-6-carboxylic acid amide

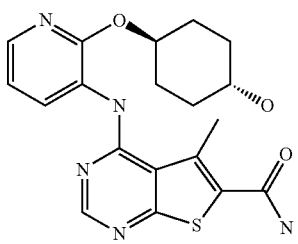 [SMILES: Cc1c(C(N)=O)sc2ncnc(Nc3cccnc3O[C@H]3CC[C@H](O)CC3)c12]

Prepared analogously to 1.4 from 0.1 g 4-[2-(trans-4-hydroxy-cyclohexyloxy)-pyridin-3-ylamino]-5-methyl-thieno[2,3-d]pyrimidine-6-carboxylic acid and ammonia in methanol (7M) in DMF. Separated from cis isomer by chromatography.
Yield: 0.008 g

Example 205

4-[2-(cis-4-Hydroxy-cyclohexyloxy)-pyridin-3-ylamino]-5-methyl-thieno[2,3-d]pyrimidine-6-carboxylic acid amide

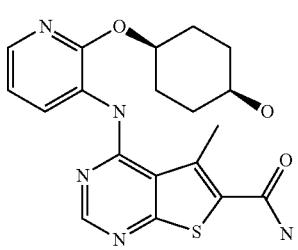 [SMILES: Cc1c(C(N)=O)sc2ncnc(Nc3cccnc3O[C@H]3CC[C@@H](O)CC3)c12]

Prepared analogously to 1.4 from 0.1 g 4-[2-(4-hydroxy-cyclohexyloxy)-pyridin-3-ylamino]-5-methyl-thieno[2,3-d]pyrimidine-6-carboxylic acid and ammonia in methanol (7M) in DMF. Separated from trans isomer by chromatography.

Yield: 0.009 g
ESI mass spectrum: m/z=400 (M+H)$^+$
R$_t$ (HPLC): 1.26 (method X)

Example 206

4-[2-(trans-4-Hydroxy-cyclohexyloxy)-pyridin-3-ylamino]-5-methyl-thieno[2,3-d]pyrimidine-6-carboxylic acid (3-dimethylamino-propyl)-amide

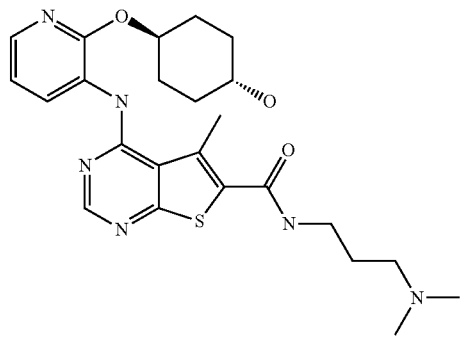 [SMILES: Cc1c(C(=O)NCCCN(C)C)sc2ncnc(Nc3cccnc3O[C@H]3CC[C@H](O)CC3)c12]

206.1 4-[2-(trans-4-Hydroxy-cyclohexyloxy)-pyridin-3-ylamino]-5-methyl-thieno[2,3-d]pyrimidine-6-carboxylic acid methylester

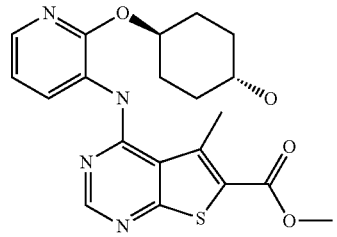

Prepared analogously to example 1.1 from 0.262 g 4-chloro-5-methyl-thieno[2,3-d]pyrimidine-6-carboxylic acid methyl ester and 0.203 g intermediate XXXXXX in dioxan.
Yield: 0.352 g
ESI mass spectrum: m/z=415 (M+H)$^+$

206.2 4-[2-(trans-4-Hydroxy-cyclohexyloxy)-pyridin-3-ylamino]-5-methyl-thieno[2,3-d]pyrimidine-6-carboxylic acid

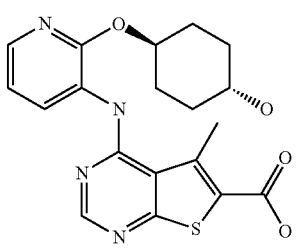 [SMILES: Cc1c(C(=O)O)sc2ncnc(Nc3cccnc3O[C@H]3CC[C@H](O)CC3)c12]

221

Prepared analogously to 58.2 from 0.352 g 4-[2-(trans-4-hydroxy-cyclohexyloxy)pyridin-3-ylamino]-5-methyl-thieno[2,3-d]pyrimidine-6-carboxylic acid methylester.

Yield: 0.083 g

ESI mass spectrum: m/z=401 (M+H)$^+$ 206.3 4-[2-(trans-4-Hydroxy-cyclohexyloxy)-pyridin-3-ylamino]-5-methyl-thieno[2,3-d]pyrimidine-6-carboxylic acid (3-dimethylamino-propyl)-amide

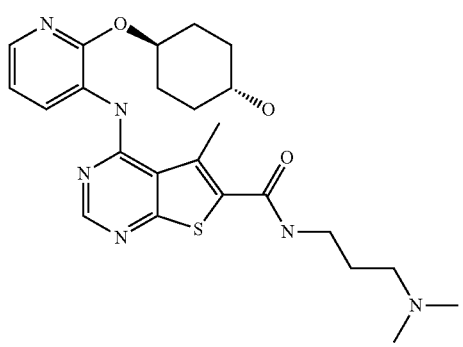 [SMILES: Cc1c(C(=O)NCCCN(C)C)sc2ncnc(Nc3cccnc3O[C@H]3CC[C@H](O)CC3)c12]

Prepared analogously to 1.4 from 0.083 g 4-[2-(trans-4-hydroxy-cyclohexyloxy)pyridin-3-ylamino]-5-methyl-thieno[2,3-d]pyrimidine-6-carboxylic acid and 26 µl N,N-dimethyl-1,3-propanediamine in THF using TBTU instead of HATU.

Yield: 0.077 g

ESI mass spectrum: m/z=485 (M+H)$^+$

R$_t$ (HPLC): 1.91 (method A)

Example 207

4-[2-(trans-4-Methoxy-cyclohexyloxy)-pyridin-3-ylamino]-5-methyl-thieno[2,3-d]pyrimidine-6-carboxylic acid amide

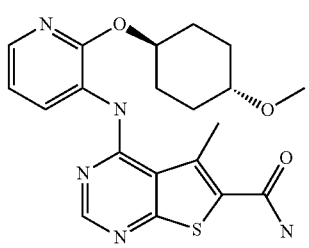 [SMILES: CO[C@H]1CC[C@H](Oc2ncccc2Nc2ncnc3sc(C(N)=O)c(C)c23)CC1]

222

207.1 4-(2-Hydroxy-pyridin-3-ylamino)-5-methyl-thieno[2,3-d]pyrimidine-6-carboxylic acid methyl ester

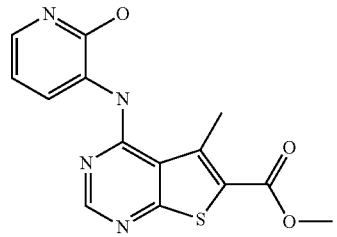 [SMILES: COC(=O)c1sc2ncnc(Nc3cccnc3O)c2c1C]

Prepared analogously to example 1.1 from 0.2 g 4-chloro-5-methyl-thieno[2,3-d]pyrimidine-6-carboxylic acid methyl ester and 0.1 g 3-amino-pyridin-2-ol in dioxan.

Yield: 0.258 g

ESI mass spectrum: m/z=317 (M+H)$^+$ 207.2 4-[2-(trans-4-Methoxy-cyclohexyloxy)-pyridin-3-ylamino]-5-methyl-thieno[2,3-d]pyrimidine-6-carboxylic acid methylester

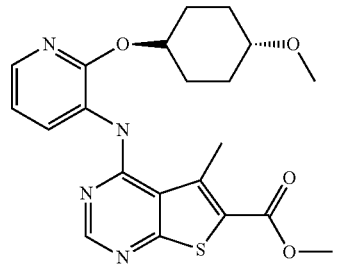

Prepared analogously to example XVI.1 from 1.215 g 4-(2-hydroxy-pyridin-3-ylamino)-5-methyl-thieno[2,3-d]pyrimidine-6-carboxylic acid methyl ester and 0.6 g cis-4-methoxy-cyclohexanol using DTAD and triphenylphosphine (polymerically bound from Aldrich).

Yield: 0.24 g

ESI mass spectrum: m/z=429 (M+H)$^+$ 207.3 4-[2-(trans-4-methoxy-cyclohexyloxy)-pyridin-3-ylamino]-5-methyl-thieno[2,3-d]pyrimidine-6-carboxylic acid

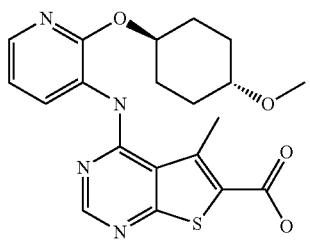 [SMILES: CO[C@H]1CC[C@H](Oc2ncccc2Nc2ncnc3sc(C(=O)O)c(C)c23)CC1]

Prepared analogously to 1.3 from 0.24 g 4-[2-(trans-4-methoxy-cyclohexyloxy)pyridin-3-ylamino]-5-methyl-thieno[2,3-d]pyrimidine-6-carboxylic acid methylester.

Yield: 0.21 g

207.4 4-[2-(trans-4-methoxy-cyclohexyloxy)-pyridin-3-ylamino]-5-methyl-thieno[2,3-d]pyrimidine-6-carboxylic acid amide

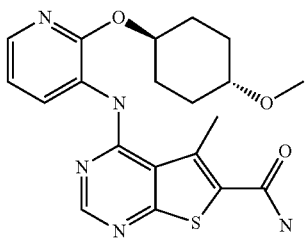

Prepared analogously to 1.4 from 0.005 g 4-[2-(trans-4-methoxy-cyclohexyloxy)pyridin-3-ylamino]-5-methyl-thieno[2,3-d]pyrimidine-6-carboxylic acid and ammonia (0.5 M in THF) in DMF using TBTU instead of HATU.

Yield: 0.034 g

ESI mass spectrum: m/z=414 (M+H)$^+$

The following compounds were prepared analogously to 1.4.:

| Example | NR1R2 | educt | Mass spectrum | HPLC (retention time) |
|---|---|---|---|---|
| 208 | (H, methyl) | Cpd. 207.3 | 428 (M + H)$^+$ | 1.83 min (Method K) |
| 209 | (H, CH2CH2O) | Cpd. 207.3 | 458 (M + H)$^+$ | 1.83 min (Method K) |
| 210 | (H, CH2CH2CH2N(CH3)2) | Cpd. 207.3 | 499 (M + H)$^+$ | 1.83 min (Method K) |

Example 211

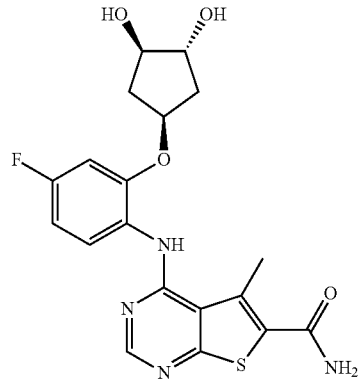

relative stereochemistry

211.1 relative stereochemistry

Intermediate XXXXXXI (243 mg), 4-chloro-5-methyl-thieno[2,3-d]pyrimidine-6-carboxylic acid methyl ester (250 mg) and p-toluenesulfonic acid (20 mg) in dioxane (3.0 ml) were heated at 110° C. for 8 h. The reaction mixture was diluted with DCM and NH$_4$OH, separated and filtered. The solid was washed with DCM and water. The filtrate was separated and the organic layer was concentrated in vacuo. The residue was suspended in water and filtered. The combined solids were washed with water and diethyl ether then dried in vacuo to give the desired product.

Yield: 366 mg 211.2

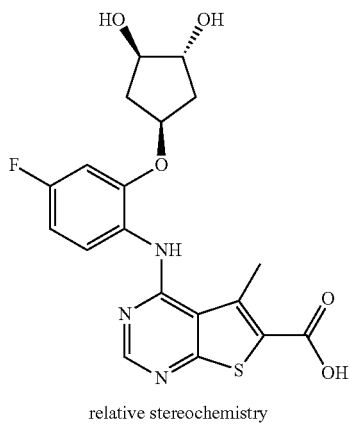
relative stereochemistry 2.0 M aq. sodium hydroxid was added to a mixture of compound 211.1 (366 mg) in ethanol (4.0 ml) and THF (4.0 ml) and stirred at rt for 4 h. The mixture was diluted with 10% aq. KHSO₄ and filtered. The filtercake was washed with water and diethyl ether and dried in vacuo to give the desired product.

Yield: 342 mg 211.3

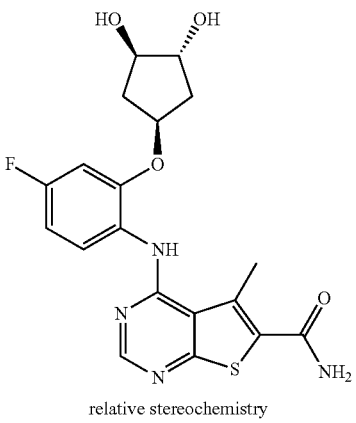
relative stereochemistry

HATU (388 mg) was added at 0° C. to a mixture of compound 211.2 (356 mg) and DIPEA (178 µl) in DMF (4.0 ml). After 30 min 7 M NH₃ in methanol (2.0 ml) was added and the mixture was allowed to warm to room temperature overnight. The reaction mixture was partitioned between EtOAc and water and filtered. The filtercake was washed with EtOAc and water, then suspended in ethanol and evaporated in vacuo. The residue was suspended in methanol, filtered and dried in vacuo to give the desired product.

Yield: 200 mg

ESI-MS: m/z=419 [M+H]⁺

R$_t$ (HPLC): 1.19 (method X)

Example 212

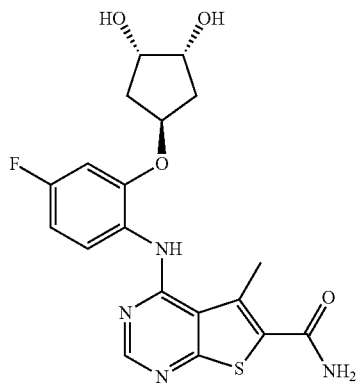
relative stereochemistry

Example 212.1

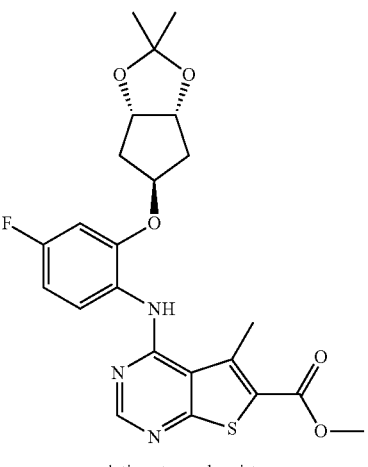
relative stereochemistry

Intermediate XXXXV (379 mg), 4-chloro-5-methyl-thieno[2,3-d]pyrimidine-6-carboxylic acid methyl ester (344 mg) and p-toluenesulfonic acid (27 mg) in dioxane (5.0 ml) were heated at 110° C. for 1 h. The reaction mixture was diluted with EtOAc and washed with 10% aq. K₂CO₃ and brine. The organic layer was concentrated in vacuo. The residue suspended in methanol and filtered to yield the desired product.

Yield: 428 mg

227

212.2

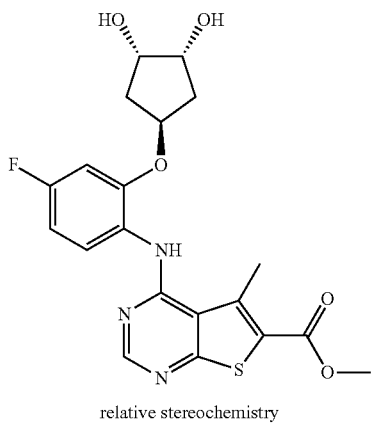 [SMILES: COC(=O)c1sc2ncnc(Nc3ccc(F)cc3O[C@@H]3C[C@@H](O)[C@@H](O)C3)c2c1C]

relative stereochemistry

2 M aq. HCl (10.0 ml) was added to compound 212.1 (672 mg) in THF (10.0 ml) and the mixture was heated at reflux. After 30 min the reaction mixture was concentrated in vacuo. The residue was partitioned between methylene chloride and 2 M aq. sodium hydroxid. The mixture was filtered. The filtercake was washed with diethyl ether and dried under vacuo to give the desired product.

Yield: 406 mg

ESI-MS: m/z=434 [M+H]$^+$ 212.3

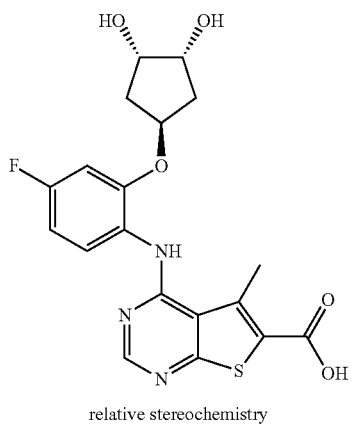 [SMILES: Cc1c(C(=O)O)sc2ncnc(Nc3ccc(F)cc3O[C@@H]3C[C@@H](O)[C@@H](O)C3)c12]

relative stereochemistry

Prepared analogously to 1.3 from 0.333 g compound 212.2.

Yield: 250 mg

228

212.4

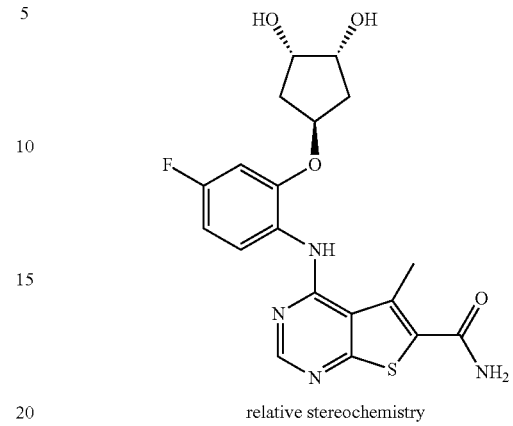

relative stereochemistry

Prepared analogously to 1.4 from 0.249 g compound 212.3 and ammonia (7 M in methanol).

Yield: 183 mg

ESI-MS: m/z=419 [M+H]$^+$

R$_t$ (HPLC): 1.2 (method X)

Example 213

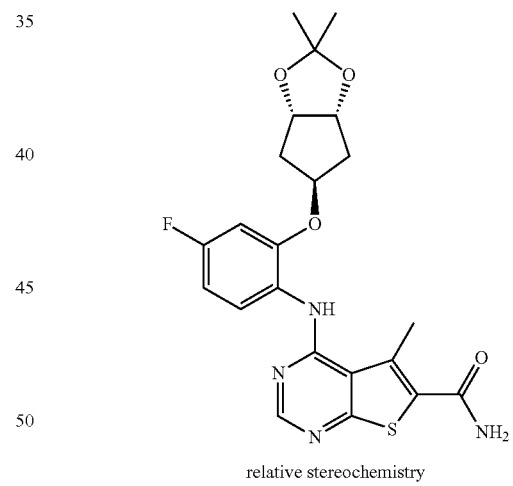

relative stereochemistry

A mixture of compound 212.4 (84 mg), 2,2-dimethoxypropan (1.0 ml) and p-toluenesulfonic acid (16 mg) in DMF (1.0 ml) was stirred at room temperature overnight. The reaction mixture was diluted with EtOAc and washed with 10% aq. K$_2$CO$_3$ and water. The organic layer was concentrated in vacuo. After triturated with diethyl ether the residue was heated in methanol/water, allowed to cool and filtered to give the desired product.

Yield: 60 mg

ESI-MS: m/z=459 [M+H]$^+$

R$_t$ (HPLC): 1.4 (method X)

Example 214

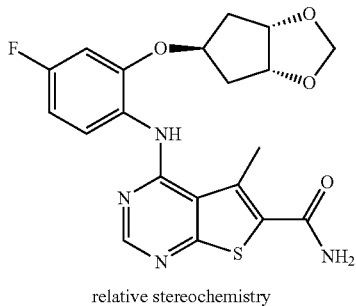 [SMILES: Cc1c(C(N)=O)sc2ncnc(Nc3ccc(F)cc3O[C@H]3C[C@@H]4OCO[C@@H]4C3)c12]

relative stereochemistry 214.1

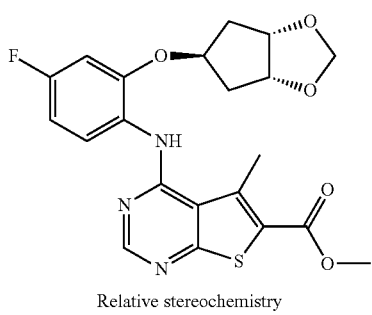 [SMILES: COC(=O)c1sc2ncnc(Nc3ccc(F)cc3O[C@H]3C[C@@H]4OCO[C@@H]4C3)c2c1C]

Relative stereochemistry

Intermediate XXXXVI (89 mg), 4-chloro-5-methyl-thieno[2,3-d]pyrimidine-6-carboxylic acid methyl ester (83 mg) and p-toluenesulfonic acid (7 mg) in dioxane (1.0 ml) were heated at 110° C. for 2 h. The reaction mixture was diluted with methylene chloride and 3 M aq. $NH_3$ and passed through a hydrophobic frit. The organic layer was concentrated in vacuo. The residue suspended in methanol and filtered to yield the desired product.

Yield: 128 mg

ESI-MS: m/z=446 [M+H]$^+$ 214.2

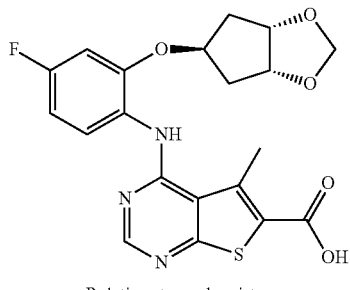

Relative stereochemistry

Compound 214.1 (126 mg) in ethanol (1.0 ml), THF (1.0 ml) and 2 M aq. sodium hydroxid (0.7 ml) were heated at reflux for 1.5 h. 2 M aq. HCl was added to the reaction mixture and filtered. The filtercake was suspended in ethanol and concentrated in vacuo to give the desired product.

Yield: 119 mg 214.3

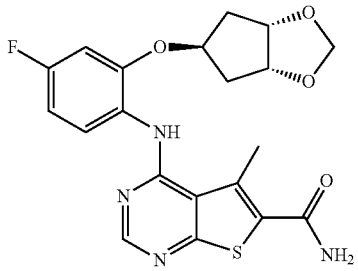

Relative stereochemistry

HATU (123 mg) was added at 0° C. to a mixture of compound 214.2 (116 mg) and DIPEA (56 µl) in DMF (1.5 ml). After 30 min 7 M $NH_3$ in methanol (0.7 ml) was added and the mixture was allowed to warm to room temperature overnight. The reaction mixture was concentrated in vacuo and re-evaporated from toluene. The residue was suspended in methanol, heated to reflux and cooled. The mixture was filtered and the filtercake was washed with diethyl ether to give the desired product.

Yield: 86 mg

ESI-MS: m/z=431 [M+H]$^+$ $R_t$ HPLC-MS: 1.32 min (Method X)

The following compound was prepared analogously to 1.4.:

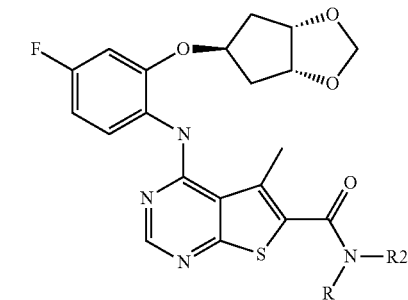

| Example | NR1R2 | educt | Mass spectrum | HPLC (retention time) |
|---------|-------|-------|---------------|------------------------|
| 215 | 2 with tBu) | Cpd. 214.2 | 516 (M + H)$^+$ | 1.93 min (Method A) |

Example 216

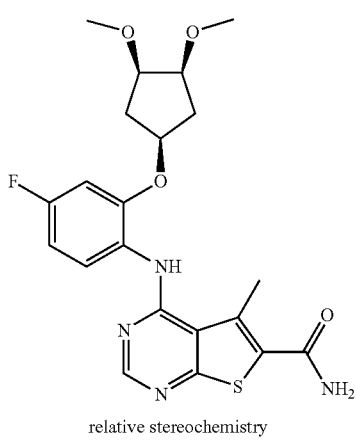 [SMILES: CO[C@H]1C[C@@H](Oc2cc(F)ccc2Nc2ncnc3sc(C(N)=O)c(C)c23)C[C@H]1OC]

relative stereochemistry 216.1

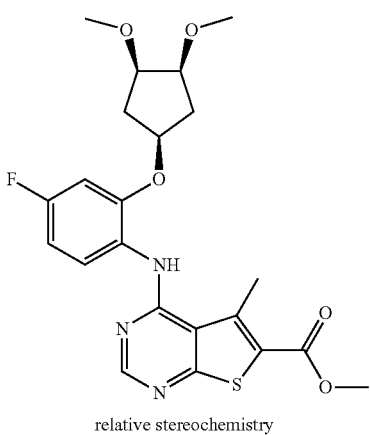 [SMILES: COC(=O)c1sc2ncnc(Nc3ccc(F)cc3O[C@@H]3C[C@H](OC)[C@H](OC)C3)c2c1C]

relative stereochemistry

Intermediate XXXXVII (360 mg), 4-chloro-5-methyl-thieno[2,3-d]pyrimidine-6-carboxylic acid methyl ester (285 mg) and p-toluenesulfonic acid (22 mg) in dioxane (3.0 ml) were heated at 110° C. for 5 h. The reaction mixture was allowed to cool, diluted with methylene chloride and 10% aq. K$_2$CO$_3$ and passed through a hydrophobic frit. The organic layer was concentrated in vacuo to give the desired product.

Yield: 430 mg 216.2

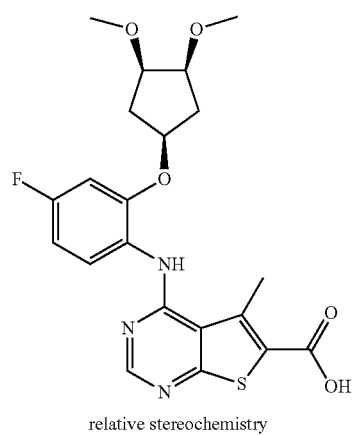 [SMILES: CO[C@H]1C[C@@H](Oc2cc(F)ccc2Nc2ncnc3sc(C(=O)O)c(C)c23)C[C@H]1OC]

relative stereochemistry

Compound 216.1 (430 mg) in methanol (5.0 ml), THF (5.0 ml) and 2 M aq. sodium hydroxid (2.4 ml) was heated at reflux for 20 min. After addition of 2 M aq.HCl the reaction mixture was concentrated in vacuo. The crude was suspended in water, filtered and washed with water. The filtercake was re-evaporated from ethanol. The residue was triturated with hot methanol, cooled, filtered and dried to give the desired product.

Yield: 346 mg 216.3

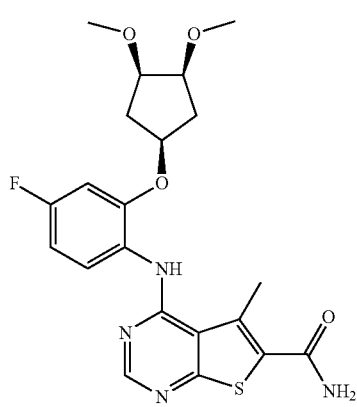

Relative stereochemistry

HATU (91 mg) was added at 0° C. to a mixture of compound 216.2 (90 mg) and DIPEA (42 µl) in DMF (1.0 ml). After 30 min 7 M NH$_3$ in methanol (1.0 ml) was added and the mixture was allowed to warm to room temperature over weekend. The reaction mixture was concentrated in vacuo. The residue was treated with ethanol and water, filtered and washed with water and diethyl ether. The filtercake was re-evaporated from DMSO to yield the desired product.

Yield: 20 mg

ESI-MS: m/z=447 [M+H]$^+$

R$_t$ HPLC-MS: 1.31 min (Method X)

The following compound was prepared analogously to 1.4.:

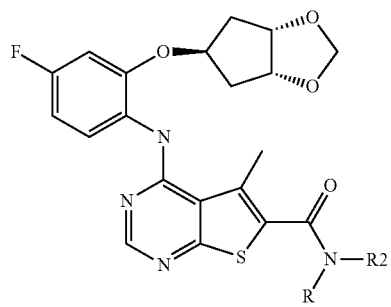

| Example | NR1R2 | educt | Mass spectrum | HPLC (retention time) |
|---|---|---|---|---|
| 217 | H, (CH$_2$)$_3$N(CH$_3$)$_2$ attached via dashed bond | Cpd. 216.2 | 532 (M + H)$^+$ | 1.25 min (Method X) |

Example 218

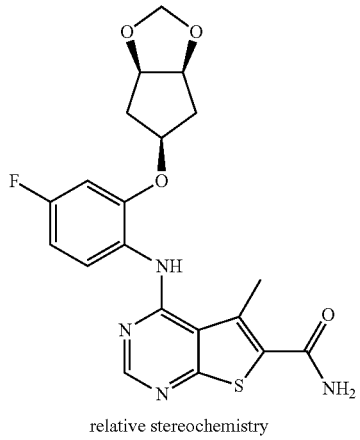 [SMILES: Cc1c(C(N)=O)sc2ncnc(Nc3ccc(F)cc3O[C@@H]3C[C@@H]4OCO[C@@H]4C3)c12]
relative stereochemistry 218.1

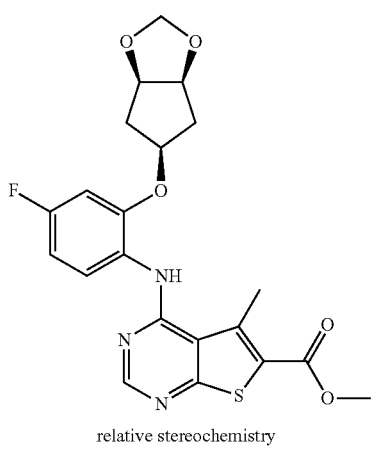 [SMILES: COC(=O)c1sc2ncnc(Nc3ccc(F)cc3O[C@@H]3C[C@@H]4OCO[C@@H]4C3)c2c1C]
relative stereochemistry

Intermediate XXXXVIII (139 mg), 4-chloro-5-methyl-thieno[2,3-d]pyrimidine-6-carboxylic acid methyl ester (128 mg) and p-toluenesulfonic acid (10 mg) in dioxane (2.0 ml) were heated at 100° C. for 2 h. The reaction mixture was allowed to cool and treated with DCM and 10% aq. K$_2$CO$_3$. The mixture separated. The organic layer was passed through a hydrophobic frit and concentrated in vacuo. The residue triturated with MeOH to yield the desired product.

Yield: 194 mg 218.2

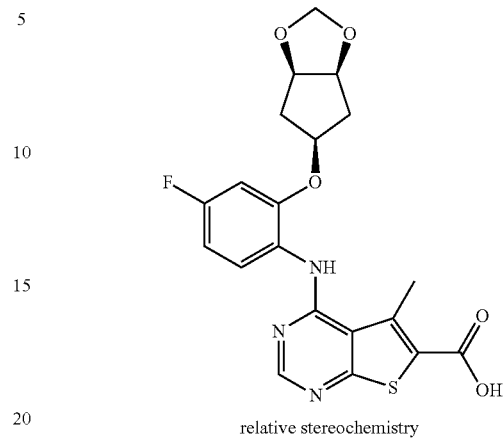
relative stereochemistry

Compound 218.1 (194 mg) in MeOH (2.5 ml), THF (2.5 ml) and 2 M aq. sodium hydroxid (1.0 ml) were heated at reflux for 30 min. The reaction mixture was allowed to cool and concentrated in vacuo. The crude was treated with 2 M aq.HCl and filtered. The filtercake was washed with water, suspended in EtOH and concentrated in vacuo to give the desired product.

Yield: 153 mg 218.3

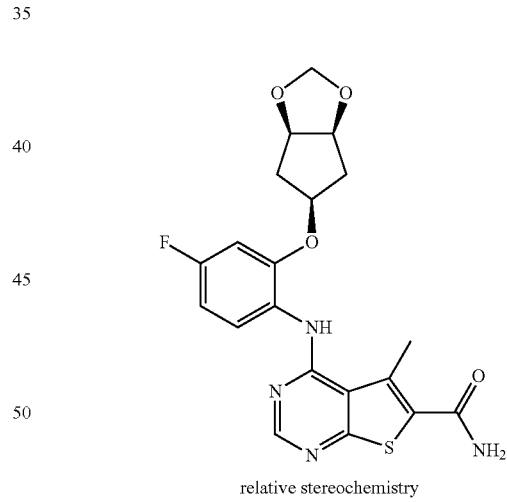
relative stereochemistry

HATU (158 mg) was added at 0° C. to a mixture of compound 218.2 (150 mg) and DIPEA (72 µl) in DMF (1.5 ml). After 30 min 7 M NH$_3$ in methanol (0.75 ml) was added and the mixture was allowed to warm to room temperature overnight. The reaction mixture was concentrated in vacu. The residue was partitioned between EtOAc and water and filtered. The filtercake was washed with water and diethyl ether and purified by chromatography to give the desired product.

Yield: 50 mg

ESI-MS: m/z=431 [M+H]$^+$

R$_t$ HPLC-MS: 1.29 min (Method X)

Example 219

219.1

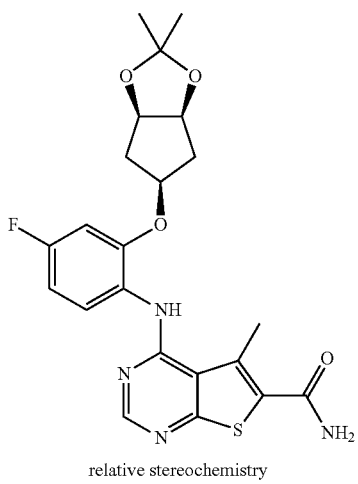 [SMILES: Cc1c(C(N)=O)sc2ncnc(Nc3ccc(F)cc3O[C@@H]3C[C@@H]4OC(C)(C)O[C@@H]4C3)c12]
relative stereochemistry

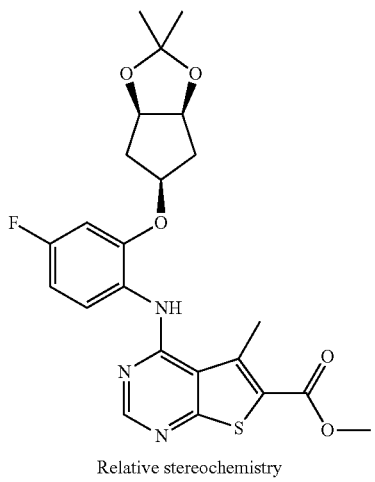 [SMILES: COC(=O)c1sc2ncnc(Nc3ccc(F)cc3O[C@@H]3C[C@@H]4OC(C)(C)O[C@@H]4C3)c2c1C]
Relative stereochemistry

Intermediate XXXXIX (363 mg), 4-chloro-5-methyl-thieno[2,3-d]pyrimidine-6-carboxylic acid methyl ester (330 mg) and p-toluenesulfonic acid (26 mg) in dioxane (5.0 ml) were heated at 110° C. for 4 h. The reaction mixture was treated with EtOAc and 10% aq. K$_2$CO$_3$. The mixture was filtered and the filtercake was washed with diethyl ether. The filtrate was separated. The organic layer was concentrated in vacuo. The crude was suspended in methanol and filtered to yield the desired product.

Yield: 615 mg

219.2

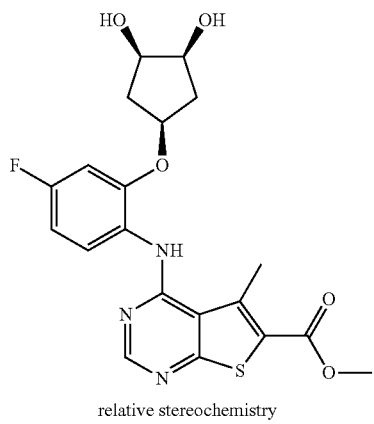 [SMILES: COC(=O)c1sc2ncnc(Nc3ccc(F)cc3O[C@H]3C[C@@H](O)[C@@H](O)C3)c2c1C]
relative stereochemistry

2 M aq. HCl (10.0 ml) was added to compound 219.1 (644 mg) in THF (10.0 ml) and the mixture was heated at reflux. After 20 min the reaction mixture was allowed to cool and concentrated in vacuo. The residue was partitioned between methylene chloride and 10% aq. K$_2$CO$_3$. The mixture was filtered. The filtercake was washed with diethyl ether and dried to give the desired product.

Yield: 531 mg

ESI-MS: m/z=434 [M+H]$^+$

219.3 relative stereochemistry

Compound 219.2 (448 mg) in EtOH (5.0 ml), THF (5.0 ml) and 2M aq. sodium hydroxid (3.0 ml) was stirred at room temperature for 1.5 h. The reaction mixture was concentrated in vacuo. The crude was treated with 10% aq. KHSO$_4$ and filtered. The filtercake was washed with water and diethyl ether and dried to give the desired product.

Yield: 372 mg 219.4

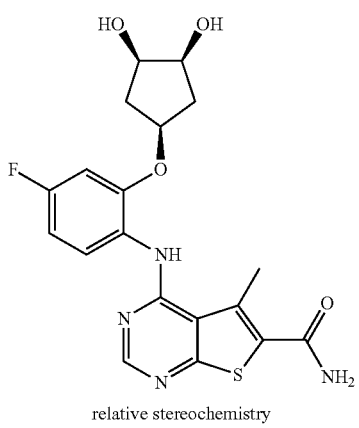 [SMILES: Cc1c(C(N)=O)sc2ncnc(Nc3ccc(F)cc3O[C@H]3C[C@@H](O)[C@@H](O)C3)c12]
relative stereochemistry

HATU (91 mg) was added at 0° C. to a mixture of compound 219.3 (82 mg) and DIPEA (42 µl) in DMF (1.0 ml). After 30 min 7 M NH₃ in methanol (0.5 ml) was added and the mixture was allowed to warm to room temperature overnight. The reaction mixture was partitioned between EtOAc and water. The organic layer was washed with brine and water. The resultant mixture was filtered. The filtercake was washed with diethyl ether, water and diethyl ether to give the desired product.

Yield: 46 mg
ESI-MS: m/z=419 [M+H]⁺
R$_t$ HPLC-MS: 1.21 min (Method X)

Example 220

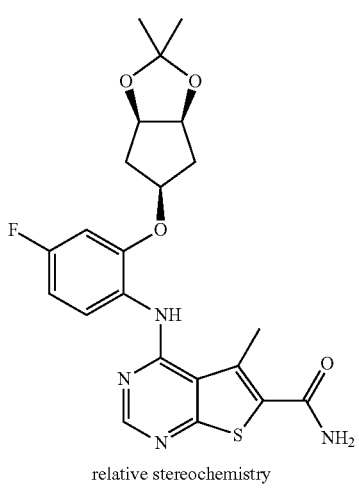 [SMILES: Cc1c(C(N)=O)sc2ncnc(Nc3ccc(F)cc3O[C@@H]3C[C@@H]4OC(C)(C)O[C@@H]4C3)c12]
relative stereochemistry

A mixture of compound 219.4 (218 mg), 2,2-dimethoxypropan (1.0 ml) and p-toluenesulfonic acid (20 mg) in DMF (1.0 ml) was stirred at room temperature overnight. Further p-toluenesulfonic acid (20 mg) was added and stirring continued at 60° C. for 45 min. The reaction mixture was diluted with 10% aq. K₂CO₃ and methanol. The mixture was filtered to give the desired product.

Yield: 177 mg
ESI-MS: m/z=459 [M+H]⁺
R$_t$ HPLC-MS: 1.35 min (Method X)

Example 221

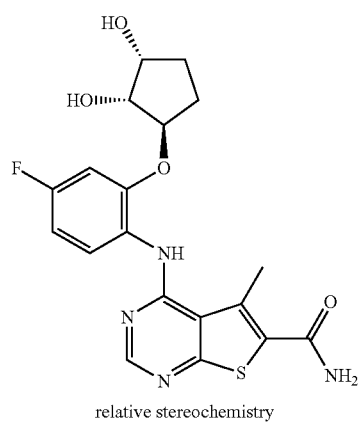 [SMILES: Cc1c(C(N)=O)sc2ncnc(Nc3ccc(F)cc3O[C@@H]3CC[C@@H](O)[C@H]3O)c12]
relative stereochemistry 221.1

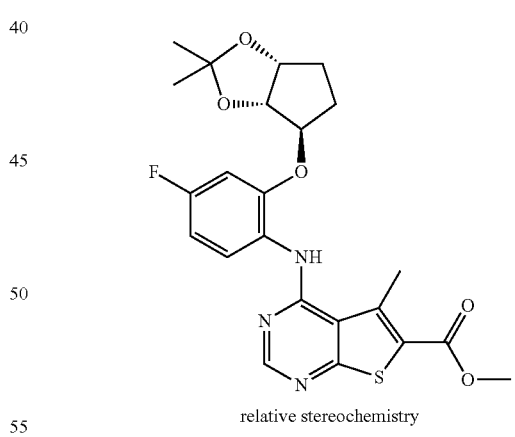
relative stereochemistry

Intermediate XXXXX (505 mg), 4-chloro-5-methylthieno[2,3-d]pyrimidine-6-carboxylic acid methyl ester (385 mg) and p-toluenesulfonic acid (60 mg) in dioxane (5.0 ml) were heated at 110° C. for 8 h. The reaction mixture was diluted with methylene chloride and 10% aq. K₂CO₃ and brine. The organic layer was passed through a hydrophobic frit and concentrated in vacuo. The residue was triturated with methanol to yield the desired product.

Yield: 488 mg 221.2

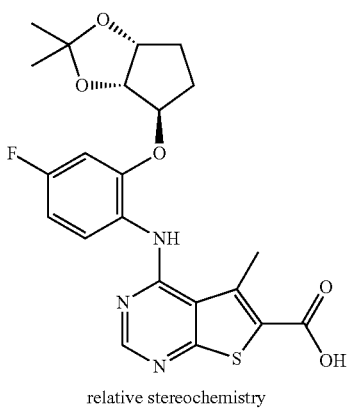 [SMILES: Cc1c(C(=O)O)sc2ncnc(Nc3ccc(F)cc3O[C@@H]3CC[C@H]4OC(C)(C)O[C@@H]34)c12]
relative stereochemistry

Compound 221.1 (488 mg) in methanol (5.0 ml), THF (5.0 ml) and 2M aq. sodium hydroxid (2.6 ml) were stirred at reflux for 30 min. The reaction mixture was allowed to cool and treated with 10% aq. KHSO$_4$. The mixture was filtered. The filtercake was washed with water and dried to give the desired product.

Yield: 600 mg 221.3

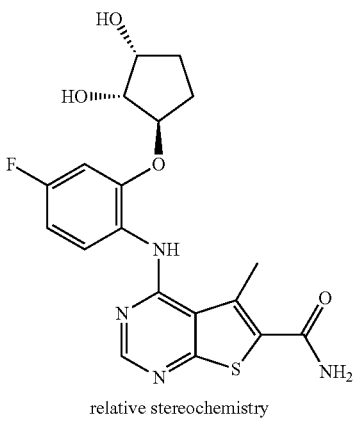 [SMILES: Cc1c(C(N)=O)sc2ncnc(Nc3ccc(F)cc3O[C@@H]3CC[C@@H](O)[C@H]3O)c12]
relative stereochemistry

HATU (228 mg) was added at 0° C. to a mixture of compound 221.2 (230 mg) and DIPEA (104 µl) in DMF (3.0 ml). After 30 min 7 M NH$_3$ in methanol (1.5 ml) was added and the mixture was allowed to warm to room temperature over weekend. The reaction mixture was concentrated in vacuo. The residue was treated with THF (3.0 ml) and 2 M aq. HCl (3 ml) at reflux for 20 min. The mixture was partitioned between EtOAc and water and filtered. The filtercake was washed with water and diethyl ether to give the desired product.

Yield: 134 mg
ESI-MS: m/z=419 [M+H]$^+$
R$_t$ HPLC-MS: 1.21 min (Method X)

Example 222

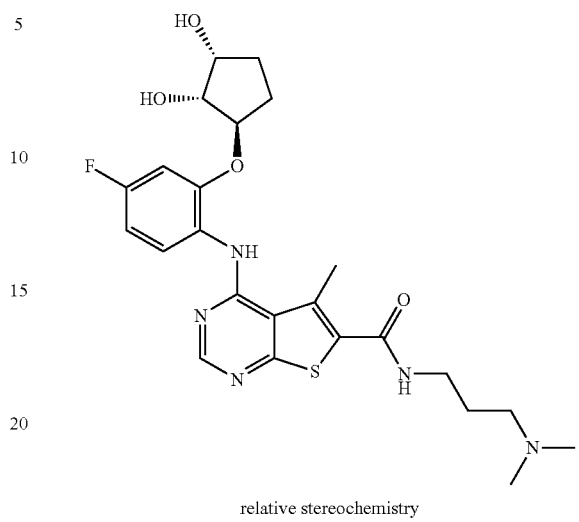
relative stereochemistry

HATU (228 mg) was added at 0° C. to a mixture of 221.2 (230 mg) and DIPEA (104 µl) in DMF (3.0 ml). After 30 min 3-dimethylaminopropylamine (315 µl) was added and the mixture was allowed to warm to room temperature over weekend. The reaction mixture was concentrated in vacuo. The residue was treated with THF (3.0 ml) and 2 M aq. HCl (3 ml) at reflux for 20 min. The mixture was partitioned between EtOAc and 10% aq. K$_2$CO$_3$. The organic layer was concentrated in vacuo. The residue was triturated with methanol, filtered and washed with diethyl ether to give the desired product.

Yield: 65 mg
ESI-MS: m/z=504 [M+H]$^+$
R$_t$ HPLC-MS: 1.18 min (Method X)

Example 223

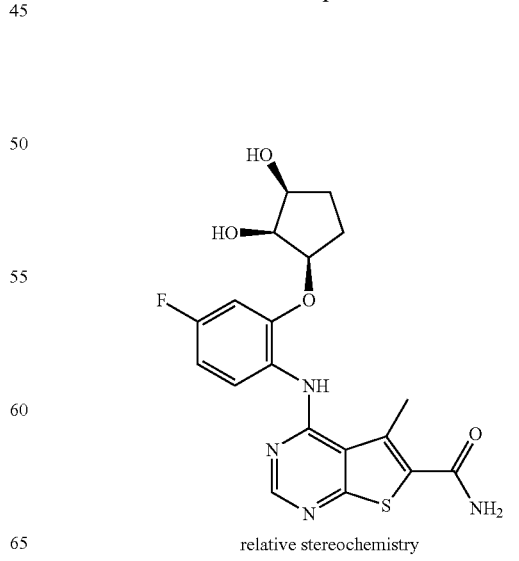
relative stereochemistry

241

223.1

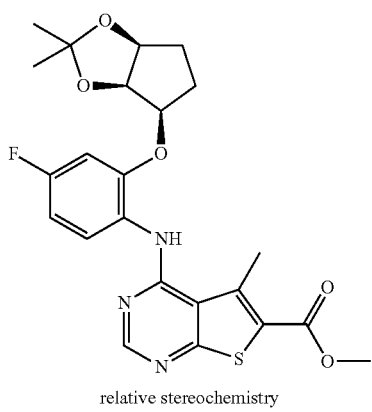 [SMILES: COC(=O)c1sc2ncnc(Nc3ccc(F)cc3O[C@@H]3CC[C@@H]4OC(C)(C)O[C@@H]43)c2c1C]
relative stereochemistry

Prepared analogously to 1.1 from intermediate 0.091 g XXXXXI and 0.076 g 4-chloro-5-methyl-thieno[2,3-d]pyrimidine-6-carboxylic acid methyl ester.

Yield: 76 mg 223.2

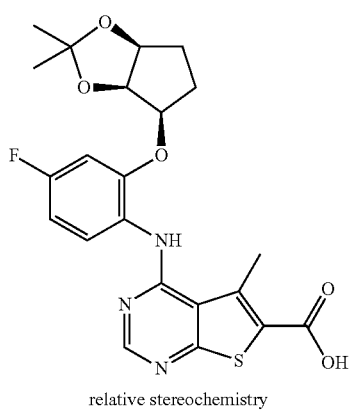 [SMILES: Cc1c(C(=O)O)sc2ncnc(Nc3ccc(F)cc3O[C@@H]3CC[C@@H]4OC(C)(C)O[C@@H]43)c12]
relative stereochemistry

Compound 223.1 (76 mg) in MeOH (0.5 ml), THF (0.5 ml) and 2M aq. sodium hydroxid (0.4 ml) were stirred at reflux for 20 min. The reaction mixture was allowed to cool and treated with 10% aq. KHSO$_4$. The mixture was filtered. The filtercake was washed with water and dried to give the desired product.

Yield: 70 mg

242

223.3

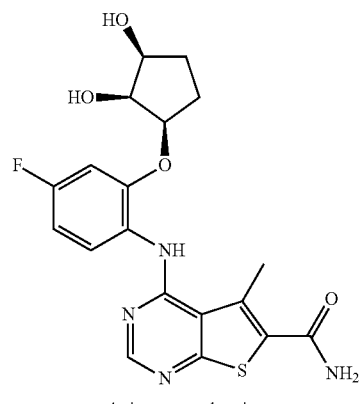
relative stereochemistry

HATU (64 mg) was added at 0° C. to a mixture of compound 223.2 (94 mg) and DIPEA (29 µl) in DMF (1.0 ml). After 30 min 7 M NH$_3$ in methanol (0.5 ml) was added and the mixture was allowed to warm to room temperature over weekend. The reaction mixture was concentrated in vacuo. The residue was treated with THF (1.0 ml) and 2 M aq. HCl (1.0 ml) at reflux for 20 min. The mixture was diluted with EtOAc and washed with water and 10% aq. K$_2$CO$_3$. The organic was concentrated in vacuo. The residue was purified by chromatography to yield the desired product.

Yield: 15 mg

ESI-MS: m/z=419 [M+H]$^+$

R$_t$ HPLC-MS: 1.20 min (Method X)

Example 224

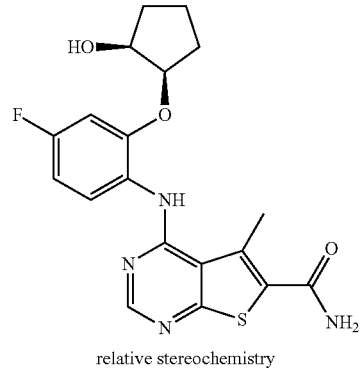 [SMILES: Cc1c(C(N)=O)sc2ncnc(Nc3ccc(F)cc3O[C@@H]3CCC[C@@H]3O)c12]
relative stereochemistry

243

224.1

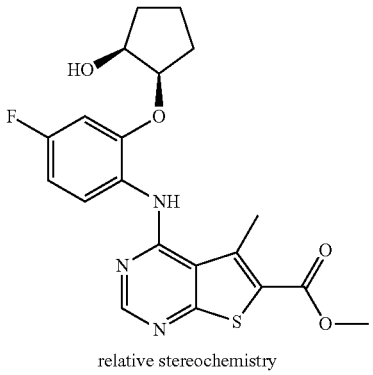 [SMILES: COC(=O)c1sc2ncnc(Nc3ccc(F)cc3O[C@@H]3CCC[C@@H]3O)c2c1C]
relative stereochemistry

Intermediate XXXXXII (384 mg), 4-chloro-5-methyl-thieno[2,3-d]pyrimidine-6-carboxylic acid methyl ester (429 mg) and p-toluenesulfonic acid (34 mg) in dioxane (5.0 ml) were heated at 110° C. for 4 h. The reaction mixture was diluted with methylene chloride and washed with 10% aq. K₂CO₃ and brine. The organic layer was passed through a hydrophobic frit and concentrated in vacuo. The residue was treated with diethyl ether, filtered and washed to yield the desired product.

Yield: 480 mg 224.2

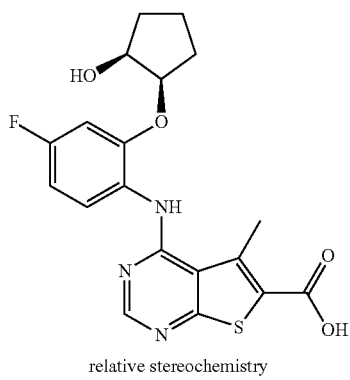 [SMILES: Cc1c(C(=O)O)sc2ncnc(Nc3ccc(F)cc3O[C@@H]3CCC[C@@H]3O)c12]
relative stereochemistry

Compound 224.1 (200 mg) in methanol (1.5 ml), THF (1.5 ml) and 2M aq. sodium hydroxid (1.3 ml) were stirred at reflux for 20 min. After addition of 2 M aq. HCl (3.0 ml) the reaction mixture was concentrated in vacuo. The residue was treated with water, filtered and washed with water. The crude was re-evaporated from ethanol before it was treated with diethyl ether. The mixture was filtered and the filtercake was washed with diethyl ether to give the desired product.

Yield: 156 mg

244

224.3

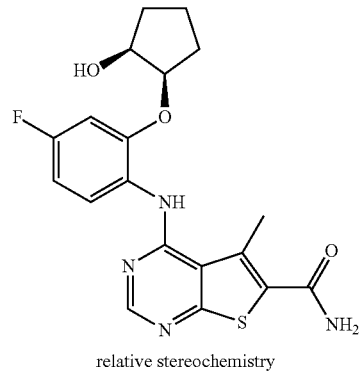 [SMILES: Cc1c(C(N)=O)sc2ncnc(Nc3ccc(F)cc3O[C@@H]3CCC[C@@H]3O)c12]
relative stereochemistry

HATU (207 mg) was added at 0° C. to a mixture of compound 224.2 (156 mg) and DIPEA (95 µl) in DMF (2.0 ml). After 30 min 7 M NH₃ in methanol (1.0 ml) was added and the mixture was allowed to warm to room temperature overnight. The reaction mixture was concentrated in vacuo and re-evaporated from toluene. The residue was treated with hot methanol. The mixture was allowed to cool, then it was filtered to yield the desired product.

Yield: 78 mg
ESI-MS: m/z=403 [M+H]⁺
R$_t$ HPLC-MS: 1.28 min (Method X)

Example 225

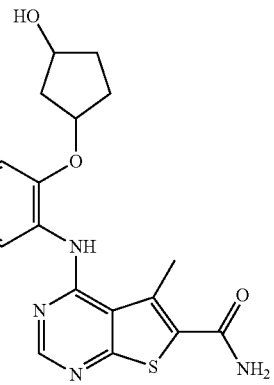

225.1

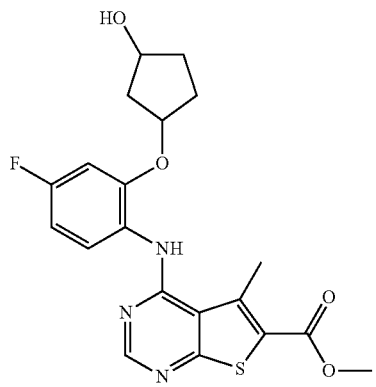 [SMILES: COC(=O)c1sc2ncnc(Nc3ccc(F)cc3OC3CCC(O)C3)c2c1C]

Intermediate XXXXXIII (990 mg), 4-chloro-5-methyl-thieno[2,3-d]pyrimidine-6-carboxylic acid methyl ester (948 mg) and p-toluenesulfonic acid (74 mg) in dioxane (10.0 ml) were heated at 110° C. for 8 h. The reaction mixture was diluted with methylene chloride and 10% aq. $K_2CO_3$. The organic layer was passed through a hydrophobic frit and concentrated in vacuo. The residue was treated with methanol to yield the desired product.

Yield: 898 mg

225.2 4-(4-fluoro-2-(3-hydroxycyclopentyloxy)phenylamino)-5-methylthieno[2,3-d]pyrimidine-6-carboxilic acid

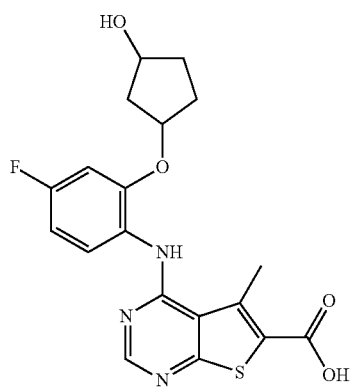 [SMILES: Cc1c(C(=O)O)sc2ncnc(Nc3ccc(F)cc3OC3CCC(O)C3)c12]

Methyl 4-(4-fluoro-2-(3-hydroxycyclopentyloxy)phenylamino)-5-methylthieno[2,3-d]pyrimidine-6-carboxylate (150 mg) in methanol (2.0 ml), THF (2.0 ml) and 2M aq. sodium hydroxid (0.9 ml) was stirred at reflux for 40 min. After addition of 2 M aq. HCl (8.0 ml) the reaction mixture was concentrated in vacuo. The aqueous layer was filtered and washed with water. The crude was re-evaporated from EtOH to give the desired product.

Yield: 141 mg

225.3. 4-(4-fluoro-2-(3-hydroxycyclopentyloxy)phenylamino)-5-methylthieno[2,3-d]pyrimidine-6-carboxamide

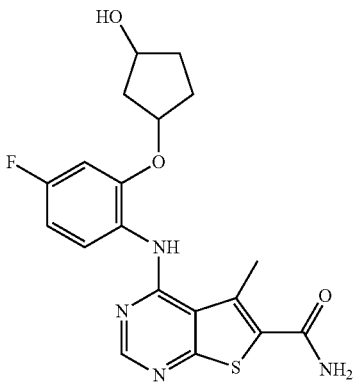 [SMILES: Cc1c(C(N)=O)sc2ncnc(Nc3ccc(F)cc3OC3CCC(O)C3)c12]

HATU (147 mg) was added at 0° C. to a mixture of 4-(4-fluoro-2-(3-hydroxycyclopentyloxy)phenylamino)-5-methylthieno[2,3-d]pyrimidine-6-carboxylic acid (130 mg) and DIPEA (67 µl) in DMF (2.0 ml). After 30 min 7 M $NH_3$ in MeOH (1.0 ml) was added and the mixture was allowed to warm to room temperature over weekend. The reaction mixture was concentrated in vacuo. The residue was treated with hot MeOH. The mixture was allowed to cool, then it was filtered to yield the desired product.

Yield: 88 mg
ESI-MS: m/z=403 $[M+H]^+$
$R_t$ HPLC-MS: 1.27 min (Method X)

Example 226

226.1

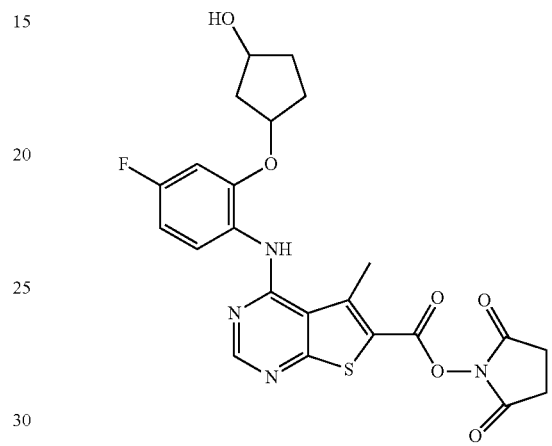

EDC (147 mg) was added to a mixture of 268 mg 4-(4-fluoro-2-(3-hydroxycyclopentyloxy)phenylamino)-5-methylthieno[2,3-d]pyrimidine-6-carboxilic acid (225.2) and N-hydroxysuccinimide (110 mg) in DMF (3.0 ml). After stirring at room temperature overnight the reaction mixture was diluted with EtoAc and washed with water and brine. The organic layer was passed through a hydrophobic frit and concentrated in vacuo to yield the desired product.

Yield: 314 mg

226.2. N-(3-(dimethylamino)propyl)-4-(4-fluoro-2-(3-hydroxycyclopentyloxy)phenylamino)-5-methylthieno[2,3-d]pyrimidine-6-carboxamide

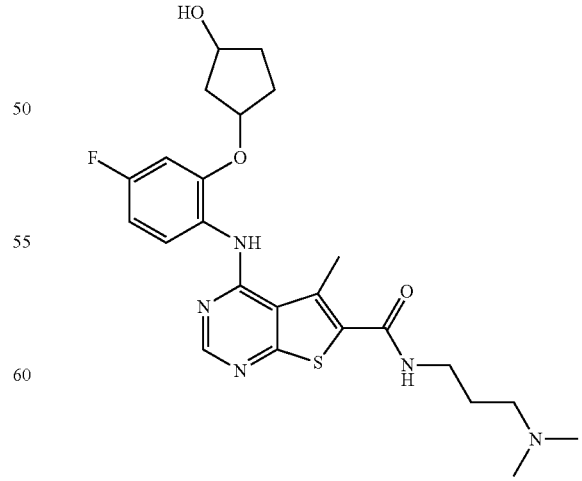

Prepared analogously to 153.2 from 0.145 g compound 226.1 and 3-dimethylaminopropylamine (200 µl)

Yield: 88 mg
ESI-MS: m/z=488 [M+H]⁺
R_t HPLC-MS: 1.22 min (Method X)

Example 227

4-(4-Fluoro-2-(3-hydroxycyclopentyloxy)phenylamino)-N-(2-hydroxyethyl)-5-methylthieno[2,3-d]pyrimidine-6-carboxamide

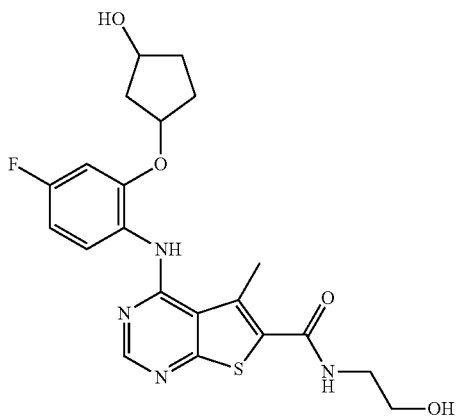 [SMILES: Cc1c(C(=O)NCCO)sc2ncnc(Nc3ccc(F)cc3OC3CCC(O)C3)c12]

Prepared analogously to 153.2 from 0.165 g compound 226.1 and 2-aminoethanol (100 μl).
Yield: 84 mg
ESI-MS: m/z=447 [m+H]⁺
R_t HPLC-MS: 1.25 min (Method X)

Example 228

{(1S,3S)-3-[2-(6-Carbamoyl-5-methyl-thieno[2,3-d]pyrimidin-4-ylamino)-5-fluoro-phenoxy]-cyclopentyl}-carbamic acid tert-butyl ester

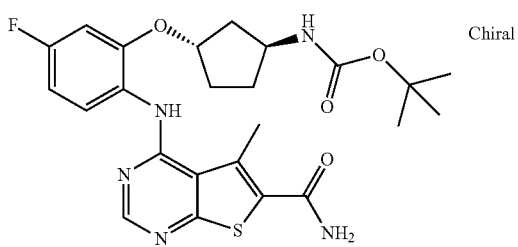 [SMILES: Cc1c(C(N)=O)sc2ncnc(Nc3ccc(F)cc3O[C@H]3CC[C@H](NC(=O)OC(C)(C)C)C3)c12]

228.1 4-[2-((1S,3S)-3-Amino-cyclopentyloxy)-4-fluoro-phenylamino]-5-methyl-thieno[2,3-d]pyrimidine-6-carboxylic acid methyl ester

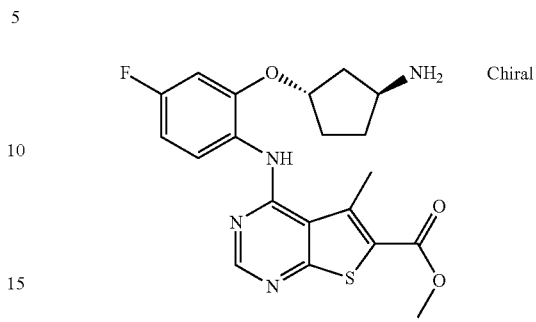

Intermediate XXXVII (155 mg), 4-chloro-5-methyl-thieno[2,3-d]pyrimidine-6-carboxylic acid methyl ester (121 mg) and p-toluenesulfonic acid (15 mg) in dioxane (3.0 ml) were heated at 110° C. for 2 hours under microwave radiation. The reaction mixture was filtered, the filtercake was washed with diisopropyl ether and dried to give the desired compound.
Yield: 150 mg
ESI-MS: m/z=417 [M+H]⁺

228.2 4-[2-((1S,3S)-3-tert-Butoxycarbonylamino-cyclopentyloxy)-4-fluoro-phenylamino]-5-methyl-thieno[2,3-d]pyrimidine-6-carboxylic acid methyl ester

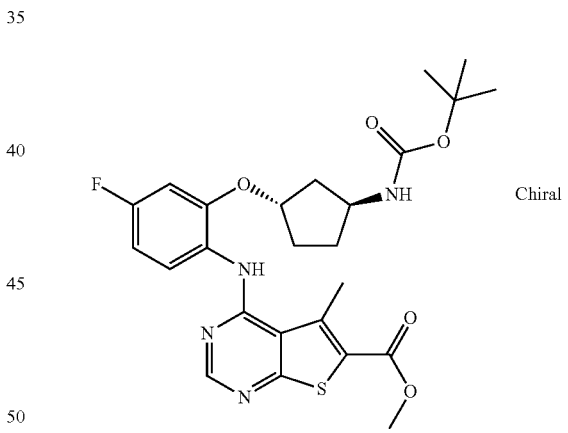

A mixture of 4-[2-((1S,3S)-3-amino-cyclopentyloxy)-4-fluoro-phenylamino]-5-methyl-thieno[2,3-d]pyrimidine-6-carboxylic acid methyl ester (150 mg), di-tert-butyl dicarbonate (173 mg) and triethylamine (145 μl) in THF (10 ml) was stirred at rt overnight. The reaction mixture was concentrated and the crude partitioned between DCM and water. The organic layer was dried, concentrated and the residue was triturated with diisopropyl ether to give the desired compound.
Yield: 113 mg
ESI-MS: m/z=517 [m+H]⁺
R_t HPLC-MS: 4.05 min (method A)
R_f (TLC): 0.29 (silica gel, DCM)

228.3 4-[2-((1S,3S)-3-tert-Butoxycarbonylamino-cyclopentyloxy)-4-fluoro-phenylamino]-5-methyl-thieno[2,3-d]pyrimidine-6-carboxylic acid

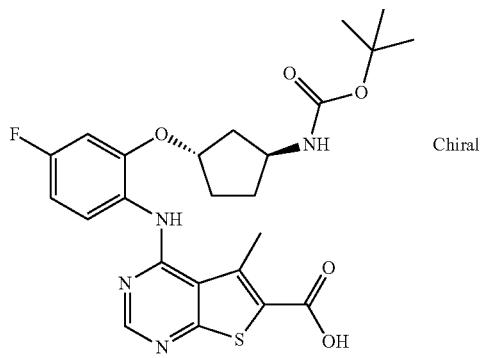 [SMILES: Cc1c(C(=O)O)sc2ncnc(Nc3ccc(F)cc3O[C@H]3CC[C@H](NC(=O)OC(C)(C)C)C3)c12]

A mixture of 4-[2-((1S,3S)-3-tert-butoxycarbonylamino-cyclopentyloxy)-4-fluoro-phenylamino]-5-methyl-thieno[2,3-d]pyrimidine-6-carboxylic acid methyl ester (100 mg) and lithium hydroxide (133 mg) in THF/MeOH/H$_2$O 1/1/1 (15 ml) was stirred at rt over the weekend. The reaction mixture was acidified with aq. HCl and extracted with DCM. The organic layer was dried, concentrated and the residue was triturated with diisopropyl ether to give the desired compound.

Yield: 57 mg
ESI-MS: m/z=503 [m+H]$^+$
R$_t$ HPLC-MS: 3.95 min (method A)

228.4 {(1S,3S)-3-[2-(6-Carbamoyl-5-methyl-thieno[2,3-d]pyrimidin-4-ylamino)-5-fluoro-phenoxy]-cyclopentyl}-carbamic acid tert-butyl ester

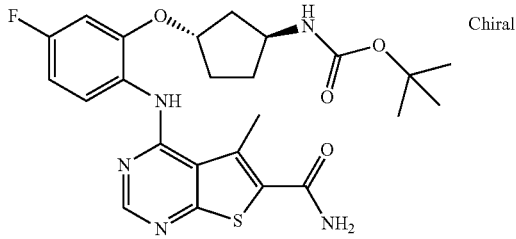 [SMILES: Cc1c(C(N)=O)sc2ncnc(Nc3ccc(F)cc3O[C@H]3CC[C@H](NC(=O)OC(C)(C)C)C3)c12]

A mixture of 4-[2-((1S,3S)-3-tert-butoxycarbonylamino-cyclopentyloxy)-4-fluoro-phenylamino]-5-methyl-thieno[2,3-d]pyrimidine-6-carboxylic acid (115 mg), TBTU (81 mg) and DIPEA (88 µl) in THF (15 ml) was stirred at rt for 30 minutes. After the addition of 0.5 M ammonia in dioxane (458 µl) and DMF the mixture was stirred at rt overnight. The reaction mixture was concentrated, diluted with water and extracted with DCM. The organic layer was concentrated and the crude was purified by chromatography to give the desired product.

Yield: 53 mg
ESI-MS: m/z=502 [M+H]$^+$
R$_t$ HPLC-MS: 2.78 min (method A)
R$_f$(TLC): 0.69 (silica gel, DCM/MeOH/NH$_3$ 80/20/1)

Example 229

4-[2-((1S,3S)-3-Amino-cyclopentyloxy)-4-fluoro-phenylamino]-5-methyl-thieno[2,3-d]pyrimidine-6-carboxylic acid amide trifluoroacetate

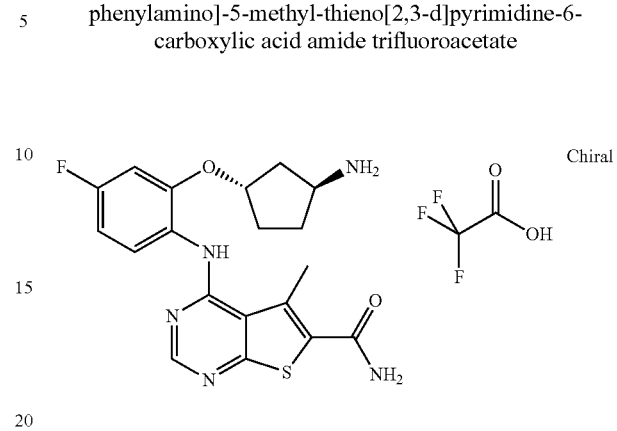

To compound 228.4 (310 mg) in DCM 815 ml) was added at 0° C. TFA (1.7 ml) and stirred at rt for 4 hours. The reaction mixture was concentrated at rt and the crude was triturated with diisopropyl ether to give the desired product.

Yield: 376 mg
ESI-MS: m/z=402 [M+H]$^+$
R$_t$ HPLC-MS: 2.56 min (method A)
R$_f$(TLC): 0.37 (silica gel, DCM/MeOH/NH$_3$ 80/20/1)

Example 230

4-[2-((1S,3S)-3-Acetylamino-cyclopentyloxy)-4-fluoro-phenylamino]-5-methyl-thieno[2,3-d]pyrimidine-6-carboxylic acid amide

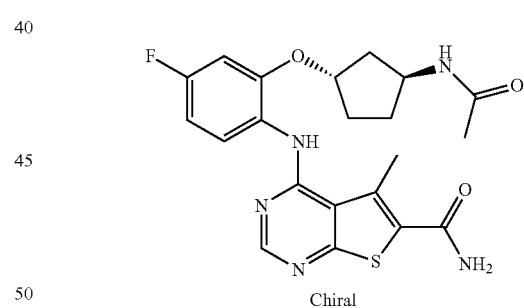

Acetyl chloride (21 µl) was added at 0° C. to a mixture of 4-[2-((1S,3S)-3-amino-cyclopentyloxy)-4-fluoro-phenylamino]-5-methyl-thieno[2,3-d]pyrimidine-6-carboxylic acid amide trifluoroacetate (cpd. 229, 206 mg) and DIPEA (348 µl) in DCM (25 ml) and stirred at rt for 4 hours. The reaction mixture was concentrated, diluted with water and extracted with DCM. The organic layer was dried, concentrated and the crude was purified by chromatography to give the desired product.

Yield: 55 mg
ESI-MS: m/z=444 [M+H]$^+$
R$_t$ HPLC-MS: 3.04 min (method A)
R$_f$(TLC): 0.74 (silica gel, DCM/MeOH 4/1)

Example 231

4-[2-((1S,3S)-3-Acetylamino-cyclopentyloxy)-4-fluoro-phenylamino]-5-methyl-thieno[2,3-d]pyrimidine-6-carboxylic acid (2-hydroxy-ethyl)-amide

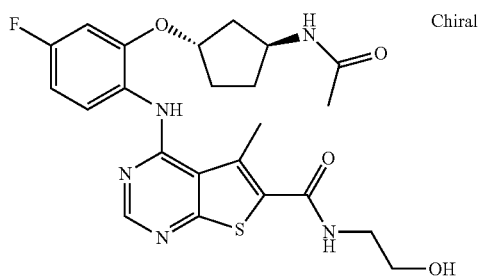 [SMILES: CC(=O)N[C@H]1CC[C@H](Oc2cc(F)ccc2Nc2ncnc3sc(C(=O)NCCO)c(C)c23)C1]

231.1 4-[2-((1S,3S)-3-Acetylamino-cyclopentyloxy)-4-fluoro-phenylamino]-5-methyl-thieno[2,3-d]pyrimidine-6-carboxylic acid methyl ester

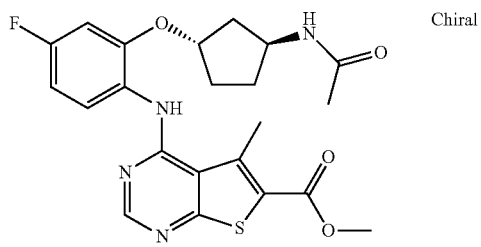 [SMILES: COC(=O)c1sc2ncnc(Nc3ccc(F)cc3O[C@H]3CC[C@H](NC(C)=O)C3)c2c1C]

Intermediate XXXXXXII (155 mg), 4-chloro-5-methyl-thieno[2,3-d]pyrimidine-6-carboxylic acid methyl ester (242 mg) and p-toluenesulfonic acid (34 mg) in dioxane (4.0 ml) were heated at 110° C. for 1 hours under microwave radiation. The reaction mixture was concentrated, washed with water and concentrated. The crude was purified by chromatography and triturated with diisopropyl ether to give the desired compound.

Yield: 196 mg

ESI-MS: m/z=459 [M+H]$^+$

R$_t$ HPLC-MS: 3.02 min (method A)

R$_f$ (TLC): 0.34 (silica gel, DCM/MeOH/NH$_3$ 90/10/1)

231.2 4-[2-((1S,3S)-3-Acetylamino-cyclopentyloxy)-4-fluoro-phenylamino]-5-methyl-thieno[2,3-d]pyrimidine-6-carboxylic acid

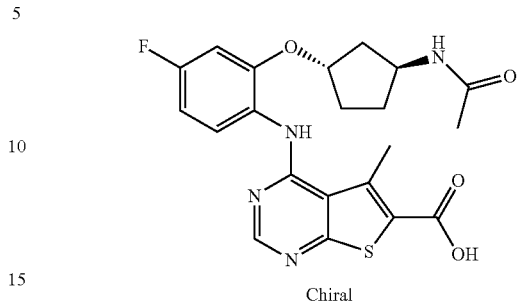

Prepared analogously to example 228.3 from 4-[2-((1S,3S)-3-acetylamino-cyclopentyloxy)-4-fluoro-phenylamino]-5-methyl-thieno[2,3-d]pyrimidine-6-carboxylic acid methyl ester, cpd.231.1 (1.44 g).

Yield: 1.15 g

ESI-MS: m/z=445 [M+H]$^+$

R$_t$ HPLC-MS: 2.72 min (method A)

231.3 4-[2-((1S,3S)-3-Acetylamino-cyclopentyloxy)-4-fluoro-phenylamino]-5-methyl-thieno[2,3-d]pyrimidine-6-carboxylic acid (2-hydroxy-ethyl)-amide

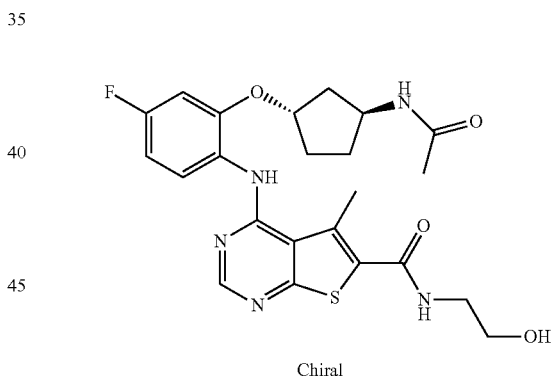

Synthesized analogously to example 225.3 from 4-[2-((1S,3S)-3-acetylamino-cyclopentyloxy)-4-fluoro-phenylamino]-5-methyl-thieno[2,3-d]pyrimidine-6-carboxylic acid (111 mg) and 2-aminoethanol (18 µl). The reaction mixture was concentrated, the residue was partitioned between DCM and water and the organic layer was dried and concentrated again. The crude was purified by chromatography to give the desired product.

Yield: 32 mg

ESI-MS: m/z=488 [M+H]$^+$

R$_t$ HPLC-MS: 2.43 min (method A)

R$_f$ (TLC): 0.21 (silica gel, DCM/MeOH/NH$_3$ 90/10/1)

The following compounds were prepared analogously to 231.3.:

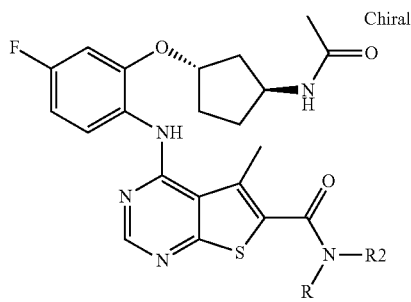
| Example | NR1R2 | educt | Mass spectrum | HPLC (retention time) |
|---|---|---|---|---|
| 232 | ![structure] | Cpd. 231.2 | 599 (M + H)+ | 2.87 (method A) |
| 233 | ![structure] | Cpd. 231.2 | 539 (M + H)+ | 2.07 min (method AC1) |
| 234 | ![structure] | Cpd. 231.2 | 541 (M + H)+ | 2.05 min (method A) |
| 235 | ![structure] | Cpd. 231.2 | 458 (M + H)+ | 2.55 min (method A) |
| 236 | ![structure] | Cpd. 231.2 | 474 (M + H)+ | 2.57 min (method A) |
| 237 | ![structure] | Cpd. 231.2 | 529 (M + H)+ | 2.07 min (method A) |
| 238 | ![structure] | Cpd. 231.2 | 499 (M + H)+ | 2.12 min (method A) |
| 239 | ![structure] | Cpd. 231.2 | 555 (M + H)+ | 2.15 min (method A) |

Example 240

4-{2-[(1S,3S)-3-(Acetyl-methyl-amino)-cyclopentyloxy]-4-fluoro-phenylamino}-5-methyl-thieno[2,3-d]pyrimidine-6-carboxylic acid amide

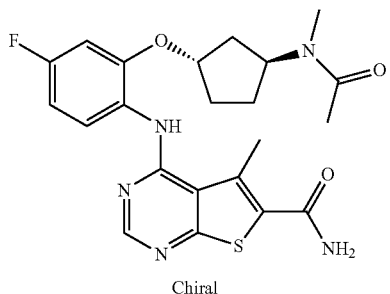 [SMILES: CC(=O)N(C)[C@H]1CC[C@H](Oc2cc(F)ccc2Nc2ncnc3sc(C(N)=O)c(C)c23)C1]

Chiral 240.1 4-{2-[(1S,3S)-3-(Acetyl-methyl-amino)-cyclopentyloxy]-4-fluoro-phenylamino}-5-methyl-thieno[2,3-d]pyrimidine-6-carboxylic acid methyl ester

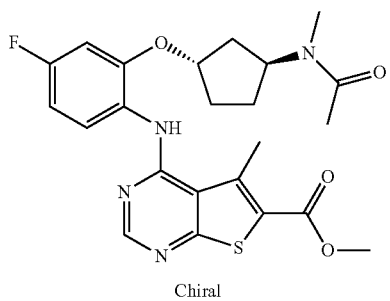 [SMILES: COC(=O)c1sc2ncnc(Nc3ccc(F)cc3O[C@H]3CC[C@H](N(C)C(C)=O)C3)c2c1C]

Chiral

Prepared analogously to example 231.1 from intermediate XXXVIII (266 mg) and 4-chloro-5-methyl-thieno[2,3-d]pyrimidine-6-carboxylic acid methyl ester (243 mg).
Yield: 242 mg
ESI-MS: m/z=473 [M+H]$^+$
$R_t$ HPLC-MS: 3.13 min (method A)
$R_f$(TLC): 0.52 (silica gel, DCM/MeOH/NH$_3$ 90/10/1)

240.2 4-{2-[(1S,3S)-3-(Acetyl-methyl-amino)-cyclopentyloxy]-4-fluoro-phenylamino}-5-methyl-thieno[2,3-d]pyrimidine-6-carboxylic acid

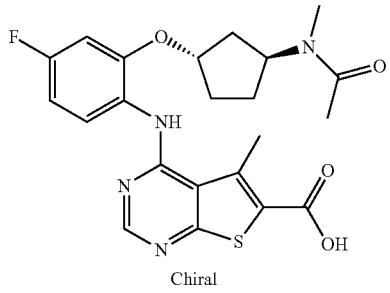 [SMILES: CC(=O)N(C)[C@H]1CC[C@H](Oc2cc(F)ccc2Nc2ncnc3sc(C(=O)O)c(C)c23)C1]

Chiral

Prepared analogously to example 228.3 from 4-{2-[(1S,3S)-3-(acetyl-methyl-amino)cyclopentyloxy]-4-fluoro-phenylamino}-5-methyl-thieno[2,3-d]pyrimidine-6-carboxylic acid methyl ester (185 mg).
Yield: 126 mg
ESI-MS: m/z=459 [M+H]$^+$
$R_t$ HPLC-MS: 2.80 min (method A)

240.3 4-{2-[(1S,3S)-3-(Acetyl-methyl-amino)-cyclopentyloxy]-4-fluoro-phenylamino}-5-methyl-thieno[2,3-d]pyrimidine-6-carboxylic acid amide

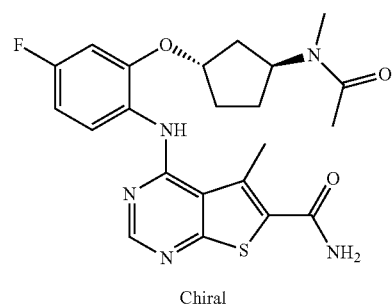 [SMILES: CC(=O)N(C)[C@H]1CC[C@H](Oc2cc(F)ccc2Nc2ncnc3sc(C(N)=O)c(C)c23)C1]

Chiral

Prepared analogously to example 225.3 from 4-{2-[(1S,3S)-3-(acetyl-methyl-amino)cyclopentyloxy]-4-fluoro-phenylamino}-5-methyl-thieno[2,3-d]pyrimidine-6-carboxylic acid (126 mg) and 0.5 M ammonia in dioxane (2.1 ml).
Yield: 37 mg
ESI-MS: m/z=458 [M+H]$^+$
$R_t$ HPLC-MS: 2.55 min (method A)
$R_f$(TLC): 0.30 (silica gel, DCM/MeOH/NH$_3$ 90/10/1)

Example 241

4-[2-(trans-3-Acetylamino-cyclobutoxy)-4-fluoro-phenylamino]-5-methyl-thieno[2,3-d]pyrimidine-6-carboxylic acid cyanomethyl-amide

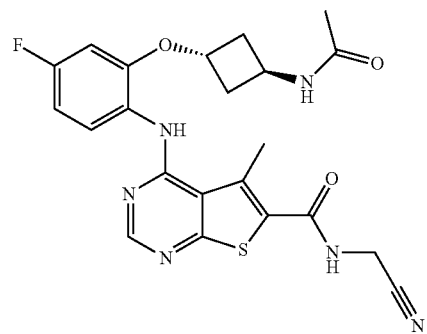 [SMILES: CC(=O)N[C@H]1C[C@H](Oc2cc(F)ccc2Nc2ncnc3sc(C(=O)NCC#N)c(C)c23)C1]

Prepared analogously to example 35.1 from compound 35.2 (80 mg) and aminoacetonitrile (14 mg).
Yield: 70 mg
ESI-MS: m/z=469 [M+H]$^+$
$R_t$ HPLC-MS: 1.61 min (method L

Example 242

Separation into 4-(4-fluoro-2-(cis-3-hydroxycyclopentyloxy)phenylamino)-5-methylthieno[2,3-d]pyrimidine-6-carboxamide and 4-(4-fluoro-2-(trans-3-hydroxycyclopentyloxy)phenylamino)-5-methylthieno[2,3-d]pyrimidine-6-carboxamide

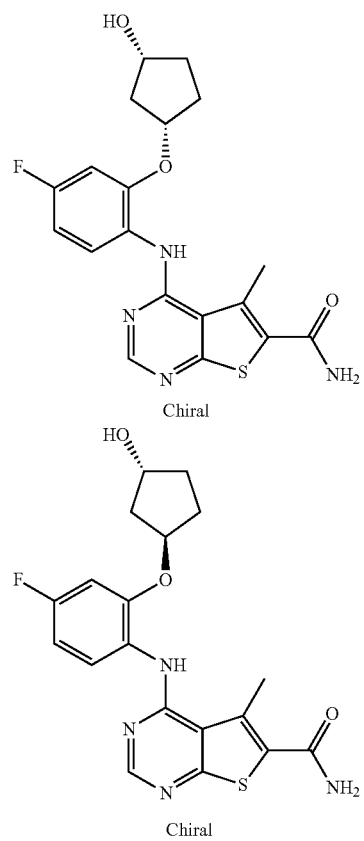

The cis/trans mixture from 225.3 (50 mg) was separated into the isomers by SFC chromatography:

Column: Daicel ASH 250 mm×4.6 mm
Mobile phase: $CO_2$/Methanol 60:40 (with addition of 0.2% Diethyl amine)
Eluting first: cis isomer; eluting second: trans isomer 4-(4-fluoro-2-(cis-3-hydroxycyclopentyloxy)phenylamino)-5-methylthieno[2,3-d]pyrimidine-6-carboxamide Yield: 5 mg
ESI-MS: m/z=403 [M+H]$^+$ 4-(4-fluoro-2-(trans-3-hydroxycyclopentyloxy)phenylamino)-5-methylthieno[2,3-d]pyrimidine-6-carboxamide Yield: 5 mg
ESI-MS: m/z=403 [M+H]$^+$

Example 243

4-(2-Cyclobutoxy-4-fluoro-phenylamino)-5-methyl-thieno[2,3-d]pyrimidine-6-carboxylic acid amide

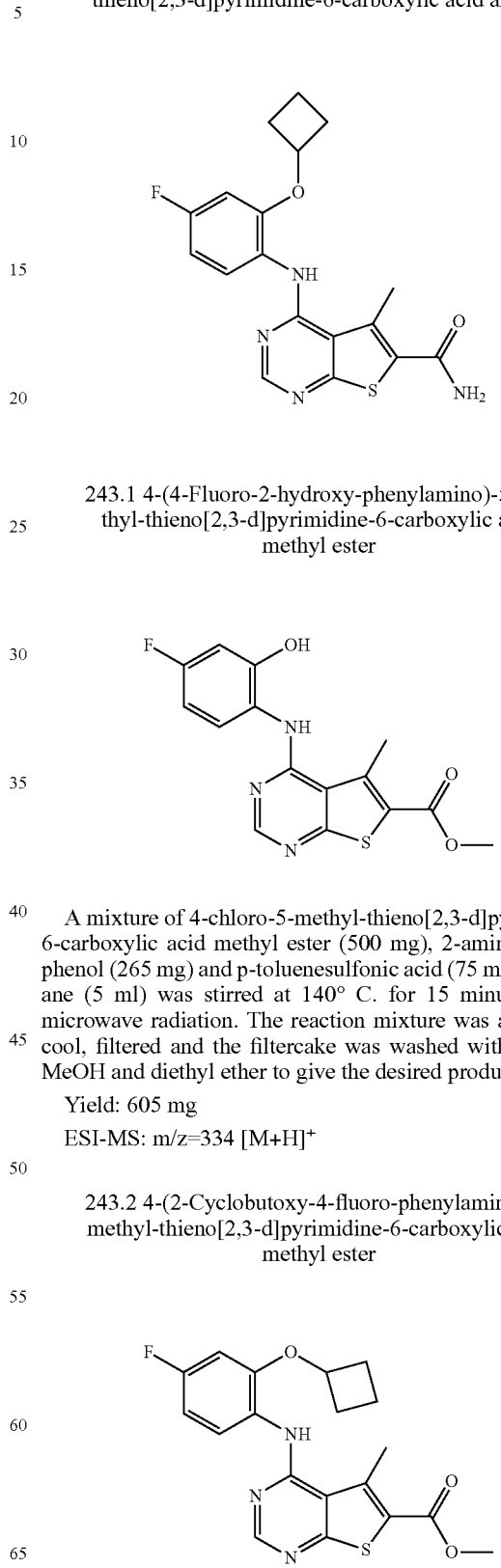

243.1 4-(4-Fluoro-2-hydroxy-phenylamino)-5-methyl-thieno[2,3-d]pyrimidine-6-carboxylic acid methyl ester A mixture of 4-chloro-5-methyl-thieno[2,3-d]pyrimidine-6-carboxylic acid methyl ester (500 mg), 2-amino-5-fluorphenol (265 mg) and p-toluenesulfonic acid (75 mg) in dioxane (5 ml) was stirred at 140° C. for 15 minutes under microwave radiation. The reaction mixture was allowed to cool, filtered and the filtercake was washed with dioxane, MeOH and diethyl ether to give the desired product.

Yield: 605 mg
ESI-MS: m/z=334 [M+H]$^+$ 243.2 4-(2-Cyclobutoxy-4-fluoro-phenylamino)-5-methyl-thieno[2,3-d]pyrimidine-6-carboxylic acid methyl ester A mixture of 4-(4-fluoro-2-hydroxy-phenylamino)-5-methyl-thieno[2,3-d]pyrimidine-6-carboxylic acid methyl ester (200 mg), potassium carbonate (166 mg) and bromocyclobutane (113 µl) in DMF (3 ml) was stirred at 60° C. over the weekend. The reaction mixture was diluted with EtOAc and washed with water and brine. The organic layer was concentrated and the residue was triturated with diethyl ether to give the desired compound.

Yield: 130 mg

243.3 4-(2-Cyclobutoxy-4-fluoro-phenylamino)-5-methyl-thieno[2,3-d]pyrimidine-6-carboxylic acid

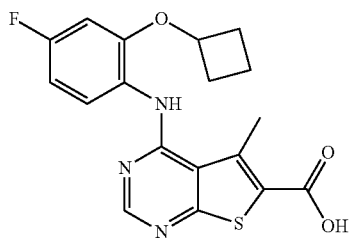 [SMILES: Cc1c(C(=O)O)sc2ncnc(Nc3ccc(F)cc3OC3CCC3)c12]

Prepared analogously to example 1.3 from 4-(2-cyclobutoxy-4-fluoro-phenylamino)-5-methyl-thieno[2,3-d]pyrimidine-6-carboxylic acid methyl ester (130 mg).

Yield: 125 mg

243.4 4-(2-Cyclobutoxy-4-fluoro-phenylamino)-5-methyl-thieno[2,3-d]pyrimidine-6-carboxylic acid amide

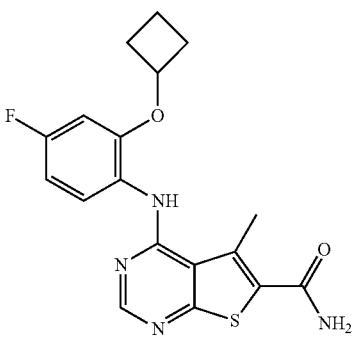 [SMILES: Cc1c(C(N)=O)sc2ncnc(Nc3ccc(F)cc3OC3CCC3)c12]

Prepared analogously to example 1.4 from 4-(2-cyclobutoxy-4-fluoro-phenylamino)-5-methyl-thieno[2,3-d]pyrimidine-6-carboxylic acid (127 mg) and 7 M ammonia in MeOH (1 ml).

Yield: 45 mg

ESI-MS: m/z=372 [M+H]+

$R_t$ HPLC-MS: 1.42 min (method X)

Example 244

4-(2-Cyclopentoxy-4-fluoro-phenylamino)-5-methyl-thieno[2,3-d]pyrimidine-6-carboxylic acid amide

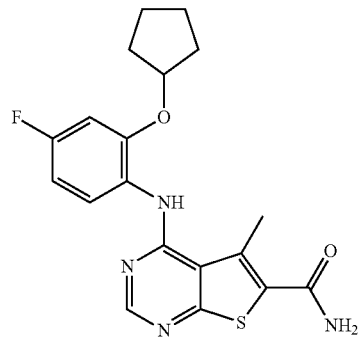 [SMILES: Cc1c(C(N)=O)sc2ncnc(Nc3ccc(F)cc3OC3CCCC3)c12]

244.1 4-(2-Cyclopentoxy-4-fluoro-phenylamino)-5-methyl-thieno[2,3-d]pyrimidine-6-carboxylic acid methyl ester

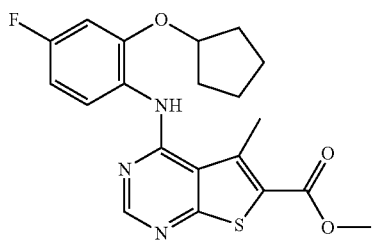 [SMILES: COC(=O)c1sc2ncnc(Nc3ccc(F)cc3OC3CCCC3)c2c1C]

Prepared analogously to example 243.2 from 4-(4-fluoro-2-hydroxy-phenylamino)-5-methyl-thieno[2,3-d]pyrimidine-6-carboxylic acid methyl ester (67 mg) and bromocyclopentane (60 mg).

Yield: 46 mg

244.2 4-(2-Cyclopentoxy-4-fluoro-phenylamino)-5-methyl-thieno[2,3-d]pyrimidine-6-carboxylic acid

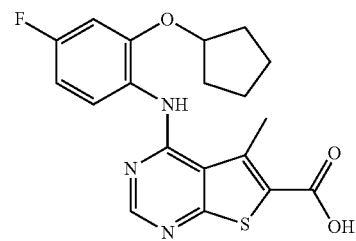 [SMILES: Cc1c(C(=O)O)sc2ncnc(Nc3ccc(F)cc3OC3CCCC3)c12]

Prepared analogously to example 1.3 from 4-(2-cyclopentoxy-4-fluoro-phenylamino)-5-methyl-thieno[2,3-d]pyrimidine-6-carboxylic acid methyl ester (73 mg).

Yield: 62 mg 244.3 4-(2-Cyclopentoxy-4-fluoro-phenylamino)-5-methyl-thieno[2,3-d]pyrimidine-6-carboxylic acid amide

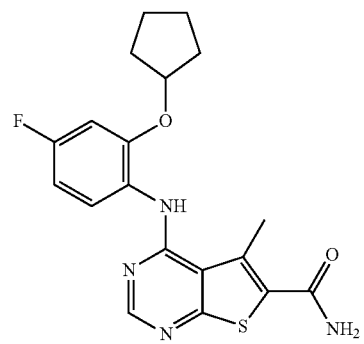 [SMILES: Cc1c(C(N)=O)sc2ncnc(Nc3ccc(F)cc3OC3CCCC3)c12]

Prepared analogously to example 1.4 from 4-(2-cyclopentoxy-4-fluoro-phenylamino)-5-methyl-thieno[2,3-d]pyrimidine-6-carboxylic acid (59 mg) and 7 M ammonia in MeOH (0.5 ml).

Yield: 27 mg
ESI-MS: m/z=387 [M+H]$^+$
R$_t$ HPLC-MS: 1.45 min (method X)

Example 245

4-[2-(trans-3-Acetylamino-cyclobutoxy)-4-fluoro-phenylamino]-5-methyl-thieno[2,3-d]pyrimidine-6-carboxylic acid (4-dimethylamino-but-2-ynyl)-amide

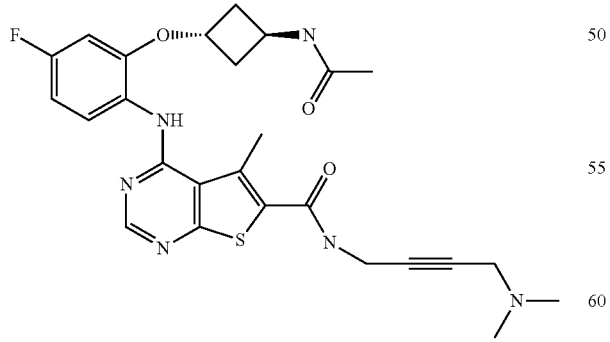

Prepared analogously to 35.3 from 0.080 g 4-[2-(trans-3-acetylamino-cyclobutoxy)-4-fluoro-phenylamino]-5-methyl-thieno[2,3-d]pyrimidine-6-carboxylic acid (cpd. 35.2) and 0.045 g 4-(dimethylamino)-but-2-ynylamin*2HCl.

Yield: 0.0075 g
ESI mass spectrum: m/z=525 (M+H)$^+$

Example 246

4-[2-(trans-3-Acetylamino-cyclobutoxy)-4-fluoro-phenylamino]-5-methyl-thieno[2,3-d]pyrimidine-6-carboxylic acid (2-amino-cyclopropyl)-amide

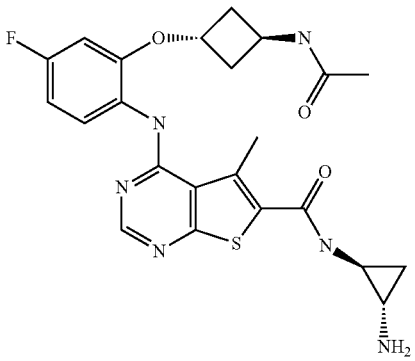 [SMILES: CC(=O)N[C@H]1C[C@H](Oc2cc(F)ccc2Nc2ncnc3sc(C(=O)N[C@H]4C[C@@H]4N)c(C)c23)C1]

246.1 [2-({4-[2-(trans-3-Acetylamino-cyclobutoxy)-4-fluoro-phenylamino]-5-methyl-thieno[2,3-d]pyrimidine-6-carbonyl}amino)-cyclopropyl]-carbamic acid tert-butyl ester

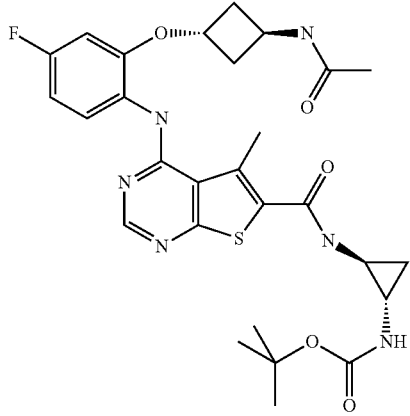 [SMILES: CC(=O)N[C@H]1C[C@H](Oc2cc(F)ccc2Nc2ncnc3sc(C(=O)N[C@H]4C[C@@H]4NC(=O)OC(C)(C)C)c(C)c23)C1]

Prepared analogously to 35.3 from 0.080 g 4-[2-(trans-3-acetylamino-cyclobutoxy)-4-fluoro-phenylamino]-5-methyl-thieno[2,3-d]pyrimidine-6-carboxylic acid (cpd. 35.2) and 0.050 g tert-butyl (1R,2R)-2-aminocyclopropylcarbamate hydrochloride.

246.2 4-[2-(trans-3-Acetylamino-cyclobutoxy)-4-fluoro-phenylamino]-5-methyl-thieno[2,3-d]pyrimidine-6-carboxylic acid (2-amino-cyclopropyl)-amide

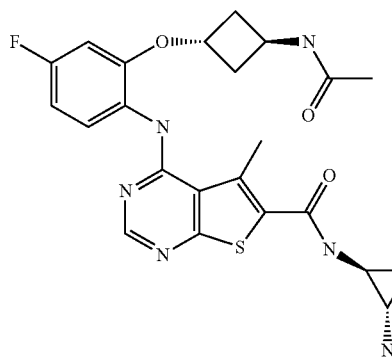

A mixture of 0.15 g [2-({4-[2-(trans-3-acetylamino-cyclobutoxy)-4-fluoro-phenylamino]-5-methyl-thieno[2,3-d]pyrimidine-6-carbonyl}amino)-cyclopropyl]-carbamic acid tert-butyl ester in 5 ml dioxane was added 1 M hydrochloric acid solution in Dioxan and was stirred at rt overnight. The reaction mixture was concentrated and the residue was purified by chromatography.

Yield: 0.014 g
ESI mass spectrum: m/z=485 (M+H)$^+$
R$_t$ (HPLC): 1.71 min (method L)

Example 247

4-[4-Fluoro-2-((1R,2R)-2-methoxy-cyclohexyloxy)-phenylamino]-5-methyl-thieno[2,3-d]pyrimidine-6-carboxylic acid methyl ester

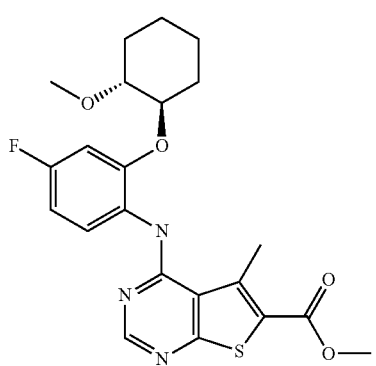

A reaction mixture of 1.00 g 4-chloro-5-methyl-thieno[2,3d]pyrimidine-6-carboxylic acid methyl ester, 1.98 g intermediate XVIII and 0.071 g p-toluenesulfonic acid in 20 ml dioxane was heated at 100° C. for 2 hours. The reaction mixture was allowed to reach rt and diluted with water. The mixture was filtered. The solid was washed with water. The solid was dried in vacuo at 65° C.

Yield: 1.75 g
ESI mass spectrum: m/z=446 (M+H)$^+$
R$_t$ (HPLC): 2.41 min (method L)

Example 248

4-[4-Fluoro-2-((1R,2R)-2-methoxy-cyclohexyloxy)-phenylamino]-5-methyl-thieno[2,3-d]pyrimidine-6-carboxylic acid

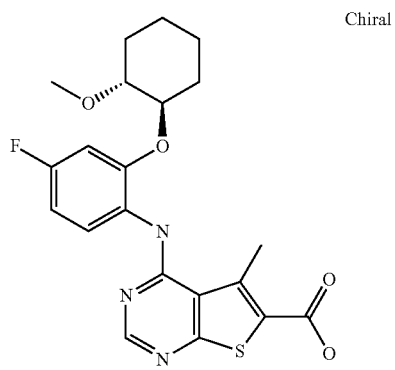 [SMILES: CO[C@@H]1CCCC[C@H]1Oc1cc(F)ccc1Nc1ncnc2sc(C(=O)O)c(C)c12]

248.1 4-[4-Fluoro-2-((1R,2R)-2-methoxy-cyclohexyloxy)-phenylamino]-5-methyl-thieno[2,3-d]pyrimidine-6-carboxylic acid methyl ester

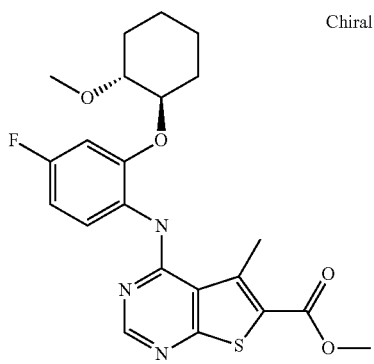 [SMILES: COC(=O)c1sc2ncnc(Nc3ccc(F)cc3O[C@@H]3CCCC[C@H]3OC)c2c1C]

Prepared analogously to 247 from 1.00 g 4-chloro-5-methyl-thieno[2,3d]pyrimidine-6-carboxylic acid methyl ester and 1.98 g intermediate XVIII.

248.2 4-[4-Fluoro-2-((1R,2R)-2-methoxy-cyclohexyloxy)-phenylamino]-5-methyl-thieno[2,3-d]pyrimidine-6-carboxylic acid

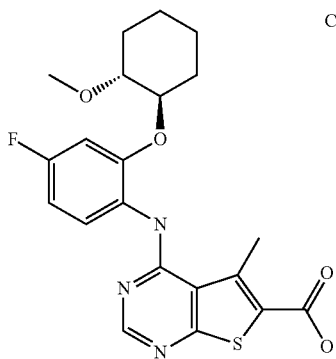

A mixture of 1.75 g 4-[4-fluoro-2-((1R,2R)-2-methoxy-cyclohexyloxy)-phenylamino]-5-10 methyl-thieno[2,3-d]pyrimidine-6-carboxylic acid methyl ester, 4M sodium hydroxide solution, 20 ml THF and 20 ml MeOH was stirred at rt overnight. The reaction mixture was acidified by addition of hydrochloric acid, diluted with 80 ml water and filtered. The solid was washed with water and dried in vacuo at 65° C.

Yield: 1.575 g
ESI mass spectrum: m/z=432 (M+H)$^+$
Rt (HPLC): 2.05 min (method L)

Example 249

4-[4-Fluoro-2-((1R,2R)-2-methoxy-cyclohexyloxy)-phenylamino]-5-methyl-thieno[2,3-d]pyrimidine-6-carboxylic acid amide

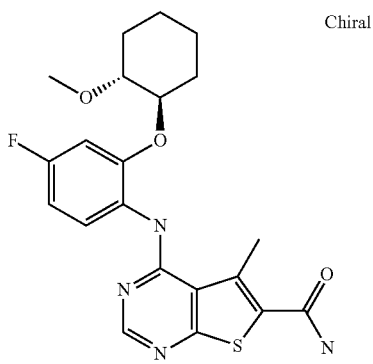 [SMILES: CO[C@@H]1CCCC[C@H]1Oc1cc(F)ccc1Nc1ncnc2sc(C(N)=O)c(C)c12]

249.1 4-[4-Fluoro-2-((1R,2R)-2-methoxy-cyclohexyloxy)-phenylamino]-5-methyl-thieno[2,3-d]pyrimidine-6-carboxylic acid methyl ester

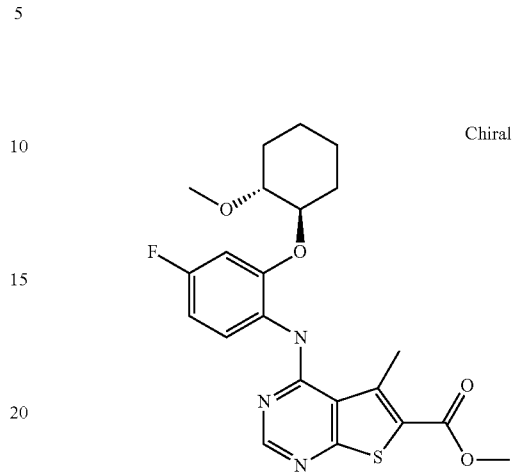

Prepared analogously to 247 from 1.00 g 4-chloro-5-methyl-thieno[2,3d]pyrimidine-6-carboxylic acid methyl ester and 1.98 g intermediate XVIII.

249.2 4-[4-Fluoro-2-((1R,2R)-2-methoxy-cyclohexyloxy)-phenylamino]-5-methyl-thieno[2,3-d]pyrimidine-6-carboxylic acid

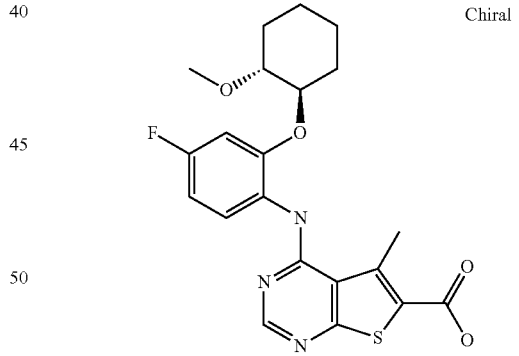

A mixture of 1.75 g 4-[4-fluoro-2-((1R,2R)-2-methoxy-cyclohexyloxy)-phenylamino]-5-methyl-thieno[2,3-d]pyrimidine-6-carboxylic acid methyl ester, 4M sodium hydroxide solution, 20 ml THF and 20 ml MeOH was stirred at rt overnight. The reaction mixture was acidified by addition of hydrochloric acid, diluted with 80 ml water and filtered. The solid was washed with water and dried in vacuo at 65° C.

Yield: 1.575 g
ESI mass spectrum: m/z=432 (M+H)$^+$
Rt (HPLC): 2.05 min (method L)

249.3 4-[4-Fluoro-2-((1R,2R)-2-methoxy-cyclohexyloxy)-phenylamino]-5-methyl-thieno[2,3-d]pyrimidine-6-carboxylic acid amide

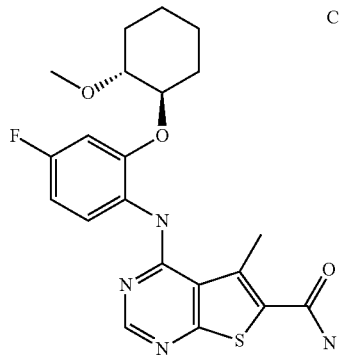

A mixture of 0.21 g 4-[4-Fluoro-2-((1R,2R)-2-methoxy-cyclohexyloxy)-phenylamino]-5-methyl-thieno[2,3-d]pyrimidine-6-carboxylic acid, 5 ml ammonia 0.5 M in dioxane, 0.22 g HATU, 0.10 ml DIPEA and 2 ml DMF was stirred at rt overnight. The reaction mixture was diluted with water and filtered. The solid was dried in vacuo at 65° C.

Yield: 0.211 g

ESI mass spectrum: m/z=431 (M+H)$^+$

Rt (HPLC): 1.80 min (method L)

The following compounds were prepared analogously to 1.4 using TBTU and TEA instead of HATU and DIPEA:

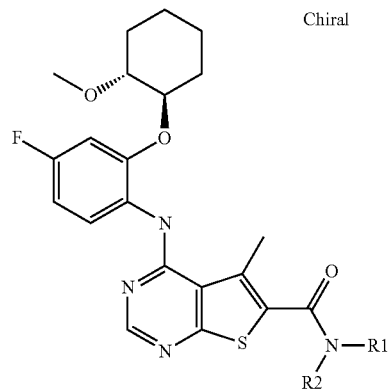

| Example | NR1R2 | educt | Mass spectrum | HPLC (retention time) |
|---|---|---|---|---|
| 250 | 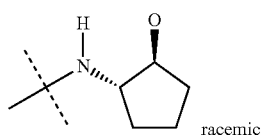 racemic | Cpd. 249.2 | 515 (M + H) | 1.86 min (Method L) |
| 251 | 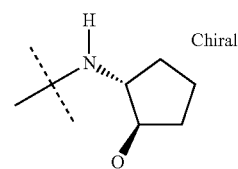 | Cpd. 249.2 | 515 (M + H) | 1.87 min (Method L) |
| 252 | 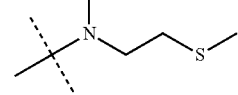 | Cpd. 249.2 | 505 (M + H) | 2.05 min (Method L) |
| 253 | 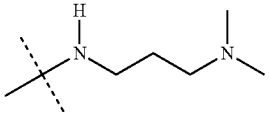 | Cpd. 249.2 | 515 (M + H) | 1.40 min (Method L) |
| 254 | 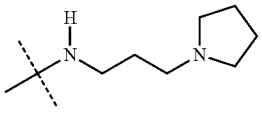 | Cpd. 249.2 | 542 (M + H) | 1.42 min (Method L) |
| 255 | | Cpd. 249.2 | 521 (M + H) | 3.67 min (Method B) |

Example 256

Pure enantiomeres of 4-[4-fluoro-2-(cis-2-hydroxy-cyclohexyloxy)-phenylamino]-5-methyl-thieno[2,3-d]pyrimidine-6-carboxylic acid methyl ester (The absolute configuration has not been determined, i.e. the compound can be either the structure shown or the other enantiomer.)

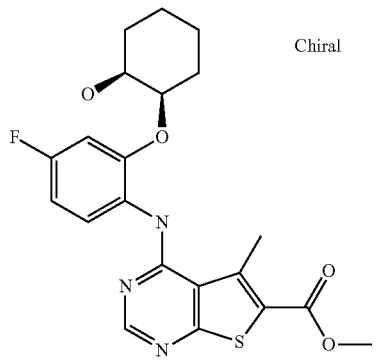 [SMILES: COC(=O)c1sc2ncnc(Nc3ccc(F)cc3O[C@@H]3CCCC[C@@H]3O)c2c1C]

Prepared analogously to 247 from 0.437 g 4-chloro-5-methyl-thieno[2,3-d]pyrimidine-6-carboxylic acid methyl ester and 0.410 g intermediate XXII.3.
Yield: 0.707 g
ESI mass spectrum: m/z=432 (M+H)$^+$
Rt (HPLC): 2.08 min (method L)

Example 257

Pure enantiomeres of 4-[4-fluoro-2-(cis-2-hydroxy-cyclohexyloxy)-phenylamino]-5-methyl-thieno[2,3-d]pyrimidine-6-carboxylic acid methyl ester (The absolute configuration has not been determined, i.e. the compound can be either the structure shown or the other enantiomer.)

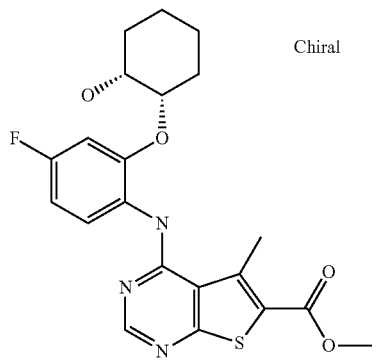 [SMILES: COC(=O)c1sc2ncnc(Nc3ccc(F)cc3O[C@H]3CCCC[C@H]3O)c2c1C]

Prepared analogously to 247 from 0.451 g 4-chloro-5-methyl-thieno[2,3-d]pyrimidine-6-carboxylic acid methyl ester and 0.420 g intermediate XXII.4
Yield: 0.783 g
ESI mass spectrum: m/z=432 (M+H)$^+$
Rt (HPLC): 2.03 min (method L)

Example 258

Pure enantiomere of 4-[4-fluoro-2-(cis-2-hydroxy-cyclohexyloxy)-phenylamino]-5-methyl-thieno[2,3-d]pyrimidine-6-carboxylic acid (The absolute configuration has not been determined, i.e. the compound can be either the structure shown or the other enantiomer.)

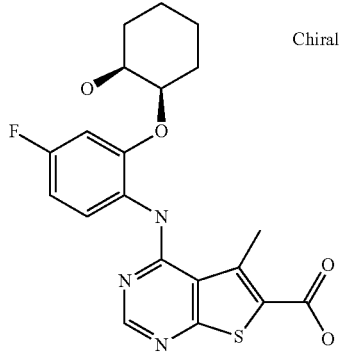 [SMILES: Cc1c(C(=O)O)sc2ncnc(Nc3ccc(F)cc3O[C@@H]3CCCC[C@@H]3O)c12]

Prepared analogously to 51.2 from 0.630 g 4-[4-fluoro-2-(−2-hydroxycyclohexyloxy)-phenylamino]-5-methyl-thieno[2,3-d]pyrimidine-6-carboxylic acid methyl ester (cpd. 256)
Yield: 0.594 g
ESI mass spectrum: m/z=418 (M+H)$^+$
Rt (HPLC): 1.78 min (method L)

The following compounds were prepared analogously to 1.4 using TBTU and TEA instead of HATU and DIPEA:

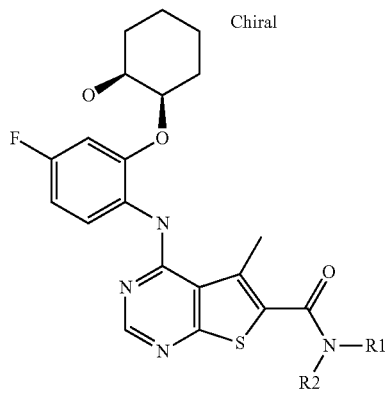

| Example | NR1R2 | educt | Mass spectrum | HPLC (retention time) |
|---|---|---|---|---|
| 259 | (H)N—piperidine-N—methyl | Cpd. 258 | 514 (M + H) | 1.31 min (Method L) |
| 260 | (H)N—(CH2)3—pyrrolidine | Cpd. 258 | 528 (M + H) | 1.31 min (Method L) |
| 261 | (H)N—(CH2)3—N(CH3)2 | Cpd. 258 | 502 (M + H) | 1.44 min (Method L) |

Example 262

Pure enantiomeres of 4-[4-fluoro-2-(cis-2-hydroxy-cyclohexyloxy)-phenylamino]-5-methyl-thieno[2,3-d]pyrimidine-6-carboxylic acid (The absolute configuration has not been determined, i.e. the compound can be either the structure shown or the other enantiomer.)

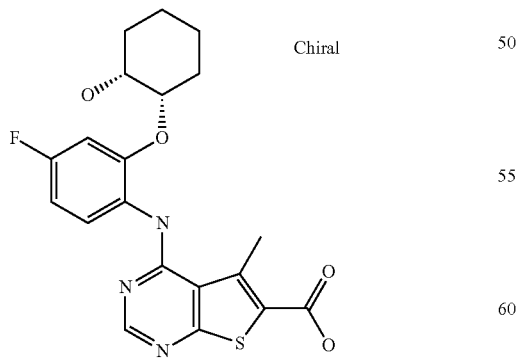

Prepared analogously to 51.2 from 0.72 g 4-[4-fluoro-2-(cis-2-hydroxycyclohexyloxy)-phenylamino]-5-methyl-thieno[2,3-d]pyrimidine-6-carboxylic acid methyl ester (cpd. 257)

Yield: 0.585 g
ESI mass spectrum: m/z=418 (M+H)⁺
Rt (HPLC): 1.77 min (method L)
The following compounds were prepared analogously to 1.4 using TBTU instead of HATU and no DIPEA:

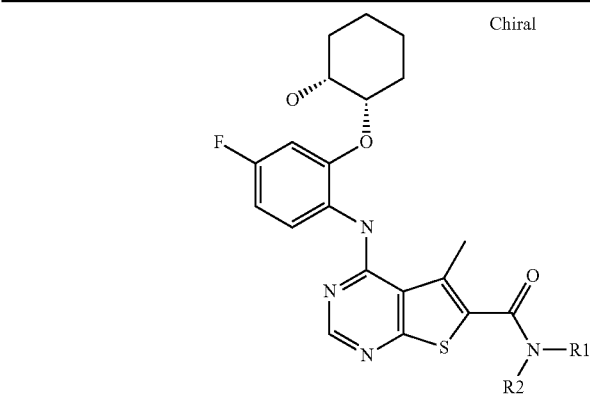

| Example | NR1R2 | educt | Mass spectrum | HPLC (retention time) |
|---|---|---|---|---|
| 263 | (H-N-propyl-pyrrolidine) | Cpd. 262 | 528 (M + H) | 1.32 min (Method L) |
| 264 | (H-N-propyl-N,N-dimethylamine) | Cpd. 262 | 502 (M + H) | 1.33 min (Method L) |

The following compound was prepared analogously to 1.4 using TBTU and TEA instead of HATU and DIPEA:

| Example | NR1R2 | educt | Mass spectrum | HPLC (retention time) |
|---|---|---|---|---|
| 265 | (H-N-(1-methylpiperidin-4-yl)) | Cpd. 262 | 514 (M + H) | 1.32 min (Method L) |

Example 266

4-[2-(trans-4-hydroxy-cyclohexyloxy)-pyridine-3-ylamino]-5-methyl-thieno[2,3-d]pyrimidine-6-carboxylic acid (2-hydroxy-ethyl)-amide

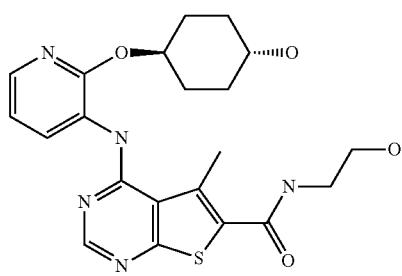 [SMILES: Cc1c(C(=O)NCCO)sc2ncnc(Nc3cccnc3O[C@H]3CC[C@H](O)CC3)c12]

266.1 4-[2-(trans-4-hydroxy-cyclohexyloxy)-pyridine-3-ylamino]-5-methyl-thieno[2,3-d]pyrimidine-6-carboxylic acid methylester

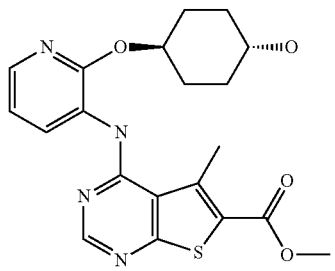 [SMILES: COC(=O)c1sc2ncnc(Nc3cccnc3O[C@H]3CC[C@H](O)CC3)c2c1C]

A reaction mixture of 2.913 g 4-chloro-5-methyl-thieno[2,3d]pyrimidine-6-carboxylic acid methyl ester, 2.5 g intermediate XXIV and 0.413 g p-toluenesulfonic acid in 60 ml dioxane was heated at 110° C. in the microwave for 1 hour. The reaction mixture was concentrated and the residue was purified by chromatography.
Yield: 1.547 g
ESI mass spectrum: m/z=415 (M+H)$^+$

266.2 4-[2-(trans-4-hydroxy-cyclohexyloxy)-pyridine-3-ylamino]-5-methyl-thieno[2,3-d]pyrimidine-6-carboxylic acid

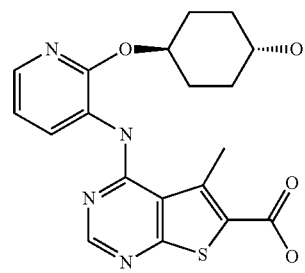 [SMILES: Cc1c(C(=O)O)sc2ncnc(Nc3cccnc3O[C@H]3CC[C@H](O)CC3)c12]

A reaction mixture of 1.541 g 4-[2-(trans-4-hydroxy-cyclohexyloxy)-pyridine-3-ylamino]-5-methyl-thieno[2,3-d]pyrimidine-6-carboxylic acid methylester, 2.00 g lithium hydroxide, 13.3 ml THF, 13.3 ml MeOH and 13.3 ml water was stirred at rt overnight. Then the mixture was acidified by addition of hydrochloric acid and extracted with DCM. The organic phase was dried, filtered and the filtrate was concentrated.
Yield: 1.683 g
ESI mass spectrum: m/z=401 (M+H)$^+$

266.3 4-[2-(trans-4-hydroxy-cyclohexyloxy)-pyridine-3-ylamino]-5-methyl-thieno[2,3-d]pyrimidine-6-carboxylic acid (2-hydroxy-ethyl)-amide

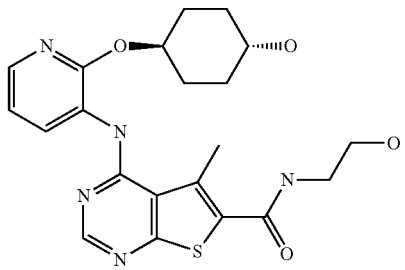 [SMILES: Cc1c(C(=O)NCCO)sc2ncnc(Nc3cccnc3O[C@H]3CC[C@H](O)CC3)c12]

Prepared analogously to 1.4 from 0.2 g 4-[2-(trans-2-hydroxy-cyclohexyloxy)pyridine-3-yl-amino]-5-methyl-thieno[2,3-d]pyrimidine-6-carboxylic acid and 36 µl ethanolamine.

Yield: 0.051 g
ESI mass spectrum: m/z=444 (M+H)$^+$
Rt (HPLC): 2.27 min (method A)

The following compounds were prepared analogously to 1.4:

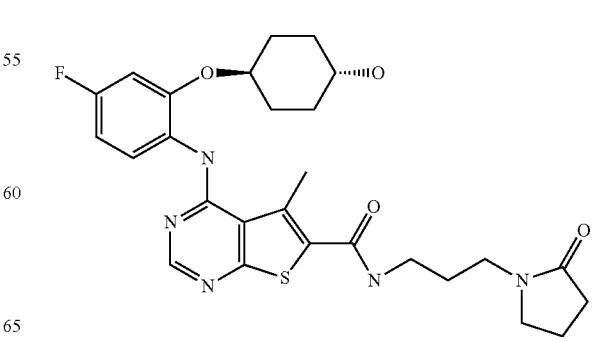

| Example | NR1R2 | educt | Mass spectrum | HPLC (retention time) |
|---|---|---|---|---|
| 267 | ![H-N-CH2-C≡C-CH2-N(CH3) · 2HCl] | Cpd. 266.3 | 495 (M + H) | 2.05 min (Method A) |
| 268 | ![H-N-(CH2)3-pyrrolidine] | Cpd. 266.3 | 511 (M + H) | 2.05 min (Method A) |
| 269 | ![H-N-piperidine-N-CH3] | Cpd. 266.3 | 497 (M + H) | 1.94 min (Method A) |
| 270 | ![H-N-(CH2)3-azetidine] | Cpd. 266.3 | 497 (M + H) | 1.24 min (Method A) |

Example 271

4-[4-Fluoro-2-(trans-4-hydroxy-cyclohexyloxy)-phenylamino]-5-methyl-thieno[2,3-d]pyrimidine-6-carboxylic acid [3-(2-oxo-pyrrolidin-1-yl)-propyl] amide

271.1 4-[4-Fluoro-2-(trans-4-hydroxy-cyclohexyloxy)-phenylamino]-5-methyl-thieno[2,3-d]pyrimidine-6-carboxylic acid

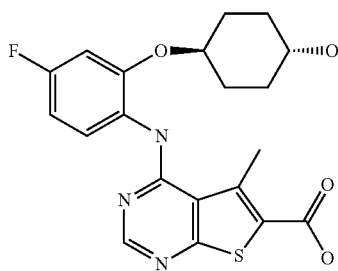 [SMILES: Cc1c(C(=O)O)sc2ncnc(Nc3ccc(F)cc3O[C@H]3CC[C@H](O)CC3)c12]

A reaction mixture of 2.56 g 4-chloro-5-methyl-thieno[2,3d]pyrimidine-6-carboxylic acid ethyl ester, 1.86 g intermediate XXVII and 0.25 g p-toluenesulfonic acid in 50 ml dioxane was heated at 100° C. for 1.5 hours. At rt the reaction mixture was diluted with water. The mixture was filtered and the solid was washed with water. The solid was dried in vacuo at 50° C. To the solid was added 10 ml THF, 10 ml MeOH, 2 ml 2M sodium hydroxide solution. This mixture was stirred at rt overnight. The mixture was concentrated, neutralized with 2M hydrochloric acid and filtered. The solid was washed with water and triturated with diethylether. The solid was dried in vacuo at 50° C.

Yield: 2.14 g

ESI mass spectrum: m/z=418 (M+H)$^+$

R$_t$ (HPLC): 2.05 min (method K)

271.2 4-[4-Fluoro-2-(trans-4-hydroxy-cyclohexyloxy)-phenylamino]-5-methyl-thieno[2,3-d]pyrimidine-6-carboxylic acid [3-(2-oxo-pyrrolidin-1-yl)-propyl]-amide

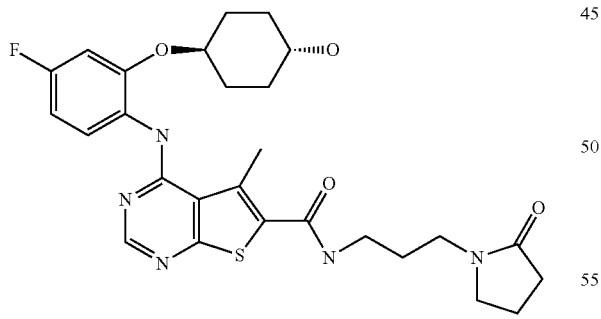

Prepared analogously to 1.4 from 0.042 g 4-[4-fluoro-2-(trans-4-hydroxycyclohexyloxy)-phenylamino]-5-methyl-thieno[2,3-d]pyrimidine-6-carboxylic acid and 0.015 g 1-(3-aminopropyl)-2-pyrrolidinone. The residue was purified by chromatography.

Yield: 0.034 g

ESI mass spectrum: m/z=542 (M+H)$^+$

Rt (HPLC): 2.18 min (method E)

Example 272

2-({-4-[4-Fluoro-2-(trans-4-methoxy-cyclohexyloxy)-phenylamino]-5-methyl-thieno[2,3-d]pyrimidine-6-carbonyl}-amino)-3-hydroxy-propionic acid methyl ester

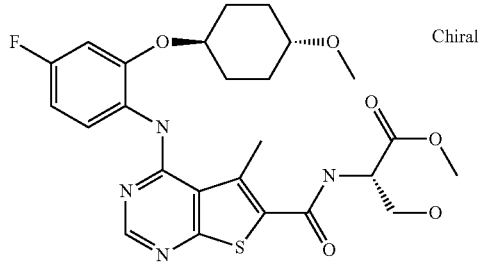 [SMILES: COC(=O)[C@H](CO)NC(=O)c1sc2ncnc(Nc3ccc(F)cc3O[C@H]3CC[C@H](OC)CC3)c2c1C]

272.1 4-[4-Fluoro-2-(trans-4-methoxy-cyclohexyloxy)-phenylamino]-5-methyl-thieno[2,3-d]pyrimidine-6-carboxylic acid methyl ester

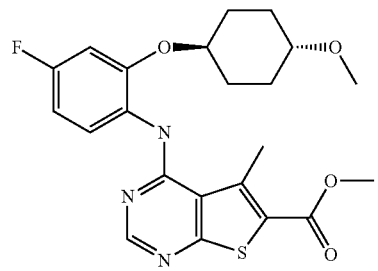 [SMILES: COC(=O)c1sc2ncnc(Nc3ccc(F)cc3O[C@H]3CC[C@H](OC)CC3)c2c1C]

A reaction mixture of 11.2 g 4-chloro-5-methyl-thieno[2,3d]pyrimidine-6-carboxylic acid methyl ester, 10.0 g intermediate XXXXXVII and 1.76 g p-toluenesulfonic acid in 95 ml dioxane was heated at 90° C. 2 hours. The reaction mixture was poured in water and filtered. The solid was washed with water and dissolved in DCM. The organic phase was dried and then filtered. The filtrate was concentrated.

Yield: 15.914 g

ESI mass spectrum: m/z=446 (M+H)

272.2 4-[4-Fluoro-2-(trans-4-methoxy-cyclohexyloxy)-phenylamino]-5-methyl-thieno[2,3-d]pyrimidine-6-carboxylic acid

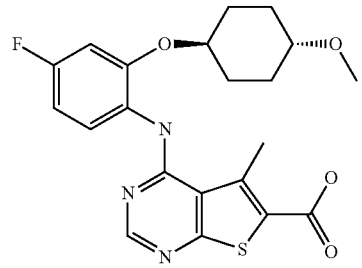 [SMILES: CO[C@H]1CC[C@H](Oc2cc(F)ccc2Nc2ncnc3sc(C(=O)O)c(C)c23)CC1]

Prepared analogously to 58.2 from 15.914 g 4-[4-fluoro-2-(trans-4-methoxycyclohexyloxy)-phenylamino]-5-methyl-thieno[2,3-d]pyrimidine-6-carboxylic acid methyl ester.

Yield: 14.54 g

ESI mass spectrum: m/z=432 (M+H)$^+$ 272.3 Methyl (2S)-2-{([4-({4-fluoro-2-[(4-methoxy-cyclohexyl)oxy]phenyl}amino)-5-methylthieno[2,3-d]pyrimidin-6-yl]formamido}-3-hydroxypropanoate

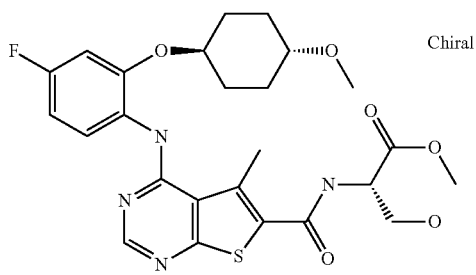 [SMILES: COC(=O)[C@H](CO)NC(=O)c1sc2ncnc(Nc3ccc(F)cc3O[C@H]3CC[C@H](OC)CC3)c2c1C]

Prepared analogously to 1.4 from 1.50 g 4-[4-fluoro-2-(trans-4-methoxycyclohexyloxy)-phenylamino]-5-methyl-thieno[2,3-d]pyrimidine-6-carboxylic acid and 0.541 g L-(+)-serine methyl ester hydrochloride.

Yield: 1.648 g

ESI mass spectrum: m/z=533 (M+H)⁺

$R_t$ (HPLC): 2.87 min (method A)

The following compounds were prepared analogously to 1.4:

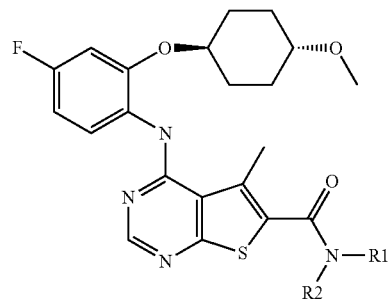

| Example | NR1R2 | educt | Mass spectrum | HPLC (retention time) |
|---|---|---|---|---|
| 273 | (Chiral) | Cpd. 272.2 | 558 (M + H) | 1.8 min (Method N) |
| 274 | (Chiral) | Cpd. 272.2 | 558 (M + H) | 1.81 min (Method N) |

The following compounds were prepared analogously to 1.4 using TBTU instead of HATU:

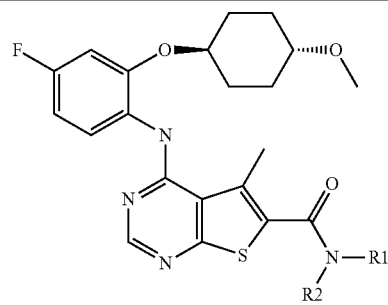

| Example | NR1R2 | educt | Mass spectrum | HPLC (retention time) |
|---|---|---|---|---|
| 275 | | Cpd. 272.2 | 556 (M + H) | 1.42 min (Method L) |

-continued
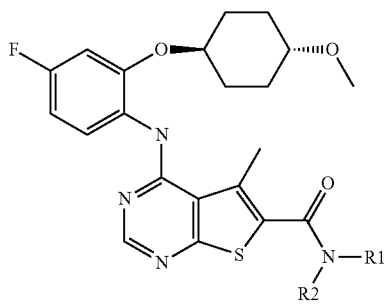
| Example | NR1R2 | educt | Mass spectrum | HPLC (retention time) |
|---|---|---|---|---|
| 276 | 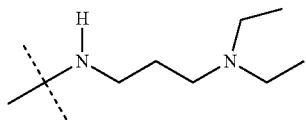 | Cpd. 272.2 | 544 (M + H) | min (Method . . . ) |
| 277 | 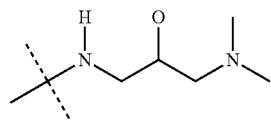 | Cpd. 272.2 | 532 (M + H) | min (Method . . . ) |
| 278 | 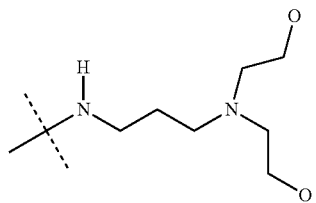 | Cpd. 272.2 | 576 (M + H) | 1.37 min (Method L) |
| 279 | 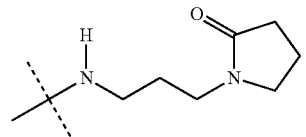 | Cpd. 272.2 | 556 (M + H) | min (Method . . . ) |
| 280 | 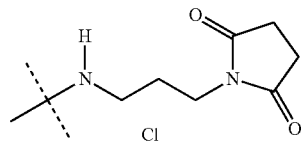 | Cpd. 272.2 | 570 (M + H) | min (Method . . . ) |

Example 281

4-[2-(4-Amino-cyclohexyloxy)-pyridin-3-ylamino]-5-methyl-thieno[2,3-d]pyrimidine-6-carboxylic acid methyl ester

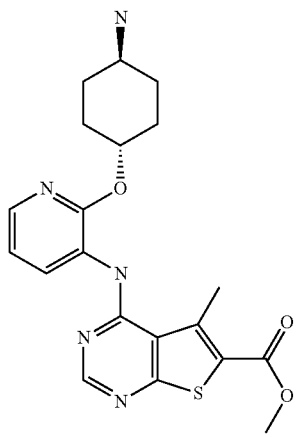 [SMILES: COC(=O)c1sc2ncnc(Nc3cccnc3O[C@H]3CC[C@H](N)CC3)c2c1C]

A reaction mixture of 0.5 g 4-chloro-5-methyl-thieno[2,3d]pyrimidine-6-carboxylic acid methyl ester, 0.636 g intermediate XXXXXXIII and 0.04 g p-toluenesulfonic acid in 10 ml isopropanol was heated at 140° C. in the microwave for 14 min. The reaction mixture was concentrated and the residue was purified by chromatography.

Yield: 0.36 g
ESI mass spectrum: m/z=414 (M+H)⁺
Rt (HPLC): 1.22 min (method K)

Example 282

4-[2-(4-Amino-cyclohexyloxy)-pyridin-3-ylamino]-5-methyl-thieno[2,3-d]pyrimidine-6-carboxylic acid

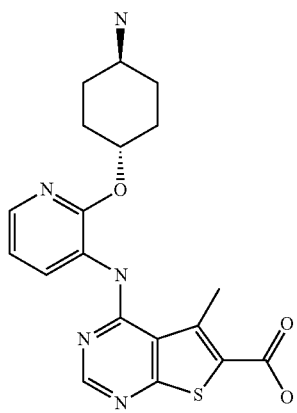

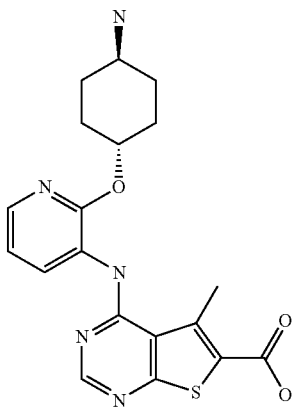

A mixture of 0.05 g 4-[2-(4-amino-cyclohexyloxy)-pyridin-3-ylamino]-5-methyl-thieno[2,3-d]pyrimidine-6-carboxylic acid methyl ester and 1M sodium hydroxide solution in 5 ml MeOH was stirred at 70° C. for 1 hour. The reaction mixture was neutralized with 1M hydrochloric acid and concentrated. The residue was dissolved in DCM and MeOH, dried and filtered. The filtrate was concentrated. The residue was triturated with diethylether.

Yield: 0.048 g
ESI mass spectrum: m/z=400 (M+H)⁺

Example 283

4-[2-(4-Amino-cyclohexyloxy)-pyridin-3-ylamino]-5-methyl-thieno[2,3-d]pyrimidine-6-carboxylic acid amide

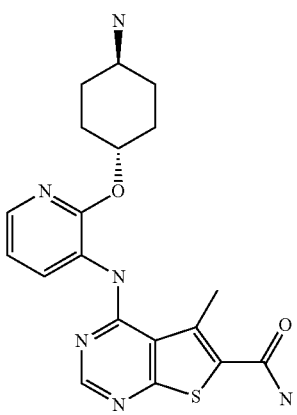 [SMILES: Cc1c(C(N)=O)sc2ncnc(Nc3cccnc3O[C@H]3CC[C@H](N)CC3)c12]

283.1 4-[2-(4-tert-Butoxycarbonylamino-cyclohexyloxy)-pyridin-3-ylamino]-5-methyl-thieno[2,3-d]pyrimidine-6-carboxylic acid methyl ester

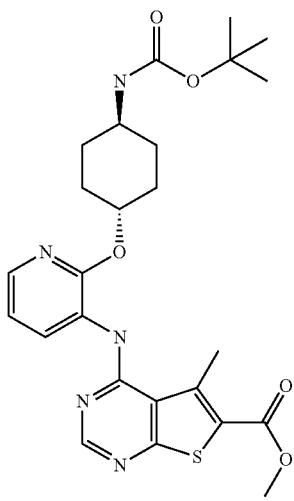 [SMILES: COC(=O)c1sc2ncnc(Nc3cccnc3O[C@H]3CC[C@H](NC(=O)OC(C)(C)C)CC3)c2c1C]

A reaction mixture of 0.2 g 4-chloro-5-methyl-thieno[2,3-d]pyrimidine-6-carboxylic acid methyl ester, 0.506 g intermediate XXXXXXIII and 0.4 ml DIPEA in 6 ml Isopropanol were heated at 140° C. in the microwave for 7 hours. The reaction mixture was cooled down overnight and filtered. The solid was washed with diethylether, the residue was dissolved in DCM+MeOH, filtered and concentrated.
Yield: 0.140 g
ESI mass spectrum: m/z=514 (M+H)+
Rt (HPLC): 2.19 min (method K)

283.2 4-[2-(4-tert-Butoxycarbonylamino-cyclohexyloxy)-pyridin-3-ylamino]-5-methyl-thieno[2,3-d]pyrimidine-6-carboxylic acid

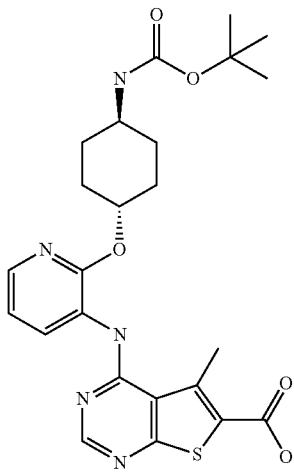 [SMILES: Cc1c(C(=O)O)sc2ncnc(Nc3cccnc3O[C@H]3CC[C@H](NC(=O)OC(C)(C)C)CC3)c12]

A mixture of 7 g 4-[2-(4-tert-butoxycarbonylamino-cyclohexyloxy)-pyridin-3-ylamino]-5-methyl-thieno[2,3-d]pyrimidine-6-carboxylic acid methyl ester and 4M sodium hydroxide solution (60 ml) and 500 mg lithium hydroxide in 60 ml MeOH was stirred at 80° C. for 5 hours. To the reaction mixture were added 65.2 ml 4M hydrochloric acid and the mixture was concentrated afterwards. The residue was triturated with water. The solid was isolated by filtration, washed with water and dried in a desiccator.
Yield: 6.8 g
ESI mass spectrum: m/z=500 (M+H)+

283.3 4-[2-(4-Amino-cyclohexyloxy)-pyridin-3-ylamino]-5-methyl-thieno[2,3-d]pyrimidine-6-carboxylic acid amide

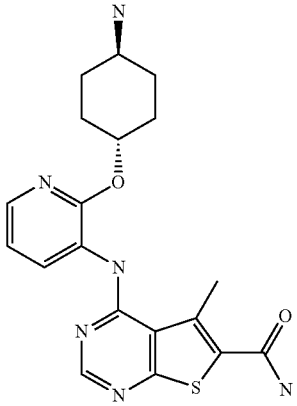 [SMILES: Cc1c(C(N)=O)sc2ncnc(Nc3cccnc3O[C@H]3CC[C@H](N)CC3)c12]

A mixture of 0.025 g 4-[2-(4-tert-butoxycarbonylamino-cyclohexyloxy)-pyridin-3-ylamino]-5-methyl-thieno[2,3-d]pyrimidine-6-carboxylic acid, 0.016 g TBTU, 17 µl DIPEA and 3 ml DMF/THF 1:1 was stirred for 30 minutes at rt. 20 µl ammonia were added and the mixture was stirred overnight. The reaction mixture was concentrated and the residue was dissolved in DCM. The organic phase was washed with water, dried and filtered. The filtrate was concentrated. The residue was dissolved in 5 ml DCM, 1 ml trifluoroacetic acid was added and the mixture was stirred at rt for 1 hour. The reaction mixture was concentrated and the residue was purified by chromatography.
Yield: 0.020 g
ESI mass spectrum: m/z=399 (M+H)+
Rt (HPLC): 1.75 min (method K)

The following compounds were prepared analogously to 283.3:

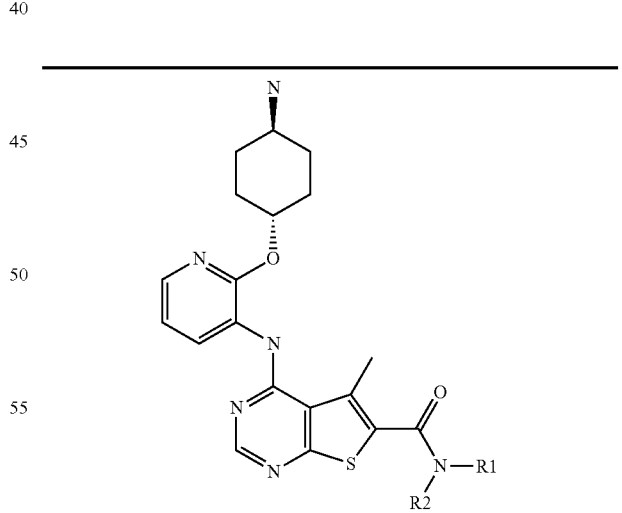

| Example | NR1R2 | educt | Mass spectrum | HPLC (retention time) |
|---|---|---|---|---|
| 284 | H, (t-Bu)(Et)N– | Cpd. 283.2 | 427 (M + H) | 1.39 min (Method K) |

-continued

| | | | | |
|---|---|---|---|---|
| 285 | 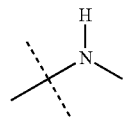 | Cpd. 283.2 | 413 (M + H) | 1.82 min (Method A) |
| 286 | 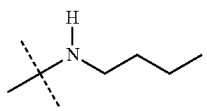 | Cpd. 283.2 | 455 (M + H) | 1.14 min (Method M) |
| 287 | 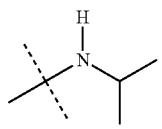 | Cpd. 283.2 | 441 (M + H) | 1.08 min (Method M) |

The following compounds were prepared analogously to 283.3 using DMF instead of DMF/THF:

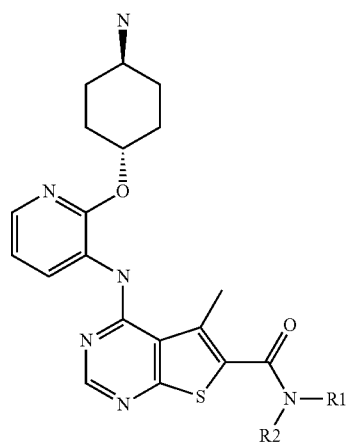

| Example | NR1R2 | educt | Mass spectrum | HPLC (retention time) |
|---|---|---|---|---|
| 288 | 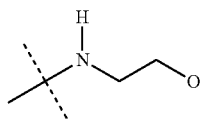 | Cpd. 283.2 | 443 (M + H) | 1.36 min (Method K) |

Example 289

4-[2-(4-Amino-cyclohexyloxy)-pyridin-3-ylamino]-5-methyl-thieno[2,3-d]pyrimidine-6-carboxylic acid propyl amide

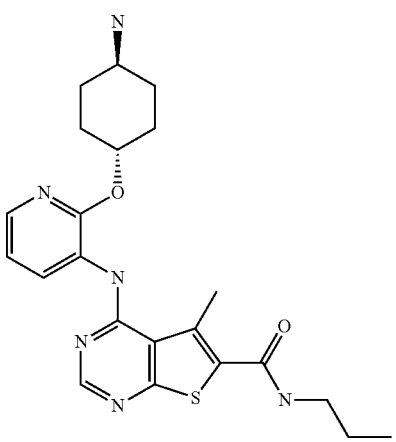 [SMILES: CCCNC(=O)c1sc2ncnc(Nc3cccnc3O[C@H]3CC[C@H](N)CC3)c2c1C]

A mixture of 0.1 g 4-[2-(4-tert-butoxycarbonylamino-cyclohexyloxy)-pyridin-3-ylamino]-5-methyl-thieno[2,3-d]pyrimidine-6-carboxylic acid, 39.689 µl chlor-trimethyl-propylenamine, 24 µl propylamine, 30.664 µl TEA and 5 ml DCM was stirred at rt overnight. The reaction mixture was washed successively with 0.1 M hydrochloric acid and 0.1 M sodium hydroxide solution, dried and filtered. The filtrate was concentrated. The residue was triturated with diethylether.

Yield: 0.050 g

ESI mass spectrum: m/z=441 (M+H)$^+$

Rt (HPLC): 1.10 min (method M)

Example 290

4-[4-Fluoro-2-(tetrahydro-cyclopenta[1,3]dioxol-5-yloxy)phenylamino]-5-methyl-thieno[2,3-d]pyrimidine-6-carboxylic acid

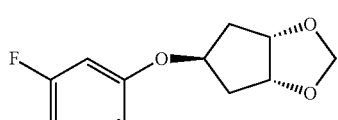

relative stereochemistry

290.1 4-[4-Fluoro-2-(tetrahydro-cyclopenta[1,3]dioxol-5-yloxy)phenylamino]-5-methyl-thieno[2,3-d]pyrimidine-6-carboxylic acid methyl ester

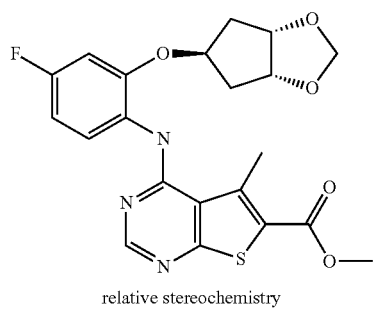 [SMILES: COC(=O)c1sc2ncnc(Nc3ccc(F)cc3O[C@H]3C[C@@H]4OCO[C@@H]4C3)c2c1C]
relative stereochemistry

A reaction mixture of 1.79 g 4-chloro-5-methyl-thieno[2,3d]pyrimidine-6-carboxylic acid methyl ester, 1.77 g intermediate XXXXVI and 0.422 g p-toluenesulfonic acid in 50 ml isopropanol was heated at 90° C. for 2 hours. The reaction mixture was poured in water and filtered. The solid was washed with water, triturated with ACN and dried in vacuo at 60° C.

Yield: 72.2 g
ESI mass spectrum: m/z=446 (M+H)$^+$
$R_t$ (HPLC): 3.30 min (method A)

290.2 4-[4-Fluoro-2-(tetrahydro-cyclopenta[1,3]dioxol-5-yloxy)phenylamino]-5-methyl-thieno[2,3-d]pyrimidine-6-carboxylic acid

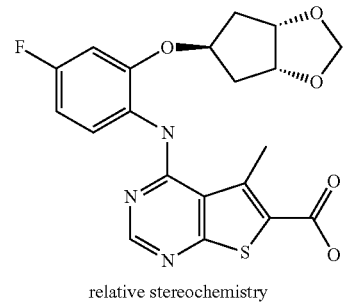 [SMILES: Cc1c(C(=O)O)sc2ncnc(Nc3ccc(F)cc3O[C@H]3C[C@@H]4OCO[C@@H]4C3)c12]
relative stereochemistry

A reaction mixture of 2.1 g 4-[4-fluoro-2-(tetrahydro-cyclopenta[1,3]dioxol-5-yloxy)phenylamino]-5-methyl-thieno[2,3-d]pyrimidine-6-carboxylic acid methyl ester and 0.56 g lithium hydroxide in 150 ml THF was stirred at rt overnight. Then the mixture was acidified by addition of 10% citric acid, concentrated and filtered. The solid was dried in vacuo at 60° C.

Yield: 1.79 g
ESI mass spectrum: m/z=432 (M+H)$^+$
$R_t$ (HPLC): 3.02 min (method A)

Example 291

4-[4-Fluoro-2-(tetrahydro-cyclopenta[1,3]dioxol-5-yloxy)phenylamino]-5-methyl-thieno[2,3-d]pyrimidine-6-carboxylic acid (3-pyrrolidin-1-yl-propyl)-amide

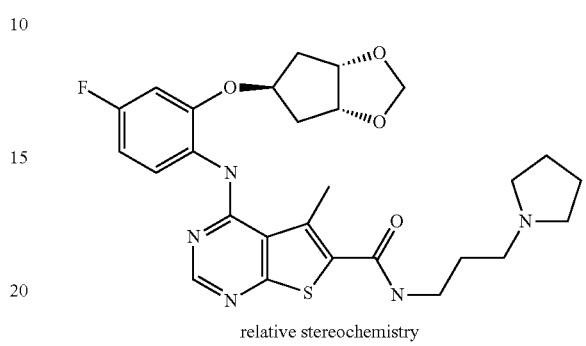
relative stereochemistry

A mixture of 0.15 g 4-[4-fluoro-2-(tetrahydro-cyclopenta[1,3]dioxol-5-yloxy)phenylamino]-5-methyl-thieno[2,3-d]pyrimidine-6-carboxylic acid, 0.045 g 1-(3-aminopropy)pyrrolidine, 0.159 g HATU and 0.097 ml TEA in 15 ml DMF was stirred at rt for 1 hour. The reaction mixture was poured on water, extracted with DCM, dried and filtered. The filtrate was concentrated. The residue was triturated with diisopropylether.

Yield: 0.110 g
ESI mass spectrum: m/z=542 (M+H)$^+$
$R_t$ (HPLC): 1.28 min (method K)

The following compound was prepared analogously to 291.3:

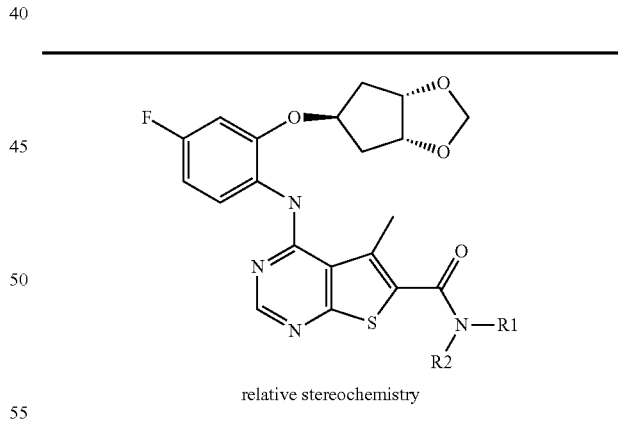
relative stereochemistry

| Example | NR1R2 | educt | Mass spectrum | HPLC (retention time) |
|---|---|---|---|---|
| 292 | H, N, piperidine-N-methyl (t-Bu) | Cpd. 291.2 | 528 (M + H) | min (Method . . . ) |

Example 293

(1S,2S) 4-{2-[2-(Cyclopropanecarbonyl-amino)-cyclopentyloxy]-4-fluoro-phenylamino}-5-methyl thieno[2,3-d]pyrimidine-6-carboxylic acid amide

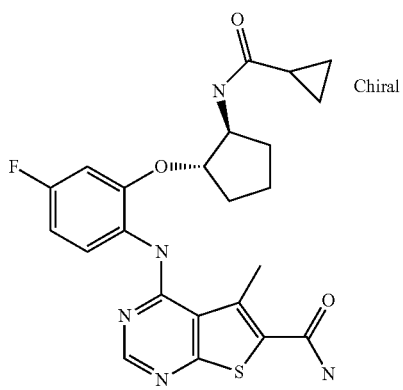 [SMILES: Cc1c(C(N)=O)sc2ncnc(Nc3ccc(F)cc3O[C@H]3CCC[C@@H]3NC(=O)C3CC3)c12]

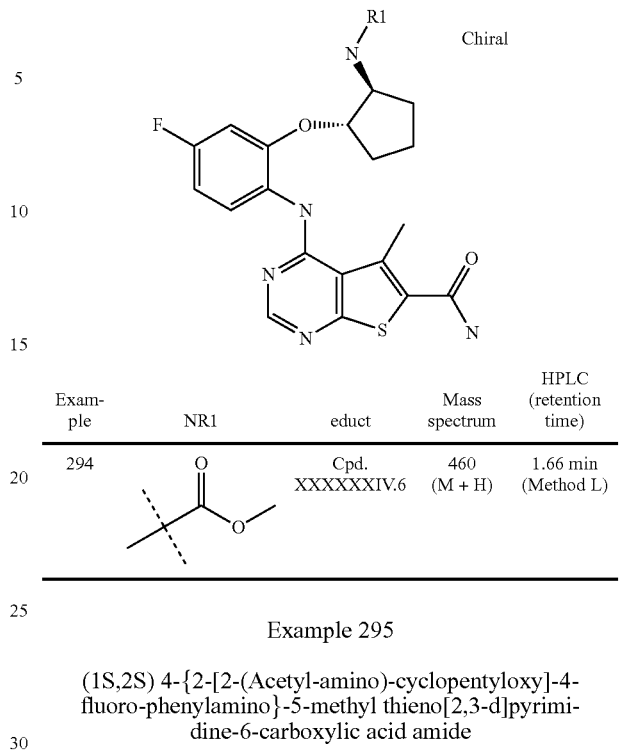

| Example | NR1 | educt | Mass spectrum | HPLC (retention time) |
|---|---|---|---|---|
| 294 | | Cpd. XXXXXXIV.6 | 460 (M + H) | 1.66 min (Method L) |

0.15 g (1S,2S) 4-[2-(2-amino-cyclopentyloxy)-4-fluoro-phenylamino]-5-methyl thieno[2,3-d]pyrimidine-6-carboxylic acid amide and 0.45 ml N,N-diisopropylethylamine were mixed with DCM. 0.047 g cyclopropanecarbonyl chloride were added to the mixture and stirred for 1 hour at rt. Then the reaction mixture was diluted with water and filtrated. The residue was dissolved in 3 ml dioxane and sodium-carbonate-solution and stirred at rt overnight.

To the mixture were added DCM and water. The mixture was filtrated and the solid was air-dried.

Yield: 0.093 g

ESI mass spectrum: m/z=470 (M+H)$^+$ $R_t$ (HPLC): 1.66 min (method L)

The following compound was prepared analogously to 293:

Example 295

(1S,2S) 4-{2-[2-(Acetyl-amino)-cyclopentyloxy]-4-fluoro-phenylamino}-5-methyl thieno[2,3-d]pyrimidine-6-carboxylic acid amide

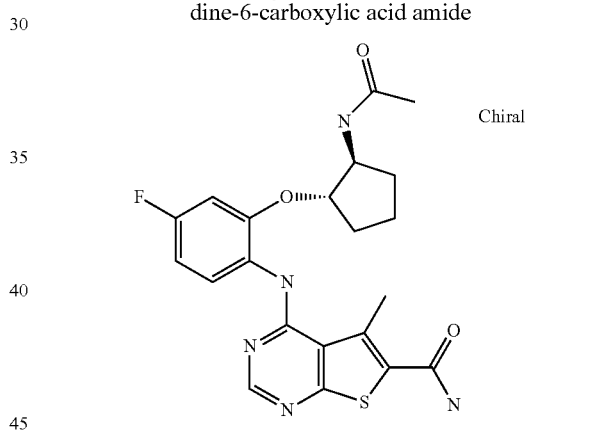

0.15 g (1S,2S) 4-[2-(2-amino-cyclopentyloxy)-4-fluoro-phenylamino]-5-methyl thieno[2,3-d]pyrimidine-6-carboxylic acid amide and 0.32 ml N,N-diisopropylethylamine were mixed with DCM. 0.027 g acetylchloride were added to the mixture and stirred for 1 hour at rt. Then the reaction mixture was diluted with water and filtrated. The solid was air-dried.

Yield: 0.14 g

ESI mass spectrum: m/z=444 (M+H)$^+$ $R_t$ (HPLC): 1.53 min (method L)

The invention claimed is:

1. A compound of Formula (I)

(I)

wherein

X is CH or N, $R^1$ is a hydrogen or halogen atom, $R^2$ is $C_{3-7}$ cycloalkyl group that is substituted with one or two substituents selected from oxo, halogen, $C_{1-3}$ alkyl, hydroxy, $C_{1-3}$ alkoxy, $C_{1-4}$ alkoxy-carbonyl, amino and morpholinyl,
wherein the hydrogen atoms of the amino group may optionally be independently replaced by a $C_{1-3}$ alkyl, $C_{1-3}$ alkoxy-$(CH_2)_m$—, $C_{1-4}$ alkoxy-carbonyl, $C_{1-3}$ alkylsulfonyl, $C_{1-3}$ alkyl-carbonyl, $C_{3-6}$-cycloalkyl-carbonyl or piperidinyl group, wherein m is 2 or 3 and wherein the piperidinyl group may optionally be substituted by a methyl group,
wherein two substituents, which are attached to the same carbon atom, together may form a —O—$(CH_2)_2$—O— group, and
wherein two substituents, which are attached to two adjacent carbon atoms, together may form a —O—$CH_2$—O— or —O—$C(CH_3)_2$—O— group, $R^3$ is a $C_{1-2}$ alkyl group and $R^4$ is a carboxy, $C_{1-3}$ alkoxy-carbonyl, aminocarbonyl, N—($C_{1-4}$ alkyl)-aminocarbonyl or N,N-[di($C_{1-4}$ alkyl)]-aminocarbonyl group,
wherein the aminocarbonyl group may be substituted with a $C_{1-3}$ alkylsulfonyl, CN, OH, $C_{1-3}$ alkoxy, $C_{3-6}$ cycloalkyl, —$CH_2$—C≡C—$CH_2$—$NH_2$, —$CH_2$—C≡C—$CH_2$—NH($C_{1-3}$ alkyl) or —$CH_2$—C≡C—$CH_2$—N($C_{1-3}$ alkyl)$_2$ group or with a piperidinyl or pyrrolidinyl group bound via a carbon atom, and
wherein the alkyl moieties of the above-mentioned N—($C_{1-4}$ alkyl)-amino-carbonyl and N,N-[di-($C_{1-4}$ alkyl)]-aminocarbonyl groups may optionally be substituted with an aminocarbonyl, N—($C_{1-3}$ alkyl)-aminocarbonyl or N,N-[di-($C_{1-3}$ alkyl)]-aminocarbonyl group or with a pyrrolidinyl, oxazolyl, imidazolyl, piperidinyl or morpholinyl group, each bound via a carbon atom, or, if the alkyl moiety is a ($C_{2-4}$alkyl), it may be substituted with a OH, CN, $C_{1-3}$ alkoxy, amino, N—($C_{1-3}$ alkyl)-amino, N,N-[di-($C_{1-3}$ alkyl)]-amino, $C_{1-5}$ alkyloxy-carbonyl-amino, morpholino, piperidino, piperazino, pyrrolidino, azetedinyl, aziridinyl or imidazolyl group, with the proviso that said ($C_{2-4}$alkyl) moiety may not be substituted on the 1-position of the alkyl moiety,
wherein each of the above-mentioned cycloalkyl, pyrrolidinyl, oxazolyl, piperidinyl, morpholinyl, piperazinyl and imidazolyl groups may be substituted with a methyl, amino, hydroxy group or $C_{1-3}$ alkoxy, or a pharmaceutically acceptable salt thereof.

2. A compound of Formula (I) according to claim 1, wherein $R^3$ is methyl, or a pharmaceutically acceptable salt thereof.

3. A compound of Formula (I) according to claim 1, wherein

X is CH and $R^1$ is a fluorine atom, or a pharmaceutically acceptable salt thereof.

4. A compound of Formula (I) according to claim 1, wherein

X is N and $R^1$ is a hydrogen atom, or a pharmaceutically acceptable salt thereof.

5. A compound of Formula (I) according to claim 1, wherein $R^4$ is carboxy, $C_{1-3}$ alkoxy-carbonyl, aminocarbonyl or N—($C_{1-3}$ alkyl)-aminocarbonyl group,
wherein, if the ($C_{1-3}$ alkyl) moiety of the above-mentioned N($C_{1-3}$alkyl)-aminocarbonyl group is a methyl group, the methyl group may optionally be substituted with a piperidinyl, N-methyl-piperidinyl or morpholinyl group, each bound via a carbon atom, and wherein, if the ($C_{1-3}$ alkyl)- moiety is an the ethyl or propyl group, the ethyl or propyl group may optionally be terminally substituted with hydroxy, methoxy, amino, N-methylamino, N,N-dimethyl-amino, morpholino, imidazolyl, 4-methyl-piperazinyl, 1-methylpyrrolidinyl, piperidinyl, pyrrolidinyl or 4-hydroxy-piperidino group, or a pharmaceutically acceptable salt thereof.

6. A compound of Formula (I) according to claim 5, wherein $R^4$ is aminocarbonyl or N—($C_{1-3}$ alkyl)-aminocarbonyl group,
wherein, if the ($C_{1-3}$ alkyl) moiety of the above-mentioned N($C_{1-3}$alkyl)-aminocarbonyl group is a methyl group, the methyl group may optionally be substituted with a piperidinyl, N-methyl-piperidinyl or morpholinyl group, each bound via a carbon atom, and wherein, if the ($C_{1-3}$ alkyl)- moiety is an ethyl or propyl group, the ethyl or propyl group may optionally be terminally substituted with hydroxy, methoxy, amino, N-methylamino, N,N-dimethyl-amino, morpholino, imidazolyl, 4-methyl-piperazinyl, 1-methylpyrrolidinyl, piperidinyl, pyrrolidinyl or 4-hydroxy-piperidino group, or a pharmaceutically acceptable salt thereof.

7. A compound of Formula (I) according to claim 1, wherein

R² is cyclopentyl substituted with one or two hydroxy or methoxy groups or with an amino, methylcarbonyl-amino, N-methyl-N-methylcarbonyl-amino group or wherein two adjacent carbon atoms are linked to each other via a —O—CH₂—O— or —O—C(CH₃)₂—O— group, or cyclohexyl substituted with one or two fluorine atoms or one or two hydroxy or methoxy groups or an oxo, $C_{1-3}$ alkoxy-carbonyl, morpholino, methyl-piperidinyl-amino or an amino group, wherein the hydrogen atoms of the amino group my optionally independently be replaced with a methyl, methylcarbonyl, 2-methoxy-ethyl or methylsulfonyl group, or wherein two adjacent carbon atoms are linked to each other via-O—C(CH₃)₂—O— group or wherein two hydrogen atoms attached to the same carbon atom are replaced by a —O—(CH₂)₂—O— group, or a pharmaceutically acceptable salt thereof.

8. A compound of formula (I) according to claim 1, wherein

R² is cyclohexyl substituted with one hydroxy or methoxy group, cyclopentyl substituted with one hydroxy, methoxy, methylcarbonyl-amino or N-methyl-N-methylcarbonyl-amino group or cyclopentyl, wherein two adjacent carbon atoms are linked to each other via a —O—CH₂—O— group, or cyclobutyl substituted with a methylcarbonyl-amino or methylcarbonyl-N(methyl)-amino group, or a pharmaceutically acceptable salt thereof.

9. A compound of Formula (I) according to claim 1 selected from a group consisting of:

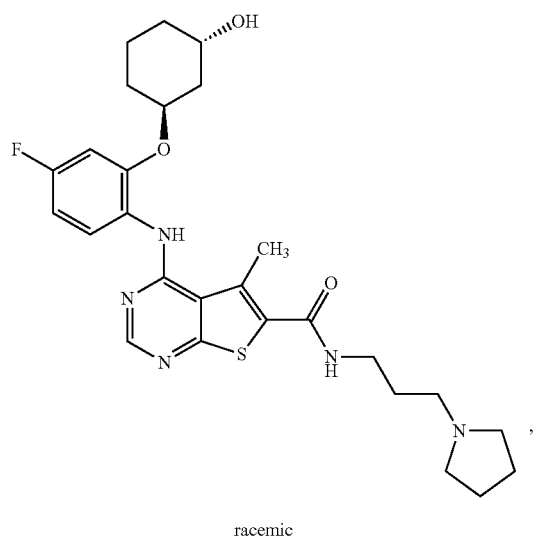

racemic

-continued

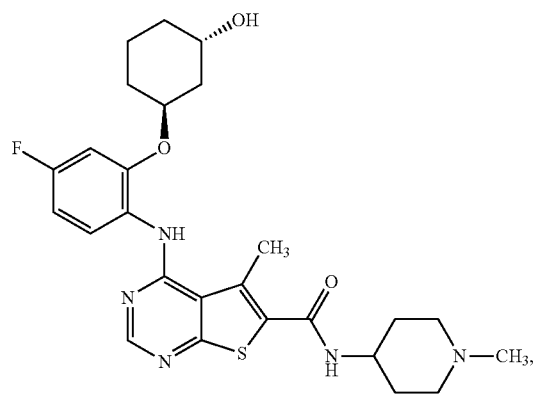

racemic

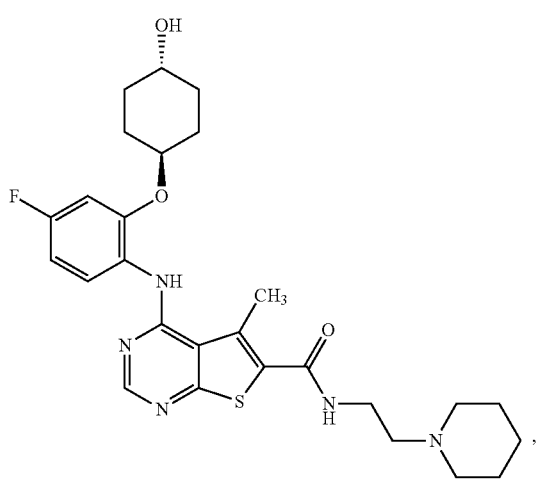

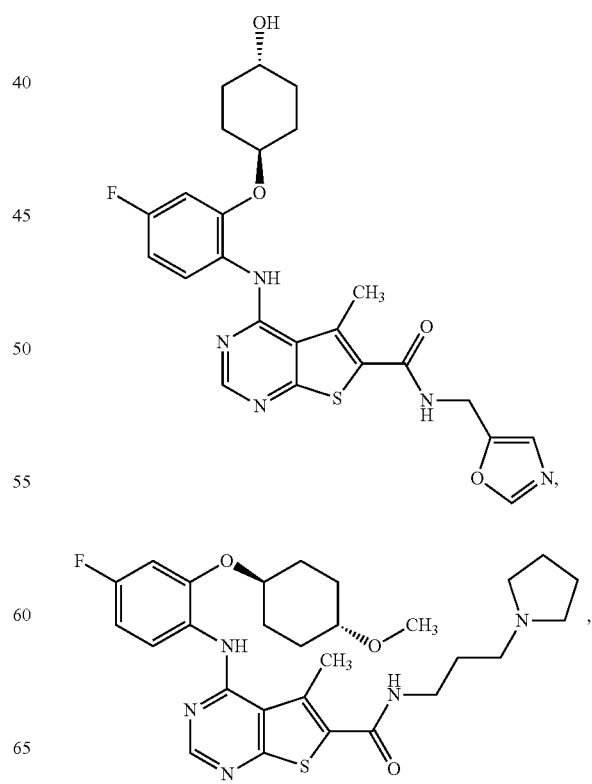

299
-continued
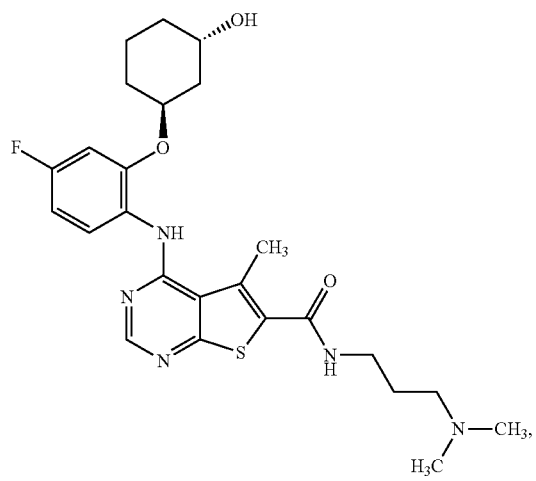
racemic
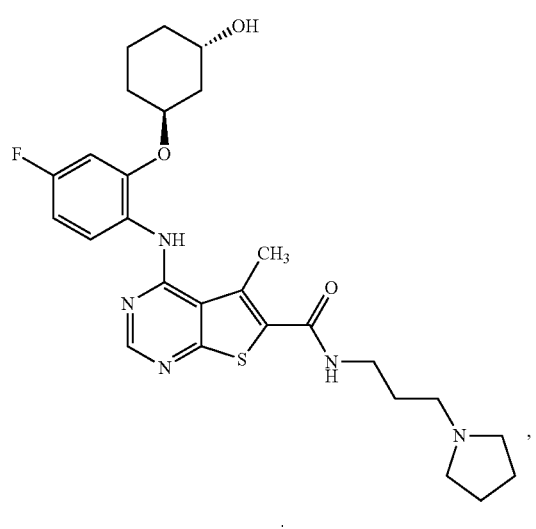
racemic
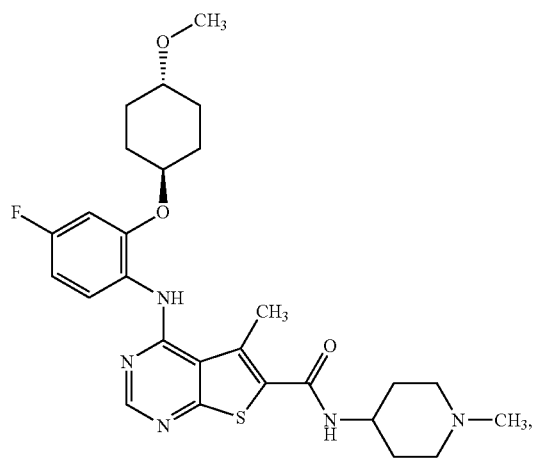
300
-continued
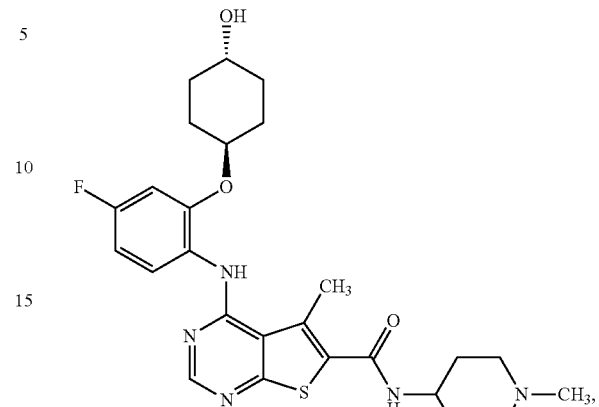
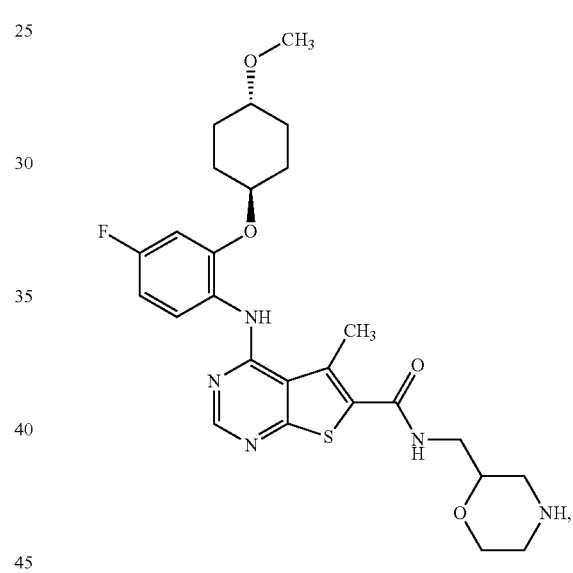
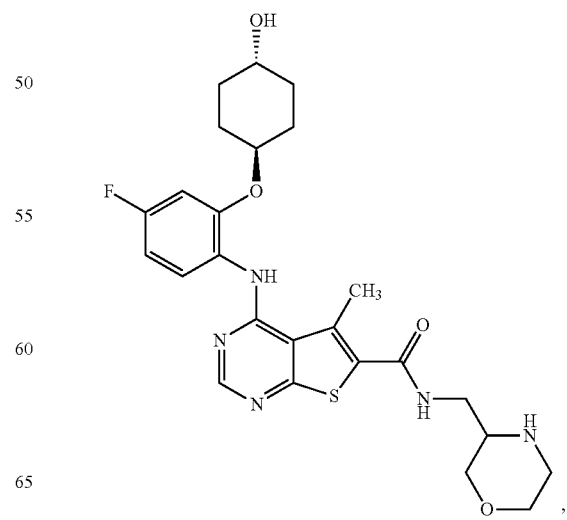

301
-continued
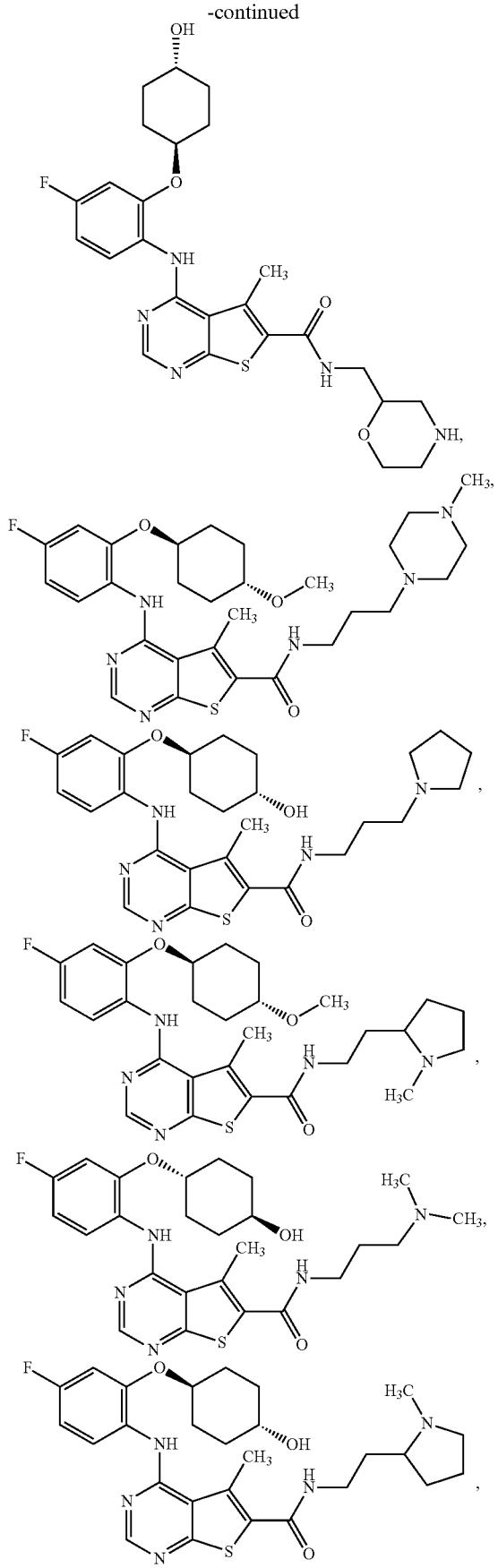
302
-continued
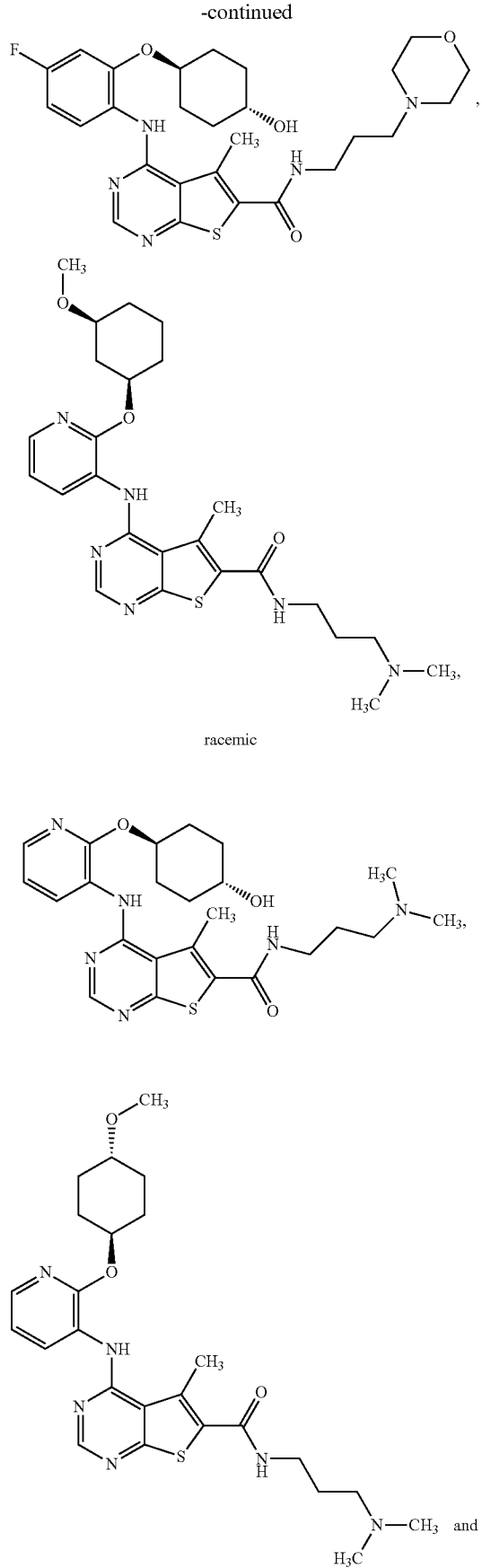
racemic

-continued

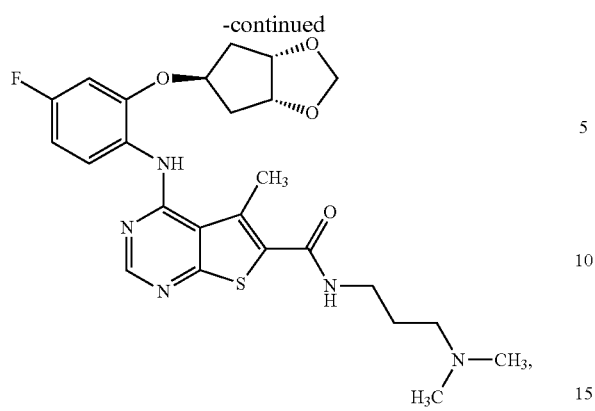

or a pharmaceutically acceptable salt thereof.

10. A pharmaceutically acceptable salt of a compound according to claim 1.

11. A pharmaceutical composition comprising a compound according to claim 1 or a pharmaceutically acceptable salt thereof and optionally a pharmaceutically acceptable carrier.

12. A pharmaceutical composition according to claim 11 further comprising an additional therapeutic agent.

13. A pharmaceutical composition according to claim 12 wherein the additional therapeutic agent is selected from an antidiabetic agent, a lipid lowering agent, a cardiovascular agent, an antihypertensive agent, a diuretic agent, a thrombocyte aggregation inhibitor, an antineoplastic agent and an anti-obesity agent.

* * * * *

SEQUENCE LISTING

<160> NUMBER OF SEQ ID NOS: 7

<210> SEQ ID NO 1
<211> LENGTH: 29
<212> TYPE: DNA
<213> ORGANISM: Homo sapiens

<400> SEQUENCE: 1
tttaggatcc gtatcttctc aaaagttgg                                29

<210> SEQ ID NO 2
<211> LENGTH: 28
<212> TYPE: DNA
<213> ORGANISM: Homo sapiens

<400> SEQUENCE: 2
ctgggtcgac tcagagtgct gtgggcgg                                 28

<210> SEQ ID NO 3
<211> LENGTH: 28
<212> TYPE: DNA
<213> ORGANISM: Homo sapiens

<400> SEQUENCE: 3
acagggatcc gtgcagaaga aaccagcc                                 28

<210> SEQ ID NO 4
<211> LENGTH: 29
<212> TYPE: DNA
<213> ORGANISM: Homo sapiens

<400> SEQUENCE: 4
gatggtcgac tcaggcgtgg tctcccacc                                29

<210> SEQ ID NO 5
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Thr Ala Thr Lys Ser Gly Ser Thr Thr Lys Asn Arg
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Phosphorylated-Ser

<400> SEQUENCE: 6

Thr Ala Thr Lys Ser Gly Ser Thr Thr Lys Asn Arg
1               5                   10

<210> SEQ ID NO 7
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Phosphorylated-Ser
<220> FEATURE:
<223> OTHER INFORMATION: C-term CONH2

```
<400> SEQUENCE: 7

Cys Thr Ala Thr Lys Ser Gly Ser Thr Thr Lys Asn Arg
 1               5                  10
```